(12) United States Patent
Mutter et al.

(10) Patent No.: US 6,703,204 B1
(45) Date of Patent: Mar. 9, 2004

(54) PROGNOSTIC CLASSIFICATION OF BREAST CANCER THROUGH DETERMINATION OF NUCLEIC ACID SEQUENCE EXPRESSION

(75) Inventors: George L. Mutter, Chestnut Hill, MA (US); Jan P. A. Baak, Tananger (NO)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/917,254

(22) Filed: Jul. 27, 2001

(65) Prior Publication Data (65)

Related U.S. Application Data

(60) Provisional application No. 60/222,093, filed on Jul. 28, 2000.

(51) Int. Cl.[7] .......................... C12Q 1/68; C12P 19/34; C07H 12/02; C07H 12/04
(52) U.S. Cl. ...................... 435/6; 435/91.2; 536/23.5; 536/24.31; 536/24.33
(58) Field of Search ..................... 435/6, 91.1, 91.2; 536/23.1, 23.5, 24.1, 24.31, 24.33

(56) References Cited

U.S. PATENT DOCUMENTS 5,622,829 A    4/1997    King et al.

FOREIGN PATENT DOCUMENTS

| EP | 1146054 A1 | 10/2001 |
|---|---|---|
| WO | WO 99/01581 A | 1/1999 |
| WO | WO 99/37771 A1 | 7/1999 |
| WO | WO 96/29430 A | 9/1999 |
| WO | WO 00/32628 A1 | 8/2000 |

OTHER PUBLICATIONS

Raport et al. Gene 163 (2), 295–299 (1995).*
Weinstein, J. et al. Molecular Cell Biology. 14(15), 3350–3363 (1994).*
Wewer, U.M. et al. Genomics 24 (2), 243–252 (1994).*
Author Unknown, The Chipping Forecast, *Nature Genetics* 21(1):1–60 (1999).
Baak et al., *Hum. Pathol.* 23:989–992 (1992).
Baak et al., *J. Cell Biochem Suppl* 17G:220–225 (1993).
Baak et al., *Pathol Res Pract* 185: 664–670 (1989).
Gwynne et al., "Microarray Analysis: the next revolution in molecular biology" *Science*, Aug. 6, 1999 Special Advertising section accessed from www.sciencemag.org/feature/e-market/benchtop/micro.shl. 11 pages.
Jannink et al., *Histopathology* 29:421–428 (1996).
Jannink et al., *Hum Pathol* 26(10): 1086–1092 (1995).
Mutter et al., *8th Int'l Workshop on Chromosomes in Solid Tumors* (Tucson, AZ) 2000.
Sainio et al, *Cell Mol. Neurobiol.* 14(5):439–457 (1994).
Theissig et al., *Anal Cell Pathol* 10:85–99 (1996).
Tosi et al., *Appl Pathol* 4:33–42 (1986).
Uyterlinde et al., *Int J Cancer* 45:1–7 (1990).
Van Diest and Baak, *Hum. Pathol.* 22:326–330 (1991).
Van Diest et al., *Hum. Pathol.* 23:603–607 (1992).
Van Diest et al., *Pathol. Res. Pract.* 188:344–349 (1992).
Wagner et al., *Nature Biotechnol.* 14:840–844 (1996).
Beattie, J. et al., Eur. J. Biochem. 239(2):479–486. (1996).
De Jong, J., et al., Journal of Pathology. 184(1):53–57 (1998) Abstract Only.
EMBL Database (EBI) Accession No. X57522—H. sapiens RING4 cD NA, Jul. 1, 1992. 2 pages.
EMBL Database (EBI) Accession No. X13839—Hum an mRNA for vascular smooth muscle alpha–actin, Mar. 13, 1989 2 pages.
EMBL Database (EBI) Accession No. Q03518, Q16149—Antigen pepti de transporter 1 (APT1) (Peptide transporter TAP1) Jun. 1, 1994. 3 pages.
EMBL Database (EBI) Accession No. P03996, P04108—Actin, aortic s mooth muscle (Apha–actin 2), Oct. 23, 1986. 3 pages.
Fodor, S.P.A., et al., Nature. 364:555–556 (Aug. 5, 1993).
Krishnan, R., et al., Cancer Research. 50(7):2164–2171 (1990) Abstract Only.
Rao, Jy, et al., Cancer Epidemiology Biomarkers & Prevention 7(11):1027–1033. (1998).
Sgroi, DC, et al., Cancer Research. 59(22):5656–5661. (1999).
Cox, C.J., et al., "Tumor marker sensitivity: single versus multiple markers in patients with breast cancer." Am. J. Clin. Pathol. 84(4):507. (1990).
Harris, A.L., et al., Gene therapy through signal transduction pathways and angiogenic growth factors as therapeutic targets in breast cancer. Cancer, American Cancer Society, Philadelphia, PA, US, 74(3 Suppl) 1021–1025 (1994).
Jiang, M., et al., "P21/WAF1/CIP1 and MDM–2 expression in breast carcinoma patients as related to prognosis." Int. J. Cancer. 74(5):529–534 (1997).
Martin, K.J., et al., "Linking gene expression patterns to therapeutic groups in breast cancer." Proceedings of the Annual Meeting of the American Association for Cancer Research. 41:311–312 (Mar. 2000).
Tanaka, T., et al., "Prognostic discrimination among neuroblastomas according to HA–RAS/TRK a gene expression a comparison of the profiles of neuroblastomas detected clinically and those detected through mass screening." Cancer. 83(8):1626–1631 (1998).

\* cited by examiner

*Primary Examiner*—Carla J. Myers
*Assistant Examiner*—Sally Sakelaris
(74) *Attorney, Agent, or Firm*—Wolf, Greenfield & Sacks, P.C.

(57) ABSTRACT

The invention provides particular sets of genes that are expressed differentially in tumors characterized as high MAI or low MAI tumors. These sets of genes can be used to discriminate between high and low MAI tumors. Diagnostic assays for classification of tumors, prediction of tumor outcome, selecting and monitoring treatment regimens and monitoring tumor progression/regression are also provided.

2 Claims, 1 Drawing Sheet

PROGNOSTIC CLASSIFICATION OF BREAST CANCER THROUGH DETERMINATION OF NUCLEIC ACID SEQUENCE EXPRESSION

RELATED APPLICATIONS

This application claims the benefit under 35 U.S.C. §119(e) of U.S. provisional application No. 60/222,093, filed Jul. 28, 2000.

FIELD OF THE INVENTION

The invention relates to nucleic acid microarray markers for cancer, particularly for breast cancer. The invention also relates to methods for diagnosing cancer as well as optimizing cancer treatment strategies.

BACKGROUND OF THE INVENTION

Breast cancer is a malignant proliferation of epithelial cells lining the ducts or lobules of the breast (Harrison's Principles of Internal Medicine 1998). Although much progress has been made toward understanding the biological basis of cancer and in its diagnosis and treatment, it is still one of the leading causes of death in the United States. Inherent difficulties in the diagnosis and treatment of cancer include among other things, the existence of many different subgroups of cancer and the concomitant variation in appropriate treatment strategies to maximize the likelihood of positive patient outcome.

The traditional method of breast cancer diagnosis and staging is through the use of biopsy examination. Once a diagnosis is made, the options for treating breast cancer are assessed with respect to the needs of the patient. These options traditionally include surgical intervention, chemotherapy, radiotherapy, and adjuvant systemic therapies. Surgical therapy may be lumpectomy or more extensive mastectomy. Adjuvants may include but are not limited to chemotherapy, radiotherapy, and endocrine therapies such as castration; administration of LHRH agonists, antiestrogens, such as tamoxifen, high-dose progestogens; adrenalectomy; and/or aromatase inhibitors (Harrison's Principles of Internal Medicine 1998).

Of key importance in the treatment of breast cancer is the selection and implementation of an appropriate combination of therapeutic approaches. For example, depending on a breast cancer patient's prognosis, therapy may include surgical intervention in combination with adjuvant therapy or it may only include surgical intervention. In addition, for some patients pretreatment with chemotherapy or radiotherapy is utilized prior to surgical intervention, but in other patients adjuvant therapies are used following surgical intervention.

It is difficult to predict from standard clinical and pathologic features the clinical course of early stage breast cancer, particularly lymph node-negative tumors in premenopausal patients. Current practice in the United States is to offer systemic chemotherapy to most of these women. Because the majority of these women would have good outcome even without chemotherapy, the rate of "over-treatment" is high. Chemotherapy itself carries a 1% mortality rate. Therefore, unnecessary deaths could be avoided if it were possible to subdivide these patients into high and low risk subgroups, and only undertake adjunctive treatment for those judged to be high risk.

Selection of a suitable treatment regimen for breast cancer is based on the subgroup of cancer. Current strategies used to make therapeutic decisions in the management of patients with breast cancer are based on several factors including hormone receptor status, her-2/neu staining, flow cytometry, and the mitotic activity index (MAI). The MAI is a widely utilized predictor of outcome in cancers, particularly in invasive breast cancer. The definition of the MAI is "the total number of mitoses counted in 10 consecutive high-power fields (objective, ×40; numeric aperture, 0.75; field diameter, 450 microns), in the most cellular area at the periphery of the tumor, with the subjectively highest mitotic activity" (Jannink et al., 1995). For the procedure, hematoxylin-eosin stained sections of breast cancer tumor are assessed for the total number of mitotic figures in ten consecutive high-power fields and based on these numbers the breast cancer is assigned to either good outcome (MAI<10) or poor outcome (MAI>10). MAI classification correlates to standard parameters such as death, recurrence, and metastases, which are known to those of ordinary skill in the art to predict clinical outcome.

Determination of appropriate treatment for an individual cancer patient is complex with a wide variety of treatments and possible treatment combinations. For example, chemotherapy is a common method of cancer treatment, with more than 50 different chemotherapeutic agents available. These therapeutic agents can be used in a wide range of dosages both singly and in combinational therapies with other chemotherapeutic agents, surgery, and/or radiotherapy.

The available methods for designing strategies for treating breast cancer patients are complex, time consuming, and inexact. The wide range of cancer subgroups and variations in disease progression limit the predictive ability of the healthcare professional. In addition, continuing development of novel treatment strategies and therapeutics will result in the addition of more variables to the already complex decision-making process involving matching the cancer patient with a treatment regimen that is appropriate and optimized for the cancer stage, extent of infiltration, tumor growth rate, and other factors central to the individual patient's prognosis. Because of the critical importance of selecting appropriate treatment regimens for breast cancer patients, the development of guidelines for treatment selection is of key interest to those in the medical community and their patients. Thus, there presently is a need for objective, reproducible, and sensitive methods for predicting breast cancer patient outcome and selecting optimal treatment regimens.

SUMMARY OF THE INVENTION

It now has been discovered that particular sets of genes are expressed differentially in tumors characterized as high MAI or low MAI tumors. These sets of genes can be used to discriminate between high and low MAI tumors. Accordingly, diagnostic assays for classification of tumors, prediction of tumor outcome, selecting and monitoring treatment regimens and monitoring tumor progression/regression can now be based on the expression of sets of genes.

According to one aspect of the invention, methods for diagnosing breast cancer in a subject suspected of having breast cancer are provided. The methods include obtaining from the subject a breast tissue sample and determining the expression of a set of nucleic acid molecules or expression products thereof in the breast tissue sample. The set of nucleic acid molecules includes at least two nucleic acid molecules selected from the group consisting of SEQ ID NOs:1–51. In preferred embodiments, the breast tissue sample suspected of being cancerous.

In some embodiments the set of nucleic acid molecules includes more than 2 and up to all of the nucleic acid molecules set forth as SEQ ID NOs:1–51, and any number of nucleic acid sequences between these two numbers. For example, in certain embodiments the set includes at least 3, 4, 5, 10, 15, 20, 30, 40 or more nucleic acid molecules of the nucleic acid molecules set forth as SEQ ID NOs:1–51.

In other embodiments, the method further includes determining the expression of the set of nucleic acid molecules or expression products thereof in a non-cancerous breast tissue sample, and comparing the expression of the set of nucleic acid molecules or expression products thereof in the breast tissue sample suspected of being cancerous and the non-cancerous breast tissue sample.

According to another aspect of the invention, methods for identifying a set of nucleic acid markers or expression products thereof are provided. The methods are effective for determining the prognosis of cancer. The methods include obtaining a plurality of tumor tissue samples from a plurality of subjects afflicted with cancer, classifying the plurality of tumor tissue samples according to mitotic activity index (MAI) into high MAI and low MAI groups and determining differences in the expression of a plurality of nucleic acid molecules or expression products thereof in the tumor tissue samples. The methods further include selecting as a set of nucleic acid markers the nucleic acid molecules or expression products thereof which are differentially expressed in the high MAI and the low MAI groups. The set of nucleic acid markers or expression products thereof effective for determining poor prognosis of cancer includes one or more nucleic acid molecules or expression products thereof which are preferentially expressed in high MAI tumor tissue samples, and wherein the set of nucleic acid markers or expression products thereof effective for determining good prognosis of cancer comprises one or more nucleic acid molecules or expression products thereof which are preferentially expressed in low MAI tumor tissue samples. In preferred embodiments, the cancer is breast cancer.

According to still another aspect of the invention, methods for selecting a course of treatment of a subject having or suspected of having cancer are provided. The methods include obtaining from the subject a tissue sample suspected of being cancerous, determining the expression of a set of nucleic acid markers or expression products thereof which are differentially expressed in high MAI tumor tissue samples to determine the MAI of the tissue sample of the subject, and selecting a course of treatment appropriate to the cancer of the subject.

In preferred embodiments the cancer is breast cancer, and in some of these embodiments the methods include determining the expression of a set of nucleic acid markers that are differentially expressed in low MAI breast tumor tissue samples.

According to yet another aspect of the invention, methods for evaluating treatment of cancer are provided. The methods include obtaining a first determination of the expression of a set of nucleic acid molecules or expression products thereof, which are differentially expressed in high MAI tumor tissue samples to determine the MAI of the tissue sample from a subject undergoing treatment for cancer, and obtaining a second determination of the expression of a set of nucleic acid molecules or expression products thereof, which are differentially expressed in high MAI tumor tissue samples to determine the MAI of the second tissue sample from the subject after obtaining the first determination. The methods also include comparing the first determination of expression to the second determination of expression as an indication of evaluation of the treatment.

In preferred embodiments the cancer is breast cancer, and in some of these embodiments the methods include determining the expression of a set of nucleic acid markers that are differentially expressed in low MAI breast tumor tissue samples.

The invention in another aspect provides solid-phase nucleic acid molecule arrays. The arrays have a cancer gene marker set that consists essentially of at least two and as many as all of the nucleic acid molecules set forth as SEQ ID NOs:1–51 fixed to a solid substrate. The set-of nucleic acid markers can include any number of nucleic acid sequences between these two numbers, selected from SEQ ID NOs:1–51. For example, in certain embodiments the set includes at least 3, 4, 5, 10, 15, 20, 30, 40 or more nucleic acid molecules of the nucleic acid molecules set forth as SEQ ID NOs:1–51. In some embodiments, the solid-phase nucleic acid molecule array also includes at least one control nucleic acid molecule.

In certain embodiments, the solid substrate includes a material selected from the group consisting of glass, silica, aluminosilicates, borosilicates, metal oxides such as alumina and nickel oxide, various clays, nitrocellulose, or nylon. Preferably the substrate is glass.

In other embodiments, the nucleic acid molecules are fixed to the solid substrate by covalent bonding.

According to yet another aspect of the invention, protein microarrays are provided. The protein microarrays include antibodies or antigen-binding fragments thereof, that specifically bind at least two different polypeptides selected from the group consisting of SEQ ID NOs:52–102, fixed to a solid substrate. In some embodiments, the microarray comprises antibodies or antigen-binding fragments thereof, that bind specifically to least 3, 4, 5, 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 51 different polypeptides selected from the group consisting of SEQ ID NOs:52–102. In certain embodiments, the microarray also includes an antibody or antigen-binding fragment thereof, that binds specifically to a cancer-associated polypeptide other than those selected from the group consisting of SEQ ID NOs:52–102, preferably a breast cancer associated polypeptide. In some embodiments, the protein microarray also includes at least one control polypeptide molecule. In further embodiments, the antibodies are monoclonal or polyclonal antibodies. In other embodiments, the antibodies arc chimeric, human, or humanized antibodies. In some embodiments, the antibodies are single chain antibodies. In still other embodimeents, the antigen-binding fragments are F(ab')$_2$, Fab, Fd, or Fv fragments.

In a further aspect of the invention, methods for identifying lead compounds for a pharmacological agent useful in the treatment of breast cancer are provided. The methods include contacting a breast cancer cell or tissue with a candidate pharmacological agent, and determining the expression of a set of nucleic acid molecules in the breast cancer cell or tissue sample under conditions which, in the absence of the candidate pharmacological agent, permit a first amount of expression of the set of nucleic acid molecules. The set of nucleic acid molecules includes at least two and as many as all of the nucleic acid molecules set forth as SEQ ID NOs:1–51. The methods also include detecting a test amount of the expression of the set of nucleic acid molecules, wherein a decrease in the test amount of expression in the presence of the candidate pharmacological agent relative to tho first amount of expression indicates that the candidate pharmacological agent is a lead compound for a pharmacological agent which is useful in the treatment of breast cancer. In preferred embodiments, the set of nucleic acid molecules is differentially expressed in high MAI breast tumor tissue samples.

In some embodiments of any of the foregoing methods and products, the differences in the expression of a the nucleic acid molecules are determined by nucleic acid hybridization or nucleic acid amplification methods. Preferably the nucleic acid hybridization is performed using a solid-phase nucleic acid molecule array. In other embodiments, the differences in the expression of the nucleic acid molecules are determined by protein expression analysis, preferably SELDI mass spectroscopy.

These and other aspects of the invention will be described in greater detail below.

DETAILED DESCRIPTION OF THE INVENTION

Figure 1:
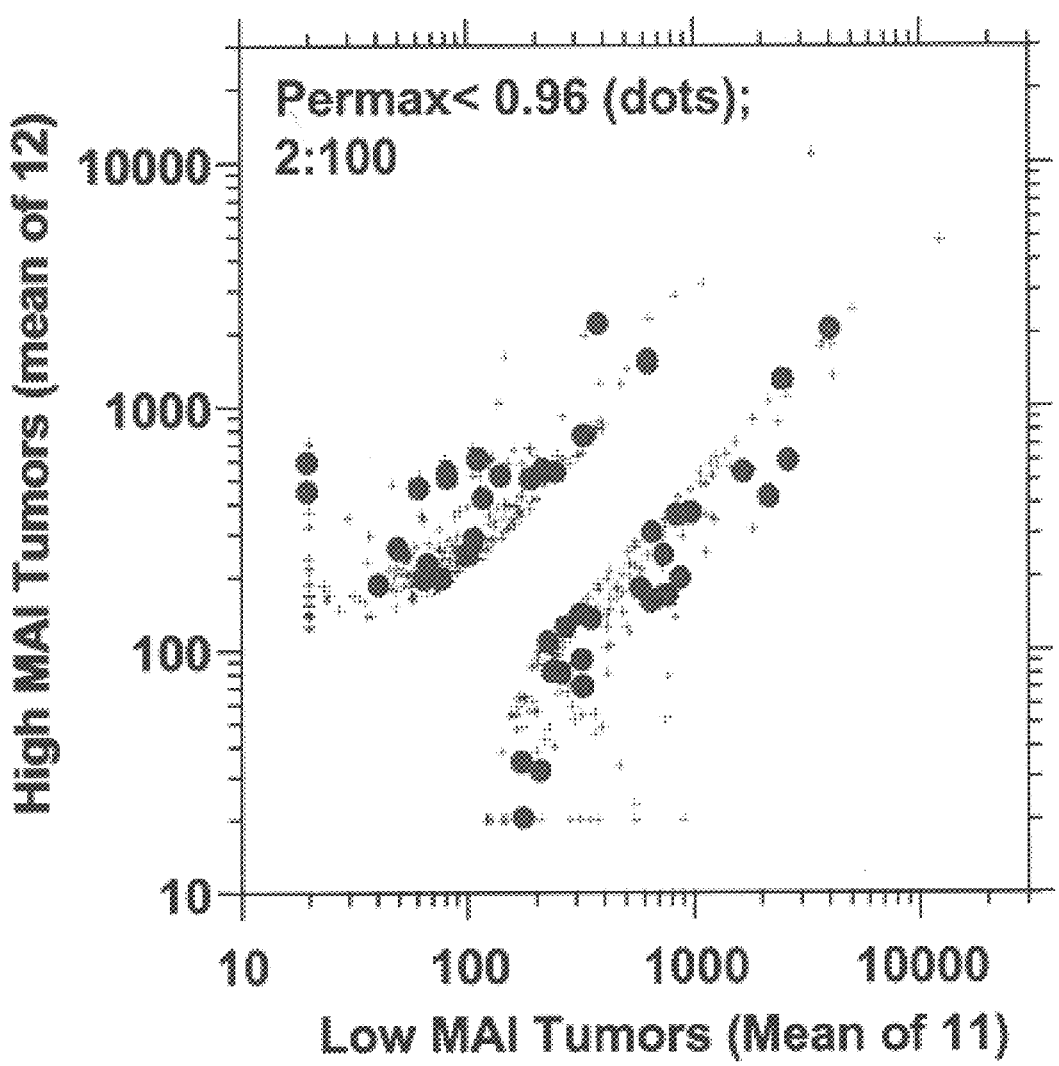
FIG. 1 is a scatterplot of gene expression level in low risk (y axis) and high risk (y axis) breast cancers. 422 genes whose mean expression between groups differs at least 2-fold and by 100 expression units are shown as small crosses. The top 51 t-test ranked genes with Permax 0.96 are indicated as solid circles, and appear in Table 1.

The invention described herein relates to the identification of a set of genes expressed in breast cancer tissue that are predictive of the clinical outcome of the cancer. Changes in cell phenotype in cancer are often the result of one or more changes in the genome expression of the cell. Some genes arm expressed in tumor calls, and not in normal cells. In addition, different genes are expressed in different subgroups of breast cancers, which have different prognoses and require different treatment regimens to optimize patient outcome. The differential expression of breast cancer genes can be examined by the assessment of nucleic acid or protein expression in the breast cancer tissue.

The genes were identified by screening nucleic acid molecules isolated from various breast cancer samples for expression of the genes present on a high-density nucleic acid microarray. The breast cancer samples were categorized with respect to their mitotic activity index (MAI) and the MAI was correlated to gene expression to identify those genes differentially expressed between low and high-MAI breast cancer tissue. The MAI has been shown to correlate with the outcome of the cancer as defined by tumor metastasis, tumor recurrence or mortality, Accordingly the genes identified permit, inter alia, rapid screening of cancer samples by nucleic acid microarray hybridization or protein expression technology to determine the expression of the specific genes and thereby to predict the outcome of the cancer. Such screening is beneficial, for example, in selecting the course of treatment to provide to the cancer patient, and to monitor the efficacy of a treatment.

The invention differs from traditional breast cancer diagnostic and classification techniques including MAI hormone receptor expression and her-2/neu expression, with respect to the speed, simplicity, and reproducibility of the cancer diagnostic assay. The invention also presents targets for drug development because it identifies genes that are differentially expressed in poor outcome breast tumors, which can be utilized in the development of drugs to treat such tumors, e.g., by reducing expression of the genes or reducing activity of proteins encoded by the genes.

The invention moves beyond the use of the MAI and simplifies prognosis determination by providing an identified set of genes whose expression in breast cancers predicts poor clinical outcome as defined by tumor metastasis, recurrence, or death. In the invention, the MAI was used in conjunction with RNA expression phenotyping performed using high density microarrays generated from quantitative expression data on over 5000 (estimated 5800) genes, which have been analyzed to identify 51 specific probe sets (genes) with divergent expression between MAI groups. The expression gene set has multifold uses including, but not limited to, the following examples, The expression gene set may be used as a prognostic tool for breast cancer patients, to make possible more finely tuned diagnosis of breast cancer and allow healthcare professionals to tailor treatment to individual patients' needs. The invention can also assess the efficacy of breast cancer treatment by determining progression or regression of breast cancer in patients before, during, and after breast cancer treatment. Another utility of the expression gene set is in the biotechnology and pharmaceutical industries' research on disease pathway discovery for therapeutic targeting. The invention can identify alterations in gene expression in breast cancer and can also be used to uncover and test candidate pharmaceutical agents to treat breast cancer.

Although the invention is described primarily with respect to breast cancer, one of ordinary skill in the art will appreciate that the invention also is useful for diagnosis and prognosis determination of cancers that can be classified into subgroups for prognosis of the cancer based on MAI. For example, MAI has been used successfully in the classification of malignant melanoma, ovarian cancer, bladder cancer, and prostatic adenocarcinoma. Thus, the methods and products of the invention also are applicable to non-breast cancers that can be classified by MAI.

The invention may also encompass cancers other than breast cancer, including but not limited to: biliary tract cancer; bladder cancer; brain cancer including glioblastomas and medulloblastomas; cervical cancer; choriocarcinoma; colon cancer; ondometial cancer; esophageal cancer; gastric cancer; hematological neoplasms including acute lymphocytic and myelogenous leukemia; multiple myeloma; AIDS-associated leukemnius and adult T-cell leukemia lymphoma; intraepithelial neoplasms including Bowen's disease and Paget's disease; liver cancer; lung cancer; lymphomas including Hodgkin's disease and lymnphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and modullar carcinoma; and renal cancer including adenocarcinoma and Wilms tumor.

As used herein, a subject is a human, non-human primate, cow, horse, pig, sheep, goat, dog, cat or rodent. In all embodiments human subjects are preferred. Preferably the subject is a human either suspected of having breast cancer, or having been diagnosed with breast cancer. In a preferred embodiment of the invention the cancer is pre-menopausal, lymph node—negative breast cancer. Methods for identifying subjects suspected of having breast cancer may include manual examination, biopsy, subject's family medical history, subject's medical history, or a number of imaging technologies such as mammography, magnetic resonance imaging, magnetic resonance spectroscopy, or positron emission tomography. Diagnostic methods for breast cancer and the clinical delineation of breast cancer diagnoses are well-known to those of skill in the medical arts.

As used herein, breast tissue sample is tissue obtained from a breast tissue biopsy using methods well-known to those of ordinary skill in the related medical arts. The phrase "suspected of being cancerous" as used herein means a breast cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radiolabeled nucleic acids.

As used herein, the phrase "determining the expression of a set of nucleic acid molecules in the breast tissue" means identifying RNA transcripts in the tissue sample by analysis of nucleic acid or protein expression in the tissue sample. As used herein, "set" refers to a group of nucleic acid molecules that include 2, 3, 4, 5, 6, 7, 8, 9, 10, 11, 12, 13, 14, 15, 16 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 different nucleic acid sequences from the group of nucleic acid sequences numbered 1 through 51 in Table 1 (SEQ ID Nos:1–51).

The expression of the set of nucleic acid molecules in the sample from the breast cancer patient can be compared to the expression of the set of nucleic acid molecules in a sample of breast tissue that is non-cancerous. As used herein, non-cancerous breast tissue means tissue determined by one of ordinary skill in the medical art to have no evidence of breast cancer based on standard diagnostic methods including, but not limited to, histologic staining and microscopic analysis.

Nucleic acid markers for cancer are nucleic acid molecules that by their presence or absence indicate the presence of absence of breast cancer. In tissue, certain nucleic acid molecules are expressed at different levels depending on whether tissue is non-cancerous or cancerous. In cancerous tissue, nucleic acid molecule expression may be correlated with MAI prognostic analysis. As described herein, breast cancer nucleic acid markers were identified by evaluating the nucleic acid molecules present in breast tumor tissue samples and comparing expression levels of the nucleic acid molecules with MAI levels determined for the tissues. An aspect of the invention is that different nucleic acid molecules are expressed in breast cancers with different MAI levels (i.e., high MAI versus low MAI) and these expression variations are identifiable by nucleic acid expression analysis, such as microarray analysis or protein expression analysis. Some nucleic acids are more likely to be, in other words, Are preferentially expressed in cancers with high MAI levels and other nucleic acids are preferentially expressed in cancers with low MAI levels. According to the invention, the corlation between the preferential expression of nucleic acid markers and MAI classification allows expression of nucleic acid markers to be used to directly categorize breast cancers as low MAI or high MAI. Thus, nucleic acid expression-based categorization of breast cancer (by measurement of nucleic acid or protein expression) as low or high MAI may be used by one of ordinary skill in the medical arts to select an appropriate treatment regimen based on a patient's specific breast cancer prognosis.

Hybridization methods for nucleic acids are well known to those of ordinary skill in the art (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols In Molecular Biology*, F. M. Ausubol, et al., eds., John Wiley & Sons, Inc., New York). The nucleic acid molecules from a breast cancer tissue sample hybridize under stringent conditions to nucleic acid markers expressed in breast cancer. In one embodiment the markers arc sets of two or more of the nucleic acid molecules as set forth in SEQ ID NOs: 1 through 51.

The breast cancer nucleic acid markers disclosed herein are known genes and fragments thereof. It may be desirable to identify variants of those genes, such as allelic variants or single nucleotide polymorphisms (SNPs) in tissues. Accordingly, methods for identifying breast cancer nucleic acid markers, including variants of the disclosed full-length cDNAs, genomic DNAs, and SNPs arc also included in the invention. The methods include contacting a nucleic acid sample (such as a cDNA library, genomic library, genornic DNA isolate, etc.) with a nucleic acid probe or primer derived from one of SEQ ID NOs:1 through 51. The nucleic acid sample and the probe or primer hybridize to complementary nucleotide sequences of nucleic acids in the sample, if any are present, allowing detection of nucleic acids related to SEQ ID NOs:1–51. Preferably the probe or primer is detectably labeled. The specific conditions, reagents, and the like can be selected by one of ordinary skill in the art to selectively identify nucleic acids related to sets of two or more of SEQ ID NOs:1 through 51. The isolated nucleic acid molecule can be sequenced according to standard procedures.

In addition to native nucleic acid markers (SEQ ID NOs:1–51), the invention also includes degenerate nucleic acids that include alternative codons to those present in the native materials. For example, seine residues are encoded by the codons TCA, AGT, TCC, TCG, TCT, and AGC. Bach of the six codons is equivalent for the purposes of encoding a serine residue. Similarly, nucleotide sequence triplets that encode other amino acid residues include, but are not limited to: CCA, CCC, CCG, and CCT (proline codons); CGA, CGC, CGG, CGT, AGA, and AGG (arginine codons); ACA, ACC, ACO, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions, and deletions of one or more nucleotides such as the allelic variants and SNPs described above. In preferred embodiments, these modified nucleic acid molecules and/or the polypeptides they encode retain at least one activity or function of the unmodified nucleic acid molecule and/or the polypeptides, such as hybridization, antibody binding, etc. In certain embodiments, the modified nucleic acid molecules encode modified polypeptides, preferably polypeptides having conservative amino acid substitutions. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. The modified nucleic acid molecules are structurally related to the unmodified nucleic acid molecules and in preferred embodiments are sufficiently structurally related to the unmodified nucleic acid molecules so that the modified and unmodified nucleic acid-molecules hybridize under stringent conditions known to one of skill in the art.

For example, modified nucleic acid molecules that encode polypeptides having single amino acid changes can be prepared for use in the methods and products disclosed herein. Each of these nucleic acid molecules can have one, two, or three nucleotide substitutions is exclusive of nucleotide changes corresponding to the degeneracy of the genetic code as described herein. Likewise, modified nucleic acid molecules that encode polypeptides having two amino acid changes can be prepared, which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the anmo acid substitutions. Additional nucleic acid molecules that encode polypeptides having additional substitutions (i.e., 3 or more), additions or deletions [e.g., by introduction of a stop codon or a splice site(s)] also can be prepared and are embraced by the invention as readily envisioned by one of ordinary skill in the art. Any of the foregoing nucleic acids can be tested by routine experimentation for retention of structural relation to or activity similar to the nucleic acids disclosed herein.

In the invention, standard hybridization techniques of microarray technology are utilized to assess patterns of nucleic acid expression and identify nucleic acid marker expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes an a fixed substrate, labeling target molecules with reporter molecules (e.g., radioactive, chemiluminescent, or fluorescent tags such as fluoresein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol.21, January 1999, the entire contents of which is incorporated by reference herein.

According to the present invention, microarray substrates may include but are not limited to glass, silica, aluminosilicates, borosilicates, metal oxides such as alumia and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length miy be determined by one of ordinary skill in the art by following art-known procedures. In one embodiment, preferred probes are sets of two or more of the nucleic acid molecules set forth as SEQ ID NO:1 though 51 (see also Table 1). Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, but are not limited to: amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photohenmical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium (Gwynne and Page. 2000). In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets are nucleic acids selected from the group, including but not limited to: DNA, genomic DNA, cDNA, RNA, mRNA and may be natural or synthetic. In all embodiments, nucleic acid molecules from human breast tissue are preferred. The tissue may be obtained from a subject or may be grown in culture (e.g. from a breast cancer cell line).

In embodiments of the invention one or more control nucleic acid molecules are attached to the substrate. Preferably, control nucleic acid molecules allow determination of factors including but not limited to nucleic acid quality and binding characteristics; reagent quality and effectiveness; hybridization success; and analysis thresholds and success. Control nucleic acids may include but are not limited to expression products of genes such as housekeeping genes or fragments thereof.

To select a set of tumor markers, the expression data generated by, for example, microarray analysis of gene expression, is preferably analyzed to determine which genes in different groups of cancer tissues are significantly differentially expressed. In the methods disclosed herein, the significance of gene expression was determined using Permax computer software, although any standard statistical page that can discriminate significant differences in expression may be used. Permax performs permutation 2-sample t-tests on large arrays of data. For high dimensional vectors of observations, the Permax software computes t-statistics for each attribute, and assesses significance using the permutation distribution of the maximum and minimum overall attributes. The main use is to determine the attributes (genes) that are the most different between two groups (e.g., high MAI tissues versus low MAI tissues), measuring "most different" using the value of the t-statistics, and their significance levels.

In one embodiment of the invention, expression of nucleic acid markers is used to select clinical treatment paradigms for breast cancer. Treatment options, as described herein, may include but are not limited to chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for breast cancer is surgery, which can be utilized either alone or in combination with any of the aforementioned treatment methods. One of ordinary skill in the medical arts may determine an appropriate treatment paradigm based on evaluation of differential expression of sets of two or more of the nucleic acid targets SEQ ID NO. 1–51. Cancers that express markers that are indicative of a more aggressive cancer or poor prognosis may be treated with more aggressive therapies.

Progression or regression of breast cancer is determined by comparison of two or more different breast cancer tissue samples taken at two or more different times from a subject. For example, progression or regression may be evaluated by assessments of expression of sets of two or more of the nucleic acid targets, including but not limited to SEQ ID NOs:1–51, in a breast cancer tissue sample from a subject before, during, and following treatment for breast cancer.

In another embodiment, novel pharmacological agents useful in the treatment of breast cancer can be identified by assessing variations in the expression of sets of two or more breast cancer nucleic acid markers, from among SEQ ID NOs:1–51, prior to and after contacting breast cancer cells or tissues with candidate pharmacological agents for the treatment of breast cancer. The cells may be grown in culture (e.g. from a breast cancer cell line), or may be obtained from a subject, (e.g. in a clinical trial of candidate pharmaceutical agents to treat breast cancer). Alterations in expression of two or more sets of breast cancer nucleic acid markers, from among SEQ ID NOs:1–51, in breast cancer cells or tissues tested before and after contact with a candidate pharmacological agent to treat breast cancer, indicate progression, regression, or stasis of the breast cancer thereby indicating efficacy of candidate agents and concomitant identification of lead compounds for therapeutic use in breast cancer.

The invention further provides efficient methods of identifying pharmacological agents or lead compounds for agents active at the level of breast cancer cellular function. Generally, the screening methods involve assaying for compounds that beneficially alter breast cancer nucleic acid molecule expression. Such methods are adaptable to automated, high throughput screening of compounds.

The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weiglt of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, the anti-breast cancer candidate agent specifically binds the cellular binding target, a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the anti-breast cancer candidate agent and one or more binding targets is detected by any convenient method available to the user. For cell-free binding type assays, a separation step is often used to separate bound from unbound components, The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of the anti-cancer agent binding to a target molecule typically encodes a directly or indirectly detectable products e.g. β-galactosidase activity, luciferase activity, and the like. For cell-free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to an anti-cancer agent binding partner, or incorporated into the structure of the binding patner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides breast cancer gene-specific binding agents, methods of identifying and making such agents, and their use in diagnosis, therapy and pharmaceutical development. For example, breast cancer gene-specific pharmacological agents are useful in a variety of diagnostic and therapeutic applications as described herein. In general, the specificity of a breast cancer gene binding to a binding agent is shown by binding equilibrium constants. Targets which are capable of selectively binding a breast cancer gene preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate breast cancer gone-specific binding. Cell-based assays include one, two and three hybrid screens, assays in which breast cancer gene-mediated transcription is inhibited or increased, etc. Cell-free assays include breast cancer gene-protein binding assays, immunoassays, etc. Other assays useful for screening agents which bind breast cancer polypeptides include fluorescence resonance energy transfer (FRET), and electrophoretic mobility shift analysis (EMSA).

In another aspect of the invention, pre- and post-treatment alterations in expression of two or more sets of breast cancer nucleic acid markers including, but not limited to, SEQ ID NOs:1–51 in breast cancer cells or tissues may be used to assess treatment parameters including, but not limited to: dosage, method of administration, timing of administration, and combination with other treatments as described herein.

Candidate pharmacological agents may include antisense oligonucleotides that selectively binds to a breast cancer nucleic acid marker molecule, as identified herein, to reduce the expression of the marker molecules in breast cancer cells and tissues. One of ordinary skill in the art can test of the effects of a reduction of expression of breast cancer nucleic acid marker sequences in vivo or in vito, to determine the efficacy of one or more antisense oligonucleotides.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an MRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

Based upon the sequences of breast cancer expressed nucleic acids, or upon allelic or homologous genomnic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases that are complementary to the target, although in certain cases modified oligonucleotides as short as 7 bases in length have been used successfully as antisense oligonucleotides (Wagner et al., 1996). Most preferably, the antisense oligonueleotides comprise a complementary sequence of 20–30 bases. Although oligonucleotides may be chosen that are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., 1994) and at which proteins are not expected to bind. Finally, although the listed sequences are cDNA sequences, one of ordinary skill in the art may easily derive the genomic DNA corresponding to the cDNA of a breast cancer expressed polypeptide. Thus, the present invention also provides for antisense oligonucleotides which are complementary to the genomic DNA corresponding to breast cancer expressed nucleic acids. Similarly, the use of antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods, which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness. The term "modified oligonucleotide" as used herein describes an oligonucleotide in which (1) at least two of its nucleotides are covalently linked via a synthetic intemucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters, and peptides.

The term "modified oligonucleotide" also encompasses oligonucleotides with a covalently modified base and/or sugar. For example, modified oligonucleotides include oligonucleotides having backbone sugars that are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, breast cancer expressed nucleic acids, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials, which are well known in the art.

Expression of breast cancer nucleic acid molecules can also be determined using protein measurement methods to determine expression of SEQ ID NOs:1–51, e.g., by determining the expression of polypeptides encoded by SEQ ID NOs:1–51 (SEQ ID NOs: 52–102, respectively). Preferred methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, antibody-capture protein arrays and immunohistochemistry-based methods such as 2-dimensional gel electrophoresis.

SELDI methodology may be used, through procedures known to those of ordinary skill in the art, to vaporize microscopic amounts of tumor protein and to create a "fingerprint" of individual proteins, thereby allowing simultaneous measurement of the abundance of many proteins in a single sample. Preferably SELDI-based assays may be utilized to classify breast cancer tumors. Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among SEQ ID NOs:1–51. Predictive models of tumor classification from SELDI measurement of multiple markers from among SEQ ID NOs:1–51 may be utilized for the SELDI strategies. In an additional embodiment a set of primary lymph node-negative premenopausal breast cancer tissues may be preferably utilized to determine the risk classification of breast cancer based on SELDI results.

The invention also involves agents such as polypeptides that bind to breast cancer-associated polypeptides, i.e., SEQ ID NOs:52–102. Such binding agents can be used, for example, in screening assays to detect the presence or absence of breast cancer-associated polypeptides and complexes of breast cancer-associated polypeptides and their binding partners and in purification protocols to isolate breast cancer-associated polypeptides and complexes of breast cancer-associated polypeptides and their binding partners. Such agents also may be used to inhibit the native activity of the breast cancer-associated polypeptides, for example, by binding to such polypeptides.

The invention, therefore, embraces peptide binding agents which, for example, can be antibodies or fragments of antibodies having the ability to selectively bind to breast cancer-associated polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CD1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to polypeptides selected from SEQ ID NOs:52–102, and complexes of both breast cancer-associated polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the breast cancer-associated polypeptide. This process can be repeated through several cycles of reselection of phage that bind to the breast cancer-associated polypeptide. Repeated rounds lead to enrichment of phage bearing particular sequences. DNA sequence analysis can be conducted to identify the sequences of the expressed polypeptides. The minimal linear portion of the sequence that binds to the breast cancer-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the breast cancer-associated polypeptides.

Thus, the breast cancer-associated polypeptides of the invention, including fragments thereof, can be used to screen peptide libraries, including phage display libraries, to identify and select peptide binding partners of the breast cancer-associated polypeptides of the invention. Such molecules can be used, as described, for screening assays, for purification protocols, for interfering directly with the functioning of breast cancer-associated polypeptides and for other purposes that will be apparent to those of ordinary skill in the art. For example, isolated breast cancer-associated polypeptides can be attached to a substrate (e.g., chromatographic media, such as polystyrene beads, a filter, or an array substrate), and then a solution suspected of containing the binding partner may be applied to the substrate. If a binding partner that can interact with breast cancer-associated polypeptides is present in the solution, then it will bind to the substrate-bound breast cancer-associated polypeptide. The binding partner then may be isolated.

As detailed herein, the foregoing antibodies and other binding molecules may be used for example, to identify tissues expressing protein or to purify protein. Antibodies also may be coupled to specific diagnostic labeling agents for imaging of cells and tissues that express breast cancer-associated polypeptides or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium.

The invention further includes protein microarrays for analyzing expression of breast cancer-associated peptides selected from SEQ ID NOs:52–102. In this aspect of the invention, standard techniques of microarray technology are utilized to assess expression of the breast cancer-associated polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760–1763, 2000.

Preferably antibodies or antigen binding fragments thereof that specifically bind polypeptides selected from the group consisting of SEQ ID NOs:52–102 are attached to the microarray substrate in accordance with standard attachment methods known in the art. These arrays can be used to quantify the expression of the polypeptides identified herein.

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

The use of such methods to determine expression of breast cancer nucleic acids from among SEQ ID NOs:1–51 and/or proteins from among SEQ ID Nos:52–102 can be done with routine methods known to those of ordinary skill in the art and the expression determined by protein measurement methods may be correlated to MAI levels and used as a prognostic method for selecting treatment strategies for breast cancer patients.

EXAMPLES

Introduction

To establish a prognostic tool for designing breast cancer treatment regimens, expression patterns in primary breast cancer specimens were assessed and correlated with: clinical outcome. Primary breast cancer tumors from premenopausal women with no lymph node metastases at the time of initial presentation were classified using the Mitotic Activity Index (MAI), which has been shown to predict disease-free survival in this type of disease. RNA was isolated, hybridized with Affymetrix HuFL human expression arrays, and analyzed to ascertain which genes discriminate the two groups.

Methods

Breast Cancers Used for RNA Microarray Expression Analysis

Primary frozen breast cancers from premenopausal women with no lymph node metastases at the time of initial presentation were assembled from material discarded following routine surgical removal for diagnostic purposes. Institutional review and human subjects approval for this project was obtained from Brigham and Women's Hospital. Fresh tissue was frozen in liquid nitrogen, and a single fragment split for confirmatory histology and RNA isolation. Individual fragments of frozen tumor tissues (estimated as 500 mg minimum) were split by fracturing under liquid nitrogen, and a portion processed for confirmatory histology using standard methods. The remaining tissue was used for synchronous RNA, protein, and DNA isolations with TRIzol reagents (Life Technologies, Inc., Rockville, Md.) using standard methods. Only tumors where the actual frozen tissue contained >50% tumor cells were used.

Mitotic Activity Index

All tumors were classified by Mitotic Activity Index (Baak et al., 1989; van Diest et al., 1991; van Diest et al., 1992(a); Uyterlinde et al., 1990; van Diest et al., 1992(b); Jannink et al., 1996; Baak et al., 1992; Baak et al., 1993) using paraffin H&E stained tissues sections prepared for diagnostic purposes at the time of excision. The MAI is the total number of mitoses counted in 10 consecutive high-power fields (objective, x40; numeric aperture, 0.75; field diameter, 450 microns) in the most cellular area at the periphery of the tumor, with the subjectively highest mitotic activity (Jannink et al., 1995). Risk groups have previously been defined using a threshold of 10 mitoses/unit area (Tosi et al., 1986; Jannink et al., 1995; Theissig et al., 1996). Tumors with MAI≧10 were assigned to the high risk group, and those with MAI≦3 to the low risk group.

Microarray Expression Analysis

RNA from 27 qualifying tumors was reverse transcribed and resultant cDNA used for in vitro transcriptional synthesis of fluorescently labeled nucleic acid probes which were then hybridized to Affymetrix HuFL human expression arrays (approximately 7100, probe sets, estimated 5800 unique genes). Hybridization images were analyzed with Affymetrix software to generate a data matrix of named probes by quantitative expression level in each tissue. RNA labeling, microarray hybridization, and microarray analysis were performed as per vendor's instructions for HuGeneFL array (Affymetrix, Santa Clara, Calif.). Four tumors were excluded from analysis because they failed to meet quality control criteria for microarray hybridization:3 cases had low hybridization signal, one case had high background.

Results

Analysis of 23 primary breast cancer specimens from premenopausal lymph node negative women were split between two prognostic groups (Low MAI, MAI≦3, n=11 and High MAI, MAI≧10, n=12) and was accomplished as follows. Affymetrix HuFL expression values were normalized by scaling so the sum of AD (AD units are the quantitative expression units used by Affymetrix) values in each sample was 3,000,000; genes for which RNA abundance was absent or marginal were reset to a value of 0, then any values less than 20 were reset to 20. The result is the GPT datastate, which was then log transformed and discriminating genes selected by t-test comparison of the logged data between low and high MAI groups. Significance cutoffs for the t-tests used Permax <0.96 based on 10,000 random permutations of the data. Permax is a data analysis software tool for testing the significance of gene expression. It has been presented by Mutter, et al., 8th International Workshop on Chromosomes in Solid Tumors, Tucson, Ariz., 2000; and is available online at biowww.dfci.harvard.edu/~gray/permax.html and from Robert J. Gray, Department of Biostatistical Science, Dana-Farber Cancer Institute, 44 Binney Street Boston, Mass. 02115. Permax details enclosed therein are incorporated by reference herein. Seventy eight of 7070 Affymetrix probe sets were selected by Pernax.

Filters for minimum divergence between the average expression values of the two groups (Low vs. High MAI) were applied as follows: ratio of means $\geq 2$, and difference between means $\geq 100$. It was determined that 51/78 genes passed these filters. The final 51 selected genes which discriminate between low and high MAI subgroups appear in Table 1 and as SEQ ID NOs:1–51. Average expression in high MAI tumors and low MAI tumors is shown as HX and LX, respectively.

TABLE 1

Gene list identifying 51 genes that discriminate low from high MAI breast cancers.

| SEQ ID NO | Short Name | GenBank Acc. No. | Permax | HX | LX | FOLDABS | DIFFABS |
|---|---|---|---|---|---|---|---|
| 1 | ABCB2 | X57522 | 0.9577 | 501 | 83 | 6.0 | 417 |
| 2 | ACTA2 | X13839 | 0.7131 | 3098 | 6152 | 2.0 | 3054 |
| 3 | AMD1 | M21154 | 0.0808 | 257 | 50 | 5.1 | 207 |
| 4 | APM2 | D45370 | 0.3317 | 590 | 2682 | 4.5 | 2092 |
| 5 | ASAH | U70063 | 0.8435 | 360 | 990 | 2.8 | 630 |
| 6 | BARD1 | U76638 | 0.5637 | 242 | 102 | 2.4 | 140 |
| 7 | CCNH | U11791 | 0.9104 | 104 | 204 | 2.0 | 100 |
| 8 | CCT2 | U91327 | 0.8801 | 280 | 109 | 2.6 | 171 |
| 9 | CDC20 | U05340 | 0.0669 | 579 | 20 | 29.0 | 559 |
| 10 | CDC34 | L22005 | 0.6979 | 182 | 41 | 4.4 | 141 |
| 11 | CDKN3 | U02681 | 0.0072 | 454 | 63 | 7.2 | 391 |
| 12 | CKS1 | X54941 | 0.8823 | 539 | 219 | 2.5 | 320 |
| 13 | CKS2 | X54942 | 0.1881 | 413 | 119 | 3.5 | 294 |
| 14 | COX7A1 | M83186 | 0.9223 | 89 | 326 | 3.6 | 236 |
| 15 | CPA3 | M73720 | 0.8234 | 132 | 357 | 2.7 | 225 |
| 16 | CPE | X51405 | 0.1984 | 80 | 243 | 3.0 | 163 |
| 17 | CX3CR1 | U20350 | 0.0317 | 70 | 328 | 4.7 | 258 |
| 18 | DLG4 | U83192 | 0.3427 | 20 | 179 | 8.9 | 159 |
| 19 | DOC1 | U53445 | 0.927 | 122 | 276 | 2.3 | 154 |
| 20 | DXS9879E | X92896 | 0.9448 | 744 | 331 | 2.3 | 413 |
| 21 | E2-EPF | M91670 | 0.9602 | 324 | 20 | 16.2 | 304 |
| 22 | ElastinAlt2 | U77846 | 0.8368 | 417 | 2210 | 5.3 | 1792 |
| 23 | GTF2A1 | U14193 | 0.7495 | 528 | 249 | 2.1 | 279 |
| 24 | GUA5MPST | U10860 | 0.6129 | 599 | 114 | 5.2 | 485 |
| 25 | H2AFX | X14850 | 0.8106 | 496 | 193 | 2.6 | 303 |
| 26 | H2BFA | M60750 | 0.2334 | 508 | 143 | 3.6 | 365 |
| 27 | Hevin | X86693 | 0.7484 | 529 | 1686 | 3.2 | 1157 |
| 28 | HNRPH2 | U01923 | 0.9056 | 106 | 231 | 2.2 | 126 |
| 29 | HPV16E1Bind | U96131 | 0.2439 | 194 | 78 | 2.5 | 116 |
| 30 | IDUA | M74715 | 0.1712 | 176 | 594 | 3.4 | 418 |
| 31 | IGF1 | X57025 | 0.9213 | 79 | 265 | 3.4 | 186 |
| 32 | IQGAP2 | U51903 | 0.9517 | 137 | 321 | 2.3 | 184 |
| 33 | ISG15 | M13755 | 0.9316 | 2133 | 386 | 5.5 | 1747 |
| 34 | JAG1 | U61276 | 0.9466 | 79 | 264 | 3.3 | 185 |
| 35 | LAMA2 | Z26653 | 0.8882 | 31 | 213 | 6.8 | 182 |
| 36 | LAMB2 | X79683 | 0.083 | 156 | 658 | 4.2 | 502 |
| 37 | LBR | L25931 | 0.5991 | 221 | 68 | 3.2 | 153 |
| 38 | MMP2 | M55593 | 0.93 | 1765 | 3670 | 2.1 | 1905 |
| 39 | MMSDH | M93405 | 0.9072 | 297 | 669 | 2.3 | 372 |
| 40 | MYH11 | AF001548 | 0.3109 | 164 | 777 | 4.7 | 612 |
| 41 | MYLK | U48959 | 0.8351 | 158 | 680 | 4.3 | 522 |
| 42 | PDE4A | L20965 | 0.8912 | 34 | 176 | 5.2 | 142 |
| 43 | SCNN1A | X76180 | 0.694 | 352 | 864 | 2.5 | 511 |
| 44 | SCYB10 | X02530 | 0.4416 | 528 | 83 | 6.4 | 445 |
| 45 | SNRPB | X17567 | 0.8965 | 1473 | 638 | 2.3 | 835 |
| 46 | STAT1 | M97936 | 0.9553 | 440 | 20 | 22.0 | 420 |
| 47 | TAF2A | X07024 | 0.6819 | 193 | 65 | 2.9 | 127 |
| 48 | TCEAL1 | M99701 | 0.5595 | 241 | 749 | 3.1 | 508 |
| 49 | TPM1 | Z24727 | 0.5676 | 1266 | 2533 | 2.0 | 1267 |
| 50 | TPS2 | M33493 | 0.3638 | 194 | 892 | 4.6 | 698 |
| 51 | UBCH10 | U73379 | 0.1972 | 1519 | 639 | 2.4 | 880 |

Several features of selected genes provide reassurance that low frequency random events were not the cause of expression differences between groups. A review of the 51 selected genes (Table 1) shows that five pairs of genes known to be co-expressed were selected independently (two carboxypeptidases, two histones, two cdc28, two ubiquitins, two laminins, and myosin/tropomyosin), and reciprocal regulation of ligand and receptor, a common regulatory pattern, occurred once (laminin and lamin receptor) amongst genes selected.

The first expectation is that genes whose expression is linked to cell division would be represented in this comparison of tumors whose mitotic activity differs systematically. This was in fact the largest category of selected genes, with expression of 11/12 cell cycle genes greatest in the high MAI group. Genes which are-preferentially expressed (at higher levels) in the low MAI group include those encoding extracellular matrix or enzymes which may remodel extracellular matrix (proteolytic enzymes).

The gene expression data presented in Table 1 can be used to generate an expression matrix of 51 selected genes by 23 tissues examined. Using standard clustering algorithms, dendrograms can be provided on the borders of the matrix (e.g., using Wards linkage and Euclidean distance) to show cluster relationships between tissues and genes. Similarly, a gene expression matrix can be generated using data normalized by standard deviation for each gene [STD(GPT)]. Dendrograms on borders of the matrix can be provided to show cluster relationships between tissues and genes. In this type of matrix, clustering of genes is based upon relative changes without bias due to absolute expression level, because each gene is expressed in standard deviation from the mean for that specific gene. However, unlike the other expression matrix described above, the absolute magnitude of expression cannot be directly inferred from this plot.

References

Harrison's Principles of Internal Medicine, 14/e, (1998) McGraw-Hill Companies, New York.

Jannink, 1, van Diest, P. J., Baak, J. P. (1995) Comparison of the prognostic value of four methods to assess mitotic activity in 186 invasive breast cancer patients: classical and random mitotic activity assessments with correction for volume percentage of epithelium. Hum Pathol Oct;26(10):1086–92.

Baak J P, van Diest P J, Ariens A T, van Beek M W, Bellot S M, Fijnheer J, van Gorp L H, Kwee W S, Los J, Peterse H C: The Multicenter Morphometric Mammary Carcinoma Project (MMMCP). A nationwide prospective study on reproducibility and prognostic power of routine quantitative assessments in The Netherlands. Pathol Res Pract 1989, 185:664–670.

van Diest P J, Baak J P: The morphometric prognostic index is the strongest prognosticator in premenopausal lymph node-negative and lymph node-positive breast cancer patients. Hum Pathol 1991, 22:326–330.

van Diest P J, Baak J P, Matze-Cok P, Bacus S S: Prediction of response to adjuvant chemotherapy in premenopausal lymph node positive breast cancer patients with morphometry, DNA flow cytometry and HER-2/neu oncoprotein expression. Preliminary results. Pathol Res Pract 1992, 188:344–349.

Uyterlinde A M, Baak J P, Schipper N W, Peterse H, Matze E, Meijer C J: Further evaluation of the prognostic value of morphometric and flow cytometric parameters in breast-cancer patients with long follow-up. Int J Cancer 1990, 45:1–7.

van Diest P J, Baak J P, Matze-Cok P, Wisse-Brekelmans E C, van Galen C M, Kurver P H, Bellot S M, Fijnheer J, van Gorp L H, Kwee W S: Reproducibility of mitosis counting in 2,469 breast cancer specimens: results from the Multicenter Morphometric Mammary Carcinoma Project. Hum Pathol 1992, 23:603–607.

Jannink I, Risberg B, van Diest P J, Baak J P: Heterogeneity of mitotic activity in breast cancer. Histopathology 1996, 29:421–428.

Baak J P, Wisse-Brekelmans E C, Kurver P H, van Gorp L H, Voorhorst F J, Miettinen O S: Regional differences in breast cancer survival are correlated with differences in differentiation and rate of proliferation. Hum Pathol 1992, 23:989–992.

Baak J P, van Diest P J, Benraadt T, Matze-Cok E, Brugghe J, Schuurmans L T, Littooy J J: The Multi-Center Morphometric Mammary Carcinoma Project (MMMCP) in The Netherlands: value of morphometrically assessed proliferation and differentiation. J Cell Biochem Suppl 1993, 17G:220–225.

Tosi P, Luzi P, Sforza V, Santopietro R, Bindi M, Tucci E, Barbini P, Baak J P: Correlation between morphometrical parameters and disease-free survival in ductal breast cancer treated only by surgery. Appl Pathol 1986, 4:33–42.

Theissig F, Baak J P, Schuurmans L, Haroske G, Meyer W, Kunze K D: 'Blind' multicenter evaluation of the prognostic value of DNA image cytometric and morphometric features in invasive breast cancer. Anal Cell Pathol 1996, 10:85–99.

The Chipping Forecast (1999) Nature Genetics, 21(1):1–60.

Gwynne, P., and Page, G., (1999) Microarray Analysis: the next revolution in Molecular Biology, Science eMarketplace, Science, August 6. (sciencemag.org/feature/e-market/benchtop/micro.shl)

Wagner et al., Nature Biotechnol. (1996) 14:840–844.

Sainio, K., Saarma, M., Nonclercq, D., Paulin, L., and Sariola, H. (1994) Antisense inhibition of low-affinity nerve growth factor receptor in kidney cultures: power and pitfalls. Cell Mol. Neurobiol. 14(5):439–457.

*Molecular Cloning: A Laboratory Manual*, (1989) J. Sambrook, et al., eds., Second Edition, Cold Spring Harbor Laboratory Press, Cold Spring Harbor, N.Y.

*Current Protocols in Molecular Biology*, (1999) F. M. Ausubel, et al., eds., John Wiley & Sons, Inc., New York.

Mutter, G. L., Baak, J. P. A., Cai, T., Fitzgerald, J., Gray, R., Gentleman, R., Gullans, S., Ibrahim, J., Neuberg, D., and Wilcox, M. Altered Gene Expression in Endometrioid Endometrial Adenocarcinomas Analyzed by High Density Microarrays. 8th International Workshop on Chromosomes in Solid Tumors (Tucson, Ariz). 2000.

The present invention is not limited in scope by the examples provided, since the examples are intended as illustrations of various aspects of the invention and other functionally equivalent embodiments are within the scope of the invention. Various modifications of the invention in addition to those shown are described herein will become apparent to those skilled in the art for the foregoing description and fall within the scope of the appended claims. The advantages and objects of the invention are not necessarily encompassed by each embodiment of the invention. All references, patents, and patent publications that are recited in this application are incorporated in their entirety herein by reference.

We claim:

1. A method for assigning primary breast cancer tissues in a subject suspected of having A breast cancer to either a high or low risk group comprising:
   a) obtaining from the subject a breast tissue sample suspected of being cancerous, and determining the expression level of at least 2 nucleic acid molecules selected from the group consisting of SEQ ID NOs:9, 17, and 36 thereof in the breast tissue sample
   b) determining the expression level of the at least 2 nucleic acid molecules selected from the group consisting of SEQ ID NOs:9, 17, and 36 in a non-cancerous breast tissue sample, and comparing the expression level of the at least 2 nucleic acid molecules in the breast tissue sample suspected of being cancerous to the non-cancerous breast tissue sample
   c) assigning the breast cancer tissue in a subject to either a high risk group by detecting an increased expression level of the nucleic acid molecule of SEQ ID NO:9
      or to a low risk group by detecting an increased expression level of the nucleic acid molecules of SEQ ID NOs:17 or 36 as determined by the comparison to the expression levels of the same nucleic acid sequences in a non-cancerous breast tissue sample.

2. A method for assigning primary breast cancer tissues in a subject suspected of having breast cancer to either a high or low risk group comprising:
   a) obtaining from the subject a breast tissue sample suspected of being cancerous, and determining the expression of all 3 nucleic acid molecules of SEQ ID NOs:9, 17, and 36 thereof in the breast tissue sample
   b) determining the expression levels of all 3 nucleic acid molecules of SEQ ID NOs:9, 17, and 36 in a non-cancerous breast tissue sample, and comparing the expression levels of the 3 nucleic acid molecules in the breast tissue sample suspected of being cancerous to those of the non-cancerous breast tissue sample
   c) assigning the breast cancer tissue in a subject to either a high risk group by detecting an increased expression level of the nucleic acid molecule in SEQ ID NO:9
      or to a low risk group by detecting an increased expression level of the nucleic acid molecules of SEQ ID NOs:17 and 36 as determined by the comparison to the expression levels of the same nucleic acid sequences in a non-cancerous breast tissue sample.

* * * * *

UNITED STATES PATENT AND TRADEMARK OFFICE
CERTIFICATE OF CORRECTION

PATENT NO. : 6,703,204 B1
DATED : March 9, 2004
INVENTOR(S) : George L. Mutter et al.

It is certified that error appears in the above-identified patent and that said Letters Patent is hereby corrected as shown below:

Column 295,
Line 33, please delete "Abreast" and replace with -- breast --.

Signed and Sealed this

Eighth Day of June, 2004

JON W. DUDAS
*Acting Director of the United States Patent and Trademark Office*

SEQUENCE LISTING

```
<160> NUMBER OF SEQ ID NOS: 102

<210> SEQ ID NO 1
<211> LENGTH: 2824
<212> TYPE: DNA
<213> ORGANISM: Homo Sapiens
```

-continued

```
<400> SEQUENCE: 1
gcggccgctt tcgatttcgc tttcccctaa atggctgagc ttctcgccag cgcaggatca      60
gcctgttcct gggactttcc gagagccccg ccctcgttcc ctcccccagc cgccagtagg     120
ggaggactcg gcggtacccg gagcttcagg ccccaccggg gcgcggagag tcccagaccc     180
ggccgggacc gggacggcgt ccgagtgcca atggctagct ctaggtgtcc cgctccccgc     240
gggtgccgct gcctccccgg agcttctctc gcatggctgg ggacagtact gctacttctc     300
gccgactggg tgctgctccg gaccgcgctg ccccgcatat tctccctgct ggtgcccacc     360
gcgctgccac tgctccgggt ctgggcggtg ggcctgagcc gctgggccgt gctctggctg     420
ggggcctgcg gggtcctcag ggcaacggtt ggctccaaga gcgaaaacgc aggtgcccag     480
ggctggctgg ctgctttgaa gccattagct gcggcactgg gcttggccct gccgggactt     540
gccttgttcc gagagctgat tcatgggga gccccgggt ccgcggatag caccaggcta     600
ctgcactggg gaagtcaccc taccgccttc gttgtcagtt atgcagcggc actgcccgca     660
gcagccctgt ggcacaaact cgggagcctc tgggtgcccg cggtcaggg cggctctgga     720
aaccctgtgc gtcggcttct aggctgcctg gctcggaga cgcgccgcct ctcgctgttc     780
ctggtcctgg tggtcctctc ctctcttggg gagatggcca ttccattctt tacgggccgc     840
ctcactgact ggattctaca agatggctca gccgatacct tcactcgaaa cttaactctc     900
atgtccattc tcaccatagc cagtgcagtg ctggagttcg tgggtgacgg gatctataac     960
aacaccatgg gccacgtgca cagccacttg cagggagagg tgtttgggc tgtcctgcgc    1020
caggagacgg agttttttcca acagaaccag acaggtaaca tcatgtctcg ggtaacagag    1080
gacacgtcca ccctgagtga ttctctgagt gagaatctga gcttatttct gtggtacctg    1140
gtgcgaggcc tatgtctctt ggggatcatg ctctggggat cagtgtccct caccatggtc    1200
accctgatca ccctgcctct gcttttcctt ctgcccaaga aggtgggaaa atggtaccag    1260
ttgctggaag tgcaggtgcg ggaatctctg gcaaagtcca gcaggtggc cattgaggct    1320
ctgtcggcca tgcctacagt tcgaagcttt gccaacgagg agggcgaagc ccagaagttt    1380
agggaaaagc tgcaagaaat aaagacactc aaccagaagg aggctgtggc ctatgcagtc    1440
aactcctgga ccactagtat ttcaggtatg ctgctgaaag tgggaatcct ctacattggt    1500
gggcagctgg tgaccagtgg ggctgtaagc agtgggaacc ttgtcacatt tgttctctac    1560
cagatgcagt tcacccaggc tgtggaggta ctgctctcca tctacccag agtacagaag    1620
gctgtgggct cctcagagaa aatatttgag tacctggacc gcacccctcg ctgcccaccc    1680
agtggtctgt tgactcccctt acacttggag ggccttgtcc agttccaaga tgtctccttt    1740
gcctacccaa accgcccaga tgtcttagtg ctacaggggc tgacattcac cctacgccct    1800
ggcgaggtga cggcgctggt gggacccaat gggtctggga gagcacagt ggctgccctg    1860
ctgcagaatc tgtaccagcc caccgggga cagctgctgt ggatgggaa gcccttccc    1920
caatatgagc accgctacct gcacaggcag gtggctgcag tgggacaaga gccacaggta    1980
tttggaagaa gtcttcaaga aaatattgcc tatggcctga cccagaagcc aactatggag    2040
gaaatcacag ctgctgcagt aaagtctggg gcccatagtt tcatctctgg actccctcag    2100
ggctatgaca cagaggtaga cgaggctggg agccagctgt cagggggtca gcgacaggca    2160
gtggcgttgg cccgagcatt gatccggaaa ccgtgtgtac ttatcctgga tgatgccacc    2220
agtgccctgg atgcaaacag ccagttacag gtggagcagc tcctgtacga aagccctgag    2280
cggtactccc gctcagtgct tctcatcacc cagcacctca gcctggtgga gcaggctgac    2340
```

-continued

```
cacatcctct ttctggaagg aggcgctatc cgggaggggg gaacccacca gcagctcatg      2400
gagaaaaagg ggtgctactg ggccatggtg caggctcctg cagatgctcc agaatgaaag      2460
ccttctcaga cctgcgcact ccatctccct ccctttcctt ctctctgtgg tggagaacca      2520
cagctgcaga gtagcagctg cctccaggat gagttacttg aaatttgcct tgagtgtgtt      2580
acctcctttc caagctcctc gtgataatgc agacttcctg gagtacaaac acaggatttg      2640
taattcctac tgtaacggag tttagagcca gggctgatgc tttggtgtgg ccagcactct      2700
gaaactgaga aatgttcaga atgtacggaa agatgatcag ctattttcaa cataactgaa      2760
ggcatatgct ggcccataaa caccctgtag gttcttgata tttataataa aattggtgtt      2820
ttgt                                                                   2824
```

<210> SEQ ID NO 2
<211> LENGTH: 1330
<212> TYPE: DNA
<213> ORGANISM: Homo Sapiens

<400> SEQUENCE: 2

```
gcagcccagc caagcactgt caggaatcct gtgaagcagc tccagctatg tgtgaagaag        60
aggacagcac tgccttggtg tgtgacaatg gctctgggct ctgtaaggcc ggctttgctg       120
gggacgatgc tcccagggct gttttcccat ccattgtggg acgtcccaga catcaggggg       180
tgatggtggg aatgggacaa aaagacagct acgtgggtga cgaagcacag agcaaaagag       240
gaatcctgac cctgaagtac ccgatagaac atggcatcat caccaactgg gacgacatgg       300
aaaagatctg gcaccactct ttctacaatg agcttcgtgt tgcccctgaa gagcatccca       360
ccctgctcac ggaggcaccc ctgaaccccca aggccaaccg ggagaaaatg actcaaatta       420
tgtttgagac tttcaatgtc ccagccatgt atgtggctat ccaggcggtg ctgtctctct       480
atgcctctgg acgcacaact ggcatcgtgc tggactctgg agatggtgtc acccacaatg       540
tccccatcta tgagggctat gccttgcccc atgccatcat gcgtctggat ctggctggcc       600
gagatctcac tgactacctc atgaagatcc tgactgagcg tggctattcc ttcgttacta       660
ctgctgagcg tgagattgtc cgggacatca aggagaaact gtgttatgta gctctggact       720 tgaaaatga gatggccact gccgcatcct catcctccct tgagaagagt tacgagttgc       780
ctgatgggca agtgatcacc atcggaaatg aacgtttccg ctgcccagag accctgttcc       840
agccatcctt catcgggatg gagtctgctg gcatccatga aaccacctac aacagcatca       900
tgaagtgtga tattgacatc aggaaggacc tctatgctaa caatgtccta tcagggggca       960
ccactatgta ccctggcatt gccgaccgaa tgcagaagga gatcacggcc ctagcaccca      1020
gcaccatgaa gatcaagatc attgcccctc cggagcgcaa atactctgtc tggatcggtg      1080
gctccatcct ggcctctctg tccaccttcc agcagatgtg gatcagcaaa caggaatacg      1140
atgaagccgg gccttccatt gtccaccgca aatgcttcta aaacactttc ctgctcctct      1200
ctgtctctag cacacaactg tgaatgtcct gtggaattat gccttcagtt ctttccaaa       1260 tcattcctag ccaaagctct gactcgttac ctatgtgttt tttaataaat ctgaaatagg      1320
ctactggtaa                                                             1330
```

<210> SEQ ID NO 3
<211>LENGTH: 1805
<212>TYPE: DNA
<213>ORGANISM: Homo Sapiens

<400> SEQUENCE: 3

```
aagagactga actgtatctg cctctatttc caaaagactc acgttcaact ttcgctcaca        60
caaagccggg aaaatttat tagtcctttt tttaaaaaaa gttaatataa aattatagca        120
aaaaaaaaaa ggaacctgaa ctttagtaac acagctggaa caatcgcagc ggcggcggca       180
gcggcgggag aagaggttta atttagttga ttttctgtgg ttgttggttg ttcgctagtc       240
tcacggtgat ggaagctgca cattttttcg aagggaccga aagctgctg gaggtttggt        300
tctcccggca gcagcccgac gcaaaccaag gatctgggga tcttcgcact atcccaagat       360
ctgagtggga catacttttg aaggatgtgc aatgttcaat cataagtgtg acaaaaactg       420
acaagcagga agcttatgta ctcagtgaga gtagcatgtt tgtctccaag agacgtttca      480
ttttgaagac atgtggtacc accctcttgc tgaaagcact ggttcccctg ttgaagcttg       540
ctaggggatta cagtgggttt gactcaattc aaagcttctt ttattctcgt aagaatttca     600
tgaagccttc tcaccaaggg tacccacacc ggaatttcca ggaagaaata gagtttctta      660
atgcaatttt cccaaatgga gcaggatatt gtatgggacg tatgaattct gactgttggt      720
acttatatac tctggatttc ccagagagtc gggtaatcag tcagccagat caaaccttgg      780
aaattctgat gagtgagctt gacccagcag ttatggacca gttctacatg aaagatggtg      840
ttactgcaaa ggatgtcact cgtgagagtg gaattcgtga cctgatacca ggttctgtca      900
ttgatgccac aatgttcaat ccttgtgggt attcgatgaa tggaatgaaa tcggatggaa      960
cttattggac tattcacatc actccagaac cagaatttc ttatgttagc tttgaaacaa      1020
acttaagtca gacctcctat gatgacctga tcaggaaagt tgtagaagtc ttcaagccag     1080
gaaaatttgt gaccaccttg tttgttaatc agagttctaa atgtcgcaca gtgcttgctt     1140
cgccccagaa gattgaaggt ttaagcgtc ttgattgcca gagtgctatg ttcaatgatt      1200
acaattttgt ttttaccagt tttgctaaga agcagcaaca acagcagagt tgattaagaa     1260
aaatgaagaa aaaacgcaaa agagaacac atgtagaagg tggtggatgc tttctagatg      1320
tcgatgctgg gggcagtgct ttccataacc accactgtgt agttcagaa agccctagat      1380
gtaatgatag tgtaatcatt ttgaattgta tgcattatta tatcaaggag ttagatatct    1440
tgcatgaatg ctctcttctg tgtttaggta ttctctgcca ctcttgctgt gaaattgaag     1500
tggatgtaga aaaaaccttt tactatatga aactttacaa cacttgtgaa agcaactcaa     1560
tttggttat gcacagtgta atatttctcc aagtatcatc caaaattccc cacagacaag      1620
gctttcgtcc tcattaggtg ttggcctcag cctaaccctc taggactgtt ctattaaatt     1680
gctgccagaa ttttacatcc agttacctcc acttttctaga acatattctt tactaatgtt   1740
attgaaacca atttctactt catactgatg ttttttggaaa cagcaattaa agtttttctt    1800
ccatg                                                                1805
```

<210> SEQ ID NO 4
<211> LENGTH: 419
<212> TYPE: DNA
<213> ORGANISM: Homo Sapiens

<400> SEQUENCE: 4

```
ctcttgacga ctccacagat accccgaagc catggcaagc aagggcttgc aggacctgaa       60
gcaacaggtg gaggggaccg cccaggaagc cgtgtcagcg gccggagcgg cagctcagca      120
agtggtggac caggccacag aggcggggca gaaagccatg gaccagctgg ccaagaccac      180
ccaggaaacc atcgacaaga ctgctaacca ggcctctgac accttctctg ggatcgggaa     240
```

```
aaaattcggc ctcctgaaat gacagcaggg agacttgggt cggcctcctg aaatgatagc      300
agggagactt gggtgacccc ccttccaggc gccatctagc acagcctggc cctgatctcc      360
gggcagccac cacctcctcg gtctgccccc tcattaaaat tcacgttccc accctgaaa       419
```

<210> SEQ ID NO 5
<211> LENGTH: 2333
<212> TYPE: DNA
<213> ORGANISM: Homo Sapiens

<400> SEQUENCE: 5

```
ggcacgaggc tagagcgatg ccgggccgga gttgcgtcgc cttagtcctc ctggctgccg       60
ccgtcagctg tgccgtcgcg cagcacgcgc cgccgtggac agaggactgc agaaaatcaa      120
cctatcctcc ttcaggacca acgtacagag gtgcagttcc atggtacacc ataaatcttg      180
acttaccacc ctacaaaaga tggcatgaat tgatgcttga caaggcacca atgctaaagg      240
ttatagtgaa ttctctgaag aatatgataa atacattcgt gccaagtgga aagttatgc       300 aggtggtgga tgaaaaattg cctggcctac ttggcaactt tcctggcccc tttgaagagg      360
aaatgaaggg tattgccgct gttactgata tacctttagg agagattatt tcattcaata      420 tttttttatga attatttacc atttgtactt caatagtagc agaagacaaa aaggtcatc      480 taatacatgg gagaaacatg gattttggag tatttcttgg gtggaacata aataatgata      540
cctgggtcat aactgagcaa ctaaaacctt aacagtgaa tttggatttc caagaaaca      600 acaaaactgt cttcaaggct tcaagctttg ctggctatgt gggcatgtta acaggattca      660
aaccaggact gttcagtctt acactgaatg aacgtttcag tataaatggt ggttatctgg      720
gtattctaga atggattctg ggaaagaaag atgccatgtg atagggttc ctcactagaa       780 cagttctgga aaatagcaca agttatgaag aagccaagaa tttattgacc aagaccaaga      840
tattggcccc agcctacttt atcctgggag gcaaccagtc tggggaaggt tgtgtgatta      900
cacgagacag aaaggaatca ttggatgtat atgaactcga tgctaagcag ggtagatggt      960
atgtggtaca aacaaattat gaccgttgga acatcccctt cttccttgat gatcgcagaa     1020
cgcctgcaaa gatgtgtctg aaccgcacca gccaagagaa tatctcattt gaaaccatgt     1080
atgatgtcct gtcaacaaaa cctgtcctca acaagctgac cgtatacaca accttgatag     1140
atgttaccaa aggtcaattc gaaacttacc tgcgggactg ccctgaccct tgtataggtt     1200
ggtgagcaca cgtctggcct acagaatgcg gcctctgaga catgaagaca ccatctccat     1260
gtgaccgaac actgcagctg tctgaccttc caaagactaa gactcgcggc aggttctctt     1320
tgagtcaata gcttgtcttc gtccatctgt tgacaaatga cagatctttt ttttttttccc    1380 cctatcagtt gattttctct atttacagat aacttcttta ggggaagtaa aacagtcatc     1440
tagaattcac tgagttttgt ttcactttga catttgggga tctggtgggc agtcgaacca     1500
tggtgaactc cacctccgtg aataaatgg agattcagcg tgggtgttga atccagcacg      1560
tctgtgtgag taacgggaca gtaaacactc cacattcttc agttttcac ttctacctac      1620 atatttgtat gttttctgt ataacagcct tttccttctg gttctaactg ctgttaaaat     1680
taatatatca ttatctttgc tgttattgac agcgatatta ttttattaca tatcattaga    1740
gggatgagac agacattcac ctgtatattt cttttaatgg gcacaaaatg ggcccttgcc    1800
tctaaatagc acttttt ggg gttcaagaag taatcagtat gcaaagcaat cttttataca    1860
ataattgaag tgttcccttt ttcataatta ctctacttcc cagtaaccct aaggaagttg    1920
```

-continued

| | |
|---|---:|
| ctaacttaaa aaactgcatc ccacgttctg ttaatttagt aaataaacaa gtcaaagact | 1980 |
| tgtggaaaat aggaagtgaa cccatatttt aaattctcat aagtagcatt gatgtaataa | 2040 |
| acaggttttt agtttgttct tcagattgat agggagtttt aaagaaattt tagtagttac | 2100 |
| taaaattatg ttactgtatt tttcagaaat caaactgctt atgaaaagta ctaatagaac | 2160 |
| ttgttaacct ttctaacctt cacgattaac tgtgaaatgt acgtcatttg tgcaagaccg | 2220 |
| tttgtccact tcattttgta taatcacagt tgtgttcctg acactcaata aacagtcact | 2280 |
| ggaaagagtg ccagtcagca gtcatgcacg ctgataaaaa aaaaaaaaaa aaa | 2333 |

<210> SEQ ID NO 6
<211> LENGTH: 2530
<212> TYPE: DNA
<213> ORGANISM: Homo Sapiens

<400> SEQUENCE: 6

| | |
|---|---:|
| cagcttccct gtggtttccc gaggcttcct tgcttcccgc tctgcgagga gcctttcatc | 60 |
| cgaaggcggg acgatgccgg ataatcggca gccgaggaac cggcagccga ggatccgctc | 120 |
| cgggaacgag cctcgttccg cgcccgccat ggaaccggat ggtcgcggtg cctgggccca | 180 |
| cagtcgcgcc gcgctcgacc gcctggagaa gctgctgcgc tgctcgcgtt gtactaacat | 240 |
| tctgagagag cctgtgtgtt taggaggatg tgagcacatc ttctgtagta attgtgtaag | 300 |
| tgactgcatt ggaactggat gtccagtgtg ttacaccccg gcctggatac aagacttgaa | 360 |
| gataaataga caactggaca gcatgattca actttgtagt aagcttcgaa atttgctaca | 420 |
| tgacaatgag ctgtcagatt tgaaagaaga taaacctagg aaaagtttgt ttaatgatgc | 480 |
| aggaaacaag aagaattcaa ttaaaatgtg gtttagccct cgaagtaaga aagtcagata | 540 |
| tgttgtgagt aaagcttcag tgcaaaccca gcctgcaata aaaaagatg caagtgctca | 600 |
| gcaagactca tatgaatttg tttccccaag tcctcctgca gatgtttctg agagggctaa | 660 |
| aaaggcttct gcaagatctg aaaaaagca aaaaagaaa actttagctg aaatcaacca | 720 |
| aaaatggaat ttagaggcag aaaaagaaga tggtgaattt gactccaaag aggaatctaa | 780 |
| gcaaaagctg gtatccttct gtagccaacc atctgttatc tccagtcctc agataaatgg | 840 |
| tgaaatagac ttactagcaa gtggctcctt gacagaatct gaatgttttg aagtttaac | 900 |
| tgaagtctct ttaccattgg ctgagcaaat agagtctcca gacactaaga gcaggaatga | 960 |
| agtagtgact cctgagaagg tctgcaaaaa ttatcttaca tctaagaaat ctttgccatt | 1020 |
| agaaataat ggaaaacgtg ccatcacaa tagactttcc agtcccattt ctaagagatg | 1080 |
| tagaaccagc attctgagca ccagtggaga ttttgttaag caaaccgtgc cctcagaaaa | 1140 |
| tataccattg cctgaatgtt cttcaccacc ttcatgcaaa cgtaaagttg gtggtacatc | 1200 |
| agggaggaaa aacagtaaca tgtccgatga attcattagt cttcaccag gtacaccacc | 1260 |
| ttctacatta agtagttcaa gttacaggca agtgatgtct agtccctcag caatgaagct | 1320 |
| gttgcccaat atggctgtga aaagaaatca tagaggagag acttgctcc atattgcttc | 1380 |
| tattaagggc gacataacctt ctgttgaata cctttacaa aatggaagtg atccaaatgt | 1440 |
| taaagaccat gctggatgga caccattgca tgaagcttgc aatcatgggc acctgaaggt | 1500 |
| agtggaatta ttgctccagc ataaggcatt ggtgaacacc accgggtatc aaaatgactc | 1560 |
| accacttcac gatgcagcca agaatgggca cgtggatata gtcaagctgt tactttccta | 1620 |
| tggagcctcc agaaatgctg ttaatatatt tggtctgcgg cctgtcgatt atacagatga | 1680 |
| tgaaagtatg aaatcgctat tgctgctacc agagaagaat gaatcatcct cagctagcca | 1740 |

-continued

```
ctgctcagta atgaacactg ggcagcgtag ggatggacct cttgtactta taggcagtgg      1800
gctgtcttca gaacaacaga aaatgctcag tgagcttgca gtaattctta aggctaaaaa      1860
atatactgag tttgacagta cagtaactca tgttgttgtt cctggtgatg cagttcaaag      1920
taccttgaag tgtatgcttg ggattctcaa tggatgctgg attctaaaat ttgaatgggt      1980
aaaagcatgt ctacgaagaa aagtatgtga acaggaagaa aagtatgaaa ttcctgaagg      2040
tccacgcaga agcaggctca acagagaaca gctgttgcca aagctgtttg atggatgcta      2100
cttctatttg tggggaacct tcaaacacca tccaaaggac aaccttatta agctcgtcac      2160
tgcaggtggg ggccagatcc tcagtagaaa gcccaagcca gacagtgacg tgactcagac      2220
catcaataca gtcgcatacc atgcgagacc cgattctgat cagcgcttct gcacacagta      2280
tatcatctat gaagatttgt gtaattatca cccagagagg gttcggcagg caaagtctg       2340 gaaggctcct tcgagctggt ttatagactg tgtgatgtcc tttgagttgc ttcctcttga      2400
cagctgaata ttataccaga tgaacatttc aaattgaatt tgcacggttt gtgagagccc      2460
agtcattgta ctgtttttaa tgttcacatt tttacaaata ggtagagtca ttcatatttg      2520
tctttgaatc                                                             2530

<210> SEQ ID NO 7
<211> LENGTH: 1203
<212> TYPE: DNA
<213> ORGANISM: Homo Sapiens

<400> SEQUENCE: 7
ggacgctgat gcgtttgggt tctcgtctgc agaccctctg gacctggtca cgattccata       60
atgtaccaca acagtagtca gaagcggcac tggaccttct ccagcgagga gcagctggca      120
agactgcggg ctgacgccaa ccgcaaattc agatgcaaag ccgtggccaa cgggaaggtt      180
cttccgaatg atccagtctt tcttgagcct catgaagaaa tgacactctg caaatactat      240 gagaaaggt tattggaatt ctgttcggtg tttaagccag caatgccaag atctgttgtg      300
ggtacggctt gtatgtattt caaacgtttt tatcttaata actcagtaat ggaatatcac      360
cccaggataa taatgctcac ttgtgcattt ttggcctgca agtagatga attcaatgta      420 tctagtcctc agtttgttgg aaacctccgg gagagtcctc ttggacagga aaggcactt      480 gaacagatac tggaatatga actacttctt atacagcaac ttaatttcca ccttattgtc      540
cacaatcctt acagaccatt tgagggcttc ctcatcgact taaagacccg ctatcccata      600
ttggagaatc cagagatttt gaggaaaaca gctgatgact tcttaatag aattgcattg      660 acggatgctt acctttatat cacaccttcc caaattgccc tgactgccat tttatctagt      720
gcctccaggg ctggaattac tatggaaagt tatttatcag agagtctgat gctgaaagag      780
aacagaactt gcctgtcaca gttactagat ataatgaaaa gcatgagaaa cttagtaaag      840
aagtatgaac cacccagatc tgaagaagtt gctgttctga acagaagtt ggagcgatgt      900 cattctgctg agcttgcact taacgtaatc acgaagaaga ggaaaggcta tgaagatgat      960
gattacgtct caaagaaatc caaacatgag gaggaagaat ggactgatga cgacctggta     1020
gaatctctct aaccatttga agttgatttc tcaatgctaa ctaatcaaga gaagtaggaa     1080
gcatatcaaa cgtttaactt tatttaaaaa gtataatgtg aaaacataaa atatattaaa     1140
acttttctat tgttttcttt ccctttcaca gtaactttat gtaaaataaa ccatcttcaa     1200
aag                                                                   1203
```

<210> SEQ ID NO 8
<211> LENGTH: 653
<212> TYPE: DNA
<213> ORGANISM: Homo Sapiens

<400> SEQUENCE: 8

| | | | | | |
|---|---|---|---|---|---|
| atggcgtccc | tttccettgc | acctgttaac | atctttaagg | caggagctga | tgaagagaga | 60 |
| gcagagacag | ctcgtctgac | ttcttttatt | ggtgccatcg | ccattggaga | cttggtaaag | 120 |
| agcaccttgg | gacccaaagg | catggacaaa | attcttctaa | gcagtggacg | agatgcctct | 180 |
| cttatggtaa | ccaatgatgg | tgccactatt | ctaaaaaaca | ttggtgttga | caatccagca | 240 |
| gctaaagttt | tagttgatat | gtcaagggtt | caagatgatg | aagttggtga | tggcactacc | 300 |
| tctgttaccg | ttttagcagc | agaattatta | agggaagcag | aatctttaat | tgcaaaaaag | 360 |
| attcatccac | agaccatcat | agcgggttgg | agagaagcca | cgaaggctgc | aagagaggcg | 420 |
| ctgttgagtt | ctgcagttga | tcatggttcc | gatgaagtta | aattccgtca | agatttaatg | 480 |
| aatattgcgg | gcacaacatt | atcctcaaaa | cttcttactc | atcacaaaga | ccactttaca | 540 |
| aagttagctg | tagaagcagt | tctcagactg | aaaggctctg | gcaacctgga | ggcaattcat | 600 |
| attatcaaga | agctaggagg | aagtttggca | gattcctatt | tagatgaagg | tat | 653 |

<210> SEQ ID NO 9
<211> LENGTH: 1686
<212> TYPE: DNA
<213> ORGANISM: Homo Sapiens

<400> SEQUENCE: 9

| | | | | | |
|---|---|---|---|---|---|
| ccacgcgtcc | gggcgtaagc | caggcgtgtt | aaagccggtc | ggaactgctc | cggagggcac | 60 |
| gggctccgta | ggcaccaact | gcaaggaccc | ctcccctgc | gggcgctccc | atggcacagt | 120 |
| tcgcgttcga | gagtgacctg | cactcgctgc | ttcagctgga | tgcacccatc | cccaatgcac | 180 |
| cccctgcgcg | ctggcagcgc | aaagccaagg | aagccgcagg | cccggccccc | tcacccatgc | 240 |
| gggccgccaa | ccgatcccac | agcgccggca | ggactccggg | ccgaactcct | ggcaaatcca | 300 |
| gttccaaggt | tcagaccact | cctagcaaac | ctggcggtga | ccgctatatc | ccccatcgca | 360 |
| gtgctgccca | gatggaggtg | gccagcttcc | tcctgagcaa | ggagaaccag | tctgaaaaca | 420 |
| gccagacgcc | caccaagaag | gaacatcaga | agcctgggc | tttgaacctg | aacggttttg | 480 |
| atgtagagga | agccaagatc | cttcggctca | gtggaaaacc | acaaaatgcg | ccagagggtt | 540 |
| atcagaacag | actgaaagta | ctctacagcc | aaaaggccac | tcctggctcc | agccggaaga | 600 |
| cctgccgtta | cattccttcc | ctgccagacc | gtatcctgga | tgcgcctgaa | atccgaaatg | 660 |
| actattacct | gaaccttgtg | gattggagtt | ctgggaatgt | actggccgtg | gcactggaca | 720 |
| acagtgtgta | cctgtggagt | gcaagctctg | gtgacatcct | gcagcttttg | caaatggagc | 780 |
| agcctgggga | atatatatcc | tctgtggcct | ggatcaaaga | gggcaactac | ttggctgtgg | 840 |
| gcaccagcag | tgctgaggtg | cagctatggg | atgtgcagca | gcagaaacgg | cttcgaaata | 900 |
| tgaccagtca | ctctgcccga | gtgggctccc | taagctggaa | cagctatatc | ctgtccagtg | 960 |
| gttcacgttc | tggccacatc | caccaccatg | atgttcgggt | agcagaacac | catgtggcca | 1020 |
| cactgagtgg | ccacagccag | gaagtgtgtg | ggctgcgctg | ggcccagat | ggacgacatt | 1080 |
| tggccagtgg | tggtaatgat | aacttggtca | atgtgtggcc | tagtgctcct | ggagagggtg | 1140 |
| gctgggttcc | tctgcagaca | ttcacccagc | atcaagggc | tgtcaaggcc | gtagcatggt | 1200 |
| gtccctggca | gtccaatgtc | ctggcaacag | gagggggcac | cagtgatcga | cacattcgca | 1260 |

-continued

```
tctggaatgt gtgctctggg gcctgtctga gtgccgtgga tgcccattcc caggtgtgct    1320
ccatcctctg gtctccccat tacaaggagc tcatctcagg ccatggcttt gcacagaacc    1380
agctagttat ttggaagtac ccaaccatgg ccaaggtggc tgaactcaaa ggtcacacat    1440
cccgggtcct gagtctgacc atgagcccag atggggccac agtggcatcc gcagcagcag    1500
atgagaccct gaggctatgg cgctgttttg agttggaccc tgcgcggcgg cgggagcggg    1560
agaaggccag tgcagccaaa agcagcctca tccaccaagg catccgctga agaccaaccc    1620
atcacctcag ttgtttttta tttttctaat aaagtcatgt ctcccttcat gttttttttt    1680
ttaaaa                                                                1686
```

<210> SEQ ID NO 10
<211> LENGTH: 1374
<212> TYPE: DNA
<213> ORGANISM: Homo Sapiens

<400> SEQUENCE: 10

```
attgcggcgg cgccagagct gctggagcgc tcgggtccc cgggcggcgg cggcggcgca      60
gaggaggagg caggcggcgg ccccggtggc tccccccgg acggtgcgcg gcccggcccg     120
tctcgcgaac tcgcggtggt cgcgcggccc cgcgctgctc cgaccccggg ccctccgcc    180 gccgccatgg ctcggccgct agtgcccagc tcgcagaagg cgctgctgct ggagctcaag    240
gggctgcagg aagagccggt cgagggattc gcgtgacac tggtggacga gggcgatcta    300
tacaactggg aggtggccat tttcgggccc ccaacacct actacgaggg cggctacttc    360
aaggcgcgcc tcaagttccc catcgactac ccatactctc caccagcctt tcggttcctg    420
accaagatgt ggcaccctaa catctacgag acggggacg tgtgtatctc catcctccac    480
ccgccggtgg acgaccccca gagcggggag ctgccctcag agaggtggaa ccccacgcag    540
aacgtcagga ccattctcct gagtgtgatc tccctcctga acgagcccaa caccttctcg    600
cccgcaaacg tggacgcctc cgtgatgtac aggaagtgga agagagcaa ggggaaggat    660 cgggagtaca cagacatcat ccggaagcag gtcctgggga ccaaggtgga cgcggagcgt    720
gacggcgtga aggtgcccac cacgctggcc gagtactgcg tgaagaccaa ggcgccggcg    780
cccgacgagg gctcagacct cttctacgac gactactacg aggacggcga ggtggaggag    840
gaggccgaca gctgcttcgg ggacgatgag atgactctg gcacggagga gtcctgacac    900
caccagaata aacttgccga gtttacctca ctagggccgg acccgtggct ccttagacga    960
cagactacct cacggaggtt ttgtgctggt ccccgtctcc tctggttgtt tcgttttggc   1020 ttttttctccc tccccatgtc tgttctgggt tttcacgtgc ttcagagaag aggggctgcc   1080
ccaccgccac tcacgtcact cggggctcgg tggacgggcc cagggtggga gcggccggcc   1140
cacctgtccc ctcgggaggg gagctgagcc cgacttctac cggggtcccc cagcttccgg   1200
actggccgca ccccggagga gccacggggg cgctgctggg aacgtgggcg gggggccgtt   1260
tcctgacact accagcctgg gaggcccagg tgtagcggtc cgaggggccc ggtcctgcct   1320
gtcagctcca ggtcctggag ccacgtccag cactgagtgg acggattcac caat         1374
```

<210> SEQ ID NO 11
<211> LENGTH: 806
<212> TYPE: DNA
<213> ORGANISM: Homo Sapiens

<400> SEQUENCE: 11

-continued

| | |
|---|---|
| cggcactggt ctcgacgtgg ggcggccagc gatggagccg cccagttcaa tacaaacaag | 60 |
| tgagtttgac tcatcagatg aagagcctat tgaagatgaa cagactccaa ttcatatatc | 120 |
| atggctatct ttgtcacgag tgaattgttc tcagtttctc ggtttatgtg ctcttccagg | 180 |
| ttgtaaattt aaagatgtta gaagaaatgt ccaaaaagat acagaagaac taaagagctg | 240 |
| tggtatacaa gacatatttg ttttctgcac cagaggggga ctgtcaaaat atagagtccc | 300 |
| aaaccttctg gatctctacc agcaatgtgg aattatcacc catcatcatc caatcgcaga | 360 |
| tggagggact cctgacatag ccagctgctg tgaaataatg gaagagctta caacctgcct | 420 |
| taaaaattac cgaaaaacct aatacactg ctatggagga cttgggagat cttgtcttgt | 480 |
| agctgcttgt ctcctactat acctgtctga cacaatatca ccagagcaag ccatagacag | 540 |
| cctgcgagac ctaagaggat ccgggcaat acagaccatc aagcaataca attatcttca | 600 |
| tgagtttcgg gacaaattag ctgcacatct atcatcaaga gattcacaat caagatctgt | 660 |
| atcaagataa aggaattcaa atagcatata tatgaccatg tctgaaatgt cagttctcta | 720 |
| gcataatttg tattgaaatg aaaccaccag tgttatcaac ttgaatgtaa atgtacatgt | 780 |
| gcagatattc ctaaagtttt attgac | 806 |

<210> SEQ ID NO 12
<211> LENGTH: 717
<212> TYPE: DNA
<213> ORGANISM: Homo Sapiens

<400> SEQUENCE: 12

| | |
|---|---|
| agagcgatca tgtcgcacaa acaaatttac tattcggaca aatacgacga cgaggagttt | 60 |
| gagtatcgac atgtcatgct gcccaaggac atagccaagc tggtccctaa aacccatctg | 120 |
| atgtctgaat ctgaatggag gaatcttggc gttcagcaga gtcagggatg ggtccattat | 180 |
| atgatccatg aaccagaacc tcacatcttg ctgttccggc gcccactacc caagaaacca | 240 |
| aagaaatgaa gctggcaagc tacttttcag cctcaagctt tacacagctg tccttacttc | 300 |
| ctaacatctt tctgataaca ttattatgtt gccttcttgt ttctcacttt gatatttaaa | 360 |
| agatgttcaa tacactgttt gaatgtgctg gtaactgctt tgcttcttga gtagagccac | 420 |
| caccaccata gcccagccag atgagtgctc tgtggaccca cagcctaagc tgagtgtgac | 480 |
| cccagaagcc acgatgtgct ctgtatccag aacacacttg gcagatggag gaagcatctg | 540 |
| agtttgagac catggctgtt acagggatca tgtaaacttg ctgttttttgt tttttctgcc | 600 |
| gggtgttgta tgtgtggtga cttgcggatt tatgtttcag tgtactggaa actttccatt | 660 |
| ttattcaaga aatctgttca tgttaaaagc cttgattaaa gaggaagttt ttataat | 717 |

<210> SEQ ID NO 13
<211> LENGTH: 627
<212> TYPE: DNA
<213> ORGANISM: Homo Sapiens

<400> SEQUENCE: 13

| | |
|---|---|
| agtctccggc gagttgttgc ctgggctgga cgtggttttg tctgctgcgc ccgctcttcg | 60 |
| cgctctcgtt tcattttctg cagcgcgcca cgaggatggc ccacaagcag atctactact | 120 |
| cggacaagta cttcgacgaa cactacgagt accggcatgt tatgttaccc agagaacttt | 180 |
| ccaaacaagt acctaaaact catctgatgt ctgaagagga gtggaggaga cttggtgtcc | 240 |
| aacagagtct aggctgggtt cattacatga ttcatgagcc agaaccacat attcttctct | 300 |
| ttagacgacc tcttccaaaa gatcaacaaa aatgaagttt atctggggat cgtcaaatct | 360 |

```
ttttcaaatt taatgtatat gtgtatataa ggtagtattc agtgaatact tgagaaatgt      420
acaaatcttt catccatacc tgtgcatgag ctgtattctt cacagcaaca gagctcagtt      480
aaatgcaact gcaagtaggt tactgtaaga tgtttaagat aaaagttctt ccagtcagtt      540
tttctcttaa gtgcctgttt gagtttactg aaacagttta cttttgttca ataaagtttg      600
tatgttgcat ttaaaaaaaa aaaaaaa                                          627

<210> SEQ ID NO 14
<211> LENGTH: 341
<212> TYPE: DNA
<213> ORGANISM: Homo Sapiens

<400> SEQUENCE: 14
aggagaaggg aggtgactcc ggcggaagag gacaaggcag aatgcaggcc cttcgggtgt       60
cccaggcgct gatccgctcc ttcagctcca ccgcccggaa ccgctttcag aaccgagtgc      120
gcgagaaaca gaagctcttc caggaggaca tgacatccc gttgtacctg aagggcggca      180
tcgttgacaa catcctgtac cgagtgacaa tgacgctgtg tctgggcggc actgtctaca      240
gcttgtactc ccttggctgg gcctccttcc ccaggaatta agaccaagaa gcctgggggg      300
cctgagagac ttgaacaagt gtcaataaac gctggcctct g                         341

<210> SEQ ID NO 15
<211> LENGTH: 1581
<212> TYPE: DNA
<213> ORGANISM: Homo Sapiens

<400> SEQUENCE: 15
ataactaaat tacattttct tggtcttttg actatgaaat agtttaccct agcaacatga       60 aaacaagag acctaagcta ttagaagaaa tgcagttcta tgtatcttgt gtgtatagtt      120
tttccctggg tggttttcaa cgaccagtga ctccttagct ggtttcctca gctgctagca      180
cttgctctgg gtacttgtcc tcaacacgtc catctgcaac aatgtgtgcc taggaaataa      240
actcaactta ctactcaccc aaccaaaatg taattttttta aacgcagcac acactgggtg      300
gattccaaag tcatgattat gctttactat gcactctgta ctattcagac cactactctc      360
attcattact gcaattaact gcacacataa ctatttttta ttgctaatta tacaccactg      420 attccactt taaaaaaaca ttagcatttg tctctaatta aatatttact gcttgtgttt      480
tacagacccg atatcaggtt cttctttaga ctgggcttat gacctgggca tcaaacacac      540
atttgccttt gagctccgag ataaaggcaa atttggtttt ctccttccag aatcccggat      600
aaagccaacg tgcagagaga ccatgctagc tgtcaaattt attgccaagt atatcctcaa      660
gcatacttcc taaagaactg ccctctgttt ggaataagcc aattaatcct ttttttgtgcc      720 tttcatcaga aagtcaatct tcagttatcc ccaaatgcag cttctatttc acctgaatcc      780
ttctcttgct catttaagtc ccatgttact gctgtttgct tttacttact ttcagtagca      840
ccataacgaa gtagctttaa gtgaaacctt taactacct ttctttgctc caagtgaagt      900
ttggacccag cagaaagcat tattttgaaa ggtgatatac agtggggcac agaaaacaaa      960
tgaaaaccct cagtttctca cagattttca ccatgtggct tcatcaattt atgtgctaat     1020
acaataaaat aaaatgcact taatgcttta aaattcatct ttttatgata aacaatattc     1080
tctgtatttc tctatagcat taataatcaa tattaatgcc attcattcag tctgttaata     1140
agaaataata tcttcaattt tcaaaaacat aatttgccta tcttttctg atagaagtag     1200
```

-continued

| acattgttta tatcttcaaa aaagcaaaag gatgtcctag caggaaataa agtggttcat | 1260 |
| atagagatga atctcagtcc tttaaataac cgatccagtt ctcatcagca taatgtacat | 1320 |
| taaattcaaa atagtttaat ttaacctgcc ataatcagaa gaaaccacct gctaaaacat | 1380 |
| ctgtttgccg gtacagacac agacaagaca gtctggtcag ctgtgacccc tgcctccta | 1440 |
| atggatagaa aggaaacctg gaaacatact gtaagttgag gacggaaagt catgttgacc | 1500 |
| aaaggcaatc agggtaactt gctgcatttg taccatttat actcctatta tttaagatag | 1560 |
| tattattgga tagcttctcc c | 1581 |

<210> SEQ ID NO 16
<211> LENGTH: 2443
<212> TYPE: DNA
<213> ORGANISM: Homo Sapiens

<400> SEQUENCE: 16

| aaatggcgtg cccgtctctc cgccggcccc ctgcctcgca gtggtttctc ctgcagctcc | 60 |
| cctgggctcc gcggccagta gtgcagcccg tggagccgcg gctttgcccg tctcctctgg | 120 |
| gtggcccag tgcgcgggct gacactcatt cagccgggga aggtgaggcg agtagaggct | 180 |
| ggtgcggaac ttgccgcccc cagcagcgcc ggcgggctaa gcccagggcc gggcagacaa | 240 |
| agaggccgc ccgcgtagga aggcacgcc ggcgcggcgg gagcgcagcg atggccgggc | 300 |
| gaggggcag cgcgctgctg gctctgtgcg gggcactggc tgcctgcggg tggctcctgg | 360 |
| gcgccgaagc ccaggagccc ggggcgcccg ggcgggcat gaggcggcgc cggcggctgc | 420 |
| agcaagagga cggcatctcc ttcgagtacc accgctaccc cgagctgcgc gaggcgctcg | 480 |
| tgtccgtgtg gctgcagtgc accgccatca gcaggattta cacggtgggg cgcagcttcg | 540 |
| agggccggga gctcctggtc atcgagctgt ccgacaaccc tggcgtccat gagcctggtg | 600 |
| agcctgaatt taaatacatt gggaatatgc atggaatga gctgttgga cgagaactgc | 660 |
| tcatttctt ggcccagtac ctatgcaacg aataccagaa ggggaacgag acaattgtca | 720 |
| acctgatcca cagtacccgc attcacatca tgccttccct gaacccagat ggctttgaga | 780 |
| aggcagcgtc tcagcctggt gaactcaagg actggtttgt gggtcgaagc aatgcccagg | 840 |
| gaatagatct gaaccggaac tttccagacc tggataggat agtgtacgtg aatgagaaag | 900 |
| aaggtggtcc aaataatcat ctgttgaaaa atatgaagaa aattgtggat caaaacacaa | 960 |
| agcttgctcc tgagaccaag gctgtcattc attggattat ggatattcct tttgtgcttt | 1020 |
| ctgccaatct ccatggagga gaccttgtgg ccaattatcc atatgatgag acgcggagtg | 1080 |
| gtagtgctca cgaatacagc tcctccccag atgacgccat tttccaaagc ttggcccggg | 1140 |
| catactcttc tttcaacccg gccatgtctg accccaatcg gccaccatgt cgcaagaatg | 1200 |
| atgatgacag cagcttttgta gatggaacca ccaacggtgg tgcttggtac agcgtacctg | 1260 |
| gagggatgca agacttcaat taccttagca gcaactgttt tgagatcacc gtggagctta | 1320 |
| gctgtgagaa gttcccacct gaagagactc tgaagaccta ctgggaggat aacaaaaact | 1380 |
| ccctcattag ctaccttgag cagatacacc gaggagttaa aggatttgtc cgagaccttc | 1440 |
| aagtaacccc aattgcgaat gccaccatct ccgtggaagg aatagaccac gatgttacat | 1500 |
| ccgcaaagga tggtgattac tggagattgc ttatacctgg aaactataaa cttacagcct | 1560 |
| cagctccagg ctatctggca ataacaaaga aagtggcagt tccttacagc cctgctgctg | 1620 |
| gggttgattt tgaactggag tcatttttctg aaaggaaaga agaggagaag gaagaattga | 1680 |
| tggaatggtg gaaatgatg tcagaaactt taaatttta aaaaggcttc tagttagctg | 1740 |

-continued

```
ctttaaatct atctatataa tgtagtatga tgtaatgtgg tcttttttt agattttgtg      1800 cagttaatac ttaacattga tttatttttt aatcatttaa atattaatca actttcctta      1860
aaataaatag cctcttaggt aaaaatataa gaacttgata tatttcattc tcttatatag      1920
tattcatttt cctacctata ttacacaaaa agtatagaa aagatttaag taattttgcc      1980
atcctaggct taaatgcaat attcctggta ttatttacaa tgcagaattt tttgagtaat      2040
tctagctttc aaaaattagt gaagttcttt tactgtaatt ggtgacaatg tcacataatg      2100
aatgctattg aaaaggttaa cagatacagc tcggagttgt gagcactcta ctgcaagact      2160
taaatagttc agtataaatt gtcgttttt tcttgtgctg actaactata agcatgatct      2220
tgttaatgca tttttgatgg gaagaaaagg tacatgttta caaagaggtt ttatgaaaag      2280
aataaaaatt gacttcttgc ttgtacatat aggagcaata ctattatatt atgtagtccg      2340
ttaacactac ttaaaagttt agggttttct cttggttgta gagtggccca gaattgcatt      2400
ctgaatgaat aaaggttaaa aaaaaatccc cagtgaaaaa aaa                       2443
```

<210> SEQ ID NO 17
<211> LENGTH: 3100
<212> TYPE: DNA
<213> ORGANISM: Homo Sapiens

<400> SEQUENCE: 17

```
actcgtctct ggtaaagtct gagcaggaca gggtggctga ctggcagatc cagaggttcc       60
cttggcagtc cacgccaggc cttcaccatg gatcagttcc ctgaatcagt gacagaaaac      120
tttgagtacg atgatttggc tgaggcctgt tatattgggg acatcgtggt ctttgggact      180
gtgttcctgt ccatattcta ctccgtcatc tttgccattg gcctggtggg aaatttgttg      240
gtagtgtttg ccctcaccaa cagcaagaag cccaagagtg tcaccgacat ttacctcctg      300
aacctggcct tgtctgatct gctgtttgta gccactttgc ccttctggac tcactatttg      360
ataaatgaaa agggcctcca caatgccatg tgcaaattca ctaccgcctt cttcttcatc      420 ggctttttg aagcatatt cttcatcacc gtcatcagca ttgataggta cctggccatc      480
gtcctggccg ccaactccat gaacaaccgg accgtgcagc atggcgtcac catcagccta      540
ggcgtctggg cagcagccat tttggtggca gcaccccagt tcatgttcac aaagcagaaa      600
gaaaatgaat gccttggtga ctaccccgag gtcctccagg aaatctggcc cgtgctccgc      660
aatgtggaaa caaattttct tggcttccta ctcccctgc tcattatgag ttattgctac      720
ttcagaatca tccagacgct gttttcctgc aagaaccaca agaaagccaa agccattaaa      780
ctgatccttc tggtggtcat cgtgttttc ctcttctgga caccctacaa cgttatgatt      840
ttcctggaga cgcttaagct ctatgacttc tttcccagtt gtgacatgag gaaggatctg      900
aggctggccc tcagtgtgac tgagacggtt gcatttagcc attgttgcct gaatcctctc      960
atctatgcat tgctgggga gaagttcaga agatacctt accacctgta tgggaaatgc     1020
ctggctgtcc tgtgtgggcg ctcagtccac gttgatttct cctcatctga atcacaaagg     1080
agcaggcatg gaagtgttct gagcagcaat tttacttacc acacgagtga tggagatgca     1140
ttgctccttc tctgaaggga atcccaaagc cttgtgtcta cagagaacct ggagttcctg     1200
aacctgatgc tgactagtga ggaaagattt tgttgttat tcttacagg cacaaaatga     1260 tggacccaat gcacacaaaa caaccctaga gtgttgttga gaattgtgct caaaattga     1320 agaatgaaca aattgaactc tttgaatgac aaagagtaga catttctctt actgcaaatg     1380
```

| | |
|---|---|
| tcatcagaac tttttggttt gcagatgaca aaaattcaac tcagactagt ttagttaaat | 1440 |
| gagggtggtg aatattgttc atattgtggc acaagcaaaa gggtgtctga gccctcaaag | 1500 |
| tgagggaaa ccagggcctg agccaagcta gaattccctc tctctgactc tcaaatcttt | 1560 |
| tagtcattat agatccccca gactttacat gacacagctt tatcaccaga gagggactga | 1620 |
| cacccatgtt tctctggccc caagggaaaa ttcccaggga agtgctctga taggccaagt | 1680 |
| ttgtatcagg tgcccatccc tggaaggtgc tgttatccat ggggaaggga tatataagat | 1740 |
| ggaagcttcc agtccaatct catggagaag cagaaataca tatttccaag aagttggatg | 1800 |
| ggtgggtact attctgatta cacaaaacaa atgccacaca tcacccttac catgtgcctg | 1860 |
| atccagcctc tcccctgatt acaccagcct cgtcttcatt aagccctctt ccatcatgtc | 1920 |
| cccaaacctg caagggctcc ccactgccta ctgcatcgag tcaaaactca atgcttggc | 1980 |
| ttctcatacg tccaccatgg ggtcctacca atagattccc cattgcctcc tccttcccaa | 2040 |
| aggactccac ccatcctatc agcctgtctc ttccatatga cctcatgcat ctccacctgc | 2100 |
| tcccaggcca gtaagggaaa tagaaaaacc ctgcccccaa ataagaaggg atggattcca | 2160 |
| accccaactc cagtagcttg ggacaaatca agcttcagtt tcctggtctg tagaagaggg | 2220 |
| ataaggtacc tttcacatag agatcatcct ttccagcatg aggaactagc caccaactct | 2280 |
| tgcaggtctc aacccttttg tctgcctctt agacttctgc tttccacacc tgcactgctg | 2340 |
| tgctgtgccc aagttgtggt gctgacaaag cttggaagag cctgcaggtg ccttggccgc | 2400 |
| gtgcatagcc cagacacaga agaggctggt tcttacgatg gcacccagtg agcactccca | 2460 |
| agtctacaga gtgatagcct tccgtaaccc aactctcctg gactgccttg aatatcccct | 2520 |
| cccagtcacc ttgtgcaagc ccctgcccat ctgggaaaat accccatcat tcatgctact | 2580 |
| gccaacctgg ggagccaggg ctatgggagc agcttttttt tcccccctag aaacgtttgg | 2640 |
| aacaatgtaa aactttaaag ctcgaaaaca attgtaataa tgctaaagaa aaagtcatcc | 2700 |
| aatctaacca catcaatatt gtcattcctg tattcacccg tccagacctt gttcacactc | 2760 |
| tcacatgttt agagttgcaa tcgtaatgta cagatggttt tataatctga tttgttttcc | 2820 |
| tcttaacgtt agaccacaaa tagtgctcgc tttctatgta gtttggtaat tatcatttta | 2880 |
| gaagactcta ccagactgtg tattcattga agtcagatgt ggtaactgtt aaattgctgt | 2940 |
| gtatctgata gctctttggc agtctatatg tttgtataat gaatgagaga ataagtcatg | 3000 |
| ttccttcaag atcatgtacc ccaatttact tgccattact caattgataa acatttaact | 3060 |
| tgtttccaat gtttagcaaa tacatatttt atagaacttc | 3100 |

<210> SEQ ID NO 18
<211> LENGTH: 3995
<212> TYPE: DNA
<213> ORGANISM: Homo Sapiens

<400> SEQUENCE: 18

| | |
|---|---|
| ggatccgcgg gacagatgag gaagggcctt aagtcactgc agccagaggg atggaggtgg | 60 |
| actgatggga gggcttctcc ggtggggtta gaagggaaaa gtagggaaag agaagtgtaa | 120 |
| ggtagatggc agaggcagag acatggaaag acagactcta gggttcctga tgatatctat | 180 |
| ctcggccaac acaaaaggga gggtacagtg gtgggggcac ccaagctagg gtgtgagtac | 240 |
| cctaagtgta ttcttctgag atgtaggcca ttcactaact cttggaacag ctacagtttc | 300 |
| acagtaggaa gacccccca gattcactgc cctcccctta gtaaagcctc tgagaccttc | 360 |
| ctgaacattc ccttctgtct ttgccctctg ttccttccag agactatgtg cccaggcaga | 420 |

-continued

```
tggattcctc ccgggcctga gaggaactgc aggaattctc ctgcctctta cccgtaaaac    480
cccaacttct ctagccctag ggcaggaagt cccaaacaat ttctacccct ttttctgcaa    540
ttctcattgg ggtgagagga ggcccaggag gagagagagc tgggctcagc ttcttttttga    600 gctgctggag ccctctgtga ggaggccctc tttgctggct tctcaggaga gtgtggctag    660
gttctgcctg cctatgggaa gagggggcca gggtgtgtgg agcaagatgg tgcggtgctg    720
gtgccttggg acctggggga atgggacagc tggtcggctc agagacggcc tactttactc    780
acagctggaa tttagtgggg agaagcagct caactccaat cctggaggat tagggagatt    840
aaagtgagag aagagagaga tgtcccagag accaagagct cccaggtcag ccctctggct    900
cctggcaccc ccactgctgc ggtgggcacc cccactcctc acagtgctgc atagcgacct    960
cttccaggcc ttgctggaca tcctggacta ttatgaggct tccctctcag agagtcagaa   1020
ataccgctac caagatgaag acacgccccc tctggagcac agcccggccc acctccccaa   1080
ccaggccaat tctcccccag tgattgtcaa cacagatacc ctagaagccc aggatatga    1140 gttgcaggtg aacgggaccg agggggagat ggaatacgag gaaatcacat tggaaagggg   1200
taactcaggt ctgggcttca gcatcgcagg tggcactgac aacccacaca tcggtgacga   1260
cccatccatt ttcatcacca agatcattcc tggtggggct gcggcccagg atggccgcct   1320
cagggtcaac gacagcatcc tgtttgtaaa tgaagtggac gtgcgcgagg tgacccactc   1380
agcggcggtg gaagccctca agaggcagg ctccatcgtt cgcctctatg tcatgcgccg    1440 gaagccccg gctgagaagg tcatggagat caagctcatc aaggggccta aggtcttgg    1500 cttcagcatc gcagggggcg tagggaacca gcacatccca ggagataata gcatctatgt   1560
aacaaagatc atcgaagggg gtgctgccca caaggatggg aggttgcaga ttggagacaa   1620
gatcctggcg gtcaacagtg tggggctaga ggacgtcatg catgaagatg ctgtggcagc   1680
cctgaagaac acgtatgatg ttgtctacct aaaggtggcc aagcccagca atgcctacct   1740
gagtgacagc tatgctcccc cagacatcac aacctcttat tcccagcacc tggacaatga   1800
gatcagtcac agcagctacc tgggcaccga ctaccccaca gccatgaccc ccacttcccc   1860
tcggcgctac tctccagtgg ccaaggacct gctcggggag gaagacattc ccgagaacc    1920 gaggcgaatt gtgatccacc ggggctccac gggcctgggc ttcaacatcg tgggtggcga   1980
ggacggtgaa ggcatcttca tctccttat cctggccggg ggccctgcag acctcagtgg    2040
ggagctgcgg aagggggacc agatcctgtc ggtcaacggt gtggacctcc gaaatgccag   2100
ccatgagcag gctgccattg ccctgaagaa tgcgggtcag acggtcacga tcatcgctca   2160
gtataaacca gaagagtaca gccgattcga ggccaagatc cacgacccttc gggaacagct   2220 catgaacagc agcctgggct cagggactgc gtccttgcgg agcaaccca aaagggtttt    2280 ctacatcagg gccctgtttg attacgacaa gaccaaggac tgcggcttcc tgagccaggc   2340
cctgagcttc cgcttttggg atgtgctgca tgtcatcgat gctagtgatg aggagtggtg   2400
gcaggcacgc cgggtccact ctgacagtga gaccgacgca attgggttca tcccccagcaa   2460 acggcgggtt gagcgacgag agtggtcaag gttaaaggcc aaggactggg gctccagctc   2520
tggatcgcag ggtcgagaag actcggttct gagctacgag acagtgacgc agatggaagt   2580
gcactatgct cgccccatca tcatccttgg gcccaccaag gaccgcgcca acgatgatct   2640
tctctccgag ttccccgaca gtttggatc ctgtgttccc catacgacac ggcccaagcg    2700
ggagtatgag atagatggcc gggattacca ctttgtgtcg tcccgggaga aaatggagaa   2760
```

-continued

| | | | | |
|---|---|---|---|---|
| ggacattcag | gcgcacaagt | tcattgaggc | cggccagtac | aacagccacc tctatgggac | 2820 |
| cagcgtccag | tccgtgcgag | aggtggcaga | gcagggaag | cactgcatcc tcgatgtctc | 2880 |
| ggccaatgcc | gtgcggcggc | tgcaggcggc | ccacctgcac | cccatcgcca tcttcatccg | 2940 |
| cccccgctcc | ctggagaatg | tgctagagat | taacaagcgg | atcacagagg agcaagcccg | 3000 |
| caaagccttc | gacagagcca | ccaagctgga | gcaggagttc | acagagtgct tctcagccat | 3060 |
| cgtggagggt | gacagctttg | aggagatcta | ccacaaggtg | aagcgtgtca tcgaggacct | 3120 |
| ctcaggcccc | tacatctggg | ttccagcccg | agagagactc | tgattcctgc cctggcttgg | 3180 |
| cctggactcg | ccctgcctcc | atcacctggg | cccttggtct | ggactgaatt gcccaagccc | 3240 |
| ttggctcccc | ccggcctccc | tcccacccct | tcttatttat | ttcctttcta actggatcca | 3300 |
| gcctgttgga | gggggacac | tcctctgcat | gtatccccgc | accccagaac tgggctcctg | 3360 |
| aacgccagga | acctggggtc | tgggggggag | ctgggctcct | tgttccgagc ccttgctcct | 3420 |
| taggatcccc | gcccccacct | gcccccaatg | cacacacaga | cccaccgggg gccacctgcc | 3480 |
| ctcccccatc | ctctcccaca | cacattccag | aagtcagggc | ccctcgagg agcacccgct | 3540 |
| gcagggatgc | agggccacag | gcctccgctc | tctcctaagg | cagggtctgg ggtcacccct | 3600 |
| gcctcatcgt | aattcccat | gttaccttga | tttctcatt | atttttccca cttttttct | 3660 |
| tctcaaaggt | ggttttttgg | ggggagaagc | agggggactcc | gcagcgggcc cctgccttcc | 3720 |
| acatgccccc | accatttttc | tttgccggtt | tgcatgagtg | gaaggtctaa atgtggcttt | 3780 |
| tttttttttt | ttcctgggaa | ttttttgggg | gaaaaggggag | ggatgggtct agggagtggg | 3840 |
| aaatgcggga | gggagggtgg | ggcagggtc | gggggtcggg | tgtccgggag ccagggaaga | 3900 |
| ctggaaatgc | tgccgccttc | tgcaattat | ttattttttt | cttttgagag agtgaaagga | 3960 |
| agagacagat | acttgaaaaa | aaaaaaaaa | aaaaa | | 3995 |

<210> SEQ ID NO 19
<211> LENGTH: 3025
<212> TYPE: DNA
<213> ORGANISM: Homo Sapiens

<400> SEQUENCE: 19

| | | | | |
|---|---|---|---|---|
| gcacgagcag | gcagttcaga | ttaaagaagc | taattgatca | agaaatcaag tctcaggagg | 60 |
| agaaggagca | agaaaaggag | aaaagggtca | ccaccctgaa | agaggagctg accaagctga | 120 |
| agtcttttgc | tttgatggtg | gtggatgaac | agcaaaggct | gacggcacag ctcacccttc | 180 |
| aaagacagaa | aatccaagag | ctgaccacaa | atgcaaagga | aacacatacc aaactagccc | 240 |
| ttgctgaagc | cagagttcag | gaggaagagc | agaaggcaac | cagactagag aaggaactgc | 300 |
| aaacgcagac | cacaaagttt | caccaagacc | aagacacaat | tatggcgaag ctcaccaatg | 360 |
| aggacagtca | aaatcgccag | cttcaacaaa | agctggcagc | actcagccgg cagattgatg | 420 |
| agttagaaga | gacaaacagg | tctttacgaa | aagcagaaga | ggagctgcaa gatataaaag | 480 |
| aaaaaatcag | taagggagaa | tatggaaacg | ctggtatcat | ggctgaagtg aagagctca | 540 |
| taaaaatgga | ggagcagtgc | agagatctca | ataagaggct | tgaagggag acgttacaga | 600 |
| gtaaagactt | taaactagag | gttgaaaaac | tcagtaaaag | aattatggct ctggaaaagt | 660 |
| tagaagacgc | tttcaacaaa | agcaaacaag | aatgctactc | tctgaaatgc aatttagaaa | 720 |
| aagaaaggat | gaccacaaag | cagttgtctc | aagaactgga | gagtttaaaa gtaaggatca | 780 |
| aagagctaga | agccattgaa | agtcggctag | aaaagacaga | attcactcta aaagaggatt | 840 |
| taactaaact | gaaaacatta | actgtgatgt | ttgtagatga | acggaaaaca atgagtgaaa | 900 |

```
aattaaagaa aactgaagat aaattacaag ctgcttcttc tcagcttcaa gtggagcaaa    960
ataaagtaac aacagttact gagaagttaa ttgaggaaac taaaagggcg ctcaagtcca   1020
aaaccgatgt agaagaaaag atgtacagcg taaccaagga gagagatgat ttaaaaaaca   1080
aattgaaagc ggaagaagag aaaggaaatg atctcctgtc aagagttaat atgttgaaaa   1140
ataggcttca atcattggaa gcaattgaga aagatttcct aaaaaacaaa ttaaatcaag   1200
actctgggaa atccacaaca gcattacacc aagaaaacaa taagattaag gagctctctc   1260
aagaagtgga aagactgaaa ctgaagctaa aggacatgaa agccattgag gatgacctca   1320
tgaaaacaga agatgaatat gagactctag aacgaaggta tgctaatgaa cgagacaaag   1380 ctcaatttt atctaaagag ctagaacatg ttaaaatgga acttgctaag tacaagttag   1440
cagaaaagac agagaccagc catgaacaat ggcttttcaa aaggcttcaa gaagaagaag   1500
ctaagtcagg gcacctctca agagaagtgg atgcattaaa agagaaaatt catgaataca   1560
tggcaactga agacctaata tgtcacctcc agggagatca ctcagtctgc aaaaaaaaac   1620
taaatcaaca agaaacagg aacagagatt taggaagaga gattgaaaac ctcactaagg   1680
agttagagag gtaccggcat ttcagtaaga gcctcaggcc tagtctcaat ggaagaagaa   1740
tttccgatcc tcaagtattt tctaaagaag ttcagacaga agcagtagac aatgaaccac   1800
ctgattacaa gagcctcatt cctctggaac gtgcagtcat caatggtcag ttatatgagg   1860
agagtgagaa tcaagacgag gaccctaatg atgagggatc tgtgctgtcc ttcaaatgca   1920
gccagtctac tccatgtcct gttaacagaa agctatggat tccctggatg aaatccaagg   1980
agggccatct tcagaatgga aaaatgcaaa ctaaacccaa tgccaacttt gtgcaacctg   2040
gagatctagt cctaagccac acacctgggc agccacttca tataaaggtt actccagacc   2100
atgtacaaaa cacagccact cttgaaatca caagtccaac cacagagagt cctcactctt   2160
acacgagtac tgcagtgata ccgaactgtg gcacgccaaa gcaaggata accatcctcc   2220 aaaacgcctc cataacacca gtaaagtcca aaacctctac cgaagacctc atgaatttag   2280
aacaaggcat gtcccccaatt accatggcaa cctttgccag agcacagacc ccagagtctt   2340
gtggttctct aactccagaa aggacaatgt ccctattcag gttttggctg tgactggttc   2400
agctagctct cctgagcagg gacgctcccc agaaccaaca gaaatcagtg ccaagcatgc   2460
gatattcaga gtctccccag accggcagtc atcatggcag tttcagcgtt caaacagcaa   2520
tagctcaagt gtgataacta ctgaggataa taaaatccac attcacttag gaagtcctta   2580
catgcaagct gtagccagcc cttcagcacc actgcaggat aaccgaactc aaggcttaat   2640
taacggggca ctaaacaaaa caaccaataa agtcaccagc agtattacta tcacaccaac   2700
agccacacct cttcctcgac aatcacaaat tacagtaagt aatatatata actgaccacg   2760
ctcaccctca tccagtccat actgatattt ttgcaaggaa ctcaatcctt ttttaatcat   2820
ccctccatat cccccaagac tgactgaact cgtactttgg gaaggtttgt gcatgaacta   2880
tacaagagta tctgaaacta actgttgcct gcatagtcat atcgagtgtg cacttactgt   2940
atatcttttc atttacatac ttgtatggaa aatatttagt ctgcacttgt ataaatacat   3000
ctttatgtat ttgaaaaaaa aaaaa                                         3025
```

<210> SEQ ID NO 20
<211> LENGTH: 599
<212> TYPE: DNA
<213> ORGANISM: Homo Sapiens

<400> SEQUENCE: 20

```
cgggacgcgg atgcagacgc aggcggaggc gctgacggcg gggatggccg gggtggccac      60
agctgccgcg ggggcgtgga cacagccgca gctccggccg gtggagctcc cccagcgcac     120
gcgccaggtc cgggcagaga cgccgcgtct gccgcagggg gtcacgaatg cggccgcaca     180
tattcaccct cagcgtgcct ttcccgaccc ccttggaggc ggaaatcgcc catgggtccc     240
tggcaccaga tgccgagccc caccaaaggg tggttgggaa ggatctcaca gtgagtggca     300
ggatcctggt cgtccgctgg aaagctgaag actgtcgcct gctccgaatt ccgtcatca      360
actttcttga ccagctttcc ctggtggtgc ggaccatgca gcgctttggg cccccgttt      420
cccgctaagc ctggcctggg caaatggagc gaggtcccac tttgcgtctc cttgtaggca     480
gtgcgtccat ccttccctag gcaggaatt cccacagttg ctactttcct gggagggcct      540
catgttttat ctggttctta aatgtttgtt actacagaaa ataaaactga ggtattatt      599
```

<210> SEQ ID NO 21
<211> LENGTH: 890
<212> TYPE: DNA
<213> ORGANISM: Homo Sapiens

<400> SEQUENCE: 21

```
ggcggaccga agaacgcagg aagggggccg gggggacccg cccccggccg gccgcagcca      60
tgaactccaa cgtggagaac ctaccccccgc acatcatccg cctggtgtac aaggaggtga    120
cgacactgac cgcagaccca cccgatggca tcaaggtctt tcccaacgag gaggacctca    180
ccgacctcca ggtcaccatc gagggccctg aggggacccc atatgctgga ggtctgttcc    240
gcatgaaact cctgctgggg aaggacttcc ctgcctcccc acccaaggc tacttcctga      300
ccaagatctt ccacccgaac gtgggcgcca atggcgagat ctgcgtcaac gtgctcaaga    360
gggactggac ggctgagctg gcatccgac acgtactgct gaccatcaag tgcctgctga     420
tccacccta ccccgagtct gcactcaacg aggaggcggg ccgcctgctc ttggagaact     480
acgaggagta tgcggctcgg gcccgtctgc tcacagagat ccacggggc gccggcgggc      540
ccagcggcag ggccgaagcc ggtcgggccc tggccagtgg cactgaagct tcctccaccg    600
accctggggc cccaggggc ccggggaggg ctgagggtcc catggccaag aagcatgctg      660
gcgagcgcga taagaagctg gcggccaaga aaaagacgga caagaagcgg gcgctgcggg     720
cgctgcggcg gctgtagtgg gctctcttcc tccttccacc gtgaccccaa cctctcctgt    780
cccctcccte caactctgtc tctaagttat ttaaattatg gctgggtcg gggagggtac      840
agggggcact gggaccctgga tttgtttttc taaataaagt tggaaaagca                890
```

<210> SEQ ID NO 22
<211> LENGTH: 1449
<212> TYPE: DNA
<213> ORGANISM: Homo Sapiens
<220> FEATURE:
<221> NAME/KEY: Unsure
<222> LOCATION: (1316)..(1316)
<223> OTHER INFORMATION: n = a, c, g, or t
<221> NAME/KEY: Unsure
<222> LOCATION: (1360)..(1360)
<223> OTHER INFORMATION: n = a, c, g, or t
<221> NAME/KEY: Unsure
<222> LOCATION: (1366)..(1367)
<223> OTHER INFORMATION: n = a, c, g, or t
<221> NAME/KEY: Unsure
<222> LOCATION: (1369)..(1369)
<223> OTHER INFORMATION: n = a, c, g, or t

<400> SEQUENCE: 22

```
agccgaaact gagaggggcc ggactcacag tgatgtgcac ctcctcccgt ccaggtgggg      60
cctgcctggg gaaagcttgt ggccggaaga gaaaatgagc ttcctaggac ccctgactca     120
cgacctcatc aacgttggtg ctactgcttg gtggagaatg taaacccttt gtaaccccat     180
cccatgcccc tccgactccc caccccagga gggaacgggc aggccgggcg gccttgcaga     240
tccacagggc aaggaaacaa gaggggagcg gccaagtgcc ccgaccagga ggcccctac      300
ttcagaggca agggccatgt ggtcctggcc ccccacccca tcccttccca ctaggagct      360
cccctccac acagcctcca tctccagggg aacttggtgc tacacgctgg tgctcttatc      420
ttcctggggg gagggaggag ggaagggtgg ccctcgggg aaccccctac ctggggctcc      480
tctaaagatg gtgcagacac ttcctgggca gtcccagctc cccctgccca ccaggaccca     540
ccgttggctg ccatccagtt ggtacccaag cacctgaagc tcaaagctg gattcgctct      600
agcatccctc ctctcctggg tccacttggc cgtctcctcc ccaccgatcg ctgttcccca     660
catctgggc gcttttgggt tggaaaacca ccccacactg gaatagcca ccttgccct       720
tgtagaatcc atccgcgcat ccgtccattc atccatcggt ccgtccatcc atgtcccag     780
ttgaccgccc ggcaccatta gctggctggg tgcacccacc atcaacctgg ttgacctgtc    840
atggccgcct gtgccctgcc tccaccccca tcctacactc cccagggcg tgcggggctg     900
tgcagactgg ggtgccaggc atcctctccc cacccgggt gtcccacat gcagtactgt      960
ataccccca tccctccctc ggtccactga acttcagagc agttcccatt cctgcccgc     1020
ccatcttttt gtgtctcgct gtgatagatc aataaatatt ttatttttg tcctggatat    1080
ttggggatta tttttgattg ttgatattct cttttggttt tattgttgtg gttcattgaa    1140
aaaaaaagat aattttttt tctgatccgg ggagctgtat ccccagtaga aaaacatt      1200
taatcactct aatataactc tggatgaaac acacctttt ttttaataag aaaagagaat    1260
taactgcttc agaaatgact aataaatgaa aacccttta aggaaactgt gtcttngctt    1320
ccttggtatg atttaatctg ccttcaactg ttggcctggn tggggnnang ggctctgctt   1380
cagggaacct ccaccaccca aattgtattt gagaggttgc ccaaccaaaa gcccctgctg   1440
cctggcttc                                                           1449
```

<210> SEQ ID NO 23
<211> LENGTH: 736
<212> TYPE: DNA
<213> ORGANISM: Homo Sapiens

<400> SEQUENCE: 23

```
cgagctggag aggtggtcgg agaagtagga acctcctgcc gggctcgtgg cggcttctgt     60
ccgctccgcg gagggaagcg ccttccccac aggacatcaa tgcaagcttg aataagaaaa    120
acaaattctt cctcctaagc catggcatat cagttataca gaaatactac tttgggaaac    180
agtcttcagg agagcctaga tgagctcata cagtctcaac agatcaccc ccaacttgcc    240
cttcaagttc tacttcagtt tgataaggct ataaatgcag cactggctca gagggtcagg    300
aacagagtca atttcagggg ctctctaaat acgtacagat tctgcgataa tgtgtggact    360
tttgtactga atgatgttga attcagagag gtgacagaac ttattaaagt ggataaagtg    420
aaaattgtag cctgtgatgg taaaaatact ggctccaata ctacgaatg aatagaaaaa    480
atatgacttt tttacaccat cttctgttat tcattgcttt tgaagagaag catagaagag    540
acttttatt tattctagaa ttgcagaaat gactacactg tgctatacca gagaattcca    600
```

```
gtagaaagaa acttgtaact ctgtagcctc ttacatcacc tttattatac agcatgaaaa      660
accataactt ttttttaagg acaaaagttg ttgccttcct aagaaccttc tttaataaac      720
tcattttaaa actctg                                                     736

<210> SEQ ID NO 24
<211> LENGTH: 2212
<212> TYPE: DNA
<213> ORGANISM: Homo Sapiens

<400> SEQUENCE: 24
tgccggctgc tcctcgacca ggcctccttc tcaacctcag cccgcggcgc cgaccctttcc     60 ggcaccctcc cgccccgtct cgtactgtcg ccgtcaccgc cgcggctccg gccctggccc     120
cgatggctct gtgcaacgga gactccaagc tggagaatgc tggaggagac cttaaggatg     180
gccaccacca ctatgaagga gctgttgtca ttctggatgt ggtgctcag tacgggaaag      240 tcatagaccg aagagtgagg gaactgttcg tgcagtctga aattttcccc ttggaaacac     300
cagcatttgc tataaaggaa caaggattcc gtgctattat catctctgga ggacctaatt    360
ctgtgtatgc tgaagatgct ccctggtttg atccagcaat attcactatt ggcaagcctg    420
ttcttggaat tgctatggt atgcagatga tgaataaggt atttggaggt actgtgcaca     480
aaaaaagtgt cagagaagat ggagttttca acattagtgt ggataataca tgttcattat     540
tcaggggcct tcagaaggaa gaagttgttt tgcttacaca tggagatagt gtagacaaag     600
tagctgatgg attcaaggtt gtggcacgtt ctggaaacat agtagcaggc atagcaaatg     660
aatctaaaaa gttatatgga gcacagttcc accctgaagt tggccttaca gaaaatggaa    720
aagtaatact gaagaatttc ctttatgata tagctggatg cagtggaacc ttcaccgtgc    780
agaacagaga acttgagtgt attcgagaga tcaaagagag agtaggcacg tcaaaagttt    840 tggtttact cagtggtgga gtagactcaa cagtttgtac agctttgcta aatcgtgctt    900
tgaaccaaga acaagtcatt gctgtgcaca ttgataatgg ctttatgaga aaacgagaaa    960
gccagtctgt tgaagaggcc ctcaaaaagc ttggaattca ggtcaaagtg ataaatgctg    1020
ctcattcttt ctacaatgga acaacaaccc taccaatatc agatgaagat agaaccccac    1080
ggaaaagaat tagcaaaacg ttaaatatga ccacaagtcc tgaagagaaa agaaaaatca    1140
ttggggatac ttttgttaag attgccaatg aagtaattgg agaaatgaac ttgaaaccag    1200
aggaggtttt ccttgcccaa ggtactttac ggcctgatct aattgaaagt gcatcccttg    1260
ttgcaagtgg caaagctgaa ctcatcaaaa cccatcacaa tgacacagag ctcatcagaa    1320
agttgagaga ggagggaaaa gtaatagaac ctctgaaaga ttttcataaa gatgaagtga    1380
gaattttggg cagagaactt ggacttccag aagagttagt ttccaggcat ccatttccag    1440
gtcctggcct ggcaatcaga gtaatatgtg ctgaagaacc ttatatttgt aaggactttc    1500
ctgaaaccaa caatattttg aaaatagtag ctgattttc tgcaagtgtt aaaaagccac    1560
ataccctatt acagagagtc aaagcctgca acagaagga ggatcaggag aagctgatgc    1620
aaattaccag tctgcattca ctgaatgcct tcttgctgcc aattaaaact gtaggtgtgc    1680
agggtgactg tcgttcctac agttacgtgt gtggaatctc cagtaaagat gaacctgact    1740
gggaatcact tattttctg gctaggctta tacctcgcat gtgtcacaac gttaacagag    1800
ttgtttatat atttggccca ccagttaaag aacctcctac agatgttact cccactttct    1860
tgacaacagg ggtgctcagt actttacgcc aagctgattt tgaggcccat aacattctca    1920
```

```
gggagtctgg gtatgctggg aaaatcagcc agatgccggt gattttgaca ccattacatt    1980
ttgatcggga cccacttcaa agcagcctt catgccagag atctgtggtt attcgaacct     2040
ttattactag tgacttcatg actggtatac ctgcaacacc tggcaatgag atccctgtag    2100
aggtggtatt aaagatggtc actgagatta agaagattcc tggtatttct cgaattatgt    2160
atgacttaac atcaaagccc ccaggaacta ctgagtggga gtaataaact tc            2212
```

<210> SEQ ID NO 25
<211> LENGTH: 1585
<212> TYPE: DNA
<213> ORGANISM: Homo Sapiens

<400> SEQUENCE: 25

```
acagcagtta cactgcggcg ggcgtctgtt ctagtgtttg agccgtcgtg cttcaccggt      60
ctacctcgct agcatgtcgg gccgcggcaa gactggcggc aaggcccgcg ccaaggccaa     120
gtcgcgctcg tcgcgcgccg gcctccagtt cccagtgggc cgtgtacacc ggctgctgcg    180
gaagggccac tacgccgagc gcgttggcgc cggcgcgcca gtgtacctgg cggcagtgct    240
ggagtacctc accgctgaga tcctggagct ggcgggcaat gcggcccgcg acaacaagaa    300
gacgcgaatc atcccccgcc acctgcagct ggccatccgc aacgacgagg agctcaacaa    360
gctgctgggc ggcgtgacga tcgcccaggg aggcgtcctg cccaacatcc aggccgtgct    420
gctgcccaag aagaccagcg ccaccgtggg gccgaaggcg ccctcgggcg gcaagaaggc    480
cacccaggcc tcccaggagt actaagaggg cccgcgccgc ggccggccgc cccagctccc    540
catgccacca caaaggccct tttaaggcc accaccgccc tcatggaaag agctgagccg    600
cttcagactg cggggcaagc gggccgcggc tcccttcccc tcccctcccc tcgcccgcct    660
tcgccgcccg gcctcgagtc cccgcccgcc cccgctcccg tcccgcaccg cctgccgcgt    720
cggcctcggg cctgccctgt ccgccgtccg ccctccggta gggttcgggc cttccggatg    780
cggcttgggc gctcttcggg gacctccgtg gcgcggaaga cccgagcctg ccggggggag    840
gccggcggcg ccgcacctgc ccgcctcggc gttcgtgact cagccgcccc atcccgagtc    900
gctaaggggc tgcggggagg ccgcagcacc ttctggaaga cttggccttc cgctctgacg    960
cagggccgag gtgggcagtc caggccgaga gccggcggcc ctgaaggtga gtgaggccct   1020
cggcagctgc agccggggtg tctggtaccc cccggcgtg gtgcttagcc caggactttc    1080
agacggccgc tggccgggag gctttggtgg gagagacgcg atcgccgatt cggtctggc    1140 gccccttctg cggccgggac ccaggccttt cacatcagct ctccctccat cttcattcat   1200
aggtctgcgc tggggccggg acgaagcact tggtaacagg cacatcttcc tcccgagtga   1260
ctgcctccta ggaggacatt taggggaggg cagaggcctg cagtttggct tcacggctgg   1320
ctatgtggac agcaagagtc gttttgcgga acgcgactgg cagccaggcc tgtcgggccc   1380
ccgacgccgc cccatttccc ttccagcaaa ctcaactcgg caatccaagc acctagatac   1440
cagcacaagt cggttaatcc ctgtctggac tgagcctccg ttggcttctg aactggaatt   1500
ctgcagctaa cccttccacg actagaacct taggcattgg ggagttttag atggactaat    1560
tttattaaag gattgttttt ttttt                                          1585
```

<210> SEQ ID NO 26
<211> LENGTH: 847
<212> TYPE: DNA
<213> ORGANISM: Homo Sapiens

<400> SEQUENCE: 26

```
agtggcttcc taacagcaga agaactaaca atccactgaa taaagaaaaa gaatgggctc        60
gatggaggaa taagaagcta gttatagtca tcggtagaat tgtgaaaggc gcaatttgat       120
tggttaaaat tgttctttga cgagccaacc aattagaaag gaaataaggt gaaggctatt       180
ttacatgtat gcgtcactga cacattgccc aatcagagct ggatattttg aattctttat       240
ttgcatgaaa ggcctataaa aggagagact ctagacacga gctttttattt aagtgcgttc      300 attctcactg ctgttattgt tttctgacag catgcctgaa ccagctaagt cagctcctgc       360
tccgaagaag ggttccaaga aggctgtgac caaggcgcag aagaaggatg caagaagcg        420 caagcgcagt cgtaaggaga gctactccgt gtatgtgtac aaggtgctaa acaggttca        480 ccccgatact ggcatctcat ccaaggccat gggcatcatg aattccttcg ttaacgacat       540
cttcgaacgc atcgcaggcg aggcttcccg tctggcccac tacaacaagc gctcgaccat      600
tacctccagg gagatccaga ccgccgtgcg tctgctgctt cccggagagc tggccaagca      660
cgcagtgtcc gaaggtacca aggctgtcac caagtataca agctccaagt aaatgtgtgc      720
ttaggtgctt taaaactcaa aggctctttt cagagccact caagtctcac ataaagagct     780
ttaatattga atttcaccgt tttctaggga ataagggaat ttttcgattt tgtaatccca     840
gcacttt                                                                847

<210> SEQ ID NO 27
<211> LENGTH: 2808
<212> TYPE: DNA
<213> ORGANISM: Homo Sapiens

<400> SEQUENCE: 27
cggcatgaga ggccagcctg ccagggaaat ccaggaatct gcaacaaaaa cgatgacagt       60
ctgaaatact ctctggtgcc aacctccaaa ttctcgtctg tcacttcaga cccccactag      120
ttgacagagc agcagaatat caactccagt agacttgaat gtgcctctgg gcaaagaagc      180
agagctaacg aggaaaggga tttaaagagt ttttcttggg tgtttgtcaa acttttattc      240
cctgtctgtg tgcagagggg attcaacttc aattttctgc agtggctctg ggtccagccc     300
cttacttaaa gatctggaaa gcatgaagac tgggcctttt ttcctatgtc tcttgggaac      360
tgcagctgca atcccgacaa atgcaagatt attatctgat cattccaaac caactgctga     420
aacggtagca cctgacaaca ctgcaatccc cagtttatgg gctgaagctg aagaaaatga      480
aaagaaaaca gcagtatcca cagaagacga ttcccaccat aaggctgaaa atcatcagt      540 actaaagtca aaagaggaaa gccatgaaca gtcagcagaa cagggcaaga gttctagcca      600
agagctggga ttgaaggatc aagaggacag tgatggtcac ttaagtgtga atttggagta      660
tgcaccaact gaaggtacat tggacataaa agaagtatg attgagcctc aggagaaaaa       720
actctcagag aacactgatt ttttggctcc tggtgttagt tccttcacag attctaacca      780
acaagaaagt atcacaaaga gagaggaaaa ccaagaacaa cctagaaatt attcacatca      840
tcagttgaac aggagcagta acatagcca aggcctaagg gatcaaggaa ccaagagca       900 ggatccaaat atttccaatg gagaagagga agaagaaaaa gagccaggtg aagttggtac      960
ccacaatgat aaccaagaaa gaagacaga attgcccagg gagcatgcta acagcaagca     1020
ggaggaagac aatacccaat ctgatgatat tttggaagag tctgatcaac caactcaagt    1080
aagcaagatt caggaggatg aattggatca gggtaaccaa gaacaagaag ataactccaa    1140
tgcagaaatg gaagaggaaa atgcatcgaa cgtcaataag cacattcaag aaactgaatg    1200
```

-continued

| | |
|---|---|
| gcagagtcaa gagggtaaaa ctggcctaga agctatcagc aaccacaaag agacagaaga | 1260 |
| aaagactgtt tctgaggctc tgctcatgga acctactgat gatggtaata ccacgcccag | 1320 |
| aaatcatgga gttgatgatg atggcgatga tgatggcgat gatggcggca ctgatggccc | 1380 |
| caggcacagt gcaagtgatg actacttcat cccaagccag gcctttctgg aggccgagag | 1440 |
| agctcaatcc attgcctatc acctcaaaat tgaggagcaa agagaaaaag tacatgaaaa | 1500 |
| tgaaaatata ggtaccactg agcctggaga gcaccaagag gccaagaaag cagagaactc | 1560 |
| atcaaatgag gaggaaacgt caagtgaagg caacatgagg gtgcatgctg tggattcttg | 1620 |
| catgagcttc cagtgtaaaa gaggccacat ctgtaaggca gaccaacagg gaaaacctca | 1680 |
| ctgtgtctgc caggatccag tgacttgtcc tccaacaaaa ccccttgatc aagtttgtgg | 1740 |
| cactgacaat cagacctatg ctagttcctg tcatctattc gctactaaat gcagactgga | 1800 |
| ggggaccaaa aaggggcatc aactccagct ggattatttt ggagcctgca atctattcc | 1860 |
| tacttgtacg gactttgaag tgattcagtt tcctctacgg atgagagact ggctcaagaa | 1920 |
| tatcctcatg cagctttatg aagccaactc tgaacatgct ggttatctaa atgagaagca | 1980 |
| gagaaataaa gtcaagaaaa tttacctgga tgaaagagg cttttggctg gggaccatcc | 2040 |
| cattgatctt ctcttaaggg actttaagaa aaactaccac atgtatgtgt atcctgtgca | 2100 |
| ctggcagttt agtgaacttg accaacaccc tatggataga gtcttgacac attctgaact | 2160 |
| tgctcctctg cgagcatctc tggtgcccat ggaacactgc ataacccgtt tctttgagga | 2220 |
| gtgtgacccc aacaaggata gcacatcac cctgaaggag tggggccact gctttggaat | 2280 |
| taaagaagag gacatagatg aaaatctctt gttttgaacg aagattttaa agaactcaac | 2340 |
| tttccagcat cctcctctgt tctaaccact tcagaaatat atgcagctgt gatacttgta | 2400 |
| gatttatatt tagcaaaatg ttagcatgta tgacaagaca atgagagtaa ttgcttgaca | 2460 |
| acaacctatg caccaggtat ttaacattaa ctttggaaac aaaaatgtac aattaagtaa | 2520 |
| agtcaacata tgcaaaatac tgtacattgt gaacagaagt ttaattcata gtaatttcac | 2580 |
| tctctgcatt gacttatgag ataattaatg attaaactat taatgataaa aataatgcat | 2640 |
| ttgtattgtt cataatatca tgtgcacttc aagaaatgg aatgctactc ttttgtggtt | 2700 |
| tacgtgtatt atttttcaata tcttaatacc ctaataaaga gtccataaaa atccaaaaaa | 2760 |
| aaaaaaaaaa aaaaaaaaaa aaaaaaaaaa aaaaaaaaaa aaaaaaa | 2808 |

<210> SEQ ID NO 28
<211> LENGTH: 2220
<212> TYPE: DNA
<213> ORGANISM: Homo Sapiens

<400> SEQUENCE: 28

| | |
|---|---|
| ggaaaattac ccggtatcgt tagagctaca ccaaaattgc attgagccaa acttgccacc | 60 |
| aagagcccaa caatcaccat gatgctgagc acggaaggca gggaggggtt cgtggtgaag | 120 |
| gtcaggggcc taccctggtc ctgctcagcc gatgaagtga tgcgcttctt ctctgattgc | 180 |
| aagatccaaa atggcacatc aggtattcgt ttcatctaca ccagagaagg cagaccaagt | 240 |
| ggtgaagcat ttgttgaact tgaatctgaa gaggaagtga aattggcttt gaagaaggac | 300 |
| agagaaacca tgggacacag atacgttgaa gtattcaagt ctaacagtgt tgaaatggat | 360 |
| tgggtgttga agcatacagg tccgaatagc cctgatactg ccaacgatgg cttcgtccgg | 420 |
| cttagaggac tcccatttgg ctgtagcaag gaagagattg ttcagttctt ttcagggttg | 480 |
| gaaattgtgc caaatgggat gacactgcca gtggactttc aggggcgaag cacagggaa | 540 |

```
gcctttgtgc agtttgcttc acaggagata gctgagaagg ccttaaagaa acacaaggaa      600
agaatagggc acaggtacat tgagatcttc aagagtagcc gagctgaagt tcgaacccac      660
tatgatcccc ctcgaaagct catggctatg cagcggccag gtccctatga taggccgggg     720
gctggcagag ggtataatag cattggcaga ggagctgggt ttgaaaggat gaggcgtggt     780
gcctatggtg gagggtatgg aggctatgat gactatggtg gctataatga tggatatggc     840
tttgggtctg atagatttgg aagagacctc aattactgtt tttcaggaat gtctgatcat     900
agatacggag atggtgggtc cagtttccag agcaccacag ggcactgtgt acacatgagg     960
gggttacctt acagagccac tgagaatgat atttataatt tcttctcacc tcttaatccc    1020
atgagagtac atattgaaat tggacccgat ggcagagtta ccggtgaggc agatgttgaa    1080
tttgctactc atgaagatgc tgtggcagct atggcaaaag acaaagctaa tatgcaacac    1140
agatatgtgg agctcttctt aaattctact gcaggaacaa gtgggggtgc ttacgatcac    1200
agctatgtag aactttttttt gaattctaca gcaggggcaa gtggtggcgc ttatggtagc    1260
caaatgatgg gagggatggg cttatccaac cagtctagtt atggaggtcc tgctagccag    1320
cagctgagtg gtggttatgg aggtggttat ggtggtcaga gcagtatgag tggatatgac    1380
caagttctgc aggaaaactc cagtgactat cagtcaaacc ttgcttaggt agagaaggag    1440
cactaaatag ctactccaga tataaaagct gtacatttgt gggagttgaa tagaatggga    1500
gggatgttta gtatatccag tatgattggt aaatgggaaa tataattgat tctgatcact    1560
cttggtcagc ttctctttct ttatctttct gtctcctttt taagaaaac gagttaagtt    1620
taacagttttt gcattacagg cttgtgattc atgcttactg taaagtggaa gttgagatta    1680
ttttaaaact tcaagctcag taattttgaa ccactgaaac attcatctag gacataataa    1740
caaagttcag tattgaccat aactgttaaa acaattttta gctttcctca agttagttat    1800
gttgtaggag tgtacctaag cagtaagcgt atttaggtta atgcagtttc acttatgtta    1860
aatgttgctc ttataccaca aatacattga aaacttcgga tgcatgttga gaaacatgcc    1920
tttctgtaaa actcaaatat aggagctgtg tctacgattc aaagtgaaaa catttggcat    1980
gtttgttaat tctagctttt tggttttaata tcctgtaagg cacgtgagtg tacactttttt   2040
ttttttttaa ggatacggga caattttaag atgtaatacc aatactttag aagtttggtc    2100
gtgtcgtttg tatgaaaatc tgaggctttg gtttaaatct ttccttgtat tgtgatttcc    2160
atttagatgt attgtactaa gtgaaacttg ttaaataaat cttccttta aaaactggaa     2220
```

<210> SEQ ID NO 29
<211> LENGTH: 2203
<212> TYPE: DNA
<213> ORGANISM: Homo Sapiens

<400> SEQUENCE: 29

```
cggcggccgc gccctggttg ggtccccact gctctcgggg gcgccatgga cgaggccgtg      60
ggcgacctga agcaggcgct tccctgtgtg gccgagtcgc caacggtcca cgtggaggtg     120
catcagcgcg gcagcagcac tgcaaagaaa gaagacataa acctgagtgt tagaaagcta    180
ctcaacagac ataatattgt gtttggtgat tacacatgga ctgagtttga tgaaccttt    240
ttgaccagaa atgtgcagtc tgtgtctatt attgacacag aattaaaggt taaagactca    300
cagcccatcg atttgagtgc atgcactgtt gcacttcaca ttttccagct gaatgaagat    360
ggccccagca gtgaaaatct ggaggaagag acagaaaaca taattgcagc aaatcactgg    420
```

-continued

```
gttctacctg cagctgaatt ccatgggctt tgggacagct tggtatacga tgtgaagtc     480 aaatcccatc tcctcgatta tgtgatgaca actttactgt tttcagacaa gaacgtcaac     540
agcaacctca tcacctggaa ccgggtggtg ctgctccacg tcctcctgg cactggaaaa      600 acatccctgt gtaaagcgtt agcccagaaa ttgacaatta gactttcaag caggtaccga     660
tatggccaat taattgaaat aaacagccac agcctctttt ctaagtggtt ttcggaaagt     720
ggcaagctgg taaccaagat gtttcagaag attcaggatt tgattgatga taaagacgcc     780
ctggtgttcg tgctgattga tgaggtggag agtctcacag ccgcccgaaa tgcctgcagg     840
gcgggcaccg agccatcaga tgccatccgc gtggtcaatg ctgtcttgac ccaaattgat     900
cagattaaaa ggcattccaa tgttgtgatt ctgaccactt ctaacatcac cgagaagatc     960
gacgtggcct tcgtggacag ggctgacatc aagcagtaca ttgggccacc ctctgcagca    1020
gccatcttca aaatctacct ctcttgtttg aagaactga tgaagtgtca gatcatatac     1080
cctcgccagc agctgctgac cctccgagag ctagagatga ttggcttcat tgaaaacaac    1140
gtgtcaaaat tgagccttct tttgaatgac atttcaagga gagcgagggg cctcagcggc    1200
cgggtcctga gaaaactccc ctttctggct catgcgctgt atgtccaggc ccccaccgtc    1260
accatagagg ggttcctcca ggccctgtct ctggcagtgg acaagcagtt tgaagagaga    1320
aagaagcttg cagcttacat ctgatcctgg gcttccccat ctggtgcttt tcccatggag    1380
aacacacaac cagtaagtga ggttgcccca cacagccgtc tcccagggaa tcccttctgc    1440
aaaccaaacg ttacttagac tgcaagctag aaagccacca aggccaggct tgttaaaag     1500 aagtgtattc tatttatgtt gttttaaaat gcatactgag agacaaacat cttgtcattt     1560
tcactgtttg taaaagataa ttcagattgt ttgtctcctt gtgaagaacc atcgaaacct    1620
gtttgttccc agcccacccc cagtggatgg gatgcataat gccagcaagt tttgtttaac    1680
agcaaaaaag gaagattaat gcaggtgtta tagaagccag aagagaaact gtgtcaccct    1740
aaagaagcat ataatcatag cattaaaat gcacacatta ctccaggtgg aaggtggcaa     1800
ttgctttctg atatcagctc gtttgattta gtgcaaaaat gttttcaaga ctatttaatg    1860
gatgtaaaaa agcctatttc tacattatac caactgagaa aaaaatggtc ggtaaagtgt    1920 tcttttcataa taaataatca agacatggtc ccatttgcag gaaaagtgca gactctgagt    1980
gttccaggga acacatgct ggacatccct tgtaacccgg tatgggcgcc cctgcattgc     2040
tgggatgttt ctgcccacgg ttttgtttgt gcaataacgt tatcacattt ctaatgagga    2100
ttcacattaa tataatataa aataaatagg tcagttactg gtctctttct gccgaatgtt    2160
atgttttgct tttatctcac agtaaaataa atataattaa aaa                      2203
```

<210> SEQ ID NO 30
<211> LENGTH: 2155
<212> TYPE: DNA
<213> ORGANISM: Homo Sapiens

<400> SEQUENCE: 30

```
gtcacatggg gtgcgcgccc agactccgac ccggaggcgg aaccggcagt gcagcccgaa      60
gccccgcagt cccccgagcac gcgtggccat cgtcccctg cgcccccgcg ccgcgctgct     120
ggcgctcctg gcctcgctcc tggccgcgcc cccggtggcc ccggccgagg ccccgcacct    180
ggtgcaggtg gacgcggccc gcgcgctgtg cccctgcgg cgcttctgga ggagcacagg     240
cttctgcccc ccgctgccac acagccaggc tgaccagtac gtcctcagct gggaccagca    300
gctcaacctc gcctatgtgg gcgccgtccc tcaccgcggc atcaagcagg tccggaccca    360
```

```
ctggctgctg gagcttgtca ccaccagggg gtccactgga cggggcctga gctacaactt      420
cacccacctg gacgggtact tggaccttct cagggagaac cagctcctcc cagggtttga      480
gctgatgggc agcgcctcgg gccacttcac tgactttgag gacaagcagc aggtgtttga     540
gtggaaggac ttggtctcca gcctggccag gagatacatc ggtaggtacg gactggcgca     600
tgtttccaag tggaacttcg agacgtggaa tgagccagac caccacgact ttgacaacgt     660
ctccatgacc atgcaaggct tcctgaacta ctacgatgcc tgctcggagg gtctgcgcgc     720
cgccagcccc gccctgcggc tgggaggccc cggcgactcc ttccacaccc caccgcgatc     780
cccgctgagc tggggcctcc tgcgccactg ccacgacggt accaacttct tcactgggga     840
ggcgggcgtg cggctggact acatctccct ccacaggaag ggtgcgcgca gctccatctc     900
catcctggag caggagaagg tcgtcgcgca gcagatccgg cagctcttcc ccaagttcgc     960
ggacaccccc atttacaacg acgaggcgga cccgctggtg ggctggtccc tgccacagcc    1020
gtggagggcg gacgtgacct acgcggccat ggtggtgaag gtcatcgcgc agcatcagaa    1080
cctgctactg gccaacacca cctccgcctt ccctacgcg ctcctgagca cgacaatgc     1140 cttcctgagc taccacccgc accccttcgc gcagcgcacg ctcaccgcgc gcttccaggt    1200
caacaacacc cgcccgccgc acgtgcagct gttgcgcaag ccggtgctca cggccatggg    1260
gctgctggcg ctgctggatg aggagcagct ctgggccgaa gtgtcgcagg ccgggaccgt    1320
cctggacagc aaccacacgg tgggcgtcct ggccagcgcc caccgccccc agggcccggc    1380
cgacgcctgg cgcgccgcgg tgctgatcta cgcgagcgac gacacccgcg cccacccccaa   1440 ccgcagcgtc gcggtgaccc tgcggctgcg cggggtgccc ccggcccgg gcctggtcta    1500 cgtcacgcgc tacctggaca cgggctctg cagccccgac ggcgagtggc ggcgcctggg    1560
ccggcccgtc ttccccacgg cagagcagtt ccggcgcatg cgcgcggctg aggacccggt    1620
ggccgcggcg ccccgcccct acccgccgg cggccgcctg accctgcgcc ccgcgctgcg    1680
gctgccgtcg cttttgctgg tgcacgtgtg tgcgcgcccc gagaagccgc ccgggcaggt    1740
cacgcggctc cgcgccctgc ccctgaccca agggcagctg gttctggtct ggtcggatga    1800
acacgtgggc tccaagtgcc tgtggacata cgagatccag ttctctcagg acggtaaggc    1860
gtacaccccg gtcagcagga agccatcgac cttcaacctc tttgtgttca gcccagacac    1920
aggtgctgtc tctggctcct accgagttcg agccctggac tactgggccc gaccaggccc    1980
cttctcggac cctgtgccgt acctggaggt ccctgtgcca gagggcccccc catccccggg   2040 caatccatga gcctgtgctg agccccagtg ggttgcacct ccaccggcag tcagcgagct    2100
ggggctgcac tgtgccatg ctgccctccc atcacccct ttgcaatata ttttt          2155
```

<210> SEQ ID NO 31
<211> LENGTH: 7260
<212> TYPE: DNA
<213> ORGANISM: Homo Sapiens

<400> SEQUENCE: 31

```
tcactgtcac tgctaaattc agagcagatt agagcctgcg caatggaata aagtcctcaa      60
aattgaaatg tgcacattgct ctcaacatct cccatctctc tggatttcct tttgcttcat   120
tattcctgct aaccaattca ttttcagact ttgtacttca gaagcaatgg gaaaaatcag    180
cagtcttcca acccaattat ttaagtgctg cttttgtgat ttcttgaagg tgaagatgca    240
caccatgtcc tcctcgcatc tcttctacct ggcgctgtgc ctgctcacct tcaccagctc    300
```

-continued

```
tgccacggct ggaccggaga cgctctgcgg ggctgagctg gtggatgctc ttcagttcgt      360
gtgtggagac agggcttttt atttcaacaa gcccacaggg tatggctcca gcagtcggag      420
ggcgcctcag acaggcatcg tggatgagtg ctgcttccgg agctgtgatc taaggaggct      480
ggagatgtat tgcgcacccc tcaagcctgc caagtcagct cgctctgtcc gtgcccagcg      540
ccacaccgac atgcccaaga cccagaagga agtacatttg aagaacgcaa gtagagggag      600
tgcaggaaac aagaactaca ggatgtagga agaccctcct gaggagtgaa gagtgacatg      660
ccaccgcagg atcctttgct ctgcacgagt tacctgttaa actttggaac acctaccaaa      720
aaataagttt gataacattt aaaagatggg cgtttccccc aatgaaatac acaagtaaac      780
attccaacat tgtctttagg agtgatttgc accttgcaaa atggtcctg gagttggtag       840 attgctgttg atctttatc aataatgttc tatagaaaag aaaaaaaaat atatatatat        900
atatatctta gtccctgcct ctcaagagcc acaaatgcat gggtgttgta tagatccagt       960
tgcactaaat tcctctctga atcttggctg ctggagccat tcattcagca accttgtcta      1020
agtggtttat gaattgtttc cttatttgca cttctttcta cacaactcgg gctgtttgtt      1080
ttacagtgtc tgataatctt gttagtctat acccaccacc tcccttcata acctttatat      1140
ttgccgaatt tggcctcctc aaaagcagca gcaagtcgtc aagaagcaca ccaattctaa      1200
cccacaagat tccatctgtg gcatttgtac caaatataag ttggatgcat tttattttag      1260
acacaaagct ttatttttcc acatcatgct tacaaaaaag aataatgcaa atagttgcaa      1320
ctttgaggcc aatcattttt aggcatatgt tttaaacata gaaagtttct tcaactcaaa      1380
agagttcctt caaatgatga gttaatgtgc aacctaatta gtaactttcc tcttttatt       1440 ttttccatat agagcactat gtaaatttag catatcaatt atacaggata tatcaaacag      1500
tatgtaaaac tctgtttttt agtataatgg tgctattttg tagtttgtta tatgaaagag      1560
tctggccaaa acgtaatac gtgaaagcaa acaataggg gaagcctgga gccaaagatg        1620
acacaagggg aagggtactg aaaacaccat ccatttggga agaaggcaa agtcccccca       1680 gttatgcctt ccaagaggaa cttcagacac aaaagtccac tgatgcaaat tggactggcg      1740
agtccagaga ggaaactgtg gaatggaaaa agcagaaggc taggaatttt agcagtcctg      1800
gtttcttttt ctcatggaag aaatgaacat ctgccagctg tgtcatggac tcaccactgt      1860
gtgaccttgg gcaagtcact tcacctctct gtgcctcagt ttcctcatct gcaaaatggg      1920
ggcaatatgt catctaccta cctcaaaggg gtggtataag gttaaaaag ataaagattc       1980 agatttttt accctgggtt gctgtaaggg tgcaacatca gggcgcttga gttgctgaga       2040
tgcaaggaat tctataaata acccattcat agcatagcta gagattggtg aattgaatgc      2100
tcctgacatc tcagttcttg tcagtgaagc tatccaaata actggccaac tagttgttaa      2160
aagctaacag ctcaatctct taaaacactt ttcaaaatat gtgggaagca tttgattttc      2220
aatttgattt tgaattctgc atttggtttt atgaatacaa agataagtga aaagagagaa      2280
aggaaaagaa aaaggagaaa aacaaagaga tttctaccag tgaaagggga attaattact      2340
ctttgttagc actcactgac tcttctatgc agttactaca tatctagtaa aaccttgttt      2400
aatactataa ataatattct attcattttg aaaacacaa tgattccttc ttttctaggc       2460
aatataagga agtgatcca aaatttgaaa tattaaaata atatctaata aaaagtcaca       2520
aagttatctt ctttaacaaa ctttactctt attcttagct gtatatacat tttttttaaa     2580
agtttgttaa aatatgcttg actagagttt cagttgaaag gcaaaaactt ccatcacaac      2640
aagaaatttc ccatgcctgc tcagaagggt agcccctagc tctctgtgaa tgtgttttat      2700
```

```
ccattcaact gaaaattggt atcaagaaag tccactggtt agtgtactag tccatcatag   2760
cctagaaaat gatccctatc tgcagatcaa gattttctca ttagaacaat gaattatcca   2820
gcattcagat ctttctagtc accttagaac tttttggtta aaagtaccca ggcttgatta   2880
tttcatgcaa attctatatt ttacattctt ggaaagtcta tatgaaaaac aaaaataaca   2940
tcttcagttt ttctcccact gggtcacctc aaggatcaga ggccaggaaa aaaaaaaag   3000 actccctgga tctctgaata tatgcaaaaa gaaggcccca tttagtggag ccagcaatcc   3060
tgttcagtca acaagtattt taactctcag tccaacatta tttgaattga gcacctcaag   3120
catgcttagc aatgttctaa tcactatgga cagatgtaaa agaaactata catcattttt   3180
gccctctgcc tgttttccag acatacaggt tctgtggaat aagatactgg actcctcttc   3240
ccaagatggc acttcttttt atttcttgtc cccagtgtgt accttttaaa attattccct   3300
ctcaacaaaa ctttataggc agtcttctgc agacttaaca tgttttctgt catagttaga   3360
tgtgataatt ctaagagtgt ctatgactta tttccttcac ttaattctat ccacagtcaa   3420
aaatccccca aggaggaaag ctgaaagatg caactgccaa tattatcttt cttaactttt   3480
tccaacacat aatcctctcc aactggatta taaataaatt gaaataact cattatacca   3540 attcactatt ttatttttta atgaattaaa actagaaaac aaattgatgc aaaccctgga   3600
agtcagttga ttactatata ctacagcaga atgactcaga tttcatagaa aggagcaacc   3660
aaaatgtcac aaccaaaact ttacaagctt tgcttcagaa ttagattgct ttataattct   3720
tgaatgaggc aatttcaaga tatttgtaaa agaacagtaa acattggtaa gaatgagctt   3780
tcaactcata ggcttatttc caatttaatt gaccatactg gatacttagg tcaaatttct   3840
gttctctctt gcccaaataa tattaaagta ttatttgaac tttttaagat gaggcagttc   3900
ccctgaaaaa gttaatgcag ctctccatca gaatccactc ttctagggat atgaaaatct   3960
cttaacaccc accctacata cacagacaca cacacacaca cacacacaca cacacacaca   4020
cacacattca ccctaaggat ccaatggaat actgaaaaga aatcacttcc ttgaaaattt   4080
tattaaaaaa caaacaaaca aacaaaaagc ctgtccaccc ttgagaatcc ttcctctcct   4140
tggaacgtca atgtttgtgt agatgaaacc atctcatgct ctgtggctcc agggtttctg   4200
ttactatttt atgcacttgg gagaaggctt agaataaaag atgtagcaca ttttgctttc   4260
ccatttattg tttggccagc tatgccaatg tggtgctatt gtttctttaa gaaagtactt   4320
gactaaaaaa aaaagaaaaa aagaaaaaaa agaaagcata gacatatttt tttaaagtat   4380
aaaaacaaca attctataga tagatggctt aataaaatag cattaggtct atctagccac   4440
caccaccttt caacttttta tcactcacaa gtagtgtact gttcaccaaa ttgtgaattt   4500
gggggtgcag gggcaggagt tggaaatttt ttaaagttag aaggctccat tgttttgttg   4560
gctctcaaac ttagcaaaat tagcaatata ttatccaatc ttctgaactt gatcaagagc   4620
atggagaata aacgcgggaa aaaagatctt ataggcaaat agaagaattt aaaagataag   4680
taagttcctt attgattttt gtgcactctg ctctaaaaca gatattcagc aagtggagaa   4740
aataagaaca aagagaaaaa atacatagat ttacctgcaa aaaatagctt ctgccaaatc   4800 cccttgggg attcttggc atttactggt ttatagaaga cattctccct tcacccagac   4860
atctcaaaga gcagtagctc tcatgaaaag caatcactga tctcatttgg gaaatgttgg   4920
aaagtatttc cttatgagat gggggttatc tactgataaa gaaagaattt atgagaaatt   4980
gttgaaagag atggctaaca atctgtgaag atttttttgtt tcttggtttt gttttttttt   5040
```

-continued

```
tttttttttac tttatacagt ctttatgaat ttcttaatgt tcaaaatgac ttggttcttt      5100 tcttctttt tttatatcag aatgaggaat aataagttaa acccacatag actctttaaa       5160
actataggct agatagaaat gtatgtttga cttgttgaag ctataatcag actatttaaa      5220
atgttttgct attttaatc ttaaaagatt gtgctaattt attagagcag aacctgtttg       5280
gctctcctca gaagaaagaa tctttccatt caaatcacat ggctttccac caatattttc      5340 aaagataaa tctgatttat gcaatggcat catttatttt aaaacagaag aattgtgaaa       5400
gtttatgccc ctcccttgca aagaccataa agtccagatc tggtagggg gcaacaacaa       5460 aaggaaaatg ttgttgattc ttggttttgg attttgtttt gttttcaatg ctagtgttta      5520
atcctgtagt acatatttgc ttattgctat tttaatattt tataagacct tcctgttagg      5580
tattagaaag tgatacatag atatctttt tgtgtaattt ctatttaaaa aagagagaag       5640
actgtcagaa gctttaagtg catatggtac aggataaaga tatcaattta aataaccaat      5700
tcctatctgg aacaatgctt ttgttttta aagaaacctc tcacagataa gacagaggcc      5760 caggggatt ttgaagctgt ctttattctg ccccatccc aacccagccc ttattatttt       5820
agtatctgcc tcagaatttt atagagggct gaccaagctg aaactctaga attaaaggaa      5880
cctcactgaa aacatatatt tcacgtgttc cctctctttt ttttcctttt tgtgagatgg      5940
ggtctcgcac tgtcccccag gctggagtgc agtggcatga tctcggctca ctgcaacctc      6000
cacctcctgg gtttaagcga ttctcctgcc tcagcctcct gagtagctgg gattacaggc      6060
acccaccact atgcccggct aatttttgg attttaata gagacggggt tttaccatgt       6120
tggccaggtt ggactcaaac tcctgacctt gtgatttgcc cgcctcagcc tcccaaattg      6180
ctgggattac aggcatgagc caccacaccc tgcccatgtg ttccctctta atgtatgatt      6240
acatggatct taaacatgat ccttctctcc tcattcttca actatctttg atggggtctt      6300 tcaagggaa aaaatccaa gctttttaa agtaaaaaa aaaaagaga ggacacaaaa          6360 ccaaatgtta ctgctcaact gaaatatgag ttaagatgga gacagagttt ctcctaataa      6420
ccggagctga attcctttc actttcaaaa acatgacctt ccacaatcct tagaatctgc      6480 cttttttat attactgagg cctaaaagta aacattactc attttatttt gcccaaaatg      6540
cactgatgta aagtaggaaa aataaaaaca gagctctaaa atcccttca agccacccat      6600 tgaccccact caccaactca tagcaaagtc acttctgtta atcccttaat ctgattttgt      6660
ttggatattt atcttgtacc cgctgctaaa cacactgcag gagggactct gaaacctcaa      6720
gctgtctact tacatctttt atctgtgtct gtgtatcatg aaaatgtcta ttcaaaatat      6780
caaaaccttt caaatatcac gcagcttata ttcagtttac ataaaggccc caaataccat      6840
gtcagatctt tttggtaaaa gagttaatga actatgagaa ttgggattac atcatgtatt      6900
ttgcctcatg tatttttatc acacttatag gccaagtgtg ataaataaac ttacagacac      6960
tgaattaatt tcccctgcta ctttgaaacc agaaaataat gactggccat tcgttacatc      7020
tgtcttagtt gaaaagcata ttttttatta aattaattct gattgtattt gaaattatta      7080
ttcaattcac ttatggcaga ggaatatcaa tcctaatgac ttctaaaaat gtaactaatt      7140
gaatcattat cttacatttta ctgttaata agcatatttt gaaatgtat ggctagagtg       7200 tcataataaa atggtatatc tttctttagt aattacaaaa aaaaaaaaa aaaaaaaaa        7260
```

<210> SEQ ID NO 32
<211> LENGTH: 5767
<212> TYPE: DNA
<213> ORGANISM: Homo Sapiens

```
<400> SEQUENCE: 32
gagggaggag agttcacttt tacttcagtg tcagcgcgcg gcggccgtgg ctggctctgg      60
cgagagagca ccgagggagt gggtcgcaga tcttcgggcg gctagggaa atcggcgaga     120 ggcgggatcc gagcgcgccg gcggggcgca gagcccgcga gcctggccag cgagggtagc    180
cgcggggggc gcgccccggg cgggcccccg gagacgcgca ggatgccaca cgaagagctg    240
ccgtcgctgc agagaccccg ctatggctct attgtggacg atgaaaggct ctctgcagag    300
gagatggatg agaggaggcg gcagaacatt gcttatgaat atctgtgcca cttagaggaa    360
gccaaaaggt ggatggaagt ttgcttagtt gaagaattgc caccaaccac tgaattggaa    420
gaagggctcc ggaatggagt ttaccttgca aagttagcca agttctttgc cccgaaaatg    480
gtatcagaga aaagatcta tgatgtggaa caaacacgtt ataagaagtc tggccttcat     540
tttcgacaca cagataatac cgtccagtgg ttaagagcga tggagtctat tggtctaccc    600
aagatatttt atccagaaac aacagatgtc tatgatcgga aaaacatacc aagaatgata    660
tattgcattc acgcactgag tttgtatctg ttcaaactag gaatagcacc ccagatccag    720
gatttgttgg gcaaagtaga cttcacagag gaggaaatca gtaatatgag aaaagaactt    780
gagaaatatg gaatacagat gccatctttc agcaaaatag tggtattct ggccaatgaa     840 ctgtccgtgg atgaagctgc attacatgct gcagttatag ccattaatga agcagttgaa    900 aaggaatag cagagcaaac cgttgtaaca ctaagaaacc caaatgcggt tttaacttta     960
gtggatgaca accttgcacc agaatatcag aaagaactct gggatgccaa aagaaaaaa    1020 gaggaaaatg caagactgaa gaatagctgt atttcagaag aagaaagaga tgcttatgaa    1080
gaactgctga cacaagcaga atccaaggc aatattaata aagtcaacag gcaggctgca    1140
gtggaccata tcaatgctgt cattccggaa ggtgaccccg agaatacgct gcttgcactg    1200
aagaaaccag aggcccagct gcctgctgtt tatccctttg ctgctgccat gtatcagaac    1260 gaactttca acctccagaa acagaacacc atgaactact ggcccacga ggagcttttg     1320 attgctgtgg aaatgttgtc tgctgttgct ttactaaacc aggccttgga aagcaacgat    1380
cttgtgtctg tgcagaatca actcagaagc cccgcaatag gcttaaacaa tctgacaag    1440 gcatatgtgg aacgttatgc aaacacacta ctctctgtta aactagaagt tttatcccaa    1500
gggcaagata acttaagctg gaatgaaatt cagaattgta ttgatatggt taatgctcaa    1560
attcaagaag aaaatgaccg agttgtagct gtagggtaca tcaatgaagc tattgatgaa    1620
gggaatcctt tgaggacttt agaaactttg ctcctaccta ctgcgaatat tagtgatgtg    1680
gacccagccc atgcccagca ctaccaggat gttttatacc atgctaaatc acagaaactc    1740
ggagactctg agagtgtttc caagtgctt tggctggatg agatacagca agccgtcgat    1800
gaggccaacg tggacgagga cagagcaaaa caatgggtta tctgtggtgg tgatgttaat    1860
cagtgtttgg aaggaaaaaa atcaagtgat attttgtctg tattgaagtc ttccacttct    1920
aatgcaaatg acataatccc ggagtgtgct gacaaatact atgatgccct tgtgaaggca    1980
aaagagctca atctgaaag agtgtctagt gacggttcat ggctcaaact caacctgcac    2040
aaaaaatatg actactatta caacactgat tcaaaagaga gttcctgggt cacacctgaa    2100
tcatgcttct ataagaatc atggctcaca ggaaaagaaa tcgaggacat tattgaggaa    2160
gtcacagtag gttacattcg tgagaatata tggtctgctt cagaagagtt gcttcttcgc    2220
tttcaagcca caagctcagg acccatcctt agggaagagt ttgaagctag aaaatcattt    2280
```

```
ttgcatgaac aagaagagaa tgtggtcaaa atacaggctt tttggaaagg atataaacaa    2340
cggaaggagt atatgcacag gcggcaaacg ttcattgata atactgattc tgttgtgaag    2400
attcagtcct ggttccgaat ggcaactgca agaaagagct atctttcaag actacagtat    2460
ttcagagatc ataataatga aattgtgaaa atacagtcac tgttgagagc gaacaaagct    2520
agagatgact acaaaacatt ggttggctct gaaaacccac cattaacagt aattcgcaaa    2580
tttgtatacc tgctggacca aagtgatttg gatttccagg aggaactaga ggttgcacga    2640
ttaagggaag aagtagtgac caagatcagg gccaatcaac agctggaaaa agacctgaac    2700
ctgatggaca tcaagattgg actgctggtg aagaacagga tcacactaga ggatgtaatt    2760
tcacacagta aaaagctgaa caagaaaaaa ggaggagaaa tggaaatact gaataacacc    2820
gacaaccaag gaataaaaag tttgagtaag gagaggagaa aaacactaga aacatatcag    2880
cagctgtttt acctttacaa gaccaaccct ttatacttgg ctaagctgat tttccagatg    2940
ccacagaaca agtccactaa atttatggat actgttattt tcacactata taattatgcc    3000
tctaatcagc gagaagaata tctacttctc aagcttttta aaactgctct ggaggaagaa    3060
ataaaatcaa aagtggacca ggtacaggac atagttactg gtaaccctac agtcatcaag    3120
atggtcgtca gcttcaatag aggtgcccgg ggacagaaca ccctgcgcca actcctggct    3180
ccagtggtaa aagagatcat cgacgacaag tcgctgatta tcaacacaaa ccctgtagag    3240
gtgtacaagg cttgggtgaa ccaactagaa acacagactg gagaggccag caagttgcct    3300
tatgatgtga ccacagaaca agctctaaca tacccagaag tgaaaaataa actggaggct    3360
tccattgaga acctgagaag ggtcaccgac aaagtcctga attctatcat ttcttccctt    3420
gatctactgc cttatggatt gaggtatata gccaaagtac tgaagaattc gatccatgag    3480
aaattccccg atgcaacaga agatgagcta ttaaagattg ttggaaacct cctgtactat    3540
cggtacatga atccagccat tgtagctcca gatggctttg atatcatcga catgacagct    3600
ggaggtcaga taaattctga ccaaaggaga aacttaggat cagtggccaa ggttcttcag    3660
cacgcagcct ccaacaagct gtttgaagga gaaaatgagc atctctcatc tatgaacaat    3720
tatttatcag agacgtatca ggaattcagg aaatatttca agaagcatg taatgtccct    3780
gagccagaag agaagtttaa tatggacaaa tacacagacc tggtgacagt cagcaaacca    3840
gtcatttata tttcaattga agaaatcatc agcacacact cactcctgtt ggaacaccag    3900
gatgcaattg cccctgagaa aaatgactta ctgagtgaat tgctgggtc gctgggagag    3960
gtgccaaccg tggaatcttt tcttggggaa ggagcagttg accccaatga ccctaacaag    4020
gcaaatacac taagtcagct ttcaaagacc gagatttctc ttgtcttgac aagcaaatat    4080
gacatagagg acggtgaagc tatagatagc cgaagcctca tgataaagac caagaagctg    4140
ataattgatg tgatccggaa ccagccaggg aacacattga cagaaatctt agagacacca    4200
gcaactgcgc aacaggaggt agaccatgcc acggacatgg tgagccgtgc aatgatagat    4260
tccaggactc cagaagaaat gaagcatagc caatctatga ttgaagatgc acagctgcct    4320
cttgagcaga agaagaggaa aatccagagg aatcttcgga cgttggaaca gactggacac    4380
gtgtcatccg aaaataaata ccaagacatt ctcaatgaga ttgccaagga tattcgaaat    4440
caaagaatct atcgtaagct tcgaaaagct gaattggcaa aacttcagca gaccctgaat    4500
gcacttaaca gaaggcagc attttatgaa gagcaaatca attattatga cacctacata    4560
aagacttgtt tagacaactt aaaaagaaaa aatactcgga gatcaattaa actagatgga    4620
aaggagaac ccaaggggc gaagagagcg aagccagtga agtacactgc agcaaagctg    4680
```

-continued

```
catgagaaag gtgtcctgct agatatagat gatcttcaaa caaaccagtt taagaatgtt      4740
acatttgata tcatagctac tgaagatgta ggcattttcg atgtaagatc aaaattcctt      4800
ggtgttgaga tggaaaaggt gcaactcaat attcaggatt tacttcagat gcaatatgaa      4860
ggagtagctg taatgaaaat gtttgataag gttaaagtga atgtaaacct tctcatatac      4920
ctgctgaaca agaagttcta tggaaagtga agtgcctaca gaaatttctt ggattctgta      4980
tcatctggat taggaaatga atttgtttaa tattttgtt tttaaacatg attgaaatca       5040
ctgcttataa atgtgtgatt ttttttaaat gaccaaaact gttctgaaga atgtacccag      5100
gtgccttttt gctaatttga tactataata gaatgagaca taaatgaat taatggaaac       5160 atatccacac tgtactgtga tataggtact ctgatttaaa actttggaca tcctgtgatc      5220
tgttttaaag ttgggggggtg ggaaatttag ctgactaggg acaaacatgt aaacctattt     5280
tcctatgaaa aaagttttaa atgtcccact tgaataacgt aattcttcat agttttttta     5340
atctatggat aaatggaaac ctaattattt gtaatgaatt atttagacag ttctaagccc      5400
tgtcttctgg gagttatcaa ttttaaagag aacttttgtg caattcaaat gaagttttta     5460
taagtaattg aaaatgacaa cacaataaca ctttctgtat aaaagtatat attttatgtg      5520
atttattcct actaaatgaa agtgcactac tgcctcatgt aaagactctt gcacgcagag      5580
cctttaagtg actaaggaac aacatagata gtgagcatag tccccacctc caccccctcac   5640 aatttatttg aatacttcaa ttgtgcctct caatttttg taatgctaaa aaatcagtat       5700
ctagatggtt tttaaatgta ttctctggaa attgttttat gtaaaataaa tgttacttaa     5760
ttccatt                                                               5767
```

<210> SEQ ID NO 33
<211> LENGTH: 634
<212> TYPE: DNA
<213> ORGANISM: Homo Sapiens

<400> SEQUENCE: 33

```
cggctgagag gcagcgaact catctttgcc agtacaggag cttgtgccgt ggcccacagc       60
ccacagccca cagccatggg ctgggacctg acggtgaaga tgctggcggg caacgaattc      120
caggtgtccc tgagcagctc catgtcggtg tcagagctga aggcgcagat cacccagaag      180
attggcgtgc acgccttcca gcagcgtctg gctgtccacc cgagcggtgt ggcgctgcag      240
gacagggtcc cccttgccag ccaggcctg ggccctggca gcacggtcct gctggtggtg       300
gacaaatgcg acgaacctct gagcatcctg gtgaggaata acaagggccg cagcagcacc      360
tacgaggtcc ggctgacgca gaccgtggcc cacctgaagc agcaagtgag cgggctggag      420
ggtgtgcagg acgacctgtt ctggctgacc ttcgagggga gcccctggga ggaccagctc      480
ccgctggggg agtacggcct caagcccctg agcaccgtgt tcatgaatct gcgcctgcgg      540
ggaggcggca cagagcctgg cgggcggagc taagggcctc caccagcatc cgagcaggat      600
caagggccgg aaataaaggc tgttgtaaga gaat                                  634
```

<210> SEQ ID NO 34
<211> LENGTH: 4855
<212> TYPE: DNA
<213> ORGANISM: Homo Sapiens

<400> SEQUENCE: 34

```
gaattcccct ccccccttttt tccatgcagc tgatctaaaa gggaataaaa ggctgcgcat      60
```

-continued

```
aatcataata ataaagaag gggagcgcga gagaaggaaa gaaagccggg aggtggaaga      120 ggaggggag cgtctcaaag aagcgatcag aataataaaa ggaggccggg ctctttgcct      180
tctggaacgg gccgctcttg aaagggcttt tgaaaagtgg tgttgttttc cagtcgtgca    240
tgctccaatc ggcggagtat attagagccg ggacgcggcc gcagggcag cggcgacggc     300 agcaccggcg gcagcaccag cgcgaacagc agcggcggcg tcccgagtgc ccgcggcggc    360
gcgcgcagcg atgcgttccc cacggacacg cggccggtcc gggcgccccc taagcctcct    420
gctcgccctg ctctgtgccc tgcgagccaa ggtgtgtggg gcctcgggtc agttcgagtt    480
ggagatcctg tccatgcaga acgtgaacgg ggagctgcag aacgggaact gctgcggcgg    540
cgcccggaac ccgggagacc gcaagtgcac ccgcgacgag tgtgacacat acttcaaagt    600
gtgcctcaag gagtatcagt cccgcgtcac ggccggggg ccctgcagct tcggctcagg     660
gtccacgcct gtcatcgggg gcaacaccttt caacctcaag gccagccgcg caacgaccc    720 gaaccgcatc gtgctgcctt tcagtttcgc ctggccgagg tcctatacgt tgcttgtgga    780
ggcgtgggat tccagtaatg acaccgttca acctgacagt attattgaaa aggcttctca    840
ctcgggcatg atcaaccca gccggcagtg gcagacgctg aagcagaaca cgggcgttgc     900
ccactttgag tatcagatcc gcgtgacctg tgatgactac tactatgct ttggctgtaa     960 taagttctgc cgccccagag atgacttctt tggacactat gcctgtgacc agaatggcaa   1020
caaaacttgc atggaaggct ggatgggccc cgaatgtaac agagctatt gccgacaagg    1080 ctgcagtcct aagcatggt cttgcaaact cccaggtgac tgcaggtgcc agtacggctg     1140
gcaaggcctg tactgtgata agtgcatccc acacccggga tgcgtccacg gcatctgtaa    1200
tgagccctgg cagtgcctct gtgagaccaa ctggggcggc cagctctgtg acaaagatct    1260
caattactgt gggactcatc agccgtgtct caacggggga acttgtagca acacaggccc    1320
tgacaaatat cagtgttcct gccctgaggg gtattcagga cccaactgtg aaattgctga    1380
gcacgcctgc ctctctgatc cctgtcacaa cagaggcagc tgtaaggaga cctccctggg   1440
ctttgagtgt gagtgttccc caggctggac cggccccaca tgctctacaa acattgatga   1500
ctgttctcct aataactgtt cccacggggg cacctgccag gacctggtta acggatttaa   1560
gtgtgtgtgc ccccccacagt ggactgggaa acgtgccca ttagatgcaa atgaatgtga    1620
ggccaaacct tgtgtaaacg ccaaatcctg taagaatctc attgccagct actactgcga   1680
ctgtcttccc ggctggatgg gtcagaattg tgacataaat attaatgact gccttggcca   1740
gtgtcagaat gacgcctcct gtcgggattt ggttaatggt tatcgctgta tctgtccacc   1800
tggctatgca ggcgatcact gtgagagaga catcgatgaa tgtgccagca cccctgttt    1860 gaatggggggt cactgtcaga atgaaatcaa cagattccag tgtctgtgtc ccactggttt   1920
ctctggaaac ctctgtcagc tggacatcga ttattgtgag cctaatccct gccagaacgg   1980
tgcccagtgc tacaaccgtg ccagtgacta tttctgcaag tgccccgagg actatgaggg   2040
caagaactgc tcacacctga agaccactg ccgcacgacc ccctgtgaag tgattgacag    2100
ctgcacagtg gccatggctt ccaacgacac acctgaaggg gtgcggtata tttcctccaa   2160
cgtctgtggt cctcacggga agtgcaagag tcagtcggga ggcaaattca cctgtgactg   2220
taacaaaggc ttcacgggaa catactgcca tgaaaatatt aatgactgtg agagcaaccc   2280
ttgtagaaac ggtggcactt gcatcgatgg tgtcaactcc tacaagtgca tctgtagtga   2340
cggctgggag ggggcctact gtgaaaccaa tattaatgac tgcagccaga ccccctgcca   2400
caatgggggc acgtgtcgcg acctggtcaa tgacttctac tgtgactgta aaaatgggtg   2460
```

-continued

```
gaaaggaaag acctgccact cacgtgacag tcagtgtgat gaggccacgt gcaacaacgg    2520
tggcacctgc tatgatgagg gggatgcttt taagtgcatg tgtcctggcg gctgggaagg    2580
aacaacctgt aacatagccc gaaacagtag ctgcctgccc aacccctgcc ataatggggg    2640
cacatgtgtg gtcaacggcg agtccttta cgtgcgtctgc aaggaaggct gggaggggcc    2700
catctgtgct cagaatacca atgactgcag ccctcatccc tgttacaaca gcggcacctg    2760
tgtggatgga gacaactggt accggtgcga atgtgccccg ggttttgctg gcccgactg     2820 cagaataaac atcaatgaat gccagtcttc accttgtgcc tttggagcga cctgtgtgga    2880
tgagatcaat ggctaccggt gtgtctgccc tccagggcac agtggtgcca agtgccagga    2940
agtttcaggg agaccttgca tcaccatggg gagtgtgata ccagatgggg ccaaatggga    3000
tgatgactgt aatacctgcc agtgcctgaa tggacggatc gcctgctcaa aggtctggtg    3060
tggccctcga ccttgcctgc tccacaaagg gcacagcgag tgcccagcg ggcagagctg     3120 catccccatc ctggacgacc agtgcttcgt ccacccctgc actggtgtgg gcgagtgtcg    3180
gtcttccagt ctccagccgg tgaagacaaa gtgcacctct gactcctatt accaggataa    3240
ctgtgcgaac atcacattta cctttaacaa ggagatgatg tcaccaggtc ttactacgga    3300
gcacatttgc agtgaattga ggaatttgaa tattttgaag aatgtttccg ctgaatattc    3360
aatctacatc gcttgcgagc cttcccttc agcgaacaat gaaatacatg tggccatttc     3420
tgctgaagat atacgggatg atgggaaccc gatcaaggaa atcactgaca aaataatcga    3480
tcttgttagt aaacgtgatg gaaacagctc gctgattgct gccgttgcag aagtaagagt    3540
tcagaggcgg cctctgaaga acagaacaga tttccttgtt cccttgctga gctctgtctt    3600
aactgtggct tggatctgtt gcttggtgac ggccttctac tggtgcctgc ggaagcggcg    3660
gaagccgggc agccacacac actcagcctc tgaggacaac accaccaaca acgtgcggga    3720
gcagctgaac cagatcaaaa accccattga gaaacatggg gccaacacgg tccccatcaa    3780
ggattacgag aacaagaact ccaaaatgtc taaaataagg acacacaatt ctgaagtaga    3840
agaggacgac atggacaaac accagcagaa agcccggtttt gccaagcagc cggcgtacac    3900
gctggtagac agagaagaga agccccccaa cggcacgccg acaaaacacc caaactggac    3960
aaacaaacag gacaacagag acttggaaag tgcccagagc ttaaaccgaa tggagtacat    4020
cgtatagcag accgcgggca ctgccgccgc taggtagagt ctgagggctt gtagttcttt    4080
aaactgtcgt gtcatactcg agtctgaggc cgttgctgac ttagaatccc tgtgttaatt    4140
tagtttgaca agctggctta cactggcaat ggtagttctg tggttggctg ggaaatcgag    4200
tggcgcatct cacagctatg caaaaagcta gtcaacagta ccctggttg tgtgtcccct     4260 tgcagccgac acgtctcgg atcaggctcc caggagctgc ccagcccct ggtactttga     4320 gctcccactt ctgccagatg tctaatggtg atgcagtctt agatcatagt tttatttata    4380
tttattgact cttgagttgt ttttgtatat tggtttatg atgacgtaca agtagttctg     4440
tatttgaaag tgcctttgca gctcagaacc acagcaacga tcacaaatga ctttattatt    4500
tatttttttt aattgtattt ttgttgttgg gggagggag actttgatgt cagcagttgc     4560
tggtaaaatg aagaatttaa agaaaaatg tccaaaagta gaactttgta tagttatgta     4620
aataattctt ttttattaat cactgtgtat atttgattta ttaacttaat aatcaagagc    4680
cttaaaacat cattccttt tatttatatg tatgtgttta gaattgaagg ttttttgatag    4740 cattgtaagc gtatggcttt attttttttga actcttctca ttacttgttg cctataagcc    4800
```
aaaaaggaaa gggtgttttg aaaatagttt attttaaaac aataggatgg gctac        4855

<210> SEQ ID NO 35
<211> LENGTH: 9534
<212> TYPE: DNA
<213> ORGANISM: Homo Sapiens

<400> SEQUENCE: 35
cagcgactcc tctggctccc gagaagtgga tccggtcgcg gccactacga tgccgggagc        60
cgccggggtc ctcctccttc tgctgctctc cggaggcctc gggggcgtac aggcgcagcg       120
gccgcagcag cagcggcagt cacaggcaca tcagcaaaga ggtttattcc ctgctgtcct       180
gaatcttgct tctaatgctc ttatcacgac caatgcaaca tgtggagaaa aggacctga        240
aatgtactgc aaattggtag aacatgtccc tgggcagcct gtgaggaacc cgcagtgtcg       300
aatctgcaat caaaacagca gcaatccaaa ccagagacac ccgattacaa atgctattga       360
tggaaagaac acttggtggc agagtcccag tattaagaat ggaatcgaat accattatgt       420
gacaattaca ctggatttac agcaggtgtt ccagatcgcg tatgtgattg tgaaggcagc       480
taactccccc cggcctggaa actggatttt ggaacgctct cttgatgatg ttgaatacaa       540
gccctggcag tatcatgctg tgacagacac ggagtgccta acgctttaca atatttatcc       600
ccgcactggg ccaccgtcat atgccaaaga tgatgaggtc atctgcactt cattttactc       660
caagatacac cccttagaaa atggagagat tcacatctct ttaatcaatg ggagaccaag       720
tgccgatgat ccttctccag aactgctaga atttacctcc gctcgctata ttcgcctgag       780
atttcagagg atccgcacac tgaatgctga cttgatgatg tttgctcaca agacccaag       840
agaaattgac cccattgtca ccagaagata ttactactcg gtcaaggata tttcagttgg       900
agggatgtgc atctgctatg gtcatgccag ggcttgtcca cttgatccag cgacaaataa       960
atctcgctgt gagtgtgagc ataacacatg tggcgatagc tgtgatcagt gctgtccagg      1020
attccatcag aaaccctgga gagctggaac ttttctaact aaaactgaat gtgaagcatg      1080
caattgtcat ggaaaagctg aagaatgcta ttatgatgaa aatgttgcca gagaaatct       1140
gagtttgaat atacgtggaa agtacattgg aggggtgtc tgcattaatt gtacccaaaa       1200
cactgctggt ataaactgcg agacatgtac agatggcttc ttcagaccca agggggtatc      1260
tccaaattat ccaaggccat gccagccatg tcattgcgat ccaattggtt ccttaaatga      1320
agtctgtgtc aaggatgaga acatgctcg acgaggtttg gcacctggat cctgtcattg       1380
caaaactggt tttggaggtg tgagctgtga tcggtgtgcc aggggctaca ctggctaccc      1440
ggactgcaaa gcctgtaact gcagtggggt agggagcaaa aatgaggatc cttgttttgg      1500
cccctgtatc tgcaaggaaa atgttgaagg aggagactgt agtcgttgca aatccggctt      1560
cttcaatttg caagaggata attggaaagg ctgcgatgag tgtttctgtt cagggggtttc      1620
aaacagatgt cagagttcct actggaccta tgcaaaaata caagatatga gtggctggta      1680
tctgactgac cttcctggcc gcattcgagt ggctccccag caggacgact ggactcacc       1740
tcagcagatc agcatcagta acgcggaggc ccggcaagcc ctgccgcaca gctactactg      1800
gagcgcgccg gctccctatc tgggaaacaa actcccagca gtaggaggac agttgacatt      1860
taccatatca tatgaccttg aagaagagga agaagataca gaacgtgttc tccagcttat      1920
gattatctta gagggtaatg acttgagcat cagcacagcc caagatgagg tgtacctgca      1980
cccatctgaa gaacatacta atgtattgtt acttaaagaa gaatcattta ccatacatgg      2040
cacacatttt ccagtccgta gaaaggaatt tatgacagtg cttgcgaatt tgaagagagt      2100

```
cctcctacaa atcacataca gctttgggat ggatgccatc ttcaggttga gctctgttaa    2160
ccttgaatcc gctgtctcct atcctactga tggaagcatt gcagcagctg tagaagtgtg    2220
tcagtgccca ccagggtata ctggctcctc ttgtgaatct tgttggccta ggcacaggcg    2280
agttaacggc actattttg gtggcatctg tgagccatgt cagtgctttg gtcatgcgga     2340
gtcctgtgat gacgtcactg gagaatgcct gaactgtaag gatcacacag gtggcccata    2400
ttgtgataaa tgtcttcctg gtttctatgg cgagcctact aaaggaacct ctgaagactg    2460
tcaaccctgt gcctgtccac tcaatatccc atccaataac tttagcccaa cgtgccattt    2520
agaccggagt cttggattga tctgtgatgg atgccctgtc gggtacacag gaccacgctg    2580
tgagaggtgt gcagaaggct attttggaca accctctgta cctggaggat catgtcagcc    2640
atgccaatgc aatgacaacc ttgacttctc catccctggc agctgtgaca gcttgtctgg    2700
ctcctgtctg atatgtaaac caggtacaac aggccggtac tgtgagctct gtgctgatgg    2760
atattttgga gatgcagttg atgcgaagaa ctgtcagccc gtcgctgta atgccggtgg     2820 ctctttctct gaggtttgcc acagtcaaac tggacagtgt gagtgcagag ccaacgttca    2880
gggtcagaga tgtgacaaat gcaaggctgg gacctttggc ctacaatcag caaggggctg    2940
tgttccctgc aactgcaatt cttttgggtc taagtcattc gactgtgaag agagtggaca    3000
atgttggtgc caacctggag tcacagggaa gaaatgtgac cgctgtgccc acggctattt    3060
caacttccaa gaaggaggct gcacagcttg tgaatgttct catctgggta taattgtga    3120 cccaaagact gggcgatgca tttgcccacc caataccatt ggagagaaat gttctaaatg    3180
tgcacccaat acctggggcc acagcattac cactggttgt aaggcttgta actgcagcac    3240
agtgggatcc ttggatttcc aatgcaatgt aaatacaggc caatgcaact gtcatccaaa    3300
attctctggt gcaaaatgta cagagtgcag tcgaggtcac tggaactacc ctcgctgcaa    3360
tctctgtgac tgcttcctcc ctgggacaga tgccacaacc tgtgattcag agactaaaaa    3420
atgctcctgt agtgatcaaa ctgggcagtg cacttgtaag gtgaatgtgg aaggcatcca    3480
ctgtgacaga tgccggcctg gcaaattcgg actcgatgcc aagaatccac ttggctgcag    3540
cagctgctat tgcttcggca ctactaccca gtgctctgaa gcaaaaggac tgatccggac    3600
gtgggtgact ctgaaggctg agcagaccat tctacccctg gtagatgagg ctctgcagca    3660
cacgaccacc aagggcattg ttttcaaca tccagagatt gttgcccaca tggacctgat     3720
gagagaagat ctccatttgg aaccttttta ttggaaactt ccagaacaat ttgaaggaaa    3780
gaagttgatg gcctatgggg gcaaactcaa gtatgcaatc tatttcgagg ctcgggaaga    3840
aacaggtttc tctacatata atcctcaagt gatcattcga gtgggacac ctactcatgc     3900 tagaattatc gtcaggcata tggctgctcc tctgattggc caattgacaa ggcatgaaat    3960
tgaaatgaca gagaaagaat ggaaatatta tgggatgat cctcgagtcc atagaactgt     4020
gacccgagaa gacttcttgg atatactata tgatattcat tacattctta tcaaagctac    4080
ttatggaaat ttcatgcgac aaagcaggat ttctgaaatc tcaatggagg tagctgaaca    4140
aggacgtgga acaacaatga ctcctccagc tgacttgatt gaaaaatgtg attgtccct     4200 gggctattct ggcctgtcct gtgaggcatg cttgccggga ttttatcgac tgcgttctca    4260
accaggtggc cgcaccctg gaccaaccct gggcacctgt gttccatgtc aatgtaatgg     4320
acacagcagc ctgtgtgacc ctgaaacatc gatatgccag aattgtcaac atcacactgc    4380
tggtgacttc tgtgaacgat gtgctcttgg atactatgga attgtcaagg gattgccaaa    4440
```

-continued

```
tgactgtcag caatgtgcct gccctctgat ttcttccagt aacaatttca gcccctcttg    4500
tgtcgcagaa ggacttgacg actaccgctg cacggcttgt ccacggggat atgaaggcca    4560
gtactgtgaa aggtgtgccc ctggctatac tggcagtcca ggcaaccctg gaggctcctg    4620
ccaagaatgt gagtgtgatc cctatggctc actgcctgtg ccctgtgacc ctgtcacagg    4680
attctgcacg tgccgacctg gagccacggg aaggaagtgt gacggctgca agcactggca    4740
tgcacgcgag ggctgggagt gtgttttttg tggagatgag tgcactggcc ttcttctcgg    4800
tgacttggct cgcctggagc agatggtcat gagcatcaac ctcactggtc cgctgcctgc    4860
gccatataaa atgctgtatg gtcttgaaaa tatgactcag gagctaaagc acttgctgtc    4920
acctcagcgg gccccagaga ggcttattca gctggcagag ggcaatctga atacactcgt    4980
gaccgaaatg aacgagctgc tgaccagggc taccaaagtg acagcagatg gcgagcagac    5040
cggacaggat gctgagagga ccaacacaag agcaaagtcc ctgggagaat tcattaagga    5100
gcttgcccgg gatgcagaag ctgtaaatga aaaagctata aaactaaatg aaactctagg    5160
aactcgagac gaggcctttg agagaaattt ggaagggctt cagaaagaga ttgaccagat    5220
gattaaagaa ctgaggagga aaaatctaga gacacaaaag gaaattgctg aagatgagtt    5280
ggtagctgca gaagcccttc tgaaaaagt gaagaagctg tttggagagt cccgggggga    5340
aaatgaagaa atggagaagg atctccggga aaaactggct gactacaaaa acaaagttga    5400
tgatgcttgg gacctttga gagaagccac agataaaatc agagaagcta atcgcctatt    5460
tgcagtaaat cagaaaaaca tgactgcatt ggagaaaaag aaggaggctg ttgagagcgg    5520
caaacgacaa attgagaaca ctttaaaaga aggcaatgac atactcgatg aagccaaccg    5580
tcttgcagat gaaatcaact ccatcataga ctatgttgaa gacatccaaa ctaaattgcc    5640
acctatgtct gaggagctta atgataaaat agatgacctc tcccaagaaa taaggacag    5700
gaagcttgct gagaaggtgt cccaggctga gagccacgca gctcagttga atgactcatc    5760
tgctgtcctt gatggaatcc ttgatgaggc taaaaacatc tccttcaatg ccactgcagc    5820
cttcaaagct tacagcaata ttaaggacta tattgatgaa gctgagaaag ttgccaaaga    5880
agccaaagat cttgcacatg aagctacaaa actggcaaca ggtcctcggg gtttattaaa    5940
ggaagatgcc aaaggctgtc ttcagaaaag cttcaggatt cttaacgaag ccaagaagtt    6000
agcaaatgat gtaaaagaaa atgaagacca tctaaatggc ttaaaaacca ggatagaaaa    6060
tgctgatgct agaaatgggg atctcttgag aactttgaat gacactttgg gaagttatc    6120
agctattcca aatgatacag ctgctaaact gcaagctgtt aaggacaaag ccagacaagc    6180
caacgacaca gctaaagatg tactggcaca gattacagag ctccaccaga acctcgatgg    6240
cctgaagaag aattacaata aactagcaga cagcgtcgcc aaaacgaatg ctgtggttaa    6300
agatccttcc aagaacaaaa tcattgccga tgcagatgcc actgtcaaaa atttagaaca    6360
ggaagctgac cggctaatag ataaactcaa acccatcaag gaacttgagg ataacctaaa    6420
gaaaacatc tctgagataa aggaattgat aaaccaagct cggaaacaag ccaattctat    6480
caaagtatct gtgtcttcag gaggtgactg cattcgaaca tacaaaccag aaatcaagaa    6540
aggaagttac aataatattg ttgtcaacgt aaagacagc gttgctgata acctcctctt    6600
ttatcttgga agtgccaaat ttattgactt tctggctata gaaatgcgta aaggcaaagt    6660
cagcttcctc tgggatgttg gatctggagt tggacgtgta gagtacccag atttgactat    6720
tgatgactca tattggtacc gtatcgtagc atcaagaact gggagaaatg gaactatttc    6780
tgtgagagcc ctggatggac ccaaagccag cattgtgccc agcacacacc attcgacgtc    6840
```

```
tcctccaggg tacacgattc tagatgtgga tgcaaatgca atgctgtttg ttggtggcct    6900
gactgggaaa ttaaagaagg ctgatgctgt acgtgtgatt acattcactg gctgcatggg    6960
agaaacatac tttgacaaca aacctatagg tttgtggaat ttccgagaaa aagaaggtga    7020
ctgcaaagga tgcactgtca gtcctcaggt ggaagatagt gagggacta ttcaatttga     7080
tggagaaggt tatgcattgg tcagccgtcc cattcgctgg taccccaaca tctccactgt    7140
catgttcaag ttcagaacat tttcttcgag tgctcttctg atgtatcttg ccacacgaga    7200
cctgagagat ttcatgagtg tggagctcac tgatgggcac ataaaagtca gttacgatct    7260
gggctcagga atggcttccg ttgtcagcaa tcaaaaccat aatgatggga atggaaatc     7320
attcactctg tcaagaattc aaaaacaagc caatatatca attgtagata tagatactaa    7380
tcaggaggag aatatagcaa cttcgtcttc tggaaacaac tttggtcttg acttgaaagc    7440
agatgacaaa atatattttg gtggcctgcc aacgctgaga aacttgagta tgaaagcaag    7500
gccagaagta aatctgaaga atattccgg ctgcctcaaa gatattgaaa tttcaagaac     7560
tccgtacaat atactcagta gtcccgatta tgttggtgtt accaaaggat gttccctgga    7620
gaatgtttac acagttagct ttcctaagcc tggttttgtg gagctctccc ctgtgccaat    7680
tgatgtagga acagaaatca acctgtcatt cagcaccaag aatgagtccg gcatcattct    7740
tttgggaagt ggagggacac cagcaccacc taggagaaaa cgaaggcaga ctggacaggc    7800
ctattatgta atactcctca acaggggccg tctggaagtg catctctcca caggggcacg    7860
aacaatgagg aaaattgtca tcagaccaga gccgaatctg tttcatgatg aagagaaca     7920
ttccgttcat gtagagcgaa ctagaggcat ctttacagtt caagtggatg aaaacagaag    7980
atacatgcaa aacctgacag ttgaacagcc tatcgaagtt aaaaagcttt tcgttggggg    8040
tgctccacct gaatttcaac cttcccccact cagaaatatt cctcctttg aaggctgcat    8100
atggaatctt gttattaact ctgtccccat ggactttgca aggcctgtgt ccttcaaaaa    8160
tgctgacatt ggtcgctgtg cccatcagaa actccgtgaa gatgaagatg gagcagctcc    8220
agctgaaata gttatccagc ctgagccagt tcccacccca gcctttccta cgcccacccc    8280
agttctgaca catggtcctt gtgctgcaga atcagaacca gctcttttga tagggagcaa    8340
gcagttcggg cttttcaagaa acagtcacat tgcaattgca tttgatgaca ccaaagttaa    8400
aaaccgtctc acaattgagt tggaagtaag aaccgaagct gaatccggct tgctttttta    8460
catggctgcg atcaatcatg ctgattttgc aacagttcag ctgagaaatg gattgcccta    8520
cttcagctat gacttgggga gtggggacac ccacaccatg atccccacca aaatcaatga    8580
tggccagtgg cacaagatta agataatgag aagtaagcaa gaaggaattc tttatgtaga    8640
tggggcttcc aacagaacca tcagtcccaa aaaagccgac atcctggatg tcgtgggaat    8700
gctgtatgtt ggtgggttac ccatcaacta cactacccga agaattggtc cagtgaccta    8760
tagcattgat ggctgcgtca ggaatctcca catggcagag gcccctgccg atctggaaca    8820
acccacctcc agcttccatg ttgggacatg ttttgcaaat gctcagaggg gaacatattt    8880
tgacggaacc ggttttgcca aagcagttgg tggattcaaa gtgggattgg accttcttgt    8940
agaatttgaa ttcgcgacaa ctacaacgac tggagttctt ctgggatca gtagtcaaaa     9000
aatggatgga atgggtattg aaatgattga tgaaaagttg atgtttcatg tggacaatgg    9060
tgcgggcaga ttcactgctg tctatgatgc tggggttcca gggcatttgt gtgatggaca    9120
atggcataaa gtcactgcca acaagatcaa acaccgcatt gagctcacag tcgatgggaa    9180
```

-continued

| | |
|---|---|
| ccaggtggaa gcccaaagcc caaacccagc atctacatca gctgacacaa atgaccctgt | 9240 |
| gtttgttgga ggcttcccag atgacctcaa gcagtttggc ctaacaacca gtattccgtt | 9300 |
| ccgaggttgc atcagatccc tgaagctcac caaaggcaca gcaagccact ggaggttaat | 9360 |
| tttgccaagg ccctggaact gaggggcgtt caacctgtat catgcccagc caactaataa | 9420 |
| aaataagtgt aacccagga agagtctgtc aaaacaagta tatcaagtaa acaaacaaa | 9480 |
| tatattttac ctatatatgt taattaaact aatttgtgca tgtacataga attc | 9534 |

<210> SEQ ID NO 36
<211> LENGTH: 5683
<212> TYPE: DNA
<213> ORGANISM: Homo Sapiens

<400> SEQUENCE: 36

| | |
|---|---|
| ccgcccggtg ttgcgctcct tcccagaatc cgctccggcc tttccttcct gccgcgattc | 60 |
| ccaactttgc tcaaagtcgc cggactctaa gctgtcggag ggaccgctgg acagacctgg | 120 |
| gaactgacag agggcctgga gggaaatagg ccaaagaccc acaggatgga gctgacctca | 180 |
| accgaaagag ggaggggaca gcctctgccc tgggaacttc gactgcccct actgctaagc | 240 |
| gtgctggctg ccacactggc acaggcccct gccccggatg tccctggctg ttccagggga | 300 |
| agctgctacc ccgccacggc cgacctgctg gtgggccgag ctgacagact gactgcctca | 360 |
| tccacttgtg gcctgaatgg ccgccagccc tactgcatcg tcagtcacct gcaggacgaa | 420 |
| aagaagtgct tcctttgtga ctcccggcgc cccttctctg ctagagacaa cccacacacc | 480 |
| catcgcatcc agaatgtagt caccagcttt gcaccacagc ggcgggcagc ttggtggcag | 540 |
| tcacagaatg gtatccctgc ggtcaccatc cagctggacc tggaggctga gtttcatttc | 600 |
| acacacctca ttatgacctt caagacattt cgccctgctg ccatgctggt cgaacgctca | 660 |
| gcagactttg gccgcacctg gcatgtgtac cgatatttct cctatcactg tgggctgac | 720 |
| ttcccaggag tcccactagc accccacgg cactgggatg atgtagtctg tgagtcccgc | 780 |
| tactcagaga ttgagccatc cactgaaggc gaggtcatct atcgtgtgct ggaccctgcc | 840 |
| atccctatcc cagaccccta cagctcacgg attcagaacc tgttgaagat caccaaccta | 900 |
| cgggtgaacc tgactcgtct acacacgttg ggagacaacc tactcgaccc acggagggag | 960 |
| atccgagaga agtactacta tgccctctat gagctggttg tacgtggcaa ctgcttctgc | 1020 |
| tacggacacg cctcagagtg tgcacccgcc caggggcac cagcccatgc tgagggcatg | 1080 |
| gtgcacggag cttgcatctg caaacacaac acacgtggcc tcaactgcga gcagtgtcag | 1140 |
| gatttctatc gtgacctgcc ctggcgtccg gctgaggacg gccatagtca tgcctgtagg | 1200 |
| aagtgtgatc ggcatgggca cacccacagc tgccacttcg acatggccgt atacctcgga | 1260 |
| tctggcaatg tgagtggagg tgtgtgtgat ggatgtcagc ataacacagc gtggcgccac | 1320 |
| tgtgagctct gtcggccctt cttctaccgt gacccaacca aggacctgcg ggatccggct | 1380 |
| gtgtgccgct cctgtgattg tgaccccatg ggttctcaag acgtggtcg ctgtgattcc | 1440 |
| catgatgacc ctgcactggg actggtctcc ggccagtgtc gctgcaaaga acacgtggtg | 1500 |
| ggcactcgct gccagcaatg ccgtgatggc ttctttgggc tcagcatcag tgacccgtct | 1560 |
| gggtgccggc gatgtcaatg taatgcacgg ggcacagtgc ctgggagcac tccttgtgac | 1620 |
| cccaacagtg gatcctgtta ctgcaaacgt ctagtgactg gacgtggatg tgaccgctgc | 1680 |
| ctgcctggcc actgggcct gagcctcgac ctgctcggct gccgccctg tgactgcgac | 1740 |
| gtgggtggtg ctttggatcc ccagtgtgat gagggcacag gtcaatgcca ctgccgccag | 1800 |

-continued

```
cacatggttg ggcgacgctg tgagcaggtg caacctggct acttccggcc cttcctggac    1860
cacctaattt gggaggctga gaacacccga gggcaggtgc tcgatgtggt ggagcgcctg    1920
gtgacccccg gggaaactcc atcctggact ggctcaggct tcgtgcgact acaggaaggt    1980
cagaccctgg agttcctggt ggcctctgtg ccgaacgcga tggactatga cctgctgctg    2040
cgcttagagc cccaggtccc tgagcaatgg gcagagttgg aactgattgt gcagcgtcca    2100
gggcctgtgc ctgcccacag cctgtgtggg catttggtgc ccagggatga tcgcatccaa    2160
gggactctgc aaccacatgc caggtacttg atatttccta atcctgtctg ccttgagcct    2220
ggtatctcct acaagctgca tctgaagctg gtacggacag ggggaagtgc ccagcctgag    2280
actccctact ctggacctgg cctgctcatt gactcgctgg tgctgctgcc ccgtgtcctg    2340
gtgctagaga tgtttagtgg gggtgatgct gctgccctgg agcgccaggc cacctttgaa    2400
cgctaccaat gccatgagga gggtctggtg cccagcaaga cttctccctc tgaggcctgc    2460
gcacccctcc tcatcagcct gtccaccctc atctacaatg gtgccctgcc atgtcagtgc    2520
aaccctcaag gttcactgag ttctgagtgc aaccctcatg gtggtcagtg cctgtgcaag    2580
cctggagtgg ttgggcgccg ctgtgacacg tgtgcccctg gctactatgg ctttggcccc    2640
acaggctgtc aagcctgcca gtgcagccca cgaggggcac tcagcagtct ctgtgaaagg    2700
accagtgggc aatgtctctg tcgaactggt gcctttgggc ttcgctgtga cgcctgccag    2760
cgtggccagt ggggattccc tagctgccgg ccatgtgtct gcaatgggca tgcagatgag    2820
tgcaacaccc acacaggcgc ttgcctgggc tgccgtgatc tcacaggggg tgagcactgt    2880
gaaaggtgca ttgctggttt ccacggggac ccacggctgc catatggggc gcagtgccgg    2940
ccctgtccct gtcctgaagg ccctgggagc caacggcact ttgctacttc ttgccaccag    3000
gatgaatatt cccagcagat tgtgtgccac tgccgggcag gctatacggg gctgcgatgt    3060
gaagcttgtg cccctgggca gtttggggac ccatcaaggc caggtggccg tgccaactg     3120 tgtgagtgca gtgggaacat tgacccaatg gatcctgatg cctgtgaccc acaccccggg    3180
caatgcctgc gctgtttaca ccacacagag gtccacact gtgcccactc gaagcctggc     3240
ttccatggcc aggctgcccg gcagagctgt caccgctgca catgcaacct gctgggcaca    3300
aatccgcagc agtgcccatc tcctgaccag tgccactgta tccaagcag tgggcagtgc    3360 ccatgcctcc ccaatgtcca ggccctagct gtagaccgct gtgccccaa cttctggaac     3420 ctcaccagtg gccatggttg ccagccttgt gcctgcctcc caagcccgga agaaggcccc    3480
acctgcaacg agttcacagg gcagtgccac tgcctgtgcg gctttggagg gcggacttgt    3540
tctgagtgcc aagagctcca ctggggagac cctgggttgc agtgccatgc ctgtgattgt    3600
gactctcgtg gaatagatac acctcagtgt caccgcttca caggtcactg cacgtgccgc    3660
ccaggggtgt ctggtgtgcg ctgtgaccag tgtgcccgtg gcttctcagg aatctttcct    3720
gcctgccatc cctgccatgc atgcttcggg gattgggacc gagtggtgca ggacttggca    3780
gcccgtacac agcgcctaga gcagcgggcg caggagttgc aacagacggg tgtgctgggt    3840
gcctttgaga gcagcttctg gcacatgcag gagaagctgg gcattgtgca gggcatcgta    3900
ggtgcccgca acacctcagc cgcctccact gcacagcttg tggaggccac agaggagctg    3960
cggcgtgaaa ttggggaggc cactgagcac ctgactcagc tcgaggcaga cctgacagat    4020
gtgcaagatg agaacttcaa tgccaaccat gcactaagtg gtctggagcg agataggctt    4080
gcacttaatc tcacactgcg gcagctcgac cagcatcttg acttgctcaa acattcaaac    4140
```

-continued

```
ttcctgggtg cctatgacag catccggcat gcccatagcc agtctgcaga ggcagaacgt    4200
cgtgccaata cctcagccct ggcagtacct agccctgtga gcaactcggc aagtgctcgg    4260
catcggacag aggcactgat ggatgctcag aaggaggact tcaacagcaa acacatggcc    4320
aaccagcggg cacttggcaa gctctctgcc atacccaca ccctgagcct gacagacata    4380
aatgagctgg tgtgtgggc ccagggattg catcatgatc gtacaagccc ttgtgggggt    4440
gccggctgtc gagatgagga tgggcagccg cgctgtgggg gcctcagctg caatggggca    4500
gcggctacag cagacctagc actgggccgg gcccggcaca cacaggcaga gctgcagcgg    4560
gcactggcag aaggtggtag catcctcagc agagtggctg agactcgtcg gcaggcaagc    4620
gaggcacagc agcgggccca ggcagccctg gacaaggcta atgcttccag gggacaggtg    4680
gaacaggcca accaggaact tcaagaactt atccagagtg tgaaggactt cctcaaccag    4740
gagggggctg atcctgatag cattgaaatg gtggccacac gggtgctaga gctctccatc    4800
ccagcttcag ctgagcagat ccagcacctg gcgggcgcga ttgcagagcg agtccggagc    4860
ctggcagatg tggatgcgat cctggcacgt actgtaggag atgtgcgtcg tgccgagcag    4920
ctactgcagg atgcacggcg ggcaaggagc tgggctgagg atgagaaaca aaggcagag    4980
acagtacagg cagcactgga ggaggcccag cgggcacagg gtattgccca gggtgccatc    5040
cgggggcag tggctgacac acgggacaca gagcagaccc tgtaccaggt acaggagagg    5100
atggcaggtg cagagcgggc actgagctct gcaggtgaaa gggctcggca gttggatgct    5160
ctcctggagg ctctgaaatt gaaacgggca ggaaatagtc tggcagcctc tacagcagaa    5220
gaaacggcag gcagtgccca gggtcgtgcc caggaggctg agcagctgct acgcggtcct    5280
ctgggtgatc agtaccagac ggtgaaggcc ctagctgagc gcaaggccca aggtgtgctg    5340
gctgcacagg caagggcaga acaactgccg gatgaggctc gggacctgtt gcaagccgct    5400
caggacaagc tgcagcggct acaggaattg aaggcacct atgaggaaaa tgagcgggca    5460
ctggagagta aggcagccca gttggacggg ttggaggcca ggatgcgcag cgtgcttcaa    5520
gccatcaact gcaggtgca gatctacaac acctgccagt gacccctgcc caaggcctac    5580
cccagttcct agcactgccc cacatgcatg tctgcctatg cactgaagag ctcttggccc    5640
ggcagggccc ccaataaacc agtgtgaacc cccaaaaaaa aaa                    5683
```

<210> SEQ ID NO 37
<211> LENGTH: 3714
<212> TYPE: DNA
<213> ORGANISM: Homo Sapiens

<400> SEQUENCE: 37

```
ccgggttgct gtgcgactat tctccgggag ccgttcgtgt caccgccgga acctggcgca     60
ggttaattat agaaatgcc aagtaggaaa tttgccgatg gtgaagtggt aagaggtcga    120
tggcctggga gttcacttta ttatgaagta gaaattctga gccacgacag cacctcccag    180
ctttacactg tgaagtataa agatggaaca gagcttgaat tgaaagagaa tgatattaag    240
ccttaactt cctttaggca aaggaaaggt ggctcaactt ccagttcccc ttccagacgc    300
cgagggagtc gatcaaggtc acgctcccga tcccctggtc gaccacctaa agtgcccgc    360
cgatctgctt ctgcttccca ccaggccgac attaaggaag caaggaggga agtggaagtt    420
aaattgactc cgctgattct gaagccattt ggaaatagca tcagcagata taatggggag    480
cctgagcata ttgagagaaa tgacgcacct cataaaaata cacaggaaaa attcagtttg    540
tcacaagaaa gcagttacat agcaacacag tatagccttc gtccaagaag agaagaagtc    600
```

```
aaattaaaag aaatagattc taaggaagaa aaatacgttg caaaagaact ggcagtgaga      660
acctttgaag tgaccccat  ccgggcaaag gacttggagt ttggaggagt acctggtgtg      720
tttctcatca tgtttggcct gcctgtgttc ctcttcctgt tgctgttgat gtgtaaacag      780
aaagatccca gtcttctgaa tttccctcct cctttgccag ctttgtatga gttatgggaa      840
accagagtat ttggggtcta cctcctgtgg tttttgattc aagtcctgtt ctacctactg      900
ccaattggaa aggttgtaga aggaacgcct cttattgatg gaagaagact caagtataga      960
ttaaatggat tctatccttt tatcctgaca tctgcagtca tcggaacatc tctcttccag     1020
ggcgtagagt ttcattacgt gtacagtcat tttcttcagt ttgcacttgc ggccactgtt     1080
ttttgtgtgg tcttgagtgt gtatctctac atgcgctctt tgaaagcgcc ccggaatgac     1140
ctgtcgcctg ccagctctgg aaatgctgtc tatgatttct tcattggccg tgaattaaac     1200
cctcgaattg gtacttttga tctcaaatac ttttgtgaat gcgccccgg  attgattgga     1260 tgggtggtta ttaacttggt gatgcttttg gctgaaatga aaatacagga ccgcgctgtt     1320
ccatccttgg ccatgatttt agttaatagt ttccagcttc tctatgtggt ggatgctctc     1380
tggaatgagg aagcgttgtt gacgaccatg acatcatcc  acgatggatt tggattcatg     1440
ctggcttttg gagacttggt gtgggttccc tttatttaca gcttccaagc ctttttattta    1500 gtcagtcatc caaatgaagt gtcttggcca atggcttctc taattattgt tctgaaactt     1560
tgtggttatg taatcttccg aggtgcaaat tctcagaaaa atgcattccg gaaaaatccc     1620
agtgatccaa agcttgcaca tttaaaaacc attcatactt caagtggaaa aaatcttcta     1680
gtttctggat ggtggggctt tgttcgccac cccaattact tgggtgatct catcatggcc     1740
ttggcgtggt ccctcccatg tggttttaac cacattctgc cttatttcta cataatttat     1800
ttcaccatgt tgcttgtcca ccgagaagct cgtgacgagt accactgtaa gaagaaatac     1860
ggcgtggctt gggaaaagta ctgtcagcgt gtgccctacc gtatatttcc atacatctac     1920
taatgctctt ctggcttttc tacaaaatac tcctgcaatt ccagctgcca tttgcaaaaa     1980
caggaaaaaa atccgaaact ttcttttgtt gcactgacag ggtctgtact tttttttttc     2040
tttttgagtc aggactatgg agccgagtag ttgatctttt aatatagccg tgtttacttg     2100
tattaactta cagttaacat aggaaaaata caagtaagga tgtgagaatt tgcattttaa     2160
tgggaaattt tcaaccctta atctgaaaac agaagacagt cttaatataa atgtactgtg     2220
aagaatgcta ttgatgttta tggtttctga ttacttttca aattttgatg ttttttttgcc    2280 agttggcttt tcttaaatga aaacactgtt ccatttaaag tacatttatg ttttattcag     2340
taagagaata gaattttcat ttgttttttct ttaaatcctt tactaattat ataatttgaa    2400
agcaaaaaga agggcctata ttaaatgctg aaagtgaaaa gtgatgacat tattagcaga     2460
cactgcttaa aggagaccat ttgtagcagt tggcttaacc tcaacttcta aaactacatt     2520
gaaaatgtaa atacatagct tagttttttg taatatatgg tgacttcaga tttttttgta    2580
cagtattttg aatgtgagat gattgtcagg actaactgtc tttttaacaa acattttca     2640 gtatttaaa  taaaattttg taaagtaatg tgaattaaaa attttggaac aattagaatt     2700
cattcactat tgtatagaag atgctgttaa acataggaa  gggtatttttt cttgatccaa    2760 agtttgtgaa tttggctttg ctacctcaat tgcaggtgtt tgtttgcctt tataaactgt     2820
tgcaaataga aaaaaaatag aataagtata tattttggga gtaacatcaa tatttaaaca    2880
tttttacaca gatcggtgtt tgaaaatttg ccatttcagg ctaatatttt tatatatttt    2940
```

-continued

```
tgactttttta aaagttcatc agtgttttg ctactgttaa gcttatgcag tttatactgt     3000 atttttatg  tatcctttat atttaccaaa cctgactccc tgtaaaggag tgctgtctta     3060
aaaacaactg aagggttaa  agtcgtttct tttagtttaa tagatgtgca taaggtagct     3120
ttagcaatta aattctagtg aagttgatat agtctcattt ttaattgtcc tgtaatggaa    3180
cagtagcaaa ttcactaaac ttttgtgttc agagttaaat tgttctcagt actttcaatg    3240
taggggaatg taataaacat agtgtgtatg tttgggtttt aattacacat tttatatatg    3300
agccatttag atatgcagtg ttaattctat actgcatttg aagtgtatgt aacttagctt    3360
atgttaatgc agtcatgaag ttggtttgct ccagcatccg gtagtcttta aacattcttt    3420
tagtgaaatt gtcattgttt tatcagtgct aatgtgtgca agcagttttt ttattttgct    3480
tttctcctgg catcagaaag tggtggcgtt ttctgtactg gattgcacca aggaagcttt    3540
tggggaggaa ggaaggacat taaattcttt ccctggtaat gaaaagagcc ctttatcaat    3600
acagtgctgc aatttctgga tatcagctac actttgtttt taagtttgtt tttgacatgt    3660
ttatttggca aattttataa tgaagttta agttgaaaat aaaatgtagc aaca           3714
```

<210> SEQ ID NO 38
<211> LENGTH: 911
<212> TYPE: DNA
<213> ORGANISM: Homo Sapiens

<400> SEQUENCE: 38

```
tctatcccag gtcacagcta cttcttcaag ggtgcctatt acctgaagct ggagaaccaa      60
agtctgaaga gcgtgaagtt tggaagcatc aaatccgact ggctaggctg ctgagctggc     120
cctggctccc acaggccctt cctctccact gccttcgata caccgggcct ggagaactag     180
agaaggaccc ggaggggcct ggcagccgtg ccttcagctc tacagctaat cagcattctc     240
actcctacct ggtaatttaa gattccgag agtggctcct cccggtgccc aagaatagat      300
gctgactgta ctcctcccag gcgccccttc cccctccaat cccaccaacc ctcagagcca    360
cccctaaaga gatccttga tatttcaac gcagccctgc tttgggctgc cctggtgctg      420
ccacacttca ggctcttctc ctttcacaac cttctgtggc tcacagaacc cttggagcca    480
atggagactg tctcaagagg gcactggtgg cccgacagcc tggcacaggg cagtgggaca    540
gggcatggcc agtggccac  tccagacccc tggcttttca ctgctggctg ccttagaacc    600
tttcttacat tagcagtttg ctttgtatgc actttgtttt tttcttgggg tcttgttttt     660
tttttccact tagaaattgc atttcctgac agaaggactc aggttgtctg aagtcactgc    720
acagtgcatc tcagcccaca tagtgatggt tcccctgttc actctactta gcatgtccct    780
accgagtctc ttctccactg gatggaggaa aaccaagccg tggcttcccg ctcagccctc    840 cctgccctc  ccttcaacca ttccccatgg gaaatgtcaa caagtatgaa taaagacacc     900
tactgagtgg c                                                          911
```

<210> SEQ ID NO 39
<211> LENGTH: 1423
<212> TYPE: DNA
<213> ORGANISM: Homo Sapiens

<400> SEQUENCE: 39

```
ctccgctatc aacaacttat taaagaaaac ttgaaagaaa ttgccaagtt aatcacattg      60
gaacaaggga agaccctagc tgatgctgaa ggagatgtat ttcgaggcct tcaggtggtt    120
gagcatgcct gtagtgtgac atccctcatg atgggagaga ccatgccatc catcaccaaa    180
```

```
gacatggacc tttattccta ccgtctgcct ctgggagtgt gtgcaggcat tgctccattc    240
aattttcctg ccatgatccc cctttggatg tttcccatgg ccatggtgtg tggaaatacc    300
ttcctaatga aaccatctga gcgagtccct ggagcaacta tgcttcttgc taagttgctc    360
caggattctg gtgccctga tggaacatta aacatcatcc atggacagca tgaagctgta    420
aattttattt gcgatcatcc ggacatcaaa gcaatcagct ttgtgggatc caacaaggca    480
ggagagtata tcttcgagag aggatcaaga catggcaaga gggttcaagc caatatggga    540
gccaagaacc atgggtagt catgccagat gccaataagg aaaatacccct gaaccagctg    600 gttggggcag catttggagc tgctggtcag cgctgcatgg ctctttcaac agcagtcctt    660
gtgggagaag ccaagaagtg gctgccagag ctggtggagc atgccaaaaa cctgagagtc    720
aatgcaggag atcagcctgg agctgatctt ggccctctga tcactcccca ggccaaagag    780
cgagtctgta atctgattga tagtggaaca aaggagggga cttccatcct tcttgatgga    840
cgaaaaatta agtgaaagg ctatgaaaat ggcaactttg ttggaccaac catcatctcg    900
aatgtcaagc caaatatgac ctgttacaaa gaggagattt ttggtccagt tcttgtggtt    960
ctggagacag aaacattgga tgaagccatc cagattgtaa ataacaaccc atatggaaat   1020
ggaactgcca tcttcaccac caatggagcc actgctcgga aatatgccca cttggtggat   1080
gttggacagg tgggagtgaa tgtccccatt ccagtgcctt tgccaatgtt ctcattcacc   1140
ggctctcgat cctccttcag gggagacacc aatttctatg caaacagggg catccaattc   1200
tacactcagt taaagaccat tacttctcag tggaaagaag aagatgctac tctttcctca   1260
cctgctgttg tcatgcctac catgggccgt tagaaacaag tttgtttaag actgactcca   1320
tcctgagtaa tctcccttta tttttgacca gcttcatttg tcagctttgc tcagatcaga   1380
tcgatgggat tggaatacat tgtaactaaa atcttaaaaa aaa                     1423
```

<210> SEQ ID NO 40
<211> LENGTH: 5574
<212> TYPE: DNA
<213> ORGANISM: Homo Sapiens

<400> SEQUENCE: 40

```
acgtactctg gcctcttctg cgtggtggtc aaccccctata aacacctgcc catctactcg     60
gagaagatcg tcgacatgta caagggcaag aagaggcacg agatgccgcc tcacatctac    120
gccatcgcag acacggccta ccggagcatg cttcaagatc gggaggacca gtccattcta    180
tgcacaggcg agtctggagc cgggaaaacc gaaaacacca agaaggtcat tcagtacctg    240
gccgtggtgg cctcctccca aagggcaag aaagacacaa gtatcacggg agagctggaa    300
aagcagcttc tacaagcaaa cccgattctg gaggctttcg gcaacgccaa aacagtgaag    360
aacgacaact cctcacgatt cggcaaattc atccgcatca acttcgacgt cacgggttac    420
atcgtgggag ccaacattga gacctatctg ctagaaaaat cacgggcaat tcgccaagcc    480
agagacgaga ggacattcca catcttttac tacatgattg ctggagccaa ggagaagatg    540
agaagtgact tgctttttgga gggcttcaac aactacacct tcctctccaa tggctttgtg    600
cccatcccag cagcccagga tgatgagatg ttccaggaaa ccgtggaggc catggcaatc    660
atgggtttca gcgaggagga gcagctatcc atattgaagg tggtatcatc ggtcctgcag    720
cttgaaaata tcgtcttcaa gaaggaaaga aacacagacc aggcgtccat gccagataac    780
acagctgctc agaaagtttg ccacctcatg ggaattaatg tgacagattt caccagatcc    840
```

-continued

| | |
|---|---|
| atcctcactc ctcgtatcaa ggttgggcga gatgtggtac agaaagctca gacaaaagaa | 900 |
| caggctgact tgctgtaga ggctttggcc aaggcaacat atgagcgcct tttccgctgg | 960 |
| atactcaccc gcgtgaacaa agccctggac aagacccatc ggcaagggc ttccttcctg | 1020 |
| gggatcctgg atatagctgg atttgagatc tttgaggtga actccttcga gcagctgtgc | 1080 |
| atcaactaca ccaacgagaa gctgcagcag ctcttcaacc acaccatgtt catcctggag | 1140 |
| caggaggagt accagcgcga gggcatcgag tggaacttca tcgactttgg gctggaccta | 1200 |
| cagccctgca tcgagctcat cgagcgaccg aacaaccctc caggtgtgct ggccctgctg | 1260 |
| gacgaggaat gctggttccc caaagccacg acaagtctt tcgtggagaa gctgtgcacg | 1320 |
| gagcagggca gccaccccaa gttccagaag cccaagcagc tcaaggacaa gactgagttc | 1380 |
| tccatcatcc attatgctgg aaggtggac tataatgcga gtgcctggct gaccaagaat | 1440 |
| atggacccgc tgaatgacaa cgtgacttcc ctgctcaatg cctcctccga caagtttgtg | 1500 |
| gccgacctgt ggaaggacgt ggaccgcatc gtgggcctgg accagatggc caagatgacg | 1560 |
| gagagctcgc tgcccagcgc ctccaagacc aagaagggca tgttccgcac agtggggcag | 1620 |
| ctgtacaagg agcagctggg caagctgatg accacgctac gcaacaccac gcccaacttc | 1680 |
| gtgcgctgca tcatccccaa ccacgagaag aggtccggca agctggatgc gttcctggtg | 1740 |
| ctggagcagc tgcggtgcaa tgggggtgctg gaaggcattc gcatctgccg gcagggcttc | 1800 |
| cccaaccgga tcgtcttcca ggagttccgc caacgctacg agatcctggc ggcgaatgcc | 1860 |
| atccccaaag gcttcatgga cgggaagcag gcctgcattc tcatgatcaa agccctggaa | 1920 |
| cttgacccca acttatacag gatagggcag agcaaaatct tcttccgaac tggcgtcctg | 1980 |
| gcccacctag aggaggagcg agatttgaag atcaccgatg tcatcatggc cttccaggcg | 2040 |
| atgtgtcgtg gctacttggc cagaaaggct tttgccaaga ggcagcagca gctgaccgcc | 2100 |
| atgaaggtga ttcagaggaa ctgcgccgcc tacctcaagc tgcggaactg gcagtggtgg | 2160 |
| aggcttttca ccaaagtgaa gccactgctg caggtgacac ggcaggagga ggagatgcag | 2220 |
| gccaaggagg atgaactgca gaagaccaag gagcggcagc agaaggcaga gaatgagctt | 2280 |
| aaggagctgg aacagaagca ctcgcagctg accgaggaga agaacctgct acaggaacag | 2340 |
| ctgcaggcag agacagagct gtatgcagag gctgaggaga tgcgggtgcg gctggcggcc | 2400 |
| aagaagcagg agctggagga gatactgcat gagatggagg cccgcctgga ggaggaggaa | 2460 |
| gacaggggcc agcagctaca ggctgaaagg aagaagatgg cccagcagat gctggacctt | 2520 |
| gaagaacagc tggaggagga ggaagctgcc aggcagaagc tgcaacttga aaggtcacg | 2580 |
| gctgaggcca agatcaagaa actggaggat gagatcctgg tcatggatga tcagaacaat | 2640 |
| aaactatcaa agaacgaaa actccttgag gagaggatta gtgacttaac gacaaatctt | 2700 |
| gcagaagagg aagaaaaggc caagaatctt accaagctga aaaacaagca tgaatctatg | 2760 |
| atttcagaac tggaagtgcg gctaaagaag aagagaagag gccgacagga gctggagaag | 2820 |
| ctgaaacgga agctggaggg tgatgccagc gacttccacg agcagatcgc tgacctccag | 2880 |
| gcgcagatcg cagagctcaa gatgcagctg gccaagaagg aggaggagct gcaggcggcc | 2940 |
| ctggccaggt tgacgatga atcgctcag aagaacaatg ccctgaagaa gatccgggag | 3000 |
| ctggagggcc acatctcaga cctccaggag gacctggact cagagcgggc cgccaggaac | 3060 |
| aaggctgaaa agcagaagcg agacctcggc gaggagctgg aggccctaaa gacagagctg | 3120 |
| gaagacacac tggacagcac agccactcag caggagctca gggccaagag ggagcaggag | 3180 |
| gtgacggtgc tgaagaaggc cctggatgaa gagacgcggt cccatgaggc tcaggtccag | 3240 |

```
gagatgaggc agaaacacgc acaggcggtg gaggagctca cagagcagct tgagcagttc    3300
aagagggcca aggcgaacct agacaagaat aagcagacgc tggagaaaga gaacgcagac    3360
ctggccgggg agctgcgggt cctgggccag gccaagcagg aggtggaaca taagaagaag    3420
aagctggagg cgcaggtgca ggagctgcag tccaagtgca gcgatgggga gcggccccgg    3480
gcggagctca atgacaaagt ccacaagctg cagaatgaag ttgagagcgt cacagggatg    3540
cttaacgagg ccgaggggaa ggccattaag ctggccaagg acgtggcgtc cctcagttcc    3600
cagctccagg acacccagga gctgcttcaa gaagaaaccc ggcagaagct caacgtgtct    3660
acgaagctgc gccagctgga ggaggagcgg aacagcctgc aagaccagct ggacgaggag    3720
atggaggcca agcagaacct ggagcgccac atctccactc tcaacatcca gctctccgac    3780
tcgaagaaga agctgcagga ctttgccagc accgtggaag ctctggaaga ggggaagaag    3840
aggttccaga aggagatcga gaacctcacc cagcagtacg aggagaaggc ggccgcttat    3900
gataaactgg aaaagaccaa gaacaggctt cagcaggagc tggacgacct ggttgttgat    3960
ttggacaacc agcggcaact cgtgtccaac ctggaaaaga gcagaggaa atttgatcag    4020 ttgttagccg aggagaaaaa catctcttcc aaatacgcgg atgagaggga cagagctgag    4080
gcagaagcca gggagaagga aaccaaggcc ctgtccctgg ctcgggccct tgaagaggcc    4140
ttggaagcca agaggaact cgagcggacc aacaaaatgc tcaaagccga aatggaagac    4200
ctggtcagct ccaaggatga cgtgggcaag aacgtccatg agctggagaa gtccaagcgg    4260 gcccctggaga cccagatgga ggagatgaag acgcagctgg aagagctgga ggacgagctg    4320
caagccacgg aggacgccaa actgcggctg gaagtcaaca tgcaggcgct caagggccag    4380
ttcgaaaggg atctccaagc ccgggacgag cagaatgagg agaagaggag gcaactgcag    4440
agacagcttc acgagtatga gacggaactg gaagacgagc gaaagcaacg tgccctggca    4500
gctgcagcaa agaagaagct ggaaggggac ctgaaagacc tggagcttca ggccgactct    4560
gccatcaagg ggagggagga agccatcaag cagctacgca aactgcaggc tcagatgaag    4620
gactttcaaa gagagctgga agatgcccgt gcctccagag atgagatctt tgccacagcc    4680
aaagagaatg agaagaaagc caagagcttg gaagcagacc tcatgcagct acaagaggac    4740
ctcgccgccg ctgagagggc tcgcaaacaa gcggacctcg agaaggagga actggcagag    4800
gagctggcca gtagcctgtc gggaaggaac gcactccagg acgagaagcg ccgcctggag    4860
gcccggatcg cccagctgga ggaggagctg gaggaggagc agggcaacat ggaggccatg    4920
agcgaccggg tccgcaaagc cacacagcag gccgagcagc tcagcaacga gctggccaca    4980
gagcgcagca cggcccagaa gaatgagagt gcccggcagc agctcgagcg gcagaacaag    5040
gagctccgga gcaagctcca cgagatggag ggggccgtca agtccaagtt caagtccacc    5100
atcgcggcgc tggaggccaa gattgcacag ctggaggagc aggtcgagca ggaggccaga    5160
gagaaacagg cggccaccaa gtcgctgaag cagaaagaca agaagctgaa ggaaatcttg    5220
ctgcaggtgg aggacgagcg caagatggcc gagcagtaca agaggcaggc agagaaaggc    5280
aatgccaggg tcaagcagct caagaggcag ctggaggagg cagaggagga gtcccagcgc    5340
atcaacgcca accgcaggaa gctgcagcgg gagctggatg aggccacgga gagcaacgag    5400
gccatgggcc gcgaggtgaa cgcactcaag agcaagctca ggcgaggaaa cgagacctct    5460
ttcgttcctt ctagaaggtc tggaggacgt agagttattg aaaatgcaga tggttctgag    5520
gaggaaacgg acactcgaga cgcagacttc aatggaacca aggccagtga ataa         5574
```

<210> SEQ ID NO 41
<211> LENGTH: 5926
<212> TYPE: DNA
<213> ORGANISM: Homo Sapiens

<400> SEQUENCE: 41

| | | | | | |
|---|---|---|---|---|---|
| ccggctgcct | ctgctgcagt | tcagagcaac | ttcaggagct | tcccagccga | gagcttcagg | 60 |
| acgcctttcc | tgtcccactg | gcccagttgc | cacaacaaac | aacagagaag | acggtgacca | 120 |
| tgggggatgt | gaagctggtt | gcctcgtcac | acatttccaa | aacctccctc | agtgtggatc | 180 |
| cctcaagagt | tgactccatg | cccctgacag | aggcccctgc | tttcattttg | cccctcgga | 240 |
| acctctgcat | caaagaagga | gccaccgcca | agttcgaagg | gcgggtccgg | ggttacccag | 300 |
| agccccaggt | gacatggcac | agaaacgggc | aacccatcac | cagcgggggc | cgcttcctgc | 360 |
| tggattgcgg | catccggggg | actttcagcc | ttgtgattca | tgctgtccat | gaggaggaca | 420 |
| ggggaaagta | tacctgtgaa | gccaccaatg | gcagtggtgc | tcgccaggtg | acagtggagt | 480 |
| tgacagtaga | aggaagtttt | gcgaagcagc | ttggtcagcc | tgttgtttcc | aaaaccttag | 540 |
| gggatagatt | ttcagcttca | gcagtggaga | cccgtcctag | catctggggg | gagtgcccac | 600 |
| caaagtttgc | taccaagctg | gccgagttg | tggtcaaaga | aggacagatg | ggacgattct | 660 |
| cctgcaagat | cactggccgg | ccccaaccgc | aggtcacctg | gctcaaggga | aatgttccac | 720 |
| tgcagccgag | tgcccgtgtg | tctgtgtctg | agaagaacgg | catgcaggtt | ctggaaatcc | 780 |
| atggagtcaa | ccaagatgac | gtgggagtgt | acacgtgcct | ggtggtgaac | gggtcgggga | 840 |
| aggcctcgat | gtcagctgaa | ctttccatcc | aaggtttgga | cagtgccaat | aggtcatttg | 900 |
| tgagagaaac | aaaagccacc | aattcagatg | tcaggaaaga | ggtgaccaat | gtaatctcaa | 960 |
| aggagtcgaa | gctggacagt | ctggaggctg | cagccaaaag | caagaactgc | tccagccccc | 1020 |
| agagaggtgg | ctccccaccc | tgggctgcaa | acagccagcc | tcagccccca | agggagtcca | 1080 |
| agctggagtc | atgcaaggac | tcgcccagaa | cggccccgca | gaccccggtc | cttcagaaga | 1140 |
| cttccagctc | catcaccctg | caggccgcaa | gagttcagcc | ggaaccaaga | gcaccaggcc | 1200 |
| tgggggtcct | atcaccttct | ggagaagaga | ggaagaggcc | agctcctccc | cgtccagcca | 1260 |
| ccttccccac | caggcagcct | ggcctgggga | gccaagatgt | tgtgagcaag | gctgctaaca | 1320 |
| ggagaatccc | catggagggc | cagagggatt | cagcattccc | caaatttgag | agcaagcccc | 1380 |
| aaagccagga | ggtcaaggaa | aatcaaactg | tcaagttcag | atgtgaagtt | ccgggattc | 1440 |
| caaagcctga | agtggcctgg | ttcctggaag | gcaccccgt | gaggagacag | gaaggcagca | 1500 |
| ttgaggtttta | tgaagatgct | ggctcccatt | acctctgcct | gctgaaagcc | cggaccaggg | 1560 |
| acagtgggac | atacagctgc | actgcttcca | acgcccaagg | ccaggtgtcc | tgtagctgga | 1620 |
| ccctccaagt | ggaaaggctt | gccgtgatgg | aggtggcccc | ctccttctcc | agtgtcctga | 1680 |
| aggactgcgc | tgttattgag | gccaggatt | ttgtgctgca | gtgctccgta | cggggaccc | 1740 |
| cagtgccccg | gatcacttgg | ctgctgaatg | ggcagcccat | ccagtacgct | cgctccacct | 1800 |
| gcgaggccgg | cgtggctgag | ctccacatcc | aggatgccct | gccggaggac | catggcacct | 1860 |
| acacctgcct | agctgagaat | gccttgggc | aggtgtcctg | cagcgcctgg | gtcaccgtcc | 1920 |
| atgaaaagaa | gagtagcagg | aagagtgagt | accttctgcc | tgtggctccc | agcaagccca | 1980 |
| ctgcacccat | cttcctgcag | ggcctctctg | atctcaaagt | catggatgga | agccaggtca | 2040 |
| ctatgactgt | ccaagtgtca | gggaatccac | ccctgaagt | catctggctg | cacaatggga | 2100 |
| atgagatcca | agagtcagag | gacttccact | ttgaacagag | aggaactcag | cacagccttt | 2160 |

```
ggatccagga agtgttcccg gaggacacgg gcacgtacac ctgcgaggcc tggaacagcg    2220
ctggagaggt ccgcacccag gccgtgctca cggtacaaga gcctcacgat ggcacccagc    2280
cctggttcat cagtaagcct cgctcagtga cagcctccct gggccagagt gtcctcatct    2340
cctgcgccat agctggtgac ccctttccta ccgtgcactg gctcagagat ggcaaagccc    2400
tctgcaaaga cactggccac ttcgaggtgc ttcagaatga ggacgtgttc accctggttc    2460
taaagaaggt gcagccctgg catgccggcc agtatgagat cctgctcaag aaccgggttg    2520
gcgaatgcag ttgccaggtg tcactgatgc tacagaacag ctctgccaga gcccttccac    2580
gggggaggga gcctgccagc tgcgaggacc tctgtggtgg aggagttggt gctgatggtg    2640
gtggtagtga ccgctatggg tccctgaggc ctggctggcc agcaagaggg cagggttggc    2700
tagaggagga agacggcgag gacgtgcgag gggtgctgaa gaggcgcgtg gagacgaggc    2760
agcacactga ggaggcgatc cgccagcagg aggtggagca gctggacttc cgagacctcc    2820
tggggaagaa ggtgagtaca aagaccctat cggaagacga cctgaaggag atcccggccg    2880
agcagatgga tttccgtgcc aacctgcagc ggcaagtgaa gccaaagact gtgtctgagg    2940
aagagaggaa ggtgcacagc ccccagcagg tcgattttcg ctctgtcctg gccaagaagg    3000
ggacttccaa gaccccgtgc ctgagaaggt gccaccgcc aaaacctgcc accccggatt     3060
ttcgctcagt gctgggtggc aagaagaaat taccagcaga gaatggcagc agcagtgccg    3120
agaccctgaa tgccaaggca gtggagagtt ccaagcccct gagcaatgca cagccttcag    3180
ggcccttgaa accgtgggc aacgccaagc ctgctgagac cctgaagcca atgggcaacg     3240
ccaagcctgc cgagaccctg aagcccatgg gcaatgccaa gctgatgag aacctgaaat     3300 ccgctagcaa agaagaactc aagaaagacg ttaagaatga tgtgaactgc aagagaggcc    3360
atgcagggac cacagataat gaaaagagat cagagagcca ggggacagcc ccagccttca    3420
agcagaagct gcaagatgtt catgtggcag agggcaagaa gctgctgctc cagtgccagg    3480
tgtcttctga cccccagcc accatcatct ggacgctgaa tggaaagacc ctcaagacca     3540
ccaagttcat catcctctcc caggaaggct cactctgctc cgtctccatc gagaaggcac    3600
tgcctgagga cagaggctta tacaagtgtg tagccaagaa tgcgctggc caggcggagt     3660 gctcctgcca agtcaccgtg gatgatgctc cagccagtga aacaccaag gccccagaga     3720 tgaaatcccg gaggcccaag agctctcttc ctcccgtgct aggaactgag agtgatgcga    3780
ctgtgaaaaa gaaacctgcc cccaagacac ctccgaaggc agcaatgccc cctcagatca    3840
tccagttccc tgaggaccag aaggtacgcg caggagagtc agtggagctg tttggcaaag    3900
tgacaggcac tcagcccatc acctgtacct ggatgaagtt ccgaaagcag atccaggaaa    3960
gcgagcacat gaaggtggag aacagcgaga tggcagcaa gctcaccatc ctggccgcgc     4020
gccaggagca ctgcggctgc tacacactgc tggtggagaa caagctgggc agcaggcagg    4080
cccaggtcaa cctcactgtc gtggataagc cagacccccc agctggcaca ccttgtgcct    4140
ctgacattcg gagctcctca ctgaccctgt cctggtatgg ctcctcatat gatggggca     4200 gtgctgtaca gtcctacagc atcgagatct gggactcagc caacaagacg tggaaggaac    4260
tagccacatg ccgcagcacc tctttcaacg tccaggacct gctgcctgac acgaatata     4320 agttccgtgt acgtgcaatc aacgtgtatg gaaccagtga gccaagccag gagtctgaac    4380
tcacaacggt aggagagaaa cctgaagagc gaaggatga gtggaggtg tcagatgatg     4440 atgagaagga gcccgaggtt gattaccgga cagtgacaat caatactgaa caaaaagtat    4500
```

-continued

```
ctgacttcta cgacattgag gagagattag gatctgggaa atttggacag gtctttcgac    4560
ttgtagaaaa gaaaactcga aaagtctggg cagggaagtt cttcaaggca tattcagcaa    4620
aagagaaaga gaatatccgg caggagatta gcatcatgaa ctgcctccac cacccctaagc   4680 tggtccagtg tgtggatgcc tttgaagaaa aggccaacat cgtcatggtc ctggagatcg    4740
tgtcaggagg ggagctgttt gagcgcatca ttgacgagga ctttgagctg acggagcgtg    4800
agtgcatcaa gtacatgcgg cagatctcgg agggagtgga gtacatccac aagcagggca   4860
tcgtgcacct ggacctcaag ccggagaaca tcatgtgtgt caacaagacg ggcaccagga   4920
tcaagctcat cgactttggt ctggccagga ggctggagaa tgcggggtct ctgaaggtcc    4980
tctttggcac cccagaattt gtggctcctg aagtgatcaa ctatgagccc atcggctacg   5040
ccacagacat gtggagcatc ggggtcatct gctacatcct agtcagtggc ctttccccct   5100
tcatgggaga caacgataac gaaaccttgg ccaacgttac ctcagccacc tgggacttcg   5160
acgacgaggc attcgatgag atctccgacg atgccaagga tttcatcagc aatctgctga   5220
agaaagatat gaaaaaccgc ctggactgca cgcagtgcct tcagcatcca tggctaatga   5280
aagataccaa gaacatggag gccaagaaac tctccaagga ccggatgaag aagtacatgg   5340
caagaaggaa atggcagaaa cgggcaatg ctgtgagagc cattggaaga ctgtcctcta   5400
tggcaatgat ctcagggctc agtggcagga aatcctcaac agggtcacca accagcccgc   5460
tcaatgcaga aaaactagaa tctgaagaag atgtgtccca gctttccttg gaggctgttg   5520
ctgaggaaaa gcctcatgta aaaccctatt tctctaagac cattcgcgat ttagaagttg   5580
tggagggaag tgctgctaga tttgactgca agattgaagg atacccagac cccgaggttg   5640
tctggttcaa agatgaccag tcaatcaggg agtcccgcca cttccagata gactacgatg   5700
aggacgggaa ctgctctttta attattagtg atgtttgcgg ggatgacgat gccaagtaca   5760
cctgcaaggc tgtcaacagt cttggagaag ccacctgcac agcagagctc attgtggaaa   5820
cgatggagga aggtgaaggg gaaggggaag aggaagaaga gtgaaacaaa gccagagaaa   5880
agcagtttct aagtcatatt aaaaggacta tttctctcaa aatcca                  5926
```

<210> SEQ ID NO 42
<211> LENGTH: 3705
<212> TYPE: DNA
<213> ORGANISM: Homo Sapiens

<400> SEQUENCE: 42

```
ggaattcccg gccgggcgca cccgcggggc cctgggctcg ctggcttgcg cgcagctgag     60
cggggtgtag gttggaaggg ccagggcccc tggggcgcaa gtgggggccg cgccatgga    120 accccgacc gtcccctcgg aaaggagcct gtctctgtca ctgcccgggc cccgggaggg   180
ccaggccacc ctgaagcctc ccccgcagca cctgtggcgg cagcctcgga cccccatccg    240
tatccagcag cgcggctact ccgacagcgc ggagcgcgcc gagcgggagc ggcagccgca   300
ccggcccata gagcgcgccg atgccatgga caccagcgac cggcccggcc tgcgcacgac   360
ccgcatgtcc tggccctcgt ccttccatgg cactggcacc ggcagcggcg cgcgggcgg    420 aggcagcagc aggcgcttcg aggcagagaa tgggccgaca ccatctcctg gccgcagccc   480
cctggactcg caggcgagcc caggactcgt gctgcacgcc ggggcggcca ccagccagcg   540
ccgggagtcg ttcctgtacc gctcagacag cgactatgac atgtcaccca agaccatgtc   600
ccggaactca tcggtcacca gcgaggcgca cgctgaagac ctcatcgtaa caccatttgc   660
tcaggtgctg gccagcctcc ggagcgtccg tagcaacttc tcactcctga ccaatgtgcc   720
```

-continued

```
cgttcccagt aacaagcggt ccccgctggg cggccccacc cctgtctgca aggccacgct    780
gtcagaagaa acgtgtcagc agttggcccg ggagactctg gaggagctgg actggtgtct    840
ggagcagctg gagaccatgc agacctatcg ctctgtcagc gagatggcct cgcacaagtt    900
caaaaggatg ttgaaccgtg agctcacaca cctgtcagaa atgagcaggt ccggaaacca    960
ggtctcagag tacatttcca caacattcct ggacaaacag aatgaagtgg agatcccatc   1020
acccacgatg aaggaacgag aaaaacagca agcgccgcga ccaagaccct ccagccgcc   1080 cccgccccct gtaccacact tacagcccat gtcccaaatc acagggttga aaaagttgat   1140
gcatagtaac agcctgaaca actctaacat tccccgattt ggggtgaaga ccgatcaaga   1200
agagctcctg gcccaagaac tggagaacct gaacaagtgg ggcctgaaca tcttttgcgt   1260
gtcggattac gctggaggcc gctcactcac ctgcatcatg tacatgatat tccaggagcg   1320
ggacctgctg aagaaattcc gcatcccggt ggacacgatg gtgacataca tgctgacgct   1380
ggaggatcac taccacgctg acgtggccta ccataacagc ctgcacgcag ctgacgtgct   1440
gcagtccacc cacgtactgc tggccacgcc tgcactagat gcagtgttca cggacctgga   1500
gattctcgcc gccctcttcg cggctgccat ccacgatgtg atcaccctg ggtctccaa   1560 ccagttcctc atcaacacca attcggagct ggcgctcatg tacaacgatg agtcggtgct   1620
cgagaatcac cacctggccg tgggcttcaa gctgctgcag gaggacaact gcgacatctt   1680
ccagaacctc agcaagcgcc agcggcagag cctacgcaag atggtcatcg acatggtgct   1740
ggccacggac atgtccaagc acatgaccct cctggctgac ctgaagacca tggtggagac   1800
caagaaagtg accagctcag gggtcctcct gctagataac tactccgacc gcatccaggt   1860
cctccggaac atggtgcact gtgccgacct cagcaaccc accaagccgc tggagctgta   1920
ccgccagtgg acagaccgca tcatggccga gttcttccag cagggtgacc gagagcgcga   1980
gcgtggcatg gaaatcagcc ccatgtgtga caagcacact gcctccgtgg agaagtctca   2040
ggtgggtttt attgactaca ttgtgcaccc attgtgggag acctgggcgg accttgtcca   2100
cccagatgcc caggagatct tggacacttt ggaggacaac cgggactggt actacagcgc   2160
catccggcag agcccatctc cgccacccga ggaggagtca aggggccag gccacccacc   2220 cctgcctgac aagttccagt ttgagctgac gctggaggag aagaggagg aagaaatatc   2280 aatggcccag ataccgtgca cagcccaaga ggcattgact gcgcagggat tgtcaggagt   2340
cgaggaagct ctggatgcaa ccatagcctg ggaggcatcc ccgcccagg agtcgttgga   2400 agttatggca caggaagcat ccctggaggc cgagctggag gcagtgtatt tgacacagca   2460
ggcacagtcc acaggcagtg cacctgtggc tccggatgag ttctcgtccc gggaggaatt   2520
cgtggttgct gtaagccaca gcagcccctc tgccctggct cttcaaagcc ccttctccc   2580 tgcttggagg accctgtctg tttcagagca tgccccgggc ctcccgggcc tccctccac   2640 ggcggccgag gtggaggccc aacgagagca ccaggctgcc aagagggctt gcagtgcctg   2700
cgcagggaca tttggggagg acacatccgc actcccagct cctggtggcg gggggtcagg   2760
tggagaccct acctgatccc cagacctctg tccctgttcc cctccactcc tccctcact   2820 cccctgctcc cccgaccacc tcctcctctg cctcaaagac tcttgtcctc ttgtccctcc   2880
tgagaaaaaa gaaaacgaaa agtggggttt ttttctgttt tctttttttc ccttttcccc   2940
ctgcccccac ccacgggggcc ttttttttgga ggtgggggct ggggaatgag gggctgaggt   3000
cccggaagga tttttatttt ttgaatttta attgtaacat ttttagaaaa agaacaaaaa   3060
```

```
aagaaaaaaa aaagaaagaa acacagcaac tgtagatgct cctgttcctg gttcccgctt    3120
tccacttcca aatccctccc ctcaccttcc cccactgccc cccaagttcc aggctcagtc    3180
ttccagccgc ctggggagtc tctacctggg cccaagcagg tgtggggcct ccttctgggc    3240
ttttcttctg aatttagagg atttctagaa cgtggtcagg aatagccatt ctaggcgggg    3300
ctggggccag ggtgggggc agtcactgtg ggaggtccca gctccagccc ccctctggtt    3360
tgctgcctcc tctcccctct aaaaaagtct tccgcttgat tttgcacaat cccggcgata    3420
ctcctggcga tactgactag aagtcaggga gctgggggag ctgttcactt taggatacgg    3480
ggggatggaa gggagcgttc acaccgccag cctcgggcct gggatttgag gagggcccta    3540
gacctcctcc actctccatc ccctttccct tccactttgg gttcactttg aattttctcc    3600
gttttttggg gcagtggctc tgatccactc acccccccgc cccgtaagtt atagccactg    3660
tggaaagtag tatgaaagtt cctcaagaaa ctaaaaatgg aattc                    3705

<210> SEQ ID NO 43
<211> LENGTH: 3151
<212> TYPE: DNA
<213> ORGANISM: Homo Sapiens

<400> SEQUENCE: 43
ccggccagcg ggcgggctcc ccagccaggc cgctgcacct gtcagggaa caagctggag        60 gagcaggacc ctagacctct gcagcccata ccaggtctca tggaggggaa caagctggag       120
gagcaggact ctagccctcc acagtccact ccagggctca tgaaggggaa caagcgtgag       180
gagcaggggc tgggccccga acctgcggcg ccccagcagc ccacggcgga ggaggaggcc       240
ctgatcgagt ccaccgctc ctaccgagag ctcttcgagt tcttctgcaa caacaccacc       300
atccacggcg ccatccgcct ggtgtgctcc cagcacaacc gcatgaagac ggccttctgg       360
gcagtgctgt ggctctgcac cttggcatg atgtactggc aattcggcct gcttttcgga       420
gagtacttca gctaccccgt cagcctcaac atcaacctca actcggacaa gctcgtcttc       480
cccgcagtga ccatctgcac cctcaatccc tacaggtacc cggaaattaa agaggagctg       540
gaggagctgg accgcatcac agagcagacg ctctttgacc tgtacaaata cagctccttc       600
accactctcg tggccggctc ccgcagccgt cgcgacctgc ggggggactct gccgcacccc       660 ttgcagcgcc tgagggtccc gcccccgcct cacgggggccc gtcgagcccg tagcgtggcc       720
tccagcttgc gggacaacaa ccccccaggtg gactggaagg actggaagat cggcttccag       780
ctgtgcaacc agaacaaatc ggactgcttc taccagacat actcatcagg ggtggatgcg       840
gtgagggagt ggtaccgctt ccactacatc aacatcctgt cgaggctgcc agagactctg       900
ccatccctgg aggaggacac gctgggcaac ttcatcttcg cctgccgctt caaccaggtc       960
tcctgcaacc aggcgaatta ctctcacttc caccacccga tgtatggaaa ctgctatact      1020
ttcaatgaca gaacaactc caacctctgg atgtcttcca tgcctggaat caacaacggt      1080
ctgtccctga tgctgcgcgc agagcagaat gacttcattc ccctgctgtc cacagtgact      1140
ggggcccggg taatggtgca cggcaggat gaacctgcct ttatggatga tggtggcttt      1200
aacttgcggc ctggcgtgga gacctccatc agcatgagga aggaaaccct ggacagactt      1260
gggggcgatt atggcgactg caccaagaat ggcagtgatg ttcctgttga gaacctttac      1320
ccttcaaagt acacacagca ggtgtgtatt cactcctgct tccaggagag catgatcaag      1380
gagtgtggct gtgcctacat cttctatccg cggccccaga acgtggagta ctgtgactac      1440
agaaagcaca gttcctgggg gtactgctac tataagctcc aggttgactt ctcctcagac      1500
```

-continued

```
cacctgggct gtttcaccaa gtgccggaag ccatgcagcg tgaccagcta ccagctctct   1560
gctggttact cacgatggcc ctcggtgaca tcccaggaat gggtcttcca gatgctatcg   1620
cgacagaaca attacaccgt caacaacaag agaaatggag tggccaaagt caacatcttc   1680
ttcaaggagc tgaactacaa aaccaattct gagtctccct ctgtcacgat ggtcaccctc   1740
ctgtccaacc tgggcagcca gtggagcctg tggttcggcc cctcggtgtt gtctgtggtg   1800
gagatggctg agctcgtctt tgacctgctg gtcatcatgt tcctcatgct gctccgaagg   1860
ttccgaagcc gatactggtc tccaggccga ggggcaggg gtgctcagga ggtagcctcc    1920
accctggcat cctcccctcc ttcccacttc tgccccacc ccatgtctct gtccttgtcc    1980
cagccaggcc ctgctccctc tccagccttg acagcccctc ccctgccta tgccaccctg    2040
ggcccccgcc catctccagg gggctctgca ggggccagtt cctccacctg tcctctgggg   2100
gggcctgag agggaaggag aggtttctca caccaaggca gatgctcctc tggtgggagg    2160
gtgctggccc tggcaagatt gaaggatgtg cagggcttcc tctcagagcc gcccaaactg   2220
ccgttgatgt gtgagggga agcaagatgg gtaagggctc aggaagttgc tccaagaaca    2280
gtagctgatg aagctgccca gaagtgcctt ggctccagcc ctgtacccct tggtactgcc   2340
tctgaacact ctggtttccc cacccaactg cggctaagtc tcttttttccc ttggatcagc  2400
caagcgaaac ttggagcttt gacaaggaac tttcctaaga accgctgat aaccaggaca    2460
aaacacaacc aagggtacac gcaggcatgc acgggtttcc tgcccagcga cggcttaagc   2520
cagcccccga ctggcctggc cacactgctc tccagtagca cagatgtctg ctcctcctct   2580
tgaacttggg tgggaaaccc cacccaaaag ccccctttgt tacttaggca attcccctc    2640
cctgactccc gagggctagg gctagagcag acccgggtaa gtaaaggcag acccagggct   2700
cctctagcct catacccgtg ccctcacaga gccatgcccc ggcacctctg ccctgtgtct   2760
ttcatacctc tacatgtctg cttgagatat ttcctcagcc tgaaagtttc cccaaccatc   2820
tgccagagaa ctcctatgca tcccttagaa ccctgctcag acaccattac ttttgtgaac   2880
gcttctgcca catcttgtct tccccaaaat tgatcactcc gccttctcct gggctcccgt   2940
agcacactat aacatctgct ggagtgttgc tgttgcacca tactttcttg tacatttgtg   3000
tctcccttcc caactagact gtaagtgcct tgcggtcagg gactgaatct tgcccgttta   3060
tgtatgctcc atgtctagcc catcatcctg cttggagcaa gtaggcagga gctcaataaa   3120
tgtttgttgc atgaaaaaaa aaaaaaaaaa a                                  3151

<210> SEQ ID NO 44
<211> LENGTH: 1172
<212> TYPE: DNA
<213> ORGANISM: Homo Sapiens

<400> SEQUENCE: 44
gagacattcc tcaattgctt agacatattc tgagcctaca gcagaggaac ctccagtctc     60
agcaccatga atcaaactgc gattctgatt tgctgcctta tctttctgac tctaagtggc    120
attcaaggag tacctctctc tagaaccgta cgctgtacct gcatcagcat tagtaatcaa    180
cctgttaatc caaggtcttt agaaaaactt gaaattattc ctgcaagcca attttgtcca    240
cgtgttgaga tcattgctac aatgaaaaag aagggtgaga agagatgtct gaatccagaa    300
tcgaaggcca tcaagaattt actgaaagca gttagcaagg aaatgtctaa aagatctcct    360
taaaaccaga ggggagcaaa atcgatgcag tgcttccaag gatggaccac acagaggctg    420
```

| | |
|---|---|
| cctctcccat cacttcccta catggagtat atgtcaagcc ataattgttc ttagtttgca | 480 |
| gttacactaa aaggtgacca atgatggtca ccaaatcagc tgctactact cctgtaggaa | 540 |
| ggttaatgtt catcatccta agctattcag taataactct accctggcac tataatgtaa | 600 |
| gctctactga ggtgctatgt tcttagtgga tgttctgacc ctgcttcaaa tatttccctc | 660 |
| acctttccca tcttccaagg gtactaagga atctttctgc tttggggttt atcagaattc | 720 |
| tcagaatctc aaataactaa aaggtatgca atcaaatctg cttttttaaag aatgctcttt | 780 |
| acttcatgga cttccactgc catcctccca aggggcccaa attctttcag tggctaccta | 840 |
| catacaattc caaacacata caggaaggta gaaatatctg aaaatgtatg tgtaagtatt | 900 |
| cttatttaat gaaagactgt acaaagtata agtcttagat gtatatattt cctatattgt | 960 |
| tttcagtgta catggaataa catgtaatta agtactatgt atcaatgagt aacaggaaaa | 1020 |
| ttttaaaaat acagatagat atatgctctg catgttacat aagataaatg tgctgaatgg | 1080 |
| ttttcaaata aaaatgaggt actctcctgg aaatattaag aaagactatc taaatgttga | 1140 |
| aagatcaaaa ggttaataaa gtaattataa ct | 1172 |

<210> SEQ ID NO 45
<211> LENGTH: 1044
<212> TYPE: DNA
<213> ORGANISM: Homo Sapiens

<400> SEQUENCE: 45

| | |
|---|---|
| gaattccctg aggaggcgaa tccggcgggt atcagagcca tcagaaccgc caccatgacg | 60 |
| gtgggcaaga gcagcaagat gctgcagcat attgattaca ggatgaggtg catcctgcag | 120 |
| gacggccgga tcttcattgg caccttcaag gcttttgaca agcacatgaa tttgatcctc | 180 |
| tgtgactgtg atgagttcag aaagatcaag ccaagaact ccaaacaagc agaaagggaa | 240 |
| gagaagcgag tcctcggtct ggtgctgctg cgagggaga atctggtctc aatgacagta | 300 |
| gagggacctc ctcccaaaga tactggtatt gctcgagttc cacttgctgg agctgccggg | 360 |
| ggcccaggga tcggcagggc tgctggcaga ggaatcccag ctggggttcc catgccccag | 420 |
| gctcctgcag gacttgctgg gccagtccgt ggggttggcg ggccatccca acaggtgatg | 480 |
| accccacaag gaagaggtac tgttgcagcc gctgcagctg ctgccacagc cagtattgcc | 540 |
| ggggctccaa cccagtaccc acctggccgt gggggtcctc cccacctat gggccgagga | 600 |
| gcaccccctc caggcatgat gggcccacct cctggtatga gacctcctat gggtccccca | 660 |
| atggggatcc cccctggaag agggactcca atgggcatgc ccctccggg aatgcggcct | 720 |
| cctccccctg ggatgcgagg ccttctttga cccttggcca cagagtatgg aagtagctcc | 780 |
| gcagaggcgt gggctcgatt cctcagggcc acgttaccac agacctgttt gtttcttatg | 840 |
| ctgttgttcg tggagtctca tgggattgtc tggtttccct tacagggccc cctcccccgg | 900 |
| gaatgcgccc accaaggccc tagactcatc ttggccctcc tcagctccct gcctgtttcc | 960 |
| cgtaaggctg tacatagtcc tttatctcc ttgtggccta tgaaactggt ttataataaa | 1020 |
| ctcttaagag aacattataa ttgc | 1044 |

<210> SEQ ID NO 46
<211> LENGTH: 2607
<212> TYPE: DNA
<213> ORGANISM: Homo Sapiens

<400> SEQUENCE: 46

| | |
|---|---|
| attaaacctc tcgccgagcc cctccgcaga ctctgcgccg gaaagtttca tttgctgtat | 60 |

```
gccatcctcg agagctgtct aggttaacgt tcgcactctg tgtatataac ctcgacagtc    120
ttggcaccta acgtgctgtg cgtagctgct cctttggttg aatccccagg cccttgttgg    180
ggcacaaggt ggcaggatgt ctcagtggta cgaacttcag cagcttgact caaaattcct    240
ggagcaggtt caccagcttt atgatgacag ttttcccatg gaaatcagac agtacctggc    300
acagtggtta gaaaagcaag actgggagca cgctgccaat gatgtttcat ttgccaccat    360
ccgttttcat gacctcctgt cacagctgga tgatcaatat agtcgctttt ctttggagaa    420
taacttcttg ctacagcata acataaggaa aagcaagcgt aatcttcagg ataattttca    480
ggaagaccca atccagatgt ctatgatcat ttacagctgt ctgaaggaag aaaggaaaat    540
tctggaaaac gcccagagat ttaatcaggc tcagtcgggg aatattcaga gcacagtgat    600
gttagacaaa cagaaagagc ttgacagtaa agtcagaaat gtgaaggaca aggttatgtg    660
tatagagcat gaaatcaaga gcctggaaga tttacaagat gaatatgact caaatgcaa     720 aaccttgcag aacagagaac acgagaccaa tggtgtggca aagagtgatc agaaacaaga    780
acagctgtta ctcaagaaga tgtatttaat gcttgacaat aagagaaagg aagtagttca    840
caaaataata gagttgctga atgtcactga acttacccag aatgccctga ttaatgatga    900
actagtggag tggaagcgga gacagcagag cgcctgtatt ggggggccgc ccaatgcttg    960
cttggatcag ctgcagaact ggttcactat agttgcggag agtctgcagc aagttcggca    1020
gcagcttaaa aagttggagg aattggaaca gaaatacacc tacgaacatg accctatcac    1080
aaaaaacaaa caagtgttat gggaccgcac cttcagtctt ttccagcagc tcattcagag    1140
ctcgtttgtg gtggaaagac agccctgcat gccaacgcac cctcagaggc cgctggtctt    1200
gaagacaggg gtccagttca ctgtgaagtt gagactgttg gtgaaattgc aagagctgaa    1260
ttataatttg aaagtcaaag tcttatttga taaagatgtg aatgagagaa atacagtaaa    1320
aggatttagg aagttcaaca ttttgggcac gcacacaaaa gtgatgaaca tggaggagtc    1380
caccaatggc agtctggcgg ctgaatttcg gcacctgcaa ttgaaagaac agaaaaatgc    1440
tggcaccaga acgaatgagg gtcctctcat cgttactgaa gagcttcact cccttagttt    1500
tgaaacccaa ttgtgccagc ctggtttggt aattgacctc gagacgacct ctctgcccgt    1560
tgtggtgatc tccaacgtca gccagctccc gagcggttgg gcctccatcc tttggtacaa    1620
catgctggtg gcggaaccca ggaatctgtc cttcttcctg actccaccat gtgcacgatg    1680
ggctcagctt tcagaagtgc tgagttggca gttttcttct gtcaccaaaa gaggtctcaa    1740
tgtggaccag ctgaacatgt gggagagaa gcttcttggt cctaacgcca gcccgatgg     1800 tctcattccg tggacgaggt tttgtaagga aaatataaat gataaaaatt ttcccttctg    1860
gctttggatt gaaagcatcc tagaactcat taaaaaacac ctgctccctc tctggaatga    1920
tgggtgcatc atgggcttca tcagcaagga gcgagagcgt gccctgttga aggaccagca    1980 gccgggacc ttcctgctgc ggttcagtga gagctcccgg aaggggcca tcacattcac      2040 atgggtggag cggtcccaga acggaggcga acctgacttc catgcggttg aaccctacac    2100
gaagaaagaa ctttctgctg ttactttccc tgacatcatt cgcaattaca agtcatggc     2160 tgctgagaat attcctgaga atccccctgaa gtatctgtat ccaaatattg acaaagacca   2220
tgcctttgga agtattact ccaggccaaa ggaagcacca gagccaatgg aacttgatgg     2280
ccctaaagga actggatata tcaagactga gttgatttct gtgtctgaag tgtaagtgaa    2340
cacagaagag tgacatgttt acaaacctca agccagcctt gctcctggct ggggcctgtt    2400
```

-continued

| | |
|---|---|
| gaagatgctt gtattttact tttccattgt aattgctatc gccatcacag ctgaacttgt | 2460 |
| tgagatcccc gtgttactgc ctatcagcat tttactactt taaaaaaaaa aaaaaaagcc | 2520 |
| aaaaaccaaa tttgtattta aggtatataa attttcccaa aactgatacc ctttgaaaaa | 2580 |
| gtataaataa aatgagcaaa agttgaa | 2607 |

<210> SEQ ID NO 47
<211> LENGTH: 5257
<212> TYPE: DNA
<213> ORGANISM: Homo Sapiens

<400> SEQUENCE: 47

| | |
|---|---|
| gaattccttt ttttttttgag ctttaaataa agcatttatt catgagcgga agcttacagt | 60 |
| ttgcatagat tcttcatacc ttatctggaa gggcgatgga aaccccaagg cactagagag | 120 |
| catcagaaga aatcagtgac atgatttgag tagggctggg ggactgggtc cctgcaccccc | 180 |
| agccacatcc tatgggcctt aggcccatac tcggagaacg agtccattgg acaaagaaca | 240 |
| tggctgagag accttctggg ggccttgaag aggccgcctc cttggtctcc tcaaccccag | 300 |
| tgtaagtctg gggaggccca aggtgagggt catgtatcgg gatgaatgta agaagcactt | 360 |
| ggcaggcttg ggggctttgg ggctgggcag cctgatcact gaactcacgg caaatgaaga | 420 |
| attgaccggg actgacggtg ccttggtaaa tgatgaaggg tgggttagga gtacagaaga | 480 |
| tgctgtggac tattcagaca tcaatgaggg ggcagaagat gaaagccgaa gataccagca | 540 |
| gacgatgggg agcttgcagc ccctttgcca ctcagattat gatgaagatg actatgatgc | 600 |
| tgattgtgaa gacattgatt gcaagttgat gcctcctcca cctccacccc cgggaccaat | 660 |
| gaagaaggat aaggaccagg attctattac tggtgagaaa gtggacttca gtagttcctc | 720 |
| tgactcagaa tctgagatgg gacctcagga agcaacacag gcagaatctg aagatggaaa | 780 |
| gctgacccctt ccattggctg ggattatgca gcatgatgcc accaagctgt tgccaagtgt | 840 |
| cacagaactt tttccagaat ttcgacctgg aaaggtgtta cgttttctac gtcttttttgg | 900 |
| accagggaag aatgtcccat ctgtttggcg gagtgctcgg agaaagagga agaagaagca | 960 |
| ccgtgagctg atacaggaag agcagatcca ggaggtggag tgctcagtag aatcagaagt | 1020 |
| cagccagaag tctttgtgga actacgacta cgctccacca ccacctccag agcagtgtct | 1080 |
| ctctgatgat gaaatcacga tgatggctcc tgtggagtcc aaattttccc aatcaactgg | 1140 |
| agatatagat aaagtgacag ataccaaacc aagagtggct gagtggcgtt atgggcctgc | 1200 |
| ccgactgtgg tatgatatgc tgggtgtccc tgaagatggc agtgggtttg actatggctt | 1260 |
| caaactgaga aagacagaac atgaacctgt gataaaatct agaatgatag aggaatttag | 1320 |
| gaaacttgag gaaaacaatg gcactgatct tctggctgat gaaaacttcc tgatggtgac | 1380 |
| acagctgcat tggaggatg atatcatctg ggatggggag gatgtcaaac acaaagggac | 1440 |
| aaaacctcag cgtgcaagcc tggcaggctg gcttccttct agcatgacta ggaatgcgat | 1500 |
| ggcttacaat gttcagcaag gttttgcagc cactcttgat gatgacaaac cttggtactc | 1560 |
| cattttttccc attgacaatg aggatctggt atatggacgc tgggaggaca atatcatttg | 1620 |
| ggatgctcag gccatgcccc ggctgttgga acctcctgtt ttgacacttg atcccaatga | 1680 |
| tgagaacctc attttggaaa ttcctgatga aaggaagag gccacctcta actccccctc | 1740 |
| caaggagagt aagaaggaat catctctgaa gaagagtcga attctcttag ggaaaacagg | 1800 |
| agtcatcaag gaggaaccac agcagaacat gtctcagcca gaagtgaaag atccatggaa | 1860 |
| tctctccaat gatgagtatt attatcccaa gcaacagggt cttcgaggca ccttttggagg | 1920 |

-continued

```
gaatattatc cagcattcaa ttcctgctgt ggaattacgg cagcccttct ttcccaccca    1980 catgggccc atcaaactcc ggcagttcca tcgcccacct ctgaaaaagt actcatttgg     2040
tgcactttct cagccaggtc cccactcagt ccaacctttg ctaaagcaca tcaaaaaaaa    2100
ggccaagatg agagaacaag agaggcaagc ttcaggtggt ggagagatgt ttttatgcg    2160 cacacctcag gacctcacag gcaaagatgg tgatcttatt cttgcagaat atagtgagga    2220
aaatggaccc ttaatgatgc aggttggcat ggcaaccaag ataaagaact attataaacg    2280
gaaacctgga aaagatcctg gagcaccaga ttgtaaatat ggggaaactg tttactgcca    2340
tacatctcct ttcctgggtt ctctccatcc tggccaattg ctgcaagcat ttgagaacaa    2400 ccttttttcgt gctccaattt atcttcataa gatgccagaa actgatttct tgatcattcg    2460
gacaagacag ggttactata ttcgggaatt agtggatatt tttgtggttg ccagcagtg    2520 tcccttgttt gaagttcctg ggcctaactc caaagggcc aatacgcata ttcgagactt     2580
tctacaggtt tttatttacc gccttttctg gaaagtaaa gatcggccac ggaggatacg    2640
aatggaagat ataaaaaag ccttccttc ccattcagaa agcagcatcc ggaagaggct      2700
aaagctctgc gctgacttca aacgcacagg gatggactca aactggtggg tgcttaagtc    2760
tgattttcgt ttaccaacgg aagaagagat cagagctatg gtgtcaccag agcagtgctg    2820
tgcttattat agcatgatag ctgcagagca acgactgaag gatgctggct atggtgagaa    2880
atcctttttt gctccagaag aagaaaatga ggaagatttc cagatgaaga ttgatgatga    2940
agttcgcact gccccttgga acaccacaag ggccttcatt gctgccatga agggcaagtg    3000
tctgctagag gtgactgggg tggcagatcc cacgggggtgt ggtgaaggat tctcctatgt    3060
gaagattcca aacaaaccaa cacagcagaa ggatgataaa gaaccgcagc cagtgaagaa    3120
gacagtgaca ggaacagatg cagaccttcg tcgccttttcc ctgaaaaatg ccaagcaact    3180
tctacgtaaa tttggtgtgc ctgaggaaga gattaaaaag ttgtcccgct gggaagtgat    3240
tgatgtggtg cgcacaatgt caacagaaca ggctcgttct ggagagggggc ccatgagtaa    3300 atttgcccgt ggatcaaggt tttctgtggc tgagcatcaa gagcgttaca agaggaatg    3360 tcagcgcatc tttgacctac agaacaaggt tctgtcatca actgaagtct tatcaactga    3420
cacagacagc agctcagctg aagatagtga ctttgaagaa atgggaaaga acattgagaa    3480
catgttgcag aacaagaaaa ccagctctca gctttcacgt gaacgggagg aacaggagcg    3540
gaaggaacta cagcgaatgc tactggcagc aggctcagca gcatccggaa acaatcacag    3600
agatgatgac acagcttccg tgactagcct taactcttct gccactggac gctgtctcaa    3660
gatttatcgc acgtttcgag atgaagaggg gaaagagtat gttcgctgtg agacagtccg    3720
aaaaccagct gtcattgatg cctatgtgcg catacggact acaaaagatg aggaattcat    3780
tcgaaaattt gcccttttttg atgaacaaca tcgggaagag atgcgaaaag aacggcggag    3840
gattcaagag caactgaggc ggcttaagag gaaccaggaa aaggagaagc ttaagggtcc    3900
tcctgagaag aagcccaaga aaatgaagga gcgtcctgac ctaaaactga aatgtggggc    3960
atgtggtgcc attggacaca tgaggactaa caaattctgc cccctctatt atcaaacaaa    4020
tgcgccacct tccaaccctg ttgccatgac agaagaacag gaggaggagt tggaaaagac    4080
agtcattcat aatgataatg aagaacttat caaggttgaa gggaccaaaa ttgtcttggg    4140
gaaacagcta attgagagtg cggatgaggt tcgcagaaaa tctctggttc tcaagttttcc    4200 taaacagcag cttcctccaa agaagaaacg gcgagttgga accactgttc actgtgacta    4260
```

-continued

```
tttgaataga cctcataagt ccatccaccg gcgccgcaca gaccctatgg tgacgctgtc    4320
gtccatcttg gagtctatca tcaatgacat gagagatctt ccaaatacat acccttcca    4380 cactccagtc aatgcaaagg ttgtaaagga ctactacaaa atcatcactc ggccaatgga    4440
cctacaaaca ctccgcgaaa acgtgcgtaa acgcctctac ccatctcggg aagagttcag    4500
agagcatctg gagctaattg tgaaaaatag tgcaacctac aatgggccaa acactcatt    4560 gactcagatc tctcaatcca tgctggatct ctgtgatgaa aaactcaaag agaaagaaga    4620
caaattagct cgcttagaga aagctatcaa ccccttgctg gatgatgatg accaagtggc    4680
gttttctttc attctggaca acattgtcac ccagaaaatg atggcagttc cagattcttg    4740
gccatttcat cacccagtta ataagaaatt tgttccagat tattacaaag tgattgtcaa    4800
tccaatggat ttagagacca tacgtaagaa catctccaag cacaagtatc agagtcggga    4860
gagctttctg gatgatgtaa accttattct ggccaacagt gttaagtata atgacaatga    4920
gtgttcatct aaagcaaatg acatagtttg cctaatccag tactgtagtt cacagataga    4980
agaattaaga ttttaatggg acggtgattt gccagcagtc cctactgaat ttcttaatta    5040
agatttgtgc ccaactgtcc tggtctctaa actggtgtca tgtttcctcc ttattccatc    5100
atgtccctga tcatagcctg ccaatctgga tgtagaactc tctgctgctc tcctggaatg    5160
atgtctacct gcatgctgcc atgcctccca ccatgacaat aattgactga agctctgaac    5220
tgtaaggcag ccccaattaa atgctttcct ttatagg                             5257
```

<210> SEQ ID NO 48
<211> LENGTH: 1174
<212> TYPE: DNA
<213> ORGANISM: Homo Sapiens

<400> SEQUENCE: 48

```
gcctgtccac catctcccta ttacccttg gtcgagaggg aaagcagaag aagtctgctg      60
gtcacacggg ggcacctcga ggagaggacg actaggagca cacggcccgg aaaggtccag    120
gtcagggaag ggaataactg tgcttgaaga agaaaattcc caacatggac aaaccacgca    180
aagaaaatga agaagagccg cagagccgcc caagaccgat gaggagaggc ctccggtgga    240
gcactctccc gaaaagcagt cccccgagga gcagtcttcg gaggagcagt cctcggagga    300
ggagttcttt cctgaggagc tcttgcctga gctcctgcct gagatgctcc tctcggagga    360
ctccctccgc aggtctttcc aggaaggacc tgtttgaggt tcgccctccc atggagcagc    420
ctccttgtgg agtaggaaaa cataaccttg aagaaggaat ctttaaagaa aggttggctc    480
gttctcgccc gcaatttaga ggggacatac atggcagaaa tttaagcaat gaggagatga    540
tacaggcagc agatgagcta aagagatgaa aagagtaag aaacaaactg atgataatgc     600
actggagggc aaaacggggc ggtccttatc ctatttaatg tgttcggcct ttaattctgt    660
tttgcctgct atagtattgc cattgccacc tggactttct gtttgcattt tcttaatgcc    720
ttttccctat ttctgaattt taacttttg tgaggcttta ttttagatgt ttagcatgta    780
actcgcttaa agttgaggtt tccccctaaa atctacaagt ttccctcttt cagtcatgag    840
ccctacacat ttgcatgaaa gatgtacata tatattgtga acgaaaaaag caattttcaa    900
atggtatata tgtatcccat tttgtaaaaa atgtatatta tatattaata tgcaaagaaa    960
aagctaaaag tatagacttc aaaggcataa cagtggttgt gtggtaagat ataggtgatt   1020 tttttaaattt ttgtttttatc tgaatttctc attttttcag gacaaacgtt ttacttgtgt   1080
tgcaaaaata tataatgaaa aaatcacaca ttttgaaga aaactgtcaa tcagcttata     1140
```
acgacaatgt ggcacttaat aaatacttgt cagg					1174

<210> SEQ ID NO 49
<211> LENGTH: 1569
<212> TYPE: DNA
<213> ORGANISM: Homo Sapiens

<400> SEQUENCE: 49

| | | | | | |
|---|---|---|---|---|---|
| caaaatctca | accatgatct | tgagatggca | aaggttttaa | atacgttttg | gaaatatact | 60 |
| cattggtata | tttcttttga | gaaggctgaa | atgtagctgg | ggacagcagg | ttgatcacaa | 120 |
| gggacgatga | tatgaggtaa | gcacacaaga | gctatggaca | agacaaggtc | taaaggattt | 180 |
| tgaatacaaa | gcagaaatat | ttcgaccttc | tcatttctgg | ggtgggagtg | gggagtgttc | 240 |
| attaagtaca | tatgcaaga | gggagtgtgg | ggagaaggtg | aaacagtaga | ctacatttat | 300 |
| ggattaagta | gggaatgtga | acaaagatgt | taaagtcatg | gcgatccggt | agacagatta | 360 |
| cacagaaggg | gaccgaagat | gaactggaca | aatactctga | ggctctcaaa | gatgcccagg | 420 |
| agaagctgga | gctggcagag | aaaaaggcca | ccgatgctga | agccgacgta | gcttctctga | 480 |
| acagacgcat | ccagctggtt | gaggaagagt | tggatcgtgc | ccaggagcgt | ctggcaacag | 540 |
| cttttgcagaa | gctggaggaa | gctgagaagg | cagcagatga | gagtgagaga | ggcatgaaag | 600 |
| tcattgagag | tcgagcccaa | aaagatgaag | aaaaaatgga | aattcaggag | atccaactga | 660 |
| aagaggccaa | gcacattgct | gaagatgccg | accgcaaata | tgaagaggtg | gcccgtaagc | 720 |
| tggtcatcat | tgagagcgac | ctggaacgtg | cagaggagcg | ggctgagctc | tcagaaggcc | 780 |
| aagtccgaca | gctggaagaa | caattaagaa | taatggatca | gaccttgaaa | gcattaatgg | 840 |
| ctgcagagga | taagtactcg | cagaaggaag | acagatatga | ggaagagatc | aaggtccttt | 900 |
| ccgacaagct | gaaggaggct | gagactcggg | ctgagtttgc | ggagaggtca | gtaactaaat | 960 |
| tggagaaaag | cattgatgac | ttagaagaga | aagtgctcat | gccaaagaag | aaaaccttag | 1020 |
| tatgcatcag | atgctggatc | agactttact | ggagttaaac | aacatgtgaa | aacctcctta | 1080 |
| gctgcgacca | cattctttca | ttttgttttg | ttttgttttg | tttttaaaca | cctgcttacc | 1140 |
| ccttaaatgc | aatttattta | cttttaccac | tgtcacagaa | acatccacaa | gataccagct | 1200 |
| aggtcagggg | gtgggaaaa | cacatacaaa | aagcaagccc | atgtcagggc | gatcctggtt | 1260 |
| caaatgtgcc | atttcccggg | ttgatgctgc | cacactttgt | agagagttta | gcaacacagt | 1320 |
| gtgcttagtc | agtgtaggaa | tcctcactaa | agcagaagaa | gttccattcc | tttctgattg | 1380 |
| gcacacgtgc | agctcatgac | aatctgtagg | ataacaatca | gtgtggattt | ccactctttt | 1440 |
| cagtccttca | tgttaaagat | ttagacacca | catacaactg | gtaaaggacg | ttttcttgag | 1500 |
| agttttaact | atatgtaaac | attgtataat | gatatggaat | aaaatgcaca | ttttaggaca | 1560 |
| ttttctaaa | | | | | | 1569 |

<210> SEQ ID NO 50
<211> LENGTH: 1081
<212> TYPE: DNA
<213> ORGANISM: Homo Sapiens

<400> SEQUENCE: 50

| | | | | | |
|---|---|---|---|---|---|
| gctgcccgtc | ctggcgagcc | gcgcctacgc | ggccctgcc | ccaggccagg | ccctgcagcg | 60 |
| agtgggcatc | gttggggtc | aggaggcccc | caggagcaag | tggccctggc | aggtgagcct | 120 |
| gagagtccgc | gaccgatact | ggatgcactt | ctgcggggc | tccctcatcc | accccagtg | 180 |

```
ggtgctgacc gcagcgcact gcgtgggacc ggacgtcaag gatctggccg ccctcagggt    240
gcaactgcgg gagcagcacc tctactacca ggaccagctg ctgccggtca gcaggatcat    300
cgtgcaccca cagttctaca ccgcccagat cggagcggac atcgccctgc tggagctgga    360
ggagccggtg aaggtctcca gccacgtcca cacggtcacc ctgccccctg cctcagagac    420
cttccccccg gggatgccgt gctgggtcac tggctgggc gatgtggaca atgatgagcg     480
cctcccaccg ccatttcctc tgaagcaggt gaaggtcccc ataatggaaa accacatttg    540
tgacgcaaaa taccaccttg cgcctacac gggagacgca gtccgcatcg tccgtgacga     600
catgctgtgt gccgggaaca cccggaggga ctcatgccag ggcgactccg agggcccct     660 ggtgtgcaag gtgaatggca cctggctgca ggcgggcgtg gtcagctggg cgagggctg     720 tgcccagccc aaccggcctg gcatctacac ccgtgtcacc tactacttgg actggatcca    780
ccactatgtc cccaaaaagc cgtgagtcag gcctggggtg tccacctggg tcactggagg    840
accagcccct cctgtccaaa acaccactgc ttcctaccca ggcggcgact gcccccaca    900 ccttccctgc cccgtcctga gtgccccttc ctgtcctaag ccccctgctc tcttctgagc    960
cccttcccct gtcctgagga ccccttccca tcctgagccc ccttccctgt cctaagcctg   1020
acgcctgcac cgggccctcc ggccctcccc tgcccaggca gctggtggtg ggcgctaatc   1080
c                                                                   1081

<210> SEQ ID NO 51
<211> LENGTH: 783
<212> TYPE: DNA
<213> ORGANISM: Homo Sapiens

<400> SEQUENCE: 51
ggcacgagcg agttcctgtc tctctgccaa cgccgcccgg atggcttccc aaaaccgcga     60
cccagccgcc actagcgtcg ccgccgcccg taaaggagct gagccgagcg ggggcgccgc    120
ccggggtccg gtgggcaaaa ggctacagca ggagctgatg accctcatga tgtctggcga    180
taaagggatt tctgccttcc ctgaatcaga caacctttc aaatgggtag ggaccatcca     240
tggagcagct ggaacagtat atgaagacct gaggtataag ctctcgctag agttccccag    300
tggctaccct tacaatgcgc ccacagtgaa gttcctcacg ccctgctatc accccaacgt    360
ggacacccag ggtaacatat gcctggacat cctgaaggaa aagtggtctg ccctgtatga    420
tgtcaggacc attctgctct ccatccagag ccttctagga gaacccaaca ttgatagtcc    480
cttgaacaca catgctgccg agctctggaa aaacccaca gcttttaaga agtacctgca    540
agaaacctac tcaaagcagg tcaccagcca ggagccctga cccaggctgc ccagcctgtc    600
cttgtgtcgt cttttaatt tttccttaga tggtctgtcc tttttgtgat ttctgtatag     660
gactctttat cttgagctgt ggtattttg ttttgttttt gtcttttaaa ttaagcctcg     720
gttgagccct tgtatattaa ataaatgcat ttttgtcctt ttttaaaaaa aaaaaaaaa    780 aaa                                                                 783

<210> SEQ ID NO 52
<211> LENGTH: 808
<212> TYPE: PRT
<213> ORGANISM: Homo Sapiens

<400> SEQUENCE: 52

Met Ala Glu Leu Leu Ala Ser Ala Gly Ser Ala Cys Ser Trp Asp Phe
  1               5                  10                  15
```

-continued

```
Pro Arg Ala Pro Pro Ser Phe Pro Pro Ala Ala Ser Arg Gly Gly
             20                  25                  30

Leu Gly Gly Thr Arg Ser Phe Arg Pro His Arg Gly Ala Glu Ser Pro
         35                  40                  45

Arg Pro Gly Arg Asp Arg Asp Gly Val Arg Val Pro Met Ala Ser Ser
     50                  55                  60

Arg Cys Pro Ala Pro Arg Gly Cys Arg Cys Leu Pro Gly Ala Ser Leu
 65                  70                  75                  80

Ala Trp Leu Gly Thr Val Leu Leu Leu Ala Asp Trp Val Leu Leu
                 85                  90                  95

Arg Thr Ala Leu Pro Arg Ile Phe Ser Leu Leu Val Pro Thr Ala Leu
                100                 105                 110

Pro Leu Leu Arg Val Trp Ala Val Gly Leu Ser Arg Trp Ala Val Leu
            115                 120                 125

Trp Leu Gly Ala Cys Gly Val Leu Arg Ala Thr Val Gly Ser Lys Ser
130                 135                 140

Glu Asn Ala Gly Ala Gln Gly Trp Leu Ala Ala Leu Lys Pro Leu Ala
145                 150                 155                 160

Ala Ala Leu Gly Leu Ala Leu Pro Gly Leu Ala Leu Phe Arg Glu Leu
                165                 170                 175

Ile Ser Trp Gly Ala Pro Gly Ser Ala Asp Ser Thr Arg Leu Leu His
            180                 185                 190

Trp Gly Ser His Pro Thr Ala Phe Val Val Ser Tyr Ala Ala Ala Leu
        195                 200                 205

Pro Ala Ala Ala Leu Trp His Lys Leu Gly Ser Leu Trp Val Pro Gly
210                 215                 220

Gly Gln Gly Gly Ser Gly Asn Pro Val Arg Arg Leu Leu Gly Cys Leu
225                 230                 235                 240

Gly Ser Glu Thr Arg Arg Leu Ser Leu Phe Leu Val Leu Val Val Leu
                245                 250                 255

Ser Ser Leu Gly Glu Met Ala Ile Pro Phe Phe Thr Gly Arg Leu Thr
            260                 265                 270

Asp Trp Ile Leu Gln Asp Gly Ser Ala Asp Thr Phe Thr Arg Asn Leu
        275                 280                 285

Thr Leu Met Ser Ile Leu Thr Ile Ala Ser Ala Val Leu Glu Phe Val
290                 295                 300

Gly Asp Gly Ile Tyr Asn Asn Thr Met Gly His Val His Ser His Leu
305                 310                 315                 320

Gln Gly Glu Val Phe Gly Ala Val Leu Arg Gln Glu Thr Glu Phe Phe
                325                 330                 335

Gln Gln Asn Gln Thr Gly Asn Ile Met Ser Arg Val Thr Glu Asp Thr
            340                 345                 350

Ser Thr Leu Ser Asp Ser Leu Ser Glu Asn Leu Ser Leu Phe Leu Trp
        355                 360                 365

Tyr Leu Val Arg Gly Leu Cys Leu Leu Gly Ile Met Leu Trp Gly Ser
    370                 375                 380

Val Ser Leu Thr Met Val Thr Leu Ile Thr Leu Pro Leu Leu Phe Leu
385                 390                 395                 400

Leu Pro Lys Lys Val Gly Lys Trp Tyr Gln Leu Leu Glu Val Gln Val
                405                 410                 415

Arg Glu Ser Leu Ala Lys Ser Ser Gln Val Ala Ile Glu Ala Leu Ser
            420                 425                 430
```

```
Ala Met Pro Thr Val Arg Ser Phe Ala Asn Glu Glu Gly Glu Ala Gln
            435                 440                 445
Lys Phe Arg Glu Lys Leu Gln Glu Ile Lys Thr Leu Asn Gln Lys Glu
        450                 455                 460
Ala Val Ala Tyr Ala Val Asn Ser Trp Thr Thr Ser Ile Ser Gly Met
465                 470                 475                 480
Leu Leu Lys Val Gly Ile Leu Tyr Ile Gly Gln Leu Val Thr Ser
                485                 490                 495
Gly Ala Val Ser Ser Gly Asn Leu Val Thr Phe Val Leu Tyr Gln Met
                500                 505                 510
Gln Phe Thr Gln Ala Val Glu Val Leu Leu Ser Ile Tyr Pro Arg Val
        515                 520                 525
Gln Lys Ala Val Gly Ser Ser Glu Lys Ile Phe Glu Tyr Leu Asp Arg
    530                 535                 540
Thr Pro Arg Cys Pro Pro Ser Gly Leu Leu Thr Pro Leu His Leu Glu
545                 550                 555                 560
Gly Leu Val Gln Phe Gln Asp Val Ser Phe Ala Tyr Pro Asn Arg Pro
                565                 570                 575
Asp Val Leu Val Leu Gln Gly Leu Thr Phe Thr Leu Arg Pro Gly Glu
            580                 585                 590
Val Thr Ala Leu Val Gly Pro Asn Gly Ser Gly Lys Ser Thr Val Ala
        595                 600                 605
Ala Leu Leu Gln Asn Leu Tyr Gln Pro Thr Gly Gly Gln Leu Leu Leu
    610                 615                 620
Asp Gly Lys Pro Leu Pro Gln Tyr Glu His Arg Tyr Leu His Arg Gln
625                 630                 635                 640
Val Ala Ala Val Gly Gln Glu Pro Gln Val Phe Gly Arg Ser Leu Gln
                645                 650                 655
Glu Asn Ile Ala Tyr Gly Leu Thr Gln Lys Pro Thr Met Glu Glu Ile
            660                 665                 670
Thr Ala Ala Ala Val Lys Ser Gly Ala His Ser Phe Ile Ser Gly Leu
        675                 680                 685
Pro Gln Gly Tyr Asp Thr Glu Val Asp Glu Ala Gly Ser Gln Leu Ser
    690                 695                 700
Gly Gly Gln Arg Gln Ala Val Ala Leu Ala Arg Ala Leu Ile Arg Lys
705                 710                 715                 720
Pro Cys Val Leu Ile Leu Asp Asp Ala Thr Ser Ala Leu Asp Ala Asn
                725                 730                 735
Ser Gln Leu Gln Val Glu Gln Leu Leu Tyr Glu Ser Pro Glu Arg Tyr
            740                 745                 750
Ser Arg Ser Val Leu Leu Ile Thr Gln His Leu Ser Leu Val Glu Gln
        755                 760                 765
Ala Asp His Ile Leu Phe Leu Glu Gly Gly Ala Ile Arg Glu Gly Gly
    770                 775                 780
Thr His Gln Gln Leu Met Glu Lys Lys Gly Cys Tyr Trp Ala Met Val
785                 790                 795                 800
Gln Ala Pro Ala Asp Ala Pro Glu
                805
```

<210> SEQ ID NO 53
<211> LENGTH: 377
<212> TYPE: PRT
<213> ORGANISM: Homo Sapiens

<400> SEQUENCE: 53

```
Met Cys Glu Glu Asp Ser Thr Ala Leu Val Cys Asp Asn Gly Ser
1               5                   10                  15
Gly Leu Cys Lys Ala Gly Phe Ala Gly Asp Asp Ala Pro Arg Ala Val
                20                  25                  30
Phe Pro Ser Ile Val Gly Arg Pro Arg His Gln Gly Val Met Val Gly
            35                  40                  45
Met Gly Gln Lys Asp Ser Tyr Val Gly Asp Glu Ala Gln Ser Lys Arg
    50                  55                  60
Gly Ile Leu Thr Leu Lys Tyr Pro Ile Glu His Gly Ile Ile Thr Asn
65                  70                  75                  80
Trp Asp Asp Met Glu Lys Ile Trp His His Ser Phe Tyr Asn Glu Leu
                85                  90                  95
Arg Val Ala Pro Glu Glu His Pro Thr Leu Leu Thr Glu Ala Pro Leu
                100                 105                 110
Asn Pro Lys Ala Asn Arg Glu Lys Met Thr Gln Ile Met Phe Glu Thr
            115                 120                 125
Phe Asn Val Pro Ala Met Tyr Val Ala Ile Gln Ala Val Leu Ser Leu
    130                 135                 140
Tyr Ala Ser Gly Arg Thr Thr Gly Ile Val Leu Asp Ser Gly Asp Gly
145                 150                 155                 160
Val Thr His Asn Val Pro Ile Tyr Glu Gly Tyr Ala Leu Pro His Ala
                165                 170                 175
Ile Met Arg Leu Asp Leu Ala Gly Arg Asp Leu Thr Asp Tyr Leu Met
                180                 185                 190
Lys Ile Leu Thr Glu Arg Gly Tyr Ser Phe Val Thr Thr Ala Glu Arg
            195                 200                 205
Glu Ile Val Arg Asp Ile Lys Glu Lys Leu Cys Tyr Val Ala Leu Asp
210                 215                 220
Phe Glu Asn Glu Met Ala Thr Ala Ala Ser Ser Ser Leu Glu Lys
225                 230                 235                 240
Ser Tyr Glu Leu Pro Asp Gly Gln Val Ile Thr Ile Gly Asn Glu Arg
                245                 250                 255
Phe Arg Cys Pro Glu Thr Leu Phe Gln Pro Ser Phe Ile Gly Met Glu
                260                 265                 270
Ser Ala Gly Ile His Glu Thr Thr Tyr Asn Ser Ile Met Lys Cys Asp
            275                 280                 285
Ile Asp Ile Arg Lys Asp Leu Tyr Ala Asn Asn Val Leu Ser Gly Gly
    290                 295                 300
Thr Thr Met Tyr Pro Gly Ile Ala Asp Arg Met Gln Lys Glu Ile Thr
305                 310                 315                 320
Ala Leu Ala Pro Ser Thr Met Lys Ile Lys Ile Ala Pro Pro Glu
                325                 330                 335
Arg Lys Tyr Ser Val Trp Ile Gly Gly Ser Ile Leu Ala Ser Leu Ser
                340                 345                 350
Thr Phe Gln Gln Met Trp Ile Ser Lys Gln Glu Tyr Asp Glu Ala Gly
            355                 360                 365
Pro Ser Ile Val His Arg Lys Cys Phe
    370                 375

<210> SEQ ID NO 54
<211> LENGTH: 334
<212> TYPE: PRT
<213> ORGANISM: Homo Sapiens
```

<400> SEQUENCE: 54

```
Met Glu Ala Ala His Phe Phe Glu Gly Thr Glu Lys Leu Leu Glu Val
1               5                   10                  15

Trp Phe Ser Arg Gln Gln Pro Asp Ala Asn Gln Gly Ser Gly Asp Leu
            20                  25                  30

Arg Thr Ile Pro Arg Ser Glu Trp Asp Ile Leu Leu Lys Asp Val Gln
        35                  40                  45

Cys Ser Ile Ile Ser Val Thr Lys Thr Asp Lys Gln Glu Ala Tyr Val
50                  55                  60

Leu Ser Glu Ser Ser Met Phe Val Ser Lys Arg Arg Phe Ile Leu Lys
65                  70                  75                  80

Thr Cys Gly Thr Thr Leu Leu Leu Lys Ala Leu Val Pro Leu Leu Lys
                85                  90                  95

Leu Ala Arg Asp Tyr Ser Gly Phe Asp Ser Ile Gln Ser Phe Phe Tyr
            100                 105                 110

Ser Arg Lys Asn Phe Met Lys Pro Ser His Gln Gly Tyr Pro His Arg
        115                 120                 125

Asn Phe Gln Glu Glu Ile Glu Phe Leu Asn Ala Ile Phe Pro Asn Gly
130                 135                 140

Ala Gly Tyr Cys Met Gly Arg Met Asn Ser Asp Cys Trp Tyr Leu Tyr
145                 150                 155                 160

Thr Leu Asp Phe Pro Glu Ser Arg Val Ile Ser Gln Pro Asp Gln Thr
                165                 170                 175

Leu Glu Ile Leu Met Ser Glu Leu Asp Pro Ala Val Met Asp Gln Phe
            180                 185                 190

Tyr Met Lys Asp Gly Val Thr Ala Lys Asp Val Thr Arg Glu Ser Gly
        195                 200                 205

Ile Arg Asp Leu Ile Pro Gly Ser Val Ile Asp Ala Thr Met Phe Asn
210                 215                 220

Pro Cys Gly Tyr Ser Met Asn Gly Met Lys Ser Asp Gly Thr Tyr Trp
225                 230                 235                 240

Thr Ile His Ile Thr Pro Glu Pro Glu Phe Ser Tyr Val Ser Phe Glu
                245                 250                 255

Thr Asn Leu Ser Gln Thr Ser Tyr Asp Asp Leu Ile Arg Lys Val Val
            260                 265                 270

Glu Val Phe Lys Pro Gly Lys Phe Val Thr Thr Leu Phe Val Asn Gln
        275                 280                 285

Ser Ser Lys Cys Arg Thr Val Leu Ala Ser Pro Gln Lys Ile Glu Gly
290                 295                 300

Phe Lys Arg Leu Asp Cys Gln Ser Ala Met Phe Asn Asp Tyr Asn Phe
305                 310                 315                 320

Val Phe Thr Ser Phe Ala Lys Lys Gln Gln Gln Gln Gln Ser
                325                 330
```

<210> SEQ ID NO 55
<211> LENGTH: 76
<212> TYPE: PRT
<213> ORGANISM: Homo Sapiens

<400> SEQUENCE: 55

```
Met Ala Ser Lys Gly Leu Gln Asp Leu Lys Gln Gln Val Glu Gly Thr
1               5                   10                  15

Ala Gln Glu Ala Val Ser Ala Ala Gly Ala Ala Ala Gln Gln Val Val
            20                  25                  30
```

```
Asp Gln Ala Thr Glu Ala Gly Gln Lys Ala Met Asp Gln Leu Ala Lys
             35                  40                  45

Thr Thr Gln Glu Thr Ile Asp Lys Thr Ala Asn Gln Ala Ser Asp Thr
 50                  55                  60

Phe Ser Gly Ile Gly Lys Lys Phe Gly Leu Leu Lys
 65                  70                  75

<210> SEQ ID NO 56
<211> LENGTH: 395
<212> TYPE: PRT
<213> ORGANISM: Homo Sapiens

<400> SEQUENCE: 56

Met Pro Gly Arg Ser Cys Val Ala Leu Val Leu Leu Ala Ala Ala Val
 1               5                  10                  15

Ser Cys Ala Val Ala Gln His Ala Pro Pro Trp Thr Glu Asp Cys Arg
             20                  25                  30

Lys Ser Thr Tyr Pro Pro Ser Gly Pro Thr Tyr Arg Gly Ala Val Pro
             35                  40                  45

Trp Tyr Thr Ile Asn Leu Asp Leu Pro Pro Tyr Lys Arg Trp His Glu
 50                  55                  60

Leu Met Leu Asp Lys Ala Pro Met Leu Lys Val Ile Val Asn Ser Leu
 65                  70                  75                  80

Lys Asn Met Ile Asn Thr Phe Val Pro Ser Gly Lys Val Met Gln Val
             85                  90                  95

Val Asp Glu Lys Leu Pro Gly Leu Leu Gly Asn Phe Pro Gly Pro Phe
             100                 105                 110

Glu Glu Glu Met Lys Gly Ile Ala Ala Val Thr Asp Ile Pro Leu Gly
             115                 120                 125

Glu Ile Ile Ser Phe Asn Ile Phe Tyr Glu Leu Phe Thr Ile Cys Thr
 130                 135                 140

Ser Ile Val Ala Glu Asp Lys Lys Gly His Leu Ile His Gly Arg Asn
 145                 150                 155                 160

Met Asp Phe Gly Val Phe Leu Gly Trp Asn Ile Asn Asn Asp Thr Trp
             165                 170                 175

Val Ile Thr Glu Gln Leu Lys Pro Leu Thr Val Asn Leu Asp Phe Gln
             180                 185                 190

Arg Asn Asn Lys Thr Val Phe Lys Ala Ser Ser Phe Ala Gly Tyr Val
             195                 200                 205

Gly Met Leu Thr Gly Phe Lys Pro Gly Leu Phe Ser Leu Thr Leu Asn
             210                 215                 220

Glu Arg Phe Ser Ile Asn Gly Gly Tyr Leu Gly Ile Leu Glu Trp Ile
 225                 230                 235                 240

Leu Gly Lys Lys Asp Ala Met Trp Ile Gly Phe Leu Thr Arg Thr Val
             245                 250                 255

Leu Glu Asn Ser Thr Ser Tyr Glu Glu Ala Lys Asn Leu Leu Thr Lys
             260                 265                 270

Thr Lys Ile Leu Ala Pro Ala Tyr Phe Ile Leu Gly Gly Asn Gln Ser
             275                 280                 285

Gly Glu Gly Cys Val Ile Thr Arg Asp Arg Lys Glu Ser Leu Asp Val
             290                 295                 300

Tyr Glu Leu Asp Ala Lys Gln Gly Arg Trp Tyr Val Val Gln Thr Asn
 305                 310                 315                 320

Tyr Asp Arg Trp Lys His Pro Phe Phe Leu Asp Asp Arg Arg Thr Pro
             325                 330                 335
```

```
Ala Lys Met Cys Leu Asn Arg Thr Ser Gln Glu Asn Ile Ser Phe Glu
            340                 345                 350

Thr Met Tyr Asp Val Leu Ser Thr Lys Pro Val Leu Asn Lys Leu Thr
            355                 360                 365

Val Tyr Thr Thr Leu Ile Asp Val Thr Lys Gly Gln Phe Glu Thr Tyr
            370                 375                 380

Leu Arg Asp Cys Pro Asp Pro Cys Ile Gly Trp
385                 390                 395

<210> SEQ ID NO 57
<211> LENGTH: 777
<212> TYPE: PRT
<213> ORGANISM: Homo Sapiens

<400> SEQUENCE: 57

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
            35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
            85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
            115                 120                 125

Arg Lys Ser Leu Phe Asn Asp Ala Gly Asn Lys Lys Asn Ser Ile Lys
    130                 135                 140

Met Trp Phe Ser Pro Arg Ser Lys Lys Val Arg Tyr Val Val Ser Lys
145                 150                 155                 160

Ala Ser Val Gln Thr Gln Pro Ala Ile Lys Lys Asp Ala Ser Ala Gln
            165                 170                 175

Gln Asp Ser Tyr Glu Phe Val Ser Pro Ser Pro Ala Asp Val Ser
            180                 185                 190

Glu Arg Ala Lys Lys Ala Ser Ala Arg Ser Gly Lys Lys Gln Lys Lys
    195                 200                 205

Lys Thr Leu Ala Glu Ile Asn Gln Lys Trp Asn Leu Glu Ala Glu Lys
    210                 215                 220

Glu Asp Gly Glu Phe Asp Ser Lys Glu Glu Ser Lys Gln Lys Leu Val
225                 230                 235                 240

Ser Phe Cys Ser Gln Pro Ser Val Ile Ser Ser Pro Gln Ile Asn Gly
            245                 250                 255

Glu Ile Asp Leu Leu Ala Ser Gly Ser Leu Thr Glu Ser Glu Cys Phe
            260                 265                 270

Gly Ser Leu Thr Glu Val Ser Leu Pro Leu Ala Glu Gln Ile Glu Ser
            275                 280                 285

Pro Asp Thr Lys Ser Arg Asn Glu Val Val Thr Pro Glu Lys Val Cys
    290                 295                 300

Lys Asn Tyr Leu Thr Ser Lys Lys Ser Leu Pro Leu Glu Asn Asn Gly
```

```
305                 310                 315                 320
Lys Arg Gly His His Asn Arg Leu Ser Ser Pro Ile Ser Lys Arg Cys
                325                 330                 335
Arg Thr Ser Ile Leu Ser Thr Ser Gly Asp Phe Val Lys Gln Thr Val
                340                 345                 350
Pro Ser Glu Asn Ile Pro Leu Pro Glu Cys Ser Ser Pro Pro Ser Cys
                355                 360                 365
Lys Arg Lys Val Gly Gly Thr Ser Gly Arg Lys Asn Ser Asn Met Ser
                370                 375                 380
Asp Glu Phe Ile Ser Leu Ser Pro Gly Thr Pro Ser Thr Leu Ser
385                 390                 395                 400
Ser Ser Ser Tyr Arg Gln Val Met Ser Ser Pro Ser Ala Met Lys Leu
                405                 410                 415
Leu Pro Asn Met Ala Val Lys Arg Asn His Arg Gly Glu Thr Leu Leu
                420                 425                 430
His Ile Ala Ser Ile Lys Gly Asp Ile Pro Ser Val Glu Tyr Leu Leu
                435                 440                 445
Gln Asn Gly Ser Asp Pro Asn Val Lys Asp His Ala Gly Trp Thr Pro
450                 455                 460
Leu His Glu Ala Cys Asn His Gly His Leu Lys Val Val Glu Leu Leu
465                 470                 475                 480
Leu Gln His Lys Ala Leu Val Asn Thr Thr Gly Tyr Gln Asn Asp Ser
                485                 490                 495
Pro Leu His Asp Ala Ala Lys Asn Gly His Val Asp Ile Val Lys Leu
                500                 505                 510
Leu Leu Ser Tyr Gly Ala Ser Arg Asn Ala Val Asn Ile Phe Gly Leu
                515                 520                 525
Arg Pro Val Asp Tyr Thr Asp Asp Glu Ser Met Lys Ser Leu Leu Leu
                530                 535                 540
Leu Pro Glu Lys Asn Glu Ser Ser Ala Ser His Cys Ser Val Met
545                 550                 555                 560
Asn Thr Gly Gln Arg Arg Asp Gly Pro Leu Val Leu Ile Gly Ser Gly
                565                 570                 575
Leu Ser Ser Glu Gln Gln Lys Met Leu Ser Glu Leu Ala Val Ile Leu
                580                 585                 590
Lys Ala Lys Lys Tyr Thr Glu Phe Asp Ser Thr Val Thr His Val Val
                595                 600                 605
Val Pro Gly Asp Ala Val Gln Ser Thr Leu Lys Cys Met Leu Gly Ile
                610                 615                 620
Leu Asn Gly Cys Trp Ile Leu Lys Phe Glu Trp Val Lys Ala Cys Leu
625                 630                 635                 640
Arg Arg Lys Val Cys Glu Gln Glu Lys Tyr Glu Ile Pro Glu Gly
                645                 650                 655
Pro Arg Arg Ser Arg Leu Asn Arg Glu Gln Leu Leu Pro Lys Leu Phe
                660                 665                 670
Asp Gly Cys Tyr Phe Tyr Leu Trp Gly Thr Phe Lys His His Pro Lys
                675                 680                 685
Asp Asn Leu Ile Lys Leu Val Thr Ala Gly Gly Gln Ile Leu Ser
                690                 695                 700
Arg Lys Pro Lys Pro Asp Ser Asp Val Thr Gln Thr Ile Asn Thr Val
705                 710                 715                 720
Ala Tyr His Ala Arg Pro Asp Ser Asp Gln Arg Phe Cys Thr Gln Tyr
                725                 730                 735
```

```
Ile Ile Tyr Glu Asp Leu Cys Asn Tyr His Pro Glu Arg Val Arg Gln
            740                 745                 750
Gly Lys Val Trp Lys Ala Pro Ser Ser Trp Phe Ile Asp Cys Val Met
            755                 760                 765
Ser Phe Glu Leu Leu Pro Leu Asp Ser
            770                 775

<210> SEQ ID NO 58
<211> LENGTH: 323
<212> TYPE: PRT
<213> ORGANISM: Homo Sapiens

<400> SEQUENCE: 58

Met Tyr His Asn Ser Ser Gln Lys Arg His Trp Thr Phe Ser Ser Glu
1               5                   10                  15
Glu Gln Leu Ala Arg Leu Arg Ala Asp Ala Asn Arg Lys Phe Arg Cys
            20                  25                  30
Lys Ala Val Ala Asn Gly Lys Val Leu Pro Asn Asp Pro Val Phe Leu
            35                  40                  45
Glu Pro His Glu Glu Met Thr Leu Cys Lys Tyr Tyr Glu Lys Arg Leu
50                  55                  60
Leu Glu Phe Cys Ser Val Phe Lys Pro Ala Met Pro Arg Ser Val Val
65                  70                  75                  80
Gly Thr Ala Cys Met Tyr Phe Lys Arg Phe Tyr Leu Asn Asn Ser Val
            85                  90                  95
Met Glu Tyr His Pro Arg Ile Ile Met Leu Thr Cys Ala Phe Leu Ala
            100                 105                 110
Cys Lys Val Asp Glu Phe Asn Val Ser Ser Pro Gln Phe Val Gly Asn
            115                 120                 125
Leu Arg Glu Ser Pro Leu Gly Gln Glu Lys Ala Leu Glu Gln Ile Leu
            130                 135                 140
Glu Tyr Glu Leu Leu Leu Ile Gln Gln Leu Asn Phe His Leu Ile Val
145                 150                 155                 160
His Asn Pro Tyr Arg Pro Phe Glu Gly Phe Leu Ile Asp Leu Lys Thr
                165                 170                 175
Arg Tyr Pro Ile Leu Glu Asn Pro Glu Ile Leu Arg Lys Thr Ala Asp
            180                 185                 190
Asp Phe Leu Asn Arg Ile Ala Leu Thr Asp Ala Tyr Leu Leu Tyr Thr
            195                 200                 205
Pro Ser Gln Ile Ala Leu Thr Ala Ile Leu Ser Ser Ala Ser Arg Ala
            210                 215                 220
Gly Ile Thr Met Glu Ser Tyr Leu Ser Glu Ser Leu Met Leu Lys Glu
225                 230                 235                 240
Asn Arg Thr Cys Leu Ser Gln Leu Leu Asp Ile Met Lys Ser Met Arg
                245                 250                 255
Asn Leu Val Lys Lys Tyr Glu Pro Pro Arg Ser Glu Val Ala Val
            260                 265                 270
Leu Lys Gln Lys Leu Glu Arg Cys His Ser Ala Glu Leu Ala Leu Asn
            275                 280                 285
Val Ile Thr Lys Lys Arg Lys Gly Tyr Glu Asp Asp Tyr Val Ser
            290                 295                 300
Lys Lys Ser Lys His Glu Glu Glu Trp Thr Asp Asp Leu Val
305                 310                 315                 320
Glu Ser Leu
```

<210> SEQ ID NO 59
<211> LENGTH: 217
<212> TYPE: PRT
<213> ORGANISM: Homo Sapiens

<400> SEQUENCE: 59

```
Met Ala Ser Leu Ser Leu Ala Pro Val Asn Ile Phe Lys Ala Gly Ala
1               5                   10                  15

Asp Glu Glu Arg Ala Glu Thr Ala Arg Leu Thr Ser Phe Ile Gly Ala
                20                  25                  30

Ile Ala Ile Gly Asp Leu Val Lys Ser Thr Leu Gly Pro Lys Gly Met
            35                  40                  45

Asp Lys Ile Leu Leu Ser Ser Gly Arg Asp Ala Ser Leu Met Val Thr
    50                  55                  60

Asn Asp Gly Ala Thr Ile Leu Lys Asn Ile Gly Val Asp Asn Pro Ala
65                  70                  75                  80

Ala Lys Val Leu Val Asp Met Ser Arg Val Gln Asp Glu Val Gly
                85                  90                  95

Asp Gly Thr Thr Ser Val Thr Val Leu Ala Ala Glu Leu Leu Arg Glu
                100                 105                 110

Ala Glu Ser Leu Ile Ala Lys Lys Ile His Pro Gln Thr Ile Ile Ala
            115                 120                 125

Gly Trp Arg Glu Ala Thr Lys Ala Ala Arg Glu Ala Leu Leu Ser Ser
    130                 135                 140

Ala Val Asp His Gly Ser Asp Glu Val Lys Phe Arg Gln Asp Leu Met
145                 150                 155                 160

Asn Ile Ala Gly Thr Thr Leu Ser Ser Lys Leu Leu Thr His His Lys
                165                 170                 175

Asp His Phe Thr Lys Leu Ala Val Glu Ala Val Leu Arg Leu Lys Gly
            180                 185                 190

Ser Gly Asn Leu Glu Ala Ile His Ile Ile Lys Lys Leu Gly Gly Ser
        195                 200                 205

Leu Ala Asp Ser Tyr Leu Asp Glu Gly
    210                 215
```

<210> SEQ ID NO 60
<211> LENGTH: 499
<212> TYPE: PRT
<213> ORGANISM: Homo Sapiens

<400> SEQUENCE: 60

```
Met Ala Gln Phe Ala Phe Glu Ser Asp Leu His Ser Leu Leu Gln Leu
1               5                   10                  15

Asp Ala Pro Ile Pro Asn Ala Pro Ala Arg Trp Gln Arg Lys Ala
                20                  25                  30

Lys Glu Ala Ala Gly Pro Ala Pro Ser Pro Met Arg Ala Ala Asn Arg
            35                  40                  45

Ser His Ser Ala Gly Arg Thr Pro Gly Arg Thr Pro Gly Lys Ser Ser
    50                  55                  60

Ser Lys Val Gln Thr Thr Pro Ser Lys Pro Gly Gly Asp Arg Tyr Ile
65                  70                  75                  80

Pro His Arg Ser Ala Ala Gln Met Glu Val Ala Ser Phe Leu Leu Ser
                85                  90                  95

Lys Glu Asn Gln Ser Glu Asn Ser Gln Thr Pro Thr Lys Lys Glu His
```

-continued

```
                100                 105                 110
Gln Lys Ala Trp Ala Leu Asn Leu Asn Gly Phe Asp Val Glu Glu Ala
            115                 120                 125
Lys Ile Leu Arg Leu Ser Gly Lys Pro Gln Asn Ala Pro Glu Gly Tyr
130                 135                 140
Gln Asn Arg Leu Lys Val Leu Tyr Ser Gln Lys Ala Thr Pro Gly Ser
145                 150                 155                 160
Ser Arg Lys Thr Cys Arg Tyr Ile Pro Ser Leu Pro Asp Arg Ile Leu
                165                 170                 175
Asp Ala Pro Glu Ile Arg Asn Asp Tyr Tyr Leu Asn Leu Val Asp Trp
            180                 185                 190
Ser Ser Gly Asn Val Leu Ala Val Ala Leu Asp Asn Ser Val Tyr Leu
        195                 200                 205
Trp Ser Ala Ser Ser Gly Asp Ile Leu Gln Leu Leu Gln Met Glu Gln
    210                 215                 220
Pro Gly Glu Tyr Ile Ser Ser Val Ala Trp Ile Lys Glu Gly Asn Tyr
225                 230                 235                 240
Leu Ala Val Gly Thr Ser Ser Ala Glu Val Gln Leu Trp Asp Val Gln
                245                 250                 255
Gln Gln Lys Arg Leu Arg Asn Met Thr Ser His Ser Ala Arg Val Gly
            260                 265                 270
Ser Leu Ser Trp Asn Ser Tyr Ile Leu Ser Ser Gly Ser Arg Ser Gly
        275                 280                 285
His Ile His His His Asp Val Arg Val Ala Glu His His Val Ala Thr
    290                 295                 300
Leu Ser Gly His Ser Gln Glu Val Cys Gly Leu Arg Trp Ala Pro Asp
305                 310                 315                 320
Gly Arg His Leu Ala Ser Gly Gly Asn Asp Asn Leu Val Asn Val Trp
                325                 330                 335
Pro Ser Ala Pro Gly Glu Gly Gly Trp Val Pro Leu Gln Thr Phe Thr
            340                 345                 350
Gln His Gln Gly Ala Val Lys Ala Val Ala Trp Cys Pro Trp Gln Ser
        355                 360                 365
Asn Val Leu Ala Thr Gly Gly Gly Thr Ser Asp Arg His Ile Arg Ile
    370                 375                 380
Trp Asn Val Cys Ser Gly Ala Cys Leu Ser Ala Val Asp Ala His Ser
385                 390                 395                 400
Gln Val Cys Ser Ile Leu Trp Ser Pro His Tyr Lys Glu Leu Ile Ser
                405                 410                 415
Gly His Gly Phe Ala Gln Asn Gln Leu Val Ile Trp Lys Tyr Pro Thr
            420                 425                 430
Met Ala Lys Val Ala Glu Leu Lys Gly His Thr Ser Arg Val Leu Ser
        435                 440                 445
Leu Thr Met Ser Pro Asp Gly Ala Thr Val Ala Ser Ala Ala Ala Asp
    450                 455                 460
Glu Thr Leu Arg Leu Trp Arg Cys Phe Glu Leu Asp Pro Ala Arg Arg
465                 470                 475                 480
Arg Glu Arg Glu Lys Ala Ser Ala Ala Lys Ser Ser Leu Ile His Gln
                485                 490                 495
Gly Ile Arg

<210> SEQ ID NO 61
<211> LENGTH: 298
```

```
<212> TYPE: PRT
<213> ORGANISM: Homo Sapiens

<400> SEQUENCE: 61

Ile Ala Ala Ala Pro Glu Leu Leu Glu Arg Ser Gly Ser Pro Gly
 1               5                  10                  15

Gly Gly Gly Ala Glu Glu Ala Gly Gly Pro Gly Gly Ser Pro
            20                  25                  30

Pro Asp Gly Ala Arg Pro Gly Pro Ser Arg Glu Leu Ala Val Val Ala
            35                  40                  45

Arg Pro Arg Ala Ala Pro Thr Pro Gly Pro Ser Ala Ala Met Ala
    50                  55                  60

Arg Pro Leu Val Pro Ser Ser Gln Lys Ala Leu Leu Leu Glu Leu Lys
 65                  70                  75                  80

Gly Leu Gln Glu Glu Pro Val Glu Gly Phe Arg Val Thr Leu Val Asp
                85                  90                  95

Glu Gly Asp Leu Tyr Asn Trp Glu Val Ala Ile Phe Gly Pro Pro Asn
                100                 105                 110

Thr Tyr Tyr Glu Gly Gly Tyr Phe Lys Ala Arg Leu Lys Phe Pro Ile
                115                 120                 125

Asp Tyr Pro Tyr Ser Pro Pro Ala Phe Arg Phe Leu Thr Lys Met Trp
    130                 135                 140

His Pro Asn Ile Tyr Glu Thr Gly Asp Val Cys Ile Ser Ile Leu His
145                 150                 155                 160

Pro Pro Val Asp Asp Pro Gln Ser Gly Glu Leu Pro Ser Glu Arg Trp
                165                 170                 175

Asn Pro Thr Gln Asn Val Arg Thr Ile Leu Leu Ser Val Ile Ser Leu
                180                 185                 190

Leu Asn Glu Pro Asn Thr Phe Ser Pro Ala Asn Val Asp Ala Ser Val
                195                 200                 205

Met Tyr Arg Lys Trp Lys Glu Ser Lys Gly Lys Asp Arg Glu Tyr Thr
    210                 215                 220

Asp Ile Ile Arg Lys Gln Val Leu Gly Thr Lys Val Asp Ala Glu Arg
225                 230                 235                 240

Asp Gly Val Lys Val Pro Thr Thr Leu Ala Glu Tyr Cys Val Lys Thr
                245                 250                 255

Lys Ala Pro Ala Pro Asp Glu Gly Ser Asp Leu Phe Tyr Asp Asp Tyr
                260                 265                 270

Tyr Glu Asp Gly Glu Val Glu Glu Ala Asp Ser Cys Phe Gly Asp
    275                 280                 285

Asp Glu Asp Asp Ser Gly Thr Glu Glu Ser
    290                 295

<210> SEQ ID NO 62
<211> LENGTH: 212
<212> TYPE: PRT
<213> ORGANISM: Homo Sapiens

<400> SEQUENCE: 62

Met Glu Pro Pro Ser Ser Ile Gln Thr Ser Glu Phe Asp Ser Asp
 1               5                  10                  15

Glu Glu Pro Ile Glu Asp Glu Gln Thr Pro Ile His Ile Ser Trp Leu
                20                  25                  30

Ser Leu Ser Arg Val Asn Cys Ser Gln Phe Leu Gly Leu Cys Ala Leu
            35                  40                  45
```

```
Pro Gly Cys Lys Phe Lys Asp Val Arg Arg Asn Val Gln Lys Asp Thr
    50                  55                  60

Glu Glu Leu Lys Ser Cys Gly Ile Gln Asp Ile Phe Val Phe Cys Thr
65                  70                  75                  80

Arg Gly Glu Leu Ser Lys Tyr Arg Val Pro Asn Leu Leu Asp Leu Tyr
                85                  90                  95

Gln Gln Cys Gly Ile Ile Thr His His His Pro Ile Ala Asp Gly Gly
            100                 105                 110

Thr Pro Asp Ile Ala Ser Cys Cys Glu Ile Met Glu Glu Leu Thr Thr
            115                 120                 125

Cys Leu Lys Asn Tyr Arg Lys Thr Leu Ile His Cys Tyr Gly Gly Leu
    130                 135                 140

Gly Arg Ser Cys Leu Val Ala Ala Cys Leu Leu Leu Tyr Leu Ser Asp
145                 150                 155                 160

Thr Ile Ser Pro Glu Gln Ala Ile Asp Ser Leu Arg Asp Leu Arg Gly
                165                 170                 175

Ser Gly Ala Ile Gln Thr Ile Lys Gln Tyr Asn Tyr Leu His Glu Phe
            180                 185                 190

Arg Asp Lys Leu Ala Ala His Leu Ser Ser Arg Asp Ser Gln Ser Arg
            195                 200                 205

Ser Val Ser Arg
    210

<210> SEQ ID NO 63
<211> LENGTH: 79
<212> TYPE: PRT
<213> ORGANISM: Homo Sapiens

<400> SEQUENCE: 63

Met Ser His Lys Gln Ile Tyr Tyr Ser Asp Lys Tyr Asp Asp Glu Glu
1               5                   10                  15

Phe Glu Tyr Arg His Val Met Leu Pro Lys Asp Ile Ala Lys Leu Val
                20                  25                  30

Pro Lys Thr His Leu Met Ser Glu Ser Glu Trp Arg Asn Leu Gly Val
            35                  40                  45

Gln Gln Ser Gln Gly Trp Val His Tyr Met Ile His Glu Pro Glu Pro
        50                  55                  60

His Ile Leu Leu Phe Arg Arg Pro Leu Pro Lys Pro Lys Lys
65                  70                  75

<210> SEQ ID NO 64
<211> LENGTH: 79
<212> TYPE: PRT
<213> ORGANISM: Homo Sapiens

<400> SEQUENCE: 64

Met Ala His Lys Gln Ile Tyr Tyr Ser Asp Lys Tyr Phe Asp Glu His
1               5                   10                  15

Tyr Glu Tyr Arg His Val Met Leu Pro Arg Glu Leu Ser Lys Gln Val
                20                  25                  30

Pro Lys Thr His Leu Met Ser Glu Glu Glu Trp Arg Arg Leu Gly Val
            35                  40                  45

Gln Gln Ser Leu Gly Trp Val His Tyr Met Ile His Glu Pro Glu Pro
        50                  55                  60

His Ile Leu Leu Phe Arg Arg Pro Leu Pro Lys Asp Gln Gln Lys
65                  70                  75
```

```
<210> SEQ ID NO 65
<211> LENGTH: 79
<212> TYPE: PRT
<213> ORGANISM: Homo Sapiens

<400> SEQUENCE: 65

Met Gln Ala Leu Arg Val Ser Gln Ala Leu Ile Arg Ser Phe Ser Ser
1               5                   10                  15

Thr Ala Arg Asn Arg Phe Gln Asn Arg Val Arg Glu Lys Gln Lys Leu
            20                  25                  30

Phe Gln Glu Asp Asn Asp Ile Pro Leu Tyr Leu Lys Gly Gly Ile Val
        35                  40                  45

Asp Asn Ile Leu Tyr Arg Val Thr Met Thr Leu Cys Leu Gly Gly Thr
    50                  55                  60

Val Tyr Ser Leu Tyr Ser Leu Gly Trp Ala Ser Phe Pro Arg Asn
65                  70                  75

<210> SEQ ID NO 66
<211> LENGTH: 417
<212> TYPE: PRT
<213> ORGANISM: Homo Sapiens

<400> SEQUENCE: 66

Met Arg Leu Ile Leu Pro Val Gly Leu Ile Ala Thr Thr Leu Ala Ile
1               5                   10                  15

Ala Pro Val Arg Phe Asp Arg Glu Lys Val Phe Arg Val Lys Pro Gln
            20                  25                  30

Asp Glu Lys Gln Ala Asp Ile Ile Lys Asp Leu Ala Lys Thr Asn Glu
        35                  40                  45

Leu Asp Phe Trp Tyr Pro Gly Ala Thr His His Val Ala Ala Asn Met
    50                  55                  60

Met Val Asp Phe Arg Val Ser Glu Lys Glu Ser Gln Ala Ile Gln Ser
65                  70                  75                  80

Ala Leu Asp Gln Asn Lys Met His Tyr Glu Ile Leu Ile His Asp Leu
            85                  90                  95

Gln Glu Glu Ile Glu Lys Gln Phe Asp Val Lys Glu Asp Ile Pro Gly
        100                 105                 110

Arg His Ser Tyr Ala Lys Tyr Asn Asn Trp Glu Lys Ile Val Ala Trp
    115                 120                 125

Thr Glu Lys Met Met Asp Lys Tyr Pro Glu Met Val Ser Arg Ile Lys
130                 135                 140

Ile Gly Ser Thr Val Glu Asp Asn Pro Leu Tyr Val Leu Lys Ile Gly
145                 150                 155                 160

Glu Lys Asn Glu Arg Arg Lys Ala Ile Phe Met Asp Cys Gly Ile His
            165                 170                 175

Ala Arg Glu Trp Val Ser Pro Ala Phe Cys Gln Trp Phe Val Tyr Gln
        180                 185                 190

Ala Thr Lys Thr Tyr Gly Arg Asn Lys Ile Met Thr Lys Leu Leu Asp
    195                 200                 205

Arg Met Asn Phe Tyr Ile Leu Pro Val Phe Asn Val Asp Gly Tyr Ile
    210                 215                 220

Trp Ser Trp Thr Lys Asn Arg Met Trp Arg Lys Asn Arg Ser Lys Asn
225                 230                 235                 240

Gln Asn Ser Lys Cys Ile Gly Thr Asp Leu Asn Arg Asn Phe Asn Ala
            245                 250                 255
```

-continued

```
Ser Trp Asn Ser Ile Pro Asn Thr Asn Asp Pro Cys Ala Asp Asn Tyr
            260                 265                 270

Arg Gly Ser Ala Pro Glu Ser Glu Lys Glu Thr Lys Ala Val Thr Asn
        275                 280                 285

Phe Ile Arg Ser His Leu Asn Glu Ile Lys Val Tyr Ile Thr Phe His
    290                 295                 300

Ser Tyr Ser Gln Met Leu Leu Phe Pro Tyr Gly Tyr Thr Ser Lys Leu
305                 310                 315                 320

Pro Pro Asn His Glu Asp Leu Ala Lys Val Ala Lys Ile Gly Thr Asp
                325                 330                 335

Val Leu Ser Thr Arg Tyr Glu Thr Arg Tyr Ile Tyr Gly Pro Ile Glu
            340                 345                 350

Ser Thr Ile Tyr Pro Ile Ser Gly Ser Ser Leu Asp Trp Ala Tyr Asp
                355                 360                 365

Leu Gly Ile Lys His Thr Phe Ala Phe Glu Leu Arg Asp Lys Gly Lys
        370                 375                 380

Phe Gly Phe Leu Leu Pro Glu Ser Arg Ile Lys Pro Thr Cys Arg Glu
385                 390                 395                 400

Thr Met Leu Ala Val Lys Phe Ile Ala Lys Tyr Ile Leu Lys His Thr
                405                 410                 415
Ser

<210> SEQ ID NO 67
<211> LENGTH: 476
<212> TYPE: PRT
<213> ORGANISM: Homo Sapiens

<400> SEQUENCE: 67

Met Ala Gly Arg Gly Gly Ser Ala Leu Leu Ala Leu Cys Gly Ala Leu
1               5                   10                  15

Ala Ala Cys Gly Trp Leu Leu Gly Ala Glu Ala Gln Glu Pro Gly Ala
            20                  25                  30

Pro Ala Ala Gly Met Arg Arg Arg Arg Leu Gln Gln Glu Asp Gly
        35                  40                  45

Ile Ser Phe Glu Tyr His Arg Tyr Pro Glu Leu Arg Glu Ala Leu Val
    50                  55                  60

Ser Val Trp Leu Gln Cys Thr Ala Ile Ser Arg Ile Tyr Thr Val Gly
65                  70                  75                  80

Arg Ser Phe Glu Gly Arg Glu Leu Leu Val Ile Glu Leu Ser Asp Asn
                85                  90                  95

Pro Gly Val His Glu Pro Gly Glu Pro Glu Phe Lys Tyr Ile Gly Asn
            100                 105                 110

Met His Gly Asn Glu Ala Val Gly Arg Glu Leu Leu Ile Phe Leu Ala
        115                 120                 125

Gln Tyr Leu Cys Asn Glu Tyr Gln Lys Gly Asn Glu Thr Ile Val Asn
    130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Met Lys Lys Ile Val Asp Gln Asn Thr Lys
```

```
            210                 215                 220
Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Ser Ala His Glu Tyr Ser Ser Ser
                260                 265                 270

Pro Asp Asp Ala Ile Phe Gln Ser Leu Ala Arg Ala Tyr Ser Ser Phe
            275                 280                 285

Asn Pro Ala Met Ser Asp Pro Asn Arg Pro Pro Cys Arg Lys Asn Asp
290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
            340                 345                 350

Thr Leu Lys Thr Tyr Trp Glu Asp Asn Lys Asn Ser Leu Ile Ser Tyr
                355                 360                 365

Leu Glu Gln Ile His Arg Gly Val Lys Gly Phe Val Arg Asp Leu Gln
370                 375                 380

Gly Asn Pro Ile Ala Asn Ala Thr Ile Ser Val Glu Gly Ile Asp His
385                 390                 395                 400

Asp Val Thr Ser Ala Lys Asp Gly Asp Tyr Trp Arg Leu Leu Ile Pro
                405                 410                 415

Gly Asn Tyr Lys Leu Thr Ala Ser Ala Pro Gly Tyr Leu Ala Ile Thr
                420                 425                 430

Lys Lys Val Ala Val Pro Tyr Ser Pro Ala Ala Gly Val Asp Phe Glu
                435                 440                 445

Leu Glu Ser Phe Ser Glu Arg Lys Glu Glu Lys Glu Glu Leu Met
            450                 455                 460

Glu Trp Trp Lys Met Met Ser Glu Thr Leu Asn Phe
465                 470                 475

<210> SEQ ID NO 68
<211> LENGTH: 355
<212> TYPE: PRT
<213> ORGANISM: Homo Sapiens

<400> SEQUENCE: 68

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
                20                  25                  30

Phe Leu Ser Ile Phe Tyr Ser Val Ile Phe Ala Ile Gly Leu Val Gly
            35                  40                  45

Asn Leu Leu Val Val Phe Ala Leu Thr Asn Ser Lys Lys Pro Lys Ser
        50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110
```

```
Phe Phe Gly Ser Ile Phe Phe Ile Thr Val Ile Ser Ile Asp Arg Tyr
            115                 120                 125

Leu Ala Ile Val Leu Ala Ala Asn Ser Met Asn Asn Arg Thr Val Gln
        130                 135                 140

His Gly Val Thr Ile Ser Leu Gly Val Trp Ala Ala Ile Leu Val
145                 150                 155                 160

Ala Ala Pro Gln Phe Met Phe Thr Lys Gln Lys Glu Asn Glu Cys Leu
            165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
            195                 200                 205

Tyr Cys Tyr Phe Arg Ile Ile Gln Thr Leu Phe Ser Cys Lys Asn His
210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
            245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
                340                 345                 350

Leu Leu Leu
        355

<210> SEQ ID NO 69
<211> LENGTH: 767
<212> TYPE: PRT
<213> ORGANISM: Homo Sapiens

<400> SEQUENCE: 69

Met Ser Gln Arg Pro Arg Ala Pro Arg Ser Ala Leu Trp Leu Leu Ala
1               5                   10                  15

Pro Pro Leu Leu Arg Trp Ala Pro Leu Leu Thr Val Leu His Ser
            20                  25                  30

Asp Leu Phe Gln Ala Leu Leu Asp Ile Leu Asp Tyr Tyr Glu Ala Ser
            35                  40                  45

Leu Ser Glu Ser Gln Lys Tyr Arg Tyr Gln Asp Glu Asp Thr Pro Pro
        50                  55                  60

Leu Glu His Ser Pro Ala His Leu Pro Asn Gln Ala Asn Ser Pro Pro
65                  70                  75                  80

Val Ile Val Asn Thr Asp Thr Leu Glu Ala Pro Gly Tyr Glu Leu Gln
                85                  90                  95

Val Asn Gly Thr Glu Gly Glu Met Glu Tyr Glu Glu Ile Thr Leu Glu
                100                 105                 110

Arg Gly Asn Ser Gly Leu Gly Phe Ser Ile Ala Gly Gly Thr Asp Asn
            115                 120                 125
```

-continued

```
Pro His Ile Gly Asp Asp Pro Ser Ile Phe Ile Thr Lys Ile Ile Pro
    130                 135                 140
Gly Gly Ala Ala Ala Gln Asp Gly Arg Leu Arg Val Asn Asp Ser Ile
145                 150                 155                 160
Leu Phe Val Asn Glu Val Asp Val Arg Glu Val Thr His Ser Ala Ala
                165                 170                 175
Val Glu Ala Leu Lys Glu Ala Gly Ser Ile Val Arg Leu Tyr Val Met
            180                 185                 190
Arg Arg Lys Pro Pro Ala Glu Lys Val Met Glu Ile Lys Leu Ile Lys
        195                 200                 205
Gly Pro Lys Gly Leu Gly Phe Ser Ile Ala Gly Gly Val Gly Asn Gln
210                 215                 220
His Ile Pro Gly Asp Asn Ser Ile Tyr Val Thr Lys Ile Ile Glu Gly
225                 230                 235                 240
Gly Ala Ala His Lys Asp Gly Arg Leu Gln Ile Gly Asp Lys Ile Leu
                245                 250                 255
Ala Val Asn Ser Val Gly Leu Glu Asp Val Met His Glu Asp Ala Val
            260                 265                 270
Ala Ala Leu Lys Asn Thr Tyr Asp Val Val Tyr Leu Lys Val Ala Lys
        275                 280                 285
Pro Ser Asn Ala Tyr Leu Ser Asp Ser Tyr Ala Pro Pro Asp Ile Thr
290                 295                 300
Thr Ser Tyr Ser Gln His Leu Asp Asn Glu Ile Ser His Ser Ser Tyr
305                 310                 315                 320
Leu Gly Thr Asp Tyr Pro Thr Ala Met Thr Pro Thr Ser Pro Arg Arg
                325                 330                 335
Tyr Ser Pro Val Ala Lys Asp Leu Leu Gly Glu Glu Asp Ile Pro Arg
            340                 345                 350
Glu Pro Arg Arg Ile Val Ile His Arg Gly Ser Thr Gly Leu Gly Phe
        355                 360                 365
Asn Ile Val Gly Gly Glu Asp Gly Glu Gly Ile Phe Ile Ser Phe Ile
370                 375                 380
Leu Ala Gly Gly Pro Ala Asp Leu Ser Gly Glu Leu Arg Lys Gly Asp
385                 390                 395                 400
Gln Ile Leu Ser Val Asn Gly Val Asp Leu Arg Asn Ala Ser His Glu
                405                 410                 415
Gln Ala Ala Ile Ala Leu Lys Asn Ala Gly Gln Thr Val Thr Ile Ile
            420                 425                 430
Ala Gln Tyr Lys Pro Glu Glu Tyr Ser Arg Phe Glu Ala Lys Ile His
        435                 440                 445
Asp Leu Arg Glu Gln Leu Met Asn Ser Ser Leu Gly Ser Gly Thr Ala
450                 455                 460
Ser Leu Arg Ser Asn Pro Lys Arg Gly Phe Tyr Ile Arg Ala Leu Phe
465                 470                 475                 480
Asp Tyr Asp Lys Thr Lys Asp Cys Gly Phe Leu Ser Gln Ala Leu Ser
                485                 490                 495
Phe Arg Phe Gly Asp Val Leu His Val Ile Asp Ala Ser Asp Glu Glu
            500                 505                 510
Trp Trp Gln Ala Arg Arg Val His Ser Asp Ser Glu Thr Asp Asp Ile
        515                 520                 525
Gly Phe Ile Pro Ser Lys Arg Arg Val Glu Arg Arg Glu Trp Ser Arg
530                 535                 540
```

```
Leu Lys Ala Lys Asp Trp Gly Ser Ser Gly Ser Gln Gly Arg Glu
545                 550                 555                 560

Asp Ser Val Leu Ser Tyr Glu Thr Val Thr Gln Met Glu Val His Tyr
                565                 570                 575

Ala Arg Pro Ile Ile Ile Leu Gly Pro Thr Lys Asp Arg Ala Asn Asp
            580                 585                 590

Asp Leu Leu Ser Glu Phe Pro Asp Lys Phe Gly Ser Cys Val Pro His
            595                 600                 605

Thr Thr Arg Pro Lys Arg Glu Tyr Glu Ile Asp Gly Arg Asp Tyr His
610                 615                 620

Phe Val Ser Ser Arg Glu Lys Met Glu Lys Asp Ile Gln Ala His Lys
625                 630                 635                 640

Phe Ile Glu Ala Gly Gln Tyr Asn Ser His Leu Tyr Gly Thr Ser Val
                645                 650                 655

Gln Ser Val Arg Glu Val Ala Glu Gln Gly Lys His Cys Ile Leu Asp
            660                 665                 670

Val Ser Ala Asn Ala Val Arg Arg Leu Gln Ala Ala His Leu His Pro
            675                 680                 685

Ile Ala Ile Phe Ile Arg Pro Arg Ser Leu Glu Asn Val Leu Glu Ile
690                 695                 700

Asn Lys Arg Ile Thr Glu Glu Gln Ala Arg Lys Ala Phe Asp Arg Ala
705                 710                 715                 720

Thr Lys Leu Glu Gln Glu Phe Thr Glu Cys Phe Ser Ala Ile Val Glu
                725                 730                 735

Gly Asp Ser Phe Glu Glu Ile Tyr His Lys Val Lys Arg Val Ile Glu
            740                 745                 750

Asp Leu Ser Gly Pro Tyr Ile Trp Val Pro Ala Arg Glu Arg Leu
755                 760                 765

<210> SEQ ID NO 70
<211> LENGTH: 752
<212> TYPE: PRT
<213> ORGANISM: Homo Sapiens

<400> SEQUENCE: 70

Met Val Val Asp Glu Gln Gln Arg Leu Thr Ala Gln Leu Thr Leu Gln
1               5                   10                  15

Arg Gln Lys Ile Gln Glu Leu Thr Thr Asn Ala Lys Glu Thr His Thr
            20                  25                  30

Lys Leu Ala Leu Ala Glu Ala Arg Val Gln Glu Glu Gln Lys Ala
        35                  40                  45

Thr Arg Leu Glu Lys Glu Leu Gln Thr Gln Thr Thr Lys Phe His Gln
50                  55                  60

Asp Gln Asp Thr Ile Met Ala Lys Leu Thr Asn Glu Asp Ser Gln Asn
65                  70                  75                  80

Arg Gln Leu Gln Gln Lys Leu Ala Ala Leu Ser Arg Gln Ile Asp Glu
                85                  90                  95

Leu Glu Glu Thr Asn Arg Ser Leu Arg Lys Ala Glu Glu Leu Gln
            100                 105                 110

Asp Ile Lys Glu Lys Ile Ser Lys Gly Glu Tyr Gly Asn Ala Gly Ile
            115                 120                 125

Met Ala Glu Val Glu Glu Leu Ile Lys Met Glu Glu Gln Cys Arg Asp
        130                 135                 140

Leu Asn Lys Arg Leu Glu Arg Glu Thr Leu Gln Ser Lys Asp Phe Lys
145                 150                 155                 160
```

-continued

```
Leu Glu Val Glu Lys Leu Ser Lys Arg Ile Met Ala Leu Glu Lys Leu
                165                 170                 175
Glu Asp Ala Phe Asn Lys Ser Lys Gln Glu Cys Tyr Ser Leu Lys Cys
            180                 185                 190
Asn Leu Glu Lys Glu Arg Met Thr Thr Lys Gln Leu Ser Gln Glu Leu
        195                 200                 205
Glu Ser Leu Lys Val Arg Ile Lys Glu Leu Glu Ala Ile Glu Ser Arg
    210                 215                 220
Leu Glu Lys Thr Glu Phe Thr Leu Lys Glu Asp Leu Thr Lys Leu Lys
225                 230                 235                 240
Thr Leu Thr Val Met Phe Val Asp Glu Arg Lys Thr Met Ser Glu Lys
            245                 250                 255
Leu Lys Lys Thr Glu Asp Lys Leu Gln Ala Ala Ser Ser Gln Leu Gln
            260                 265                 270
Val Glu Gln Asn Lys Val Thr Val Thr Glu Lys Leu Ile Glu Glu
            275                 280                 285
Thr Lys Arg Ala Leu Lys Ser Lys Thr Asp Val Glu Glu Lys Met Tyr
    290                 295                 300
Ser Val Thr Lys Glu Arg Asp Asp Leu Lys Asn Lys Leu Lys Ala Glu
305                 310                 315                 320
Glu Glu Lys Gly Asn Asp Leu Leu Ser Arg Val Asn Met Leu Lys Asn
            325                 330                 335
Arg Leu Gln Ser Leu Glu Ala Ile Glu Lys Asp Phe Leu Lys Asn Lys
        340                 345                 350
Leu Asn Gln Asp Ser Gly Lys Ser Thr Thr Ala Leu His Gln Glu Asn
    355                 360                 365
Asn Lys Ile Lys Glu Leu Ser Gln Glu Val Glu Arg Leu Lys Leu Lys
370                 375                 380
Leu Lys Asp Met Lys Ala Ile Glu Asp Asp Leu Met Lys Thr Glu Asp
385                 390                 395                 400
Glu Tyr Glu Thr Leu Glu Arg Arg Tyr Ala Asn Glu Arg Asp Lys Ala
            405                 410                 415
Gln Phe Leu Ser Lys Glu Leu Glu His Val Lys Met Glu Leu Ala Lys
            420                 425                 430
Tyr Lys Leu Ala Glu Lys Thr Glu Thr Ser His Glu Gln Trp Leu Phe
        435                 440                 445
Lys Arg Leu Gln Glu Glu Ala Lys Ser Gly His Leu Ser Arg Glu
    450                 455                 460
Val Asp Ala Leu Lys Glu Lys Ile His Glu Tyr Met Ala Thr Glu Asp
465                 470                 475                 480
Leu Ile Cys His Leu Gln Gly Asp His Ser Val Cys Lys Lys Leu
            485                 490                 495
Asn Gln Gln Glu Asn Arg Asn Arg Asp Leu Gly Arg Glu Ile Glu Asn
            500                 505                 510
Leu Thr Lys Glu Leu Glu Arg Tyr Arg His Phe Ser Lys Ser Leu Arg
        515                 520                 525
Pro Ser Leu Asn Gly Arg Arg Ile Ser Asp Pro Gln Val Phe Ser Lys
    530                 535                 540
Glu Val Gln Thr Glu Ala Val Asp Asn Glu Pro Pro Asp Tyr Lys Ser
545                 550                 555                 560
Leu Ile Pro Leu Glu Arg Ala Val Ile Asn Gly Gln Leu Tyr Glu Glu
            565                 570                 575
```

```
Ser Glu Asn Gln Asp Glu Asp Pro Asn Asp Glu Gly Ser Val Leu Ser
            580                 585                 590

Phe Lys Cys Ser Gln Ser Thr Pro Cys Pro Val Asn Arg Lys Leu Trp
        595                 600                 605

Ile Pro Trp Met Lys Ser Lys Glu Gly His Leu Gln Asn Gly Lys Met
    610                 615                 620

Gln Thr Lys Pro Asn Ala Asn Phe Val Gln Pro Gly Asp Leu Val Leu
625                 630                 635                 640

Ser His Thr Pro Gly Gln Pro Leu His Ile Lys Val Thr Pro Asp His
            645                 650                 655

Val Gln Asn Thr Ala Thr Leu Glu Ile Thr Ser Pro Thr Thr Glu Ser
        660                 665                 670

Pro His Ser Tyr Thr Ser Thr Ala Val Ile Pro Asn Cys Gly Thr Pro
    675                 680                 685

Lys Gln Arg Ile Thr Ile Leu Gln Asn Ala Ser Ile Thr Pro Val Lys
690                 695                 700

Ser Lys Thr Ser Thr Glu Asp Leu Met Asn Leu Glu Gln Gly Met Ser
705                 710                 715                 720

Pro Ile Thr Met Ala Thr Phe Ala Arg Ala Gln Thr Pro Glu Ser Cys
            725                 730                 735

Gly Ser Leu Thr Pro Glu Arg Thr Met Ser Leu Phe Arg Phe Trp Leu
            740                 745                 750

<210> SEQ ID NO 71
<211> LENGTH: 105
<212> TYPE: PRT
<213> ORGANISM: Homo Sapiens

<400> SEQUENCE: 71

Met Gln Thr Gln Ala Glu Ala Leu Thr Ala Gly Met Ala Gly Val Ala
1               5                   10                  15

Thr Ala Ala Ala Gly Ala Trp Thr Gln Pro Gln Leu Arg Pro Val Glu
            20                  25                  30

Leu Pro Gln Arg Thr Arg Gln Val Arg Ala Glu Thr Pro Arg Leu Pro
        35                  40                  45

Gln Gly Val Thr Asn Ala Ala Ala His Ile His Pro Gln Arg Ala Phe
    50                  55                  60

Pro Asp Pro Leu Gly Gly Asn Arg Pro Trp Val Pro Gly Thr Arg
65                  70                  75                  80

Cys Arg Ala Pro Pro Lys Gly Gly Trp Glu Gly Ser His Ser Glu Trp
            85                  90                  95

Gln Asp Pro Gly Arg Pro Leu Glu Ser
            100                 105

<210> SEQ ID NO 72
<211> LENGTH: 225
<212> TYPE: PRT
<213> ORGANISM: Homo Sapiens

<400> SEQUENCE: 72

Met Asn Ser Asn Val Glu Asn Leu Pro Pro His Ile Ile Arg Leu Val
1               5                   10                  15

Tyr Lys Glu Val Thr Thr Leu Thr Ala Asp Pro Pro Asp Gly Ile Lys
            20                  25                  30

Val Phe Pro Asn Glu Glu Asp Leu Thr Asp Leu Gln Val Thr Ile Glu
        35                  40                  45
```

-continued

```
Gly Pro Glu Gly Thr Pro Tyr Ala Gly Leu Phe Arg Met Lys Leu
    50                  55                  60

Leu Leu Gly Lys Asp Phe Pro Ala Ser Pro Lys Gly Tyr Phe Leu
65                  70                  75                  80

Thr Lys Ile Phe His Pro Asn Val Gly Asn Gly Glu Ile Cys Val
                85                  90                  95

Asn Val Leu Lys Arg Asp Trp Thr Ala Glu Leu Gly Ile Arg His Val
            100                 105                 110

Leu Leu Thr Ile Lys Cys Leu Leu Ile His Pro Asn Pro Glu Ser Ala
            115                 120                 125

Leu Asn Glu Glu Ala Gly Arg Leu Leu Leu Glu Asn Tyr Glu Glu Tyr
    130                 135                 140

Ala Ala Arg Ala Arg Leu Leu Thr Glu Ile His Gly Gly Ala Gly Gly
145                 150                 155                 160

Pro Ser Gly Arg Ala Glu Ala Gly Arg Ala Leu Ala Ser Gly Thr Glu
                165                 170                 175

Ala Ser Ser Thr Asp Pro Gly Ala Pro Gly Gly Pro Gly Gly Ala Glu
            180                 185                 190

Gly Pro Met Ala Lys Lys His Ala Gly Glu Arg Asp Lys Lys Leu Ala
        195                 200                 205

Ala Lys Lys Lys Thr Asp Lys Lys Arg Ala Leu Arg Ala Leu Arg Arg
    210                 215                 220

Leu
225

<210> SEQ ID NO 73
<211> LENGTH: 208
<212> TYPE: PRT
<213> ORGANISM: Homo Sapiens

<400> SEQUENCE: 73

Pro His Pro Met Pro Leu Arg Leu Pro Thr Pro Gly Gly Asn Gly Gln
1               5                   10                  15

Ala Gly Arg Pro Cys Arg Ser Thr Gly Gln Gly Asn Lys Arg Gly Ala
            20                  25                  30

Ala Lys Cys Pro Asp Gln Glu Ala Pro Tyr Phe Arg Gly Lys Gly His
        35                  40                  45

Val Val Leu Ala Pro His Pro Ile Pro Ser His Leu Gly Ala Pro Pro
    50                  55                  60

Pro His Ser Leu His Leu Gln Gly Asn Leu Val Leu His Ala Gly Ala
65                  70                  75                  80

Leu Ile Phe Leu Gly Gly Arg Arg Glu Gly Trp Pro Leu Gly Glu
                85                  90                  95

Pro Pro Thr Trp Gly Ser Ser Lys Asp Gly Ala Asp Thr Ser Trp Ala
            100                 105                 110

Val Pro Ala Pro Pro Ala His Gln Asp Pro Pro Leu Ala Ala Ile Gln
        115                 120                 125

Leu Val Pro Lys His Leu Lys Pro Gln Ser Trp Ile Arg Ser Ser Ile
    130                 135                 140

Pro Pro Leu Leu Gly Pro Leu Gly Arg Leu Leu Pro Thr Asp Arg Cys
145                 150                 155                 160

Ser Pro His Leu Gly Arg Phe Trp Val Gly Lys Pro Pro His Thr Gly
                165                 170                 175

Asn Ser His Leu Ala Pro Cys Arg Ile His Pro Arg Ile Arg Pro Phe
            180                 185                 190
```

```
Ile His Arg Ser Val His Pro Cys Pro Gln Leu Thr Ala Arg His His
            195                 200                 205

<210> SEQ ID NO 74
<211> LENGTH: 109
<212> TYPE: PRT
<213> ORGANISM: Homo Sapiens

<400> SEQUENCE: 74

Met Ala Tyr Gln Leu Tyr Arg Asn Thr Thr Leu Gly Asn Ser Leu Gln
1               5                   10                  15

Glu Ser Leu Asp Glu Leu Ile Gln Ser Gln Gln Ile Thr Pro Gln Leu
            20                  25                  30

Ala Leu Gln Val Leu Leu Gln Phe Asp Lys Ala Ile Asn Ala Ala Leu
        35                  40                  45

Ala Gln Arg Val Arg Asn Arg Val Asn Phe Arg Gly Ser Leu Asn Thr
    50                  55                  60

Tyr Arg Phe Cys Asp Asn Val Trp Thr Phe Val Leu Asn Asp Val Glu
65                  70                  75                  80

Phe Arg Glu Val Thr Glu Leu Ile Lys Val Asp Lys Val Lys Ile Val
                85                  90                  95

Ala Cys Asp Gly Lys Asn Thr Gly Ser Asn Thr Thr Glu
            100                 105

<210> SEQ ID NO 75
<211> LENGTH: 693
<212> TYPE: PRT
<213> ORGANISM: Homo Sapiens

<400> SEQUENCE: 75

Met Ala Leu Cys Asn Gly Asp Ser Lys Leu Glu Asn Ala Gly Gly Asp
1               5                   10                  15

Leu Lys Asp Gly His His His Tyr Glu Gly Ala Val Val Ile Leu Asp
            20                  25                  30

Ala Gly Ala Gln Tyr Gly Lys Val Ile Asp Arg Arg Val Arg Glu Leu
        35                  40                  45

Phe Val Gln Ser Glu Ile Phe Pro Leu Glu Thr Pro Ala Phe Ala Ile
    50                  55                  60

Lys Glu Gln Gly Phe Arg Ala Ile Ile Ser Gly Gly Pro Asn Ser
65                  70                  75                  80

Val Tyr Ala Glu Asp Ala Pro Trp Phe Asp Pro Ala Ile Phe Thr Ile
                85                  90                  95

Gly Lys Pro Val Leu Gly Ile Cys Tyr Gly Met Gln Met Met Asn Lys
            100                 105                 110

Val Phe Gly Gly Thr Val His Lys Lys Ser Val Arg Glu Asp Gly Val
        115                 120                 125

Phe Asn Ile Ser Val Asp Asn Thr Cys Ser Leu Phe Arg Gly Leu Gln
    130                 135                 140

Lys Glu Glu Val Val Leu Leu Thr His Gly Asp Ser Val Asp Lys Val
145                 150                 155                 160

Ala Asp Gly Phe Lys Val Val Ala Arg Ser Gly Asn Ile Val Ala Gly
                165                 170                 175

Ile Ala Asn Glu Ser Lys Lys Leu Tyr Gly Ala Gln Phe His Pro Glu
            180                 185                 190

Val Gly Leu Thr Glu Asn Gly Lys Val Ile Leu Lys Asn Phe Leu Tyr
        195                 200                 205
```

```
Asp Ile Ala Gly Cys Ser Gly Thr Phe Thr Val Gln Asn Arg Glu Leu
    210                 215                 220

Glu Cys Ile Arg Glu Ile Lys Glu Arg Val Gly Thr Ser Lys Val Leu
225                 230                 235                 240

Val Leu Leu Ser Gly Val Asp Ser Thr Val Cys Thr Ala Leu Leu
                245                 250                 255

Asn Arg Ala Leu Asn Gln Gln Val Ile Ala Val His Ile Asp Asn
            260                 265                 270

Gly Phe Met Arg Lys Arg Glu Ser Gln Ser Val Glu Glu Ala Leu Lys
        275                 280                 285

Lys Leu Gly Ile Gln Val Lys Val Ile Asn Ala Ala His Ser Phe Tyr
    290                 295                 300

Asn Gly Thr Thr Thr Leu Pro Ile Ser Asp Glu Asp Arg Thr Pro Arg
305                 310                 315                 320

Lys Arg Ile Ser Lys Thr Leu Asn Met Thr Thr Ser Pro Glu Glu Lys
                325                 330                 335

Arg Lys Ile Ile Gly Asp Thr Phe Val Lys Ile Ala Asn Glu Val Ile
            340                 345                 350

Gly Glu Met Asn Leu Lys Pro Glu Glu Val Phe Leu Ala Gln Gly Thr
        355                 360                 365

Leu Arg Pro Asp Leu Ile Glu Ser Ala Ser Leu Val Ala Ser Gly Lys
    370                 375                 380

Ala Glu Leu Ile Lys Thr His His Asn Asp Thr Glu Leu Ile Arg Lys
385                 390                 395                 400

Leu Arg Glu Glu Gly Lys Val Ile Glu Pro Leu Lys Asp Phe His Lys
                405                 410                 415

Asp Glu Val Arg Ile Leu Gly Arg Glu Leu Gly Leu Pro Glu Glu Leu
            420                 425                 430

Val Ser Arg His Pro Phe Pro Gly Pro Gly Leu Ala Ile Arg Val Ile
        435                 440                 445

Cys Ala Glu Glu Pro Tyr Ile Cys Lys Asp Phe Pro Glu Thr Asn Asn
    450                 455                 460

Ile Leu Lys Ile Val Ala Asp Phe Ser Ala Ser Val Lys Lys Pro His
465                 470                 475                 480

Thr Leu Leu Gln Arg Val Lys Ala Cys Thr Thr Glu Glu Asp Gln Glu
                485                 490                 495

Lys Leu Met Gln Ile Thr Ser Leu His Ser Leu Asn Ala Phe Leu Leu
            500                 505                 510

Pro Ile Lys Thr Val Gly Val Gln Gly Asp Cys Arg Ser Tyr Ser Tyr
        515                 520                 525

Val Cys Gly Ile Ser Ser Lys Asp Glu Pro Asp Trp Glu Ser Leu Ile
    530                 535                 540

Phe Leu Ala Arg Leu Ile Pro Arg Met Cys His Asn Val Asn Arg Val
545                 550                 555                 560

Val Tyr Ile Phe Gly Pro Pro Val Lys Glu Pro Thr Asp Val Thr
                565                 570                 575

Pro Thr Phe Leu Thr Thr Gly Val Leu Ser Thr Leu Arg Gln Ala Asp
            580                 585                 590

Phe Glu Ala His Asn Ile Leu Arg Glu Ser Gly Tyr Ala Gly Lys Ile
        595                 600                 605

Ser Gln Met Pro Val Ile Leu Thr Pro Leu His Phe Asp Arg Asp Pro
610                 615                 620
```

```
Leu Gln Lys Gln Pro Ser Cys Gln Arg Ser Val Val Ile Arg Thr Phe
625                 630                 635                 640

Ile Thr Ser Asp Phe Met Thr Gly Ile Pro Ala Thr Pro Gly Asn Glu
                645                 650                 655

Ile Pro Val Glu Val Val Leu Lys Met Val Thr Glu Ile Lys Lys Ile
                660                 665                 670

Pro Gly Ile Ser Arg Ile Met Tyr Asp Leu Thr Ser Lys Pro Pro Gly
            675                 680                 685

Thr Thr Glu Trp Glu
            690

<210> SEQ ID NO 76
<211> LENGTH: 143
<212> TYPE: PRT
<213> ORGANISM: Homo Sapiens

<400> SEQUENCE: 76

Met Ser Gly Arg Gly Lys Thr Gly Gly Lys Ala Arg Ala Lys Ala Lys
1               5                   10                  15

Ser Arg Ser Ser Arg Ala Gly Leu Gln Phe Pro Val Gly Arg Val His
                20                  25                  30

Arg Leu Leu Arg Lys Gly His Tyr Ala Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Gly Val Thr Ile Ala Gln Gly Gly Val Leu Pro Asn Ile
                100                 105                 110

Gln Ala Val Leu Leu Pro Lys Lys Thr Ser Ala Thr Val Gly Pro Lys
            115                 120                 125

Ala Pro Ser Gly Gly Lys Lys Ala Thr Gln Ala Ser Gln Glu Tyr
        130                 135                 140

<210> SEQ ID NO 77
<211> LENGTH: 126
<212> TYPE: PRT
<213> ORGANISM: Homo Sapiens

<400> SEQUENCE: 77

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Ser Arg Lys Glu Ser Tyr Ser Val Tyr Val Tyr Lys Val Leu Lys Gln
            35                  40                  45

Val His Pro Asp Thr Gly Ile Ser Ser Lys Ala Met Gly Ile Met Asn
        50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
                100                 105                 110
```

-continued

```
Ser Glu Gly Thr Lys Ala Val Thr Lys Tyr Thr Ser Lys
            115                 120                 125

<210> SEQ ID NO 78
<211> LENGTH: 664
<212> TYPE: PRT
<213> ORGANISM: Homo Sapiens

<400> SEQUENCE: 78

Met Lys Thr Gly Pro Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
                20                  25                  30

Glu Thr Val Ala Pro Asp Asn Thr Ala Ile Pro Ser Leu Trp Ala Glu
            35                  40                  45

Ala Glu Glu Asn Glu Lys Glu Thr Ala Val Ser Thr Glu Asp Asp Ser
        50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
            260                 265                 270

Asn Ala Glu Met Glu Glu Glu Asn Ala Ser Asn Val Asn Lys His Ile
        275                 280                 285

Gln Glu Thr Glu Trp Gln Ser Gln Glu Gly Lys Thr Gly Leu Glu Ala
    290                 295                 300

Ile Ser Asn His Lys Glu Thr Glu Lys Thr Val Ser Glu Ala Leu
305                 310                 315                 320

Leu Met Glu Pro Thr Asp Asp Gly Asn Thr Thr Pro Arg Asn His Gly
                325                 330                 335

Val Asp Asp Asp Gly Asp Asp Gly Asp Asp Gly Thr Asp Gly
            340                 345                 350

Pro Arg His Ser Ala Ser Asp Asp Tyr Phe Ile Pro Ser Gln Ala Phe
        355                 360                 365
```

```
Leu Glu Ala Glu Arg Ala Gln Ser Ile Ala Tyr His Leu Lys Ile Glu
    370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
                405                 410                 415
Glu Glu Thr Ser Ser Glu Gly Asn Met Arg Val His Ala Val Asp Ser
                420                 425                 430
Cys Met Ser Phe Gln Cys Lys Arg Gly His Ile Cys Lys Ala Asp Gln
            435                 440                 445
Gln Gly Lys Pro His Cys Val Cys Gln Asp Pro Val Thr Cys Pro Pro
450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                485                 490                 495
Lys Gly His Gln Leu Gln Leu Asp Tyr Phe Gly Ala Cys Lys Ser Ile
            500                 505                 510
Pro Thr Cys Thr Asp Phe Glu Val Ile Gln Phe Pro Leu Arg Met Arg
        515                 520                 525
Asp Trp Leu Lys Asn Ile Leu Met Gln Leu Tyr Glu Ala Asn Ser Glu
    530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                565                 570                 575
Leu Leu Arg Asp Phe Lys Lys Asn Tyr His Met Tyr Val Tyr Pro Val
            580                 585                 590
His Trp Gln Phe Ser Glu Leu Asp Gln His Pro Met Asp Arg Val Leu
        595                 600                 605
Thr His Ser Glu Leu Ala Pro Leu Arg Ala Ser Leu Val Pro Met Glu
    610                 615                 620
His Cys Ile Thr Arg Phe Phe Glu Glu Cys Asp Pro Asn Lys Asp Lys
625                 630                 635                 640
His Ile Thr Leu Lys Glu Trp Gly His Cys Phe Gly Ile Lys Glu Glu
                645                 650                 655
Asp Ile Asp Glu Asn Leu Leu Phe
                660

<210> SEQ ID NO 79
<211> LENGTH: 460
<212> TYPE: PRT
<213> ORGANISM: Homo Sapiens

<400> SEQUENCE: 79

Ala Lys Leu Ala Thr Lys Ser Pro Thr Ile Thr Met Met Leu Ser Thr
1               5                   10                  15
Glu Gly Arg Glu Gly Phe Val Val Lys Val Arg Gly Leu Pro Trp Ser
                20                  25                  30
Cys Ser Ala Asp Glu Val Met Arg Phe Phe Ser Asp Cys Lys Ile Gln
            35                  40                  45
Asn Gly Thr Ser Gly Ile Arg Phe Ile Tyr Thr Arg Glu Gly Arg Pro
        50                  55                  60
Ser Gly Glu Ala Phe Val Glu Leu Glu Ser Glu Glu Glu Val Lys Leu
```

-continued

```
65                      70                      75                      80
Ala Leu Lys Lys Asp Arg Glu Thr Met Gly His Arg Tyr Val Glu Val
                    85                      90                      95

Phe Lys Ser Asn Ser Val Glu Met Asp Trp Val Leu Lys His Thr Gly
                100                     105                     110

Pro Asn Ser Pro Asp Thr Ala Asn Asp Gly Phe Val Arg Leu Arg Gly
                115                     120                     125

Leu Pro Phe Gly Cys Ser Lys Glu Glu Ile Val Gln Phe Phe Ser Gly
            130                     135                     140

Leu Glu Ile Val Pro Asn Gly Met Thr Leu Pro Val Asp Phe Gln Gly
145                     150                     155                     160

Arg Ser Thr Gly Glu Ala Phe Val Gln Phe Ala Ser Gln Glu Ile Ala
                    165                     170                     175

Glu Lys Ala Leu Lys Lys His Lys Glu Arg Ile Gly His Arg Tyr Ile
                180                     185                     190

Glu Ile Phe Lys Ser Ser Arg Ala Glu Val Arg Thr His Tyr Asp Pro
                195                     200                     205

Pro Arg Lys Leu Met Ala Met Gln Arg Pro Gly Pro Tyr Asp Arg Pro
            210                     215                     220

Gly Ala Gly Arg Gly Tyr Asn Ser Ile Gly Arg Gly Ala Gly Phe Glu
225                     230                     235                     240

Arg Met Arg Arg Gly Ala Tyr Gly Gly Tyr Gly Gly Tyr Asp Asp
                    245                     250                     255

Tyr Gly Gly Tyr Asn Asp Gly Tyr Gly Phe Gly Ser Asp Arg Phe Gly
                260                     265                     270

Arg Asp Leu Asn Tyr Cys Phe Ser Gly Met Ser Asp His Arg Tyr Gly
            275                     280                     285

Asp Gly Gly Ser Ser Phe Gln Ser Thr Thr Gly His Cys Val His Met
290                     295                     300

Arg Gly Leu Pro Tyr Arg Ala Thr Glu Asn Asp Ile Tyr Asn Phe Phe
305                     310                     315                     320

Ser Pro Leu Asn Pro Met Arg Val His Ile Glu Ile Gly Pro Asp Gly
                325                     330                     335

Arg Val Thr Gly Glu Ala Asp Val Glu Phe Ala Thr His Glu Asp Ala
                340                     345                     350

Val Ala Ala Met Ala Lys Asp Lys Ala Asn Met Gln His Arg Tyr Val
                355                     360                     365

Glu Leu Phe Leu Asn Ser Thr Ala Gly Thr Ser Gly Gly Ala Tyr Asp
            370                     375                     380

His Ser Tyr Val Glu Leu Phe Leu Asn Ser Thr Ala Gly Ala Ser Gly
385                     390                     395                     400

Gly Ala Tyr Gly Ser Gln Met Met Gly Met Gly Leu Ser Asn Gln
                    405                     410                     415

Ser Ser Tyr Gly Gly Pro Ala Ser Gln Gln Leu Ser Gly Tyr Gly
                420                     425                     430

Gly Gly Tyr Gly Gly Gln Ser Ser Met Ser Gly Tyr Asp Gln Val Leu
                435                     440                     445

Gln Glu Asn Ser Ser Asp Tyr Gln Ser Asn Leu Ala
450                     455                     460

<210> SEQ ID NO 80
<211> LENGTH: 432
<212> TYPE: PRT
<213> ORGANISM: Homo Sapiens
```

<400> SEQUENCE: 80

```
Met Asp Glu Ala Val Gly Asp Leu Lys Gln Ala Leu Pro Cys Val Ala
1               5                   10                  15

Glu Ser Pro Thr Val His Val Glu Val His Gln Arg Gly Ser Ser Thr
            20                  25                  30

Ala Lys Lys Glu Asp Ile Asn Leu Ser Val Arg Lys Leu Leu Asn Arg
        35                  40                  45

His Asn Ile Val Phe Gly Asp Tyr Thr Trp Thr Glu Phe Asp Glu Pro
    50                  55                  60

Phe Leu Thr Arg Asn Val Gln Ser Val Ser Ile Ile Asp Thr Glu Leu
65                  70                  75                  80

Lys Val Lys Asp Ser Gln Pro Ile Asp Leu Ser Ala Cys Thr Val Ala
                85                  90                  95

Leu His Ile Phe Gln Leu Asn Glu Asp Gly Pro Ser Ser Glu Asn Leu
            100                 105                 110

Glu Glu Glu Thr Glu Asn Ile Ile Ala Ala Asn His Trp Val Leu Pro
        115                 120                 125

Ala Ala Glu Phe His Gly Leu Trp Asp Ser Leu Val Tyr Asp Val Glu
    130                 135                 140

Val Lys Ser His Leu Leu Asp Tyr Val Met Thr Thr Leu Leu Phe Ser
145                 150                 155                 160

Asp Lys Asn Val Asn Ser Asn Leu Ile Thr Trp Asn Arg Val Val Leu
                165                 170                 175

Leu His Gly Pro Pro Gly Thr Gly Lys Thr Ser Leu Cys Lys Ala Leu
            180                 185                 190

Ala Gln Lys Leu Thr Ile Arg Leu Ser Ser Arg Tyr Arg Tyr Gly Gln
        195                 200                 205

Leu Ile Glu Ile Asn Ser His Ser Leu Phe Ser Lys Trp Phe Ser Glu
    210                 215                 220

Ser Gly Lys Leu Val Thr Lys Met Phe Gln Lys Ile Gln Asp Leu Ile
225                 230                 235                 240

Asp Asp Lys Asp Ala Leu Val Phe Val Leu Ile Asp Glu Val Glu Ser
                245                 250                 255

Leu Thr Ala Ala Arg Asn Ala Cys Arg Ala Gly Thr Glu Pro Ser Asp
            260                 265                 270

Ala Ile Arg Val Val Asn Ala Val Leu Thr Gln Ile Asp Gln Ile Lys
        275                 280                 285

Arg His Ser Asn Val Val Ile Leu Thr Thr Ser Asn Ile Thr Glu Lys
    290                 295                 300

Ile Asp Val Ala Phe Val Asp Arg Ala Asp Ile Lys Gln Tyr Ile Gly
305                 310                 315                 320

Pro Pro Ser Ala Ala Ile Phe Lys Ile Tyr Leu Ser Cys Leu Glu
                325                 330                 335

Glu Leu Met Lys Cys Gln Ile Ile Tyr Pro Arg Gln Leu Leu Thr
            340                 345                 350

Leu Arg Glu Leu Glu Met Ile Gly Phe Ile Glu Asn Asn Val Ser Lys
        355                 360                 365

Leu Ser Leu Leu Leu Asn Asp Ile Ser Arg Lys Ser Glu Gly Leu Ser
    370                 375                 380

Gly Arg Val Leu Arg Lys Leu Pro Phe Leu Ala His Ala Leu Tyr Val
385                 390                 395                 400

Gln Ala Pro Thr Val Thr Ile Glu Gly Phe Leu Gln Ala Leu Ser Leu
```

-continued

```
                     405                 410                 415
Ala Val Asp Lys Gln Phe Glu Glu Arg Lys Lys Leu Ala Ala Tyr Ile
                420                 425                 430

<210> SEQ ID NO 81
<211> LENGTH: 653
<212> TYPE: PRT
<213> ORGANISM: Homo Sapiens

<400> SEQUENCE: 81

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
                20                  25                  30

Gln Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
                100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350
```

```
Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 82
<211> LENGTH: 153
<212> TYPE: PRT
<213> ORGANISM: Homo Sapiens

<400> SEQUENCE: 82

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80
```

-continued

```
Ser Ser Ser Arg Arg Ala Pro Gln Thr Gly Ile Val Asp Glu Cys Cys
            85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
            130                 135                 140

Ser Ala Gly Asn Lys Asn Tyr Arg Met
145                 150

<210> SEQ ID NO 83
<211> LENGTH: 1575
<212> TYPE: PRT
<213> ORGANISM: Homo Sapiens

<400> SEQUENCE: 83

Met Pro His Glu Glu Leu Pro Ser Leu Gln Arg Pro Arg Tyr Gly Ser
1               5                   10                  15

Ile Val Asp Asp Glu Arg Leu Ser Ala Glu Glu Met Asp Glu Arg Arg
            20                  25                  30

Arg Gln Asn Ile Ala Tyr Glu Tyr Leu Cys His Leu Glu Glu Ala Lys
            35                  40                  45

Arg Trp Met Glu Val Cys Leu Val Glu Leu Pro Pro Thr Thr Glu
    50                  55                  60

Leu Glu Glu Gly Leu Arg Asn Gly Val Tyr Leu Ala Lys Leu Ala Lys
65                  70                  75                  80

Phe Phe Ala Pro Lys Met Val Ser Glu Lys Ile Tyr Asp Val Glu
                85                  90                  95

Gln Thr Arg Tyr Lys Lys Ser Gly Leu His Phe Arg His Thr Asp Asn
            100                 105                 110

Thr Val Gln Trp Leu Arg Ala Met Glu Ser Ile Gly Leu Pro Lys Ile
            115                 120                 125

Phe Tyr Pro Glu Thr Thr Asp Val Tyr Asp Arg Lys Asn Ile Pro Arg
            130                 135                 140

Met Ile Tyr Cys Ile His Ala Leu Ser Leu Tyr Leu Phe Lys Leu Gly
145                 150                 155                 160

Ile Ala Pro Gln Ile Gln Asp Leu Leu Gly Lys Val Asp Phe Thr Glu
                165                 170                 175

Glu Glu Ile Ser Asn Met Arg Lys Glu Leu Glu Lys Tyr Gly Ile Gln
            180                 185                 190

Met Pro Ser Phe Ser Lys Ile Gly Gly Ile Leu Ala Asn Glu Leu Ser
            195                 200                 205

Val Asp Glu Ala Leu His Ala Ala Val Ile Ala Ile Asn Glu Ala
            210                 215                 220

Val Glu Lys Gly Ile Ala Glu Gln Thr Val Thr Leu Arg Asn Pro
225                 230                 235                 240

Asn Ala Val Leu Thr Leu Val Asp Asp Asn Leu Ala Pro Glu Tyr Gln
                245                 250                 255

Lys Glu Leu Trp Asp Ala Lys Lys Lys Glu Glu Asn Ala Arg Leu
            260                 265                 270

Lys Asn Ser Cys Ile Ser Glu Glu Arg Asp Ala Tyr Glu Glu Leu
            275                 280                 285

Leu Thr Gln Ala Glu Ile Gln Gly Asn Ile Asn Lys Val Asn Arg Gln
```

-continued

```
              290                 295                 300
Ala Ala Val Asp His Ile Asn Ala Val Ile Pro Glu Gly Asp Pro Glu
305                 310                 315                 320
Asn Thr Leu Leu Ala Leu Lys Lys Pro Glu Ala Gln Leu Pro Ala Val
                325                 330                 335
Tyr Pro Phe Ala Ala Ala Met Tyr Gln Asn Glu Leu Phe Asn Leu Gln
                340                 345                 350
Lys Gln Asn Thr Met Asn Tyr Leu Ala His Glu Glu Leu Leu Ile Ala
                355                 360                 365
Val Glu Met Leu Ser Ala Val Ala Leu Leu Asn Gln Ala Leu Glu Ser
370                 375                 380
Asn Asp Leu Val Ser Val Gln Asn Gln Leu Arg Ser Pro Ala Ile Gly
385                 390                 395                 400
Leu Asn Asn Leu Asp Lys Ala Tyr Val Glu Arg Tyr Ala Asn Thr Leu
                405                 410                 415
Leu Ser Val Lys Leu Glu Val Leu Ser Gln Gly Gln Asp Asn Leu Ser
                420                 425                 430
Trp Asn Glu Ile Gln Asn Cys Ile Asp Met Val Asn Ala Gln Ile Gln
                435                 440                 445
Glu Glu Asn Asp Arg Val Val Ala Val Gly Tyr Ile Asn Glu Ala Ile
450                 455                 460
Asp Glu Gly Asn Pro Leu Arg Thr Leu Glu Thr Leu Leu Pro Thr
465                 470                 475                 480
Ala Asn Ile Ser Asp Val Asp Pro Ala His Ala Gln His Tyr Gln Asp
                485                 490                 495
Val Leu Tyr His Ala Lys Ser Gln Lys Leu Gly Asp Ser Glu Ser Val
                500                 505                 510
Ser Lys Val Leu Trp Leu Asp Glu Ile Gln Gln Ala Val Asp Glu Ala
                515                 520                 525
Asn Val Asp Glu Asp Arg Ala Lys Gln Trp Val Thr Leu Val Val Asp
530                 535                 540
Val Asn Gln Cys Leu Glu Gly Lys Lys Ser Ser Asp Ile Leu Ser Val
545                 550                 555                 560
Leu Lys Ser Ser Thr Ser Asn Ala Asn Asp Ile Ile Pro Glu Cys Ala
                565                 570                 575
Asp Lys Tyr Tyr Asp Ala Leu Val Lys Ala Lys Glu Leu Lys Ser Glu
                580                 585                 590
Arg Val Ser Ser Asp Gly Ser Trp Leu Lys Leu Asn Leu His Lys Lys
                595                 600                 605
Tyr Asp Tyr Tyr Asn Thr Asp Ser Lys Glu Ser Ser Trp Val Thr
                610                 615                 620
Pro Glu Ser Cys Phe Tyr Lys Glu Ser Trp Leu Thr Gly Lys Glu Ile
625                 630                 635                 640
Glu Asp Ile Ile Glu Glu Val Thr Val Gly Tyr Ile Arg Glu Asn Ile
                645                 650                 655
Trp Ser Ala Ser Glu Glu Leu Leu Arg Phe Gln Ala Thr Ser Ser
                660                 665                 670
Gly Pro Ile Leu Arg Glu Glu Phe Glu Ala Arg Lys Ser Phe Leu His
                675                 680                 685
Glu Gln Glu Glu Asn Val Val Lys Ile Gln Ala Phe Trp Lys Gly Tyr
                690                 695                 700
Lys Gln Arg Lys Glu Tyr Met His Arg Arg Gln Thr Phe Ile Asp Asn
705                 710                 715                 720
```

-continued

```
Thr Asp Ser Val Val Lys Ile Gln Ser Trp Phe Arg Met Ala Thr Ala
                725                 730                 735
Arg Lys Ser Tyr Leu Ser Arg Leu Gln Tyr Phe Arg Asp His Asn Asn
            740                 745                 750
Glu Ile Val Lys Ile Gln Ser Leu Leu Arg Ala Asn Lys Ala Arg Asp
            755                 760                 765
Asp Tyr Lys Thr Leu Val Gly Ser Glu Asn Pro Pro Leu Thr Val Ile
770                 775                 780
Arg Lys Phe Val Tyr Leu Leu Asp Gln Ser Asp Leu Asp Phe Gln Glu
785                 790                 795                 800
Glu Leu Glu Val Ala Arg Leu Arg Glu Glu Val Val Thr Lys Ile Arg
                805                 810                 815
Ala Asn Gln Gln Leu Glu Lys Asp Leu Asn Leu Met Asp Ile Lys Ile
                820                 825                 830
Gly Leu Leu Val Lys Asn Arg Ile Thr Leu Glu Asp Val Ile Ser His
                835                 840                 845
Ser Lys Lys Leu Asn Lys Lys Gly Gly Glu Met Glu Ile Leu Asn
850                 855                 860
Asn Thr Asp Asn Gln Gly Ile Lys Ser Leu Ser Lys Glu Arg Arg Lys
865                 870                 875                 880
Thr Leu Glu Thr Tyr Gln Gln Leu Phe Tyr Leu Leu Gln Thr Asn Pro
                885                 890                 895
Leu Tyr Leu Ala Lys Leu Ile Phe Gln Met Pro Gln Asn Lys Ser Thr
                900                 905                 910
Lys Phe Met Asp Thr Val Ile Phe Thr Leu Tyr Asn Tyr Ala Ser Asn
                915                 920                 925
Gln Arg Glu Glu Tyr Leu Leu Leu Lys Leu Phe Lys Thr Ala Leu Glu
                930                 935                 940
Glu Glu Ile Lys Ser Lys Val Asp Gln Val Gln Asp Ile Val Thr Gly
945                 950                 955                 960
Asn Pro Thr Val Ile Lys Met Val Val Ser Phe Asn Arg Gly Ala Arg
                965                 970                 975
Gly Gln Asn Thr Leu Arg Gln Leu Leu Ala Pro Val Val Lys Glu Ile
                980                 985                 990
Ile Asp Asp Lys Ser Leu Ile Ile Asn Thr Asn Pro Val Glu Val Tyr
                995                1000                1005
Lys Ala Trp Val Asn Gln Leu Glu Thr Gln Thr Gly Glu Ala Ser
                1010                1015                1020
Lys Leu Pro Tyr Asp Val Thr Thr Glu Gln Ala Leu Thr Tyr Pro
                1025                1030                1035
Glu Val Lys Asn Lys Leu Glu Ala Ser Ile Glu Asn Leu Arg Arg
                1040                1045                1050
Val Thr Asp Lys Val Leu Asn Ser Ile Ile Ser Ser Leu Asp Leu
                1055                1060                1065
Leu Pro Tyr Gly Leu Arg Tyr Ile Ala Lys Val Leu Lys Asn Ser
                1070                1075                1080
Ile His Glu Lys Phe Pro Ala Thr Glu Asp Glu Leu Leu Lys
                1085                1090                1095
Ile Val Gly Asn Leu Leu Tyr Tyr Arg Tyr Met Asn Pro Ala Ile
                1100                1105                1110
Val Ala Pro Asp Gly Phe Asp Ile Ile Asp Met Thr Ala Gly Gly
                1115                1120                1125
```

-continued

```
Gln Ile Asn Ser Asp Gln Arg Arg Asn Leu Gly Ser Val Ala Lys
    1130                1135                1140

Val Leu Gln His Ala Ala Ser Asn Lys Leu Phe Glu Gly Glu Asn
    1145                1150                1155

Glu His Leu Ser Ser Met Asn Asn Tyr Leu Ser Glu Thr Tyr Gln
    1160                1165                1170

Glu Phe Arg Lys Tyr Phe Lys Glu Ala Cys Asn Val Pro Glu Pro
    1175                1180                1185

Glu Glu Lys Phe Asn Met Asp Lys Tyr Thr Asp Leu Val Thr Val
    1190                1195                1200

Ser Lys Pro Val Ile Tyr Ile Ser Ile Glu Glu Ile Ile Ser Thr
    1205                1210                1215

His Ser Leu Leu Leu Glu His Gln Asp Ala Ile Ala Pro Glu Lys
    1220                1225                1230

Asn Asp Leu Leu Ser Glu Leu Leu Gly Ser Leu Gly Glu Val Pro
    1235                1240                1245

Thr Val Glu Ser Phe Leu Gly Glu Gly Ala Val Asp Pro Asn Asp
    1250                1255                1260

Pro Asn Lys Ala Asn Thr Leu Ser Gln Leu Ser Lys Thr Glu Ile
    1265                1270                1275

Ser Leu Val Leu Thr Ser Lys Tyr Asp Ile Glu Asp Gly Glu Ala
    1280                1285                1290

Ile Asp Ser Arg Ser Leu Met Ile Lys Thr Lys Lys Leu Ile Ile
    1295                1300                1305

Asp Val Ile Arg Asn Gln Pro Gly Asn Thr Leu Thr Glu Ile Leu
    1310                1315                1320

Glu Thr Pro Ala Thr Ala Gln Gln Glu Val Asp His Ala Thr Asp
    1325                1330                1335

Met Val Ser Arg Ala Met Ile Asp Ser Arg Thr Pro Glu Glu Met
    1340                1345                1350

Lys His Ser Gln Ser Met Ile Glu Asp Ala Gln Leu Pro Leu Glu
    1355                1360                1365

Gln Lys Lys Arg Lys Ile Gln Arg Asn Leu Arg Thr Leu Glu Gln
    1370                1375                1380

Thr Gly His Val Ser Ser Glu Asn Lys Tyr Gln Asp Ile Leu Asn
    1385                1390                1395

Glu Ile Ala Lys Asp Ile Arg Asn Gln Arg Ile Tyr Arg Lys Leu
    1400                1405                1410

Arg Lys Ala Glu Leu Ala Lys Leu Gln Gln Thr Leu Asn Ala Leu
    1415                1420                1425

Asn Lys Lys Ala Ala Phe Tyr Glu Glu Gln Ile Asn Tyr Tyr Asp
    1430                1435                1440

Thr Tyr Ile Lys Thr Cys Leu Asp Asn Leu Lys Arg Lys Asn Thr
    1445                1450                1455

Arg Arg Ser Ile Lys Leu Asp Gly Lys Gly Glu Pro Lys Gly Ala
    1460                1465                1470

Lys Arg Ala Lys Pro Val Lys Tyr Thr Ala Ala Lys Leu His Glu
    1475                1480                1485

Lys Gly Val Leu Leu Asp Ile Asp Asp Leu Gln Thr Asn Gln Phe
    1490                1495                1500

Lys Asn Val Thr Phe Asp Ile Ile Ala Thr Glu Asp Val Gly Ile
    1505                1510                1515

Phe Asp Val Arg Ser Lys Phe Leu Gly Val Glu Met Glu Lys Val
```

```
                1520              1525              1530
        Gln Leu Asn Ile Gln Asp Leu Leu Gln Met Gln Tyr Glu Gly Val
                1535              1540              1545

Ala Val Met Lys Met Phe Asp Lys Val Lys Val Asn Val Asn Leu
                1550              1555              1560

Leu Ile Tyr Leu Leu Asn Lys Lys Phe Tyr Gly Lys
                1565              1570              1575

<210> SEQ ID NO 84
<211> LENGTH: 165
<212> TYPE: PRT
<213> ORGANISM: Homo Sapiens

<400> SEQUENCE: 84

Met Gly Trp Asp Leu Thr Val Lys Met Leu Ala Gly Asn Glu Phe Gln
1               5                   10                  15

Val Ser Leu Ser Ser Met Ser Val Ser Glu Leu Lys Ala Gln Ile
            20                  25                  30

Thr Gln Lys Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
        115                 120                 125

Lys Pro Leu Glu Asp Gln Leu Pro Leu Gly Glu Tyr Gly Leu Lys Pro
    130                 135                 140

Leu Ser Thr Val Phe Met Asn Leu Arg Leu Arg Gly Gly Gly Thr Glu
145                 150                 155                 160

Pro Gly Gly Arg Ser
            165

<210> SEQ ID NO 85
<211> LENGTH: 1218
<212> TYPE: PRT
<213> ORGANISM: Homo Sapiens

<400> SEQUENCE: 85

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
```

-continued

```
                100                 105                 110
Arg Gly Asn Asp Pro Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
            130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
            165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
            195                 200                 205

His Tyr Ala Cys Asp Gln Asn Gly Asn Lys Thr Cys Met Glu Gly Trp
            210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
            245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
            275                 280                 285

Gly Gly Gln Leu Cys Asp Lys Asp Leu Asn Tyr Cys Gly Thr His Gln
            290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
            325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
            405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
            450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
            485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525
```

```
Cys Glu Pro Asn Pro Cys Gln Asn Gly Ala Gln Cys Tyr Asn Arg Ala
    530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
        595                 600                 605
Ser Gly Gly Lys Phe Thr Cys Asp Cys Asn Lys Gly Phe Thr Gly Thr
    610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
                645                 650                 655
Asp Gly Trp Glu Gly Ala Tyr Cys Glu Thr Asn Ile Asn Asp Cys Ser
            660                 665                 670
Gln Asn Pro Cys His Asn Gly Gly Thr Cys Arg Asp Leu Val Asn Asp
        675                 680                 685
Phe Tyr Cys Asp Cys Lys Asn Gly Trp Lys Gly Lys Thr Cys His Ser
    690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
                725                 730                 735
Gly Thr Thr Cys Asn Ile Ala Arg Asn Ser Ser Cys Leu Pro Asn Pro
            740                 745                 750
Cys His Asn Gly Gly Thr Cys Val Val Asn Gly Glu Ser Phe Thr Cys
        755                 760                 765
Val Cys Lys Glu Gly Trp Glu Gly Pro Ile Cys Ala Gln Asn Thr Asn
    770                 775                 780
Asp Cys Ser Pro His Pro Cys Tyr Asn Ser Gly Thr Cys Val Asp Gly
785                 790                 795                 800
Asp Asn Trp Tyr Arg Cys Glu Cys Ala Pro Gly Phe Ala Gly Pro Asp
                805                 810                 815
Cys Arg Ile Asn Ile Asn Glu Cys Gln Ser Ser Pro Cys Ala Phe Gly
            820                 825                 830
Ala Thr Cys Val Asp Glu Ile Asn Gly Tyr Arg Cys Val Cys Pro Pro
        835                 840                 845
Gly His Ser Gly Ala Lys Cys Gln Glu Val Ser Gly Arg Pro Cys Ile
    850                 855                 860
Thr Met Gly Ser Val Ile Pro Asp Gly Ala Lys Trp Asp Asp Asp Cys
865                 870                 875                 880
Asn Thr Cys Gln Cys Leu Asn Gly Arg Ile Ala Cys Ser Lys Val Trp
                885                 890                 895
Cys Gly Pro Arg Pro Cys Leu Leu His Lys Gly His Ser Glu Cys Pro
            900                 905                 910
Ser Gly Gln Ser Cys Ile Pro Ile Leu Asp Asp Gln Cys Phe Val His
        915                 920                 925
Pro Cys Thr Gly Val Gly Glu Cys Arg Ser Ser Ser Leu Gln Pro Val
    930                 935                 940
```

-continued

```
Lys Thr Lys Cys Thr Ser Asp Ser Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
                980                 985                 990

Ser Ala Glu Tyr Ser Ile Tyr Ile Ala Cys Glu Pro Ser Pro Ser Ala
            995                 1000                1005

Asn Asn Glu Ile His Val Ala Ile Ser Ala Glu Asp Ile Arg Asp
        1010                1015                1020

Asp Gly Asn Pro Ile Lys Glu Ile Thr Asp Lys Ile Ile Asp Leu
        1025                1030                1035

Val Ser Lys Arg Asp Gly Asn Ser Ser Leu Ile Ala Ala Val Ala
        1040                1045                1050

Glu Val Arg Val Gln Arg Arg Pro Leu Lys Asn Arg Thr Asp Phe
        1055                1060                1065

Leu Val Pro Leu Leu Ser Ser Val Leu Thr Val Ala Trp Ile Cys
        1070                1075                1080

Cys Leu Val Thr Ala Phe Tyr Trp Cys Leu Arg Lys Arg Arg Lys
        1085                1090                1095

Pro Gly Ser His Thr His Ser Ala Ser Glu Asp Asn Thr Thr Asn
        1100                1105                1110

Asn Val Arg Glu Gln Leu Asn Gln Ile Lys Asn Pro Ile Glu Lys
        1115                1120                1125

His Gly Ala Asn Thr Val Pro Ile Lys Asp Tyr Glu Asn Lys Asn
        1130                1135                1140

Ser Lys Met Ser Lys Ile Arg Thr His Asn Ser Glu Val Glu Glu
        1145                1150                1155

Asp Asp Met Asp Lys His Gln Gln Lys Ala Arg Phe Ala Lys Gln
        1160                1165                1170

Pro Ala Tyr Thr Leu Val Asp Arg Glu Glu Lys Pro Pro Asn Gly
        1175                1180                1185

Thr Pro Thr Lys His Pro Asn Trp Thr Asn Lys Gln Asp Asn Arg
        1190                1195                1200

Asp Leu Glu Ser Ala Gln Ser Leu Asn Arg Met Glu Tyr Ile Val
        1205                1210                1215

<210> SEQ ID NO 86
<211> LENGTH: 3110
<212> TYPE: PRT
<213> ORGANISM: Homo Sapiens

<400> SEQUENCE: 86

Met Pro Gly Ala Ala Gly Val Leu Leu Leu Leu Leu Ser Gly Gly
1               5                   10                  15

Leu Gly Gly Val Gln Ala Gln Arg Pro Gln Gln Arg Gln Ser Gln
                20                  25                  30

Ala His Gln Gln Arg Gly Leu Phe Pro Ala Val Leu Asn Leu Ala Ser
            35                  40                  45

Asn Ala Leu Ile Thr Thr Asn Ala Thr Cys Gly Glu Lys Gly Pro Glu
        50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95
```

```
His Pro Ile Thr Asn Ala Ile Asp Gly Lys Asn Thr Trp Trp Gln Ser
            100                 105                 110
Pro Ser Ile Lys Asn Gly Ile Glu Tyr His Tyr Val Thr Ile Thr Leu
        115                 120                 125
Asp Leu Gln Gln Val Phe Gln Ile Ala Tyr Val Ile Val Lys Ala Ala
    130                 135                 140
Asn Ser Pro Arg Pro Gly Asn Trp Ile Leu Glu Arg Ser Leu Asp Asp
145                 150                 155                 160
Val Glu Tyr Lys Pro Trp Gln Tyr His Ala Val Thr Asp Thr Glu Cys
                165                 170                 175
Leu Thr Leu Tyr Asn Ile Tyr Pro Arg Thr Gly Pro Pro Ser Tyr Ala
            180                 185                 190
Lys Asp Asp Glu Val Ile Cys Thr Ser Phe Tyr Ser Lys Ile His Pro
        195                 200                 205
Leu Glu Asn Gly Glu Ile His Ile Ser Leu Ile Asn Gly Arg Pro Ser
    210                 215                 220
Ala Asp Asp Pro Ser Pro Glu Leu Leu Glu Phe Thr Ser Ala Arg Tyr
225                 230                 235                 240
Ile Arg Leu Arg Phe Gln Arg Ile Arg Thr Leu Asn Ala Asp Leu Met
                245                 250                 255
Met Phe Ala His Lys Asp Pro Arg Glu Ile Asp Pro Ile Val Thr Arg
            260                 265                 270
Arg Tyr Tyr Ser Val Lys Asp Ile Ser Val Gly Gly Met Cys Ile
        275                 280                 285
Cys Tyr Gly His Ala Arg Ala Cys Pro Leu Asp Pro Ala Thr Asn Lys
    290                 295                 300
Ser Arg Cys Glu Cys Glu His Asn Thr Cys Gly Asp Ser Cys Asp Gln
305                 310                 315                 320
Cys Cys Pro Gly Phe His Gln Lys Pro Trp Arg Ala Gly Thr Phe Leu
                325                 330                 335
Thr Lys Thr Glu Cys Glu Ala Cys Asn Cys His Gly Lys Ala Glu Glu
            340                 345                 350
Cys Tyr Tyr Asp Glu Asn Val Ala Arg Arg Asn Leu Ser Leu Asn Ile
        355                 360                 365
Arg Gly Lys Tyr Ile Gly Gly Gly Val Cys Ile Asn Cys Thr Gln Asn
    370                 375                 380
Thr Ala Gly Ile Asn Cys Glu Thr Cys Thr Asp Gly Phe Phe Arg Pro
385                 390                 395                 400
Lys Gly Val Ser Pro Asn Tyr Pro Arg Pro Cys Gln Pro Cys His Cys
                405                 410                 415
Asp Pro Ile Gly Ser Leu Asn Glu Val Cys Val Lys Asp Glu Lys His
            420                 425                 430
Ala Arg Arg Gly Leu Ala Pro Gly Ser Cys His Cys Lys Thr Gly Phe
        435                 440                 445
Gly Gly Val Ser Cys Asp Arg Cys Ala Arg Gly Tyr Thr Gly Tyr Pro
    450                 455                 460
Asp Cys Lys Ala Cys Asn Cys Ser Gly Leu Gly Ser Lys Asn Glu Asp
465                 470                 475                 480
Pro Cys Phe Gly Pro Cys Ile Cys Lys Glu Asn Val Glu Gly Gly Asp
                485                 490                 495
Cys Ser Arg Cys Lys Ser Gly Phe Phe Asn Leu Gln Glu Asp Asn Trp
            500                 505                 510
```

-continued

```
Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
        530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
        595                 600                 605

Asp Leu Glu Glu Glu Glu Asp Thr Glu Arg Val Leu Gln Leu Met
        610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
        675                 680                 685

Thr Tyr Ser Phe Gly Met Asp Ala Ile Phe Arg Leu Ser Ser Val Asn
        690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Val Asn Gly Thr Ile Phe Gly Gly
            740                 745                 750

Ile Cys Glu Pro Cys Gln Cys Phe Gly His Ala Glu Ser Cys Asp Asp
        755                 760                 765

Val Thr Gly Glu Cys Leu Asn Cys Lys Asp His Thr Gly Gly Pro Tyr
770                 775                 780

Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
                805                 810                 815

Asn Phe Ser Pro Thr Cys His Leu Asp Arg Ser Leu Gly Leu Ile Cys
            820                 825                 830

Asp Gly Cys Pro Val Gly Tyr Thr Gly Pro Arg Cys Glu Arg Cys Ala
        835                 840                 845

Glu Gly Tyr Phe Gly Gln Pro Ser Val Pro Gly Gly Ser Cys Gln Pro
        850                 855                 860

Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
                885                 890                 895

Tyr Cys Glu Leu Cys Ala Asp Gly Tyr Phe Gly Asp Ala Val Asp Ala
            900                 905                 910

Lys Asn Cys Gln Pro Cys Arg Cys Asn Ala Gly Gly Ser Phe Ser Glu
        915                 920                 925

Val Cys His Ser Gln Thr Gly Gln Cys Glu Cys Arg Ala Asn Val Gln
```

-continued

```
              930                 935                 940
Gly Gln Arg Cys Asp Lys Cys Lys Ala Gly Thr Phe Gly Leu Gln Ser
945                 950                 955                 960
Ala Arg Gly Cys Val Pro Cys Asn Cys Asn Ser Phe Gly Ser Lys Ser
                965                 970                 975
Phe Asp Cys Glu Glu Ser Gly Gln Cys Trp Cys Gln Pro Gly Val Thr
            980                 985                 990
Gly Lys Lys Cys Asp Arg Cys Ala His Gly Tyr Phe Asn Phe Gln Glu
        995                 1000                1005
Gly Gly Cys Thr Ala Cys Glu Cys Ser His Leu Gly Asn Asn Cys
    1010                1015                1020
Asp Pro Lys Thr Gly Arg Cys Ile Cys Pro Pro Asn Thr Ile Gly
    1025                1030                1035
Glu Lys Cys Ser Lys Cys Ala Pro Asn Thr Trp Gly His Ser Ile
    1040                1045                1050
Thr Thr Gly Cys Lys Ala Cys Asn Cys Ser Thr Val Gly Ser Leu
    1055                1060                1065
Asp Phe Gln Cys Asn Val Asn Thr Gly Gln Cys Asn Cys His Pro
    1070                1075                1080
Lys Phe Ser Gly Ala Lys Cys Thr Glu Cys Ser Arg Gly His Trp
    1085                1090                1095
Asn Tyr Pro Arg Cys Asn Leu Cys Asp Cys Phe Leu Pro Gly Thr
    1100                1105                1110
Asp Ala Thr Thr Cys Asp Ser Glu Thr Lys Lys Cys Ser Cys Ser
    1115                1120                1125
Asp Gln Thr Gly Gln Cys Thr Cys Lys Val Asn Val Glu Gly Ile
    1130                1135                1140
His Cys Asp Arg Cys Arg Pro Gly Lys Phe Gly Leu Asp Ala Lys
    1145                1150                1155
Asn Pro Leu Gly Cys Ser Ser Cys Tyr Cys Phe Gly Thr Thr Thr
    1160                1165                1170
Gln Cys Ser Glu Ala Lys Gly Leu Ile Arg Thr Trp Val Thr Leu
    1175                1180                1185
Lys Ala Glu Gln Thr Ile Leu Pro Leu Val Asp Glu Ala Leu Gln
    1190                1195                1200
His Thr Thr Thr Lys Gly Ile Val Phe Gln His Pro Glu Ile Val
    1205                1210                1215
Ala His Met Asp Leu Met Arg Glu Asp Leu His Leu Glu Pro Phe
    1220                1225                1230
Tyr Trp Lys Leu Pro Glu Gln Phe Glu Gly Lys Lys Leu Met Ala
    1235                1240                1245
Tyr Gly Gly Lys Leu Lys Tyr Ala Ile Tyr Phe Glu Ala Arg Glu
    1250                1255                1260
Glu Thr Gly Phe Ser Thr Tyr Asn Pro Gln Val Ile Ile Arg Gly
    1265                1270                1275
Gly Thr Pro Thr His Ala Arg Ile Ile Val Arg His Met Ala Ala
    1280                1285                1290
Pro Leu Ile Gly Gln Leu Thr Arg His Glu Ile Glu Met Thr Glu
    1295                1300                1305
Lys Glu Trp Lys Tyr Tyr Gly Asp Asp Pro Arg Val His Arg Thr
    1310                1315                1320
Val Thr Arg Glu Asp Phe Leu Asp Ile Leu Tyr Asp Ile His Tyr
    1325                1330                1335
```

-continued

```
Ile Leu Ile Lys Ala Thr Tyr Gly Asn Phe Met Arg Gln Ser Arg
    1340                1345                1350

Ile Ser Glu Ile Ser Met Glu Val Ala Glu Gln Gly Arg Gly Thr
    1355                1360                1365

Thr Met Thr Pro Pro Ala Asp Leu Ile Glu Lys Cys Asp Cys Pro
    1370                1375                1380

Leu Gly Tyr Ser Gly Leu Ser Cys Glu Ala Cys Leu Pro Gly Phe
    1385                1390                1395

Tyr Arg Leu Arg Ser Gln Pro Gly Gly Arg Thr Pro Gly Pro Thr
    1400                1405                1410

Leu Gly Thr Cys Val Pro Cys Gln Cys Asn Gly His Ser Ser Leu
    1415                1420                1425

Cys Asp Pro Glu Thr Ser Ile Cys Gln Asn Cys Gln His His Thr
    1430                1435                1440

Ala Gly Asp Phe Cys Glu Arg Cys Ala Leu Gly Tyr Tyr Gly Ile
    1445                1450                1455

Val Lys Gly Leu Pro Asn Asp Cys Gln Gln Cys Ala Cys Pro Leu
    1460                1465                1470

Ile Ser Ser Ser Asn Asn Phe Ser Pro Ser Cys Val Ala Glu Gly
    1475                1480                1485

Leu Asp Asp Tyr Arg Cys Thr Ala Cys Pro Arg Gly Tyr Glu Gly
    1490                1495                1500

Gln Tyr Cys Glu Arg Cys Ala Pro Gly Tyr Thr Gly Ser Pro Gly
    1505                1510                1515

Asn Pro Gly Gly Ser Cys Gln Glu Cys Glu Cys Asp Pro Tyr Gly
    1520                1525                1530

Ser Leu Pro Val Pro Cys Asp Pro Val Thr Gly Phe Cys Thr Cys
    1535                1540                1545

Arg Pro Gly Ala Thr Gly Arg Lys Cys Asp Gly Cys Lys His Trp
    1550                1555                1560

His Ala Arg Glu Gly Trp Glu Cys Val Phe Cys Gly Asp Glu Cys
    1565                1570                1575

Thr Gly Leu Leu Leu Gly Asp Leu Ala Arg Leu Glu Gln Met Val
    1580                1585                1590

Met Ser Ile Asn Leu Thr Gly Pro Leu Pro Ala Pro Tyr Lys Met
    1595                1600                1605

Leu Tyr Gly Leu Glu Asn Met Thr Gln Glu Leu Lys His Leu Leu
    1610                1615                1620

Ser Pro Gln Arg Ala Pro Glu Arg Leu Ile Gln Leu Ala Glu Gly
    1625                1630                1635

Asn Leu Asn Thr Leu Val Thr Glu Met Asn Glu Leu Leu Thr Arg
    1640                1645                1650

Ala Thr Lys Val Thr Ala Asp Gly Glu Gln Thr Gly Gln Asp Ala
    1655                1660                1665

Glu Arg Thr Asn Thr Arg Ala Lys Ser Leu Gly Glu Phe Ile Lys
    1670                1675                1680

Glu Leu Ala Arg Asp Ala Glu Ala Val Asn Glu Lys Ala Ile Lys
    1685                1690                1695

Leu Asn Glu Thr Leu Gly Thr Arg Asp Glu Ala Phe Glu Arg Asn
    1700                1705                1710

Leu Glu Gly Leu Gln Lys Glu Ile Asp Gln Met Ile Lys Glu Leu
    1715                1720                1725
```

```
Arg Arg Lys Asn Leu Glu Thr Gln Lys Glu Ile Ala Glu Asp Glu
        1730                1735                1740

Leu Val Ala Ala Glu Ala Leu Leu Lys Lys Val Lys Lys Leu Phe
        1745                1750                1755

Gly Glu Ser Arg Gly Glu Asn Glu Glu Met Glu Lys Asp Leu Arg
        1760                1765                1770

Glu Lys Leu Ala Asp Tyr Lys Asn Lys Val Asp Asp Ala Trp Asp
        1775                1780                1785

Leu Leu Arg Glu Ala Thr Asp Lys Ile Arg Glu Ala Asn Arg Leu
        1790                1795                1800

Phe Ala Val Asn Gln Lys Asn Met Thr Ala Leu Glu Lys Lys Lys
        1805                1810                1815

Glu Ala Val Glu Ser Gly Lys Arg Gln Ile Glu Asn Thr Leu Lys
        1820                1825                1830

Glu Gly Asn Asp Ile Leu Asp Glu Ala Asn Arg Leu Ala Asp Glu
        1835                1840                1845

Ile Asn Ser Ile Ile Asp Tyr Val Glu Asp Ile Gln Thr Lys Leu
        1850                1855                1860

Pro Pro Met Ser Glu Glu Leu Asn Asp Lys Ile Asp Asp Leu Ser
        1865                1870                1875

Gln Glu Ile Lys Asp Arg Lys Leu Ala Glu Lys Val Ser Gln Ala
        1880                1885                1890

Glu Ser His Ala Ala Gln Leu Asn Asp Ser Ser Ala Val Leu Asp
        1895                1900                1905

Gly Ile Leu Asp Glu Ala Lys Asn Ile Ser Phe Asn Ala Thr Ala
        1910                1915                1920

Ala Phe Lys Ala Tyr Ser Asn Ile Lys Asp Tyr Ile Asp Glu Ala
        1925                1930                1935

Glu Lys Val Ala Lys Glu Ala Lys Asp Leu Ala His Glu Ala Thr
        1940                1945                1950

Lys Leu Ala Thr Gly Pro Arg Gly Leu Leu Lys Glu Asp Ala Lys
        1955                1960                1965

Gly Cys Leu Gln Lys Ser Phe Arg Ile Leu Asn Glu Ala Lys Lys
        1970                1975                1980

Leu Ala Asn Asp Val Lys Glu Asn Glu Asp His Leu Asn Gly Leu
        1985                1990                1995

Lys Thr Arg Ile Glu Asn Ala Asp Ala Arg Asn Gly Asp Leu Leu
        2000                2005                2010

Arg Thr Leu Asn Asp Thr Leu Gly Lys Leu Ser Ala Ile Pro Asn
        2015                2020                2025

Asp Thr Ala Ala Lys Leu Gln Ala Val Lys Asp Lys Ala Arg Gln
        2030                2035                2040

Ala Asn Asp Thr Ala Lys Asp Val Leu Ala Gln Ile Thr Glu Leu
        2045                2050                2055

His Gln Asn Leu Asp Gly Leu Lys Lys Asn Tyr Asn Lys Leu Ala
        2060                2065                2070

Asp Ser Val Ala Lys Thr Asn Ala Val Val Lys Asp Pro Ser Lys
        2075                2080                2085

Asn Lys Ile Ile Ala Asp Ala Asp Ala Thr Val Lys Asn Leu Glu
        2090                2095                2100

Gln Glu Ala Asp Arg Leu Ile Asp Lys Leu Lys Pro Ile Lys Glu
        2105                2110                2115

Leu Glu Asp Asn Leu Lys Lys Asn Ile Ser Glu Ile Lys Glu Leu
```

-continued

```
            2120                2125                2130
Ile Asn Gln Ala Arg Lys Gln Ala Asn Ser Ile Lys Val Ser Val
        2135                2140                2145
Ser Ser Gly Gly Asp Cys Ile Arg Thr Tyr Lys Pro Glu Ile Lys
    2150                2155                2160
Lys Gly Ser Tyr Asn Asn Ile Val Val Asn Val Lys Thr Ala Val
    2165                2170                2175
Ala Asp Asn Leu Leu Phe Tyr Leu Gly Ser Ala Lys Phe Ile Asp
    2180                2185                2190
Phe Leu Ala Ile Glu Met Arg Lys Gly Lys Val Ser Phe Leu Trp
    2195                2200                2205
Asp Val Gly Ser Gly Val Gly Arg Val Glu Tyr Pro Asp Leu Thr
    2210                2215                2220
Ile Asp Asp Ser Tyr Trp Tyr Arg Ile Val Ala Ser Arg Thr Gly
    2225                2230                2235
Arg Asn Gly Thr Ile Ser Val Arg Ala Leu Asp Gly Pro Lys Ala
    2240                2245                2250
Ser Ile Val Pro Ser Thr His His Ser Thr Ser Pro Pro Gly Tyr
    2255                2260                2265
Thr Ile Leu Asp Val Asp Ala Asn Ala Met Leu Phe Val Gly Gly
    2270                2275                2280
Leu Thr Gly Lys Leu Lys Lys Ala Asp Ala Val Arg Val Ile Thr
    2285                2290                2295
Phe Thr Gly Cys Met Gly Glu Thr Tyr Phe Asp Asn Lys Pro Ile
    2300                2305                2310
Gly Leu Trp Asn Phe Arg Glu Lys Glu Gly Asp Cys Lys Gly Cys
    2315                2320                2325
Thr Val Ser Pro Gln Val Glu Asp Ser Glu Gly Thr Ile Gln Phe
    2330                2335                2340
Asp Gly Glu Gly Tyr Ala Leu Val Ser Arg Pro Ile Arg Trp Tyr
    2345                2350                2355
Pro Asn Ile Ser Thr Val Met Phe Lys Phe Arg Thr Phe Ser Ser
    2360                2365                2370
Ser Ala Leu Leu Met Tyr Leu Ala Thr Arg Asp Leu Arg Asp Phe
    2375                2380                2385
Met Ser Val Glu Leu Thr Asp Gly His Ile Lys Val Ser Tyr Asp
    2390                2395                2400
Leu Gly Ser Gly Met Ala Ser Val Val Ser Asn Gln Asn His Asn
    2405                2410                2415
Asp Gly Lys Trp Lys Ser Phe Thr Leu Ser Arg Ile Gln Lys Gln
    2420                2425                2430
Ala Asn Ile Ser Ile Val Asp Ile Asp Thr Asn Gln Glu Glu Asn
    2435                2440                2445
Ile Ala Thr Ser Ser Ser Gly Asn Asn Phe Gly Leu Asp Leu Lys
    2450                2455                2460
Ala Asp Asp Lys Ile Tyr Phe Gly Gly Leu Pro Thr Leu Arg Asn
    2465                2470                2475
Leu Ser Met Lys Ala Arg Pro Glu Val Asn Leu Lys Lys Tyr Ser
    2480                2485                2490
Gly Cys Leu Lys Asp Ile Glu Ile Ser Arg Thr Pro Tyr Asn Ile
    2495                2500                2505
Leu Ser Ser Pro Asp Tyr Val Gly Val Thr Lys Gly Cys Ser Leu
    2510                2515                2520
```

-continued

```
Glu Asn Val Tyr Thr Val Ser Phe Pro Lys Pro Gly Phe Val Glu
2525                2530                2535

Leu Ser Pro Val Pro Ile Asp Val Gly Thr Glu Ile Asn Leu Ser
2540                2545                2550

Phe Ser Thr Lys Asn Glu Ser Gly Ile Ile Leu Leu Gly Ser Gly
2555                2560                2565

Gly Thr Pro Ala Pro Pro Arg Arg Lys Arg Arg Gln Thr Gly Gln
2570                2575                2580

Ala Tyr Tyr Val Ile Leu Leu Asn Arg Gly Arg Leu Glu Val His
2585                2590                2595

Leu Ser Thr Gly Ala Arg Thr Met Arg Lys Ile Val Ile Arg Pro
2600                2605                2610

Glu Pro Asn Leu Phe His Asp Gly Arg Glu His Ser Val His Val
2615                2620                2625

Glu Arg Thr Arg Gly Ile Phe Thr Val Gln Val Asp Glu Asn Arg
2630                2635                2640

Arg Tyr Met Gln Asn Leu Thr Val Glu Gln Pro Ile Glu Val Lys
2645                2650                2655

Lys Leu Phe Val Gly Gly Ala Pro Pro Glu Phe Gln Pro Ser Pro
2660                2665                2670

Leu Arg Asn Ile Pro Pro Phe Glu Gly Cys Ile Trp Asn Leu Val
2675                2680                2685

Ile Asn Ser Val Pro Met Asp Phe Ala Arg Pro Val Ser Phe Lys
2690                2695                2700

Asn Ala Asp Ile Gly Arg Cys Ala His Gln Lys Leu Arg Glu Asp
2705                2710                2715

Glu Asp Gly Ala Ala Pro Ala Glu Ile Val Ile Gln Pro Glu Pro
2720                2725                2730

Val Pro Thr Pro Ala Phe Pro Thr Pro Thr Pro Val Leu Thr His
2735                2740                2745

Gly Pro Cys Ala Ala Glu Ser Glu Pro Ala Leu Leu Ile Gly Ser
2750                2755                2760

Lys Gln Phe Gly Leu Ser Arg Asn Ser His Ile Ala Ile Ala Phe
2765                2770                2775

Asp Asp Thr Lys Val Lys Asn Arg Leu Thr Ile Glu Leu Glu Val
2780                2785                2790

Arg Thr Glu Ala Glu Ser Gly Leu Leu Phe Tyr Met Ala Ala Ile
2795                2800                2805

Asn His Ala Asp Phe Ala Thr Val Gln Leu Arg Asn Gly Leu Pro
2810                2815                2820

Tyr Phe Ser Tyr Asp Leu Gly Ser Gly Asp Thr His Thr Met Ile
2825                2830                2835

Pro Thr Lys Ile Asn Asp Gly Gln Trp His Lys Ile Lys Ile Met
2840                2845                2850

Arg Ser Lys Gln Glu Gly Ile Leu Tyr Val Asp Gly Ala Ser Asn
2855                2860                2865

Arg Thr Ile Ser Pro Lys Lys Ala Asp Ile Leu Asp Val Val Gly
2870                2875                2880

Met Leu Tyr Val Gly Gly Leu Pro Ile Asn Tyr Thr Thr Arg Arg
2885                2890                2895

Ile Gly Pro Val Thr Tyr Ser Ile Asp Gly Cys Val Arg Asn Leu
2900                2905                2910
```

-continued

```
His Met Ala Glu Ala Pro Ala Asp Leu Glu Gln Pro Thr Ser Ser
    2915                2920                2925

Phe His Val Gly Thr Cys Phe Ala Asn Ala Gln Arg Gly Thr Tyr
    2930                2935                2940

Phe Asp Gly Thr Gly Phe Ala Lys Ala Val Gly Phe Lys Val
    2945                2950                2955

Gly Leu Asp Leu Leu Val Glu Phe Glu Phe Ala Thr Thr Thr Thr
    2960                2965                2970

Thr Gly Val Leu Leu Gly Ile Ser Ser Gln Lys Met Asp Gly Met
    2975                2980                2985

Gly Ile Glu Met Ile Asp Glu Lys Leu Met Phe His Val Asp Asn
    2990                2995                3000

Gly Ala Gly Arg Phe Thr Ala Val Tyr Asp Ala Gly Val Pro Gly
    3005                3010                3015

His Leu Cys Asp Gly Gln Trp His Lys Val Thr Ala Asn Lys Ile
    3020                3025                3030

Lys His Arg Ile Glu Leu Thr Val Asp Gly Asn Gln Val Glu Ala
    3035                3040                3045

Gln Ser Pro Asn Pro Ala Ser Thr Ser Ala Asp Thr Asn Asp Pro
    3050                3055                3060

Val Phe Val Gly Gly Phe Pro Asp Asp Leu Lys Gln Phe Gly Leu
    3065                3070                3075

Thr Thr Ser Ile Pro Phe Arg Gly Cys Ile Arg Ser Leu Lys Leu
    3080                3085                3090

Thr Lys Gly Thr Ala Ser His Trp Arg Leu Ile Leu Pro Arg Pro
    3095                3100                3105

Trp Asn
    3110

<210> SEQ ID NO 87
<211> LENGTH: 1798
<212> TYPE: PRT
<213> ORGANISM: Homo Sapiens

<400> SEQUENCE: 87

Met Glu Leu Thr Ser Thr Glu Arg Gly Arg Gly Gln Pro Leu Pro Trp
1               5                   10                  15

Glu Leu Arg Leu Pro Leu Leu Ser Val Leu Ala Ala Thr Leu Ala
                20                  25                  30

Gln Ala Pro Ala Pro Asp Val Pro Gly Cys Ser Arg Gly Ser Cys Tyr
            35                  40                  45

Pro Ala Thr Ala Asp Leu Leu Val Gly Arg Ala Asp Arg Leu Thr Ala
        50                  55                  60

Ser Ser Thr Cys Gly Leu Asn Gly Arg Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Thr His Arg Ile Gln Asn Val Val
            100                 105                 110

Thr Ser Phe Ala Pro Gln Arg Arg Ala Ala Trp Trp Gln Ser Gln Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160
```

-continued

```
Leu Val Glu Arg Ser Ala Asp Phe Gly Arg Thr Trp His Val Tyr Arg
                165                 170                 175
Tyr Phe Ser Tyr His Cys Gly Ala Asp Phe Pro Gly Val Pro Leu Ala
            180                 185                 190
Pro Pro Arg His Trp Asp Val Val Cys Glu Ser Arg Tyr Ser Glu
            195                 200                 205
Ile Glu Pro Ser Thr Glu Gly Glu Val Ile Tyr Arg Val Leu Asp Pro
        210                 215                 220
Ala Ile Pro Ile Pro Asp Pro Tyr Ser Ser Arg Ile Gln Asn Leu Leu
225                 230                 235                 240
Lys Ile Thr Asn Leu Arg Val Asn Leu Thr Arg Leu His Thr Leu Gly
                245                 250                 255
Asp Asn Leu Leu Asp Pro Arg Arg Glu Ile Arg Glu Lys Tyr Tyr Tyr
            260                 265                 270
Ala Leu Tyr Glu Leu Val Val Arg Gly Asn Cys Phe Cys Tyr Gly His
            275                 280                 285
Ala Ser Glu Cys Ala Pro Ala Pro Gly Ala Pro Ala His Ala Glu Gly
        290                 295                 300
Met Val His Gly Ala Cys Ile Cys Lys His Asn Thr Arg Gly Leu Asn
305                 310                 315                 320
Cys Glu Gln Cys Gln Asp Phe Tyr Arg Asp Leu Pro Trp Arg Pro Ala
                325                 330                 335
Glu Asp Gly His Ser His Ala Cys Arg Lys Cys Asp Arg His Gly His
            340                 345                 350
Thr His Ser Cys His Phe Asp Met Ala Val Tyr Leu Gly Ser Gly Asn
            355                 360                 365
Val Ser Gly Gly Val Cys Asp Gly Cys Gln His Asn Thr Ala Trp Arg
        370                 375                 380
His Cys Glu Leu Cys Arg Pro Phe Phe Tyr Arg Asp Pro Thr Lys Asp
385                 390                 395                 400
Leu Arg Asp Pro Ala Val Cys Arg Ser Cys Asp Cys Asp Pro Met Gly
                405                 410                 415
Ser Gln Asp Gly Gly Arg Cys Asp Ser His Asp Asp Pro Ala Leu Gly
            420                 425                 430
Leu Val Ser Gly Gln Cys Arg Cys Lys Glu His Val Val Gly Thr Arg
            435                 440                 445
Cys Gln Gln Cys Arg Asp Gly Phe Phe Gly Leu Ser Ile Ser Asp Pro
        450                 455                 460
Ser Gly Cys Arg Arg Cys Gln Cys Asn Ala Arg Gly Thr Val Pro Gly
465                 470                 475                 480
Ser Thr Pro Cys Asp Pro Asn Ser Gly Ser Cys Tyr Cys Lys Arg Leu
                485                 490                 495
Val Thr Gly Arg Gly Cys Asp Arg Cys Leu Pro Gly His Trp Gly Leu
            500                 505                 510
Ser Leu Asp Leu Leu Gly Cys Arg Pro Cys Asp Cys Asp Val Gly Gly
            515                 520                 525
Ala Leu Asp Pro Gln Cys Asp Glu Gly Thr Gly Gln Cys His Cys Arg
        530                 535                 540
Gln His Met Val Gly Arg Arg Cys Glu Gln Val Gln Pro Gly Tyr Phe
545                 550                 555                 560
Arg Pro Phe Leu Asp His Leu Ile Trp Glu Ala Glu Asn Thr Arg Gly
                565                 570                 575
```

```
-continued

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
            595                 600                 605

Glu Phe Leu Val Ala Ser Val Pro Asn Ala Met Asp Tyr Asp Leu Leu
            610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Arg Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
                675                 680                 685

Tyr Lys Leu His Leu Lys Leu Val Arg Thr Gly Gly Ser Ala Gln Pro
                690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
                755                 760                 765

Leu Ile Ser Leu Ser Thr Leu Ile Tyr Asn Gly Ala Leu Pro Cys Gln
770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Thr Cys
                805                 810                 815

Ala Pro Gly Tyr Tyr Gly Phe Gly Pro Thr Gly Cys Gln Ala Cys Gln
                820                 825                 830

Cys Ser Pro Arg Gly Ala Leu Ser Ser Leu Cys Glu Arg Thr Ser Gly
                835                 840                 845

Gln Cys Leu Cys Arg Thr Gly Ala Phe Gly Leu Arg Cys Asp Ala Cys
                850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp Leu Thr Gly Gly Glu His Cys Glu Arg Cys Ile Ala Gly Phe
                900                 905                 910

His Gly Asp Pro Arg Leu Pro Tyr Gly Ala Gln Cys Arg Pro Cys Pro
                915                 920                 925

Cys Pro Glu Gly Pro Gly Ser Gln Arg His Phe Ala Thr Ser Cys His
                930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly Gln Phe Gly Asp Pro
                965                 970                 975

Ser Arg Pro Gly Gly Arg Cys Gln Leu Cys Glu Cys Ser Gly Asn Ile
                980                 985                 990

Asp Pro Met Asp Pro Asp Ala Cys  Asp Pro His Pro Gly  Gln Cys Leu
```

-continued

```
               995                1000               1005
Arg Cys  Leu His His Thr Glu  Gly Pro His Cys Ala  His Ser Lys
    1010             1015              1020

Pro Gly  Phe His Gly Gln Ala  Ala Arg Gln Ser Cys  His Arg Cys
    1025             1030              1035

Thr Cys  Asn Leu Leu Gly Thr  Asn Pro Gln Gln Cys  Pro Ser Pro
    1040             1045              1050

Asp Gln  Cys His Cys Asp Pro  Ser Ser Gly Gln Cys  Pro Cys Leu
    1055             1060              1065

Pro Asn  Val Gln Ala Leu Ala  Val Asp Arg Cys Ala  Pro Asn Phe
    1070             1075              1080

Trp Asn  Leu Thr Ser Gly His  Gly Cys Gln Pro Cys  Ala Cys Leu
    1085             1090              1095

Pro Ser  Pro Glu Glu Gly Pro  Thr Cys Asn Glu Phe  Thr Gly Gln
    1100             1105              1110

Cys His  Cys Leu Cys Gly Phe  Gly Gly Arg Thr Cys  Ser Glu Cys
    1115             1120              1125

Gln Glu  Leu His Trp Gly Asp  Pro Gly Leu Gln Cys  His Ala Cys
    1130             1135              1140

Asp Cys  Asp Ser Arg Gly Ile  Asp Thr Pro Gln Cys  His Arg Phe
    1145             1150              1155

Thr Gly  His Cys Thr Cys Arg  Pro Gly Val Ser Gly  Val Arg Cys
    1160             1165              1170

Asp Gln  Cys Ala Arg Gly Phe  Ser Gly Ile Phe Pro  Ala Cys His
    1175             1180              1185

Pro Cys  His Ala Cys Phe Gly  Asp Trp Asp Arg Val  Val Gln Asp
    1190             1195              1200

Leu Ala  Ala Arg Thr Gln Arg  Leu Glu Gln Arg Ala  Gln Glu Leu
    1205             1210              1215

Gln Gln  Thr Gly Val Leu Gly  Ala Phe Glu Ser Ser  Phe Trp His
    1220             1225              1230

Met Gln  Glu Lys Leu Gly Ile  Val Gln Gly Ile Val  Gly Ala Arg
    1235             1240              1245

Asn Thr  Ser Ala Ala Ser Thr  Ala Gln Leu Val Glu  Ala Thr Glu
    1250             1255              1260

Glu Leu  Arg Arg Glu Ile Gly  Glu Ala Thr Glu His  Leu Thr Gln
    1265             1270              1275

Leu Glu  Ala Asp Leu Thr Asp  Val Gln Asp Glu Asn  Phe Asn Ala
    1280             1285              1290

Asn His  Ala Leu Ser Gly Leu  Glu Arg Asp Arg Leu  Ala Leu Asn
    1295             1300              1305

Leu Thr  Leu Arg Gln Leu Asp  Gln His Leu Asp Leu  Leu Lys His
    1310             1315              1320

Ser Asn  Phe Leu Gly Ala Tyr  Asp Ser Ile Arg His  Ala His Ser
    1325             1330              1335

Gln Ser  Ala Glu Ala Glu Arg  Arg Ala Asn Thr Ser  Ala Leu Ala
    1340             1345              1350

Val Pro  Ser Pro Val Ser Asn  Ser Ala Ser Ala Arg  His Arg Thr
    1355             1360              1365

Glu Ala  Leu Met Asp Ala Gln  Lys Glu Asp Phe Asn  Ser Lys His
    1370             1375              1380

Met Ala  Asn Gln Arg Ala Leu  Gly Lys Leu Ser Ala  His Thr His
    1385             1390              1395
```

```
Thr Leu Ser Leu Thr Asp Ile Asn Glu Leu Val Cys Gly Ala Gln
1400                1405                1410

Gly Leu His His Asp Arg Thr Ser Pro Cys Gly Gly Ala Gly Cys
1415                1420                1425

Arg Asp Glu Asp Gly Gln Pro Arg Cys Gly Gly Leu Ser Cys Asn
1430                1435                1440

Gly Ala Ala Ala Thr Ala Asp Leu Ala Leu Gly Arg Ala Arg His
1445                1450                1455

Thr Gln Ala Glu Leu Gln Arg Ala Leu Ala Glu Gly Gly Ser Ile
1460                1465                1470

Leu Ser Arg Val Ala Glu Thr Arg Arg Gln Ala Ser Glu Ala Gln
1475                1480                1485

Gln Arg Ala Gln Ala Ala Leu Asp Lys Ala Asn Ala Ser Arg Gly
1490                1495                1500

Gln Val Glu Gln Ala Asn Gln Glu Leu Gln Glu Leu Ile Gln Ser
1505                1510                1515

Val Lys Asp Phe Leu Asn Gln Glu Gly Ala Asp Pro Asp Ser Ile
1520                1525                1530

Glu Met Val Ala Thr Arg Val Leu Glu Leu Ser Ile Pro Ala Ser
1535                1540                1545

Ala Glu Gln Ile Gln His Leu Ala Gly Ala Ile Ala Glu Arg Val
1550                1555                1560

Arg Ser Leu Ala Asp Val Asp Ala Ile Leu Ala Arg Thr Val Gly
1565                1570                1575

Asp Val Arg Arg Ala Glu Gln Leu Leu Gln Asp Ala Arg Arg Ala
1580                1585                1590

Arg Ser Trp Ala Glu Asp Glu Lys Gln Lys Ala Glu Thr Val Gln
1595                1600                1605

Ala Ala Leu Glu Glu Ala Gln Arg Ala Gln Gly Ile Ala Gln Gly
1610                1615                1620

Ala Ile Arg Gly Ala Val Ala Asp Thr Arg Asp Thr Glu Gln Thr
1625                1630                1635

Leu Tyr Gln Val Gln Glu Arg Met Ala Gly Ala Glu Arg Ala Leu
1640                1645                1650

Ser Ser Ala Gly Glu Arg Ala Arg Gln Leu Asp Ala Leu Leu Glu
1655                1660                1665

Ala Leu Lys Leu Lys Arg Ala Gly Asn Ser Leu Ala Ala Ser Thr
1670                1675                1680

Ala Glu Glu Thr Ala Gly Ser Ala Gln Gly Arg Ala Gln Glu Ala
1685                1690                1695

Glu Gln Leu Leu Arg Gly Pro Leu Gly Asp Gln Tyr Gln Thr Val
1700                1705                1710

Lys Ala Leu Ala Glu Arg Lys Ala Gln Gly Val Leu Ala Ala Gln
1715                1720                1725

Ala Arg Ala Glu Gln Leu Pro Asp Glu Ala Arg Asp Leu Leu Gln
1730                1735                1740

Ala Ala Gln Asp Lys Leu Gln Arg Leu Gln Glu Leu Glu Gly Thr
1745                1750                1755

Tyr Glu Glu Asn Glu Arg Ala Leu Glu Ser Lys Ala Ala Gln Leu
1760                1765                1770

Asp Gly Leu Glu Ala Arg Met Arg Ser Val Leu Gln Ala Ile Asn
1775                1780                1785
```

-continued

```
Leu Gln  Val Gln Ile Tyr Asn  Thr Cys Gln
    1790             1795

<210> SEQ ID NO 88
<211> LENGTH: 615
<212> TYPE: PRT
<213> ORGANISM: Homo Sapiens

<400> SEQUENCE: 88

Met Pro Ser Arg Lys Phe Ala Asp Gly Glu Val Val Arg Gly Arg Trp
1               5                   10                  15

Pro Gly Ser Ser Leu Tyr Tyr Glu Val Glu Ile Leu Ser His Asp Ser
                20                  25                  30

Thr Ser Gln Leu Tyr Thr Val Lys Tyr Lys Asp Gly Thr Glu Leu Glu
            35                  40                  45

Leu Lys Glu Asn Asp Ile Lys Pro Leu Thr Ser Phe Arg Gln Arg Lys
50                  55                  60

Gly Gly Ser Thr Ser Ser Pro Ser Arg Arg Gly Ser Arg Ser
65                  70                  75                  80

Arg Ser Arg Ser Arg Ser Pro Gly Arg Pro Lys Ser Ala Arg Arg
                85                  90                  95

Ser Ala Ser Ala Ser His Gln Ala Asp Ile Lys Glu Ala Arg Arg Glu
                100                 105                 110

Val Glu Val Lys Leu Thr Pro Leu Ile Leu Lys Pro Phe Gly Asn Ser
            115                 120                 125

Ile Ser Arg Tyr Asn Gly Glu Pro Glu His Ile Glu Arg Asn Asp Ala
130                 135                 140

Pro His Lys Asn Thr Gln Glu Lys Phe Ser Leu Ser Gln Glu Ser Ser
145                 150                 155                 160

Tyr Ile Ala Thr Gln Tyr Ser Leu Arg Pro Arg Arg Glu Glu Val Lys
                165                 170                 175

Leu Lys Glu Ile Asp Ser Lys Glu Glu Lys Tyr Val Ala Lys Glu Leu
            180                 185                 190

Ala Val Arg Thr Phe Glu Val Thr Pro Ile Arg Ala Lys Asp Leu Glu
        195                 200                 205

Phe Gly Gly Val Pro Gly Val Phe Leu Ile Met Phe Gly Leu Pro Val
210                 215                 220

Phe Leu Phe Leu Leu Leu Met Cys Lys Gln Lys Asp Pro Ser Leu
225                 230                 235                 240

Leu Asn Phe Pro Pro Pro Leu Pro Ala Leu Tyr Glu Leu Trp Glu Thr
                245                 250                 255

Arg Val Phe Gly Val Tyr Leu Leu Trp Phe Leu Ile Gln Val Leu Phe
            260                 265                 270

Tyr Leu Leu Pro Ile Gly Lys Val Val Glu Gly Thr Pro Leu Ile Asp
        275                 280                 285

Gly Arg Arg Leu Lys Tyr Arg Leu Asn Gly Phe Tyr Pro Phe Ile Leu
290                 295                 300

Thr Ser Ala Val Ile Gly Thr Ser Leu Phe Gln Gly Val Glu Phe His
305                 310                 315                 320

Tyr Val Tyr Ser His Phe Leu Gln Phe Ala Leu Ala Ala Thr Val Phe
                325                 330                 335

Cys Val Val Leu Ser Val Tyr Leu Tyr Met Arg Ser Leu Lys Ala Pro
            340                 345                 350

Arg Asn Asp Leu Ser Pro Ala Ser Ser Gly Asn Ala Val Tyr Asp Phe
        355                 360                 365
```

-continued

```
Phe Ile Gly Arg Glu Leu Asn Pro Arg Ile Gly Thr Phe Asp Leu Lys
    370                 375                 380
Tyr Phe Cys Glu Leu Arg Pro Gly Leu Ile Gly Trp Val Val Ile Asn
385                 390                 395                 400
Leu Val Met Leu Leu Ala Glu Met Lys Ile Gln Asp Arg Ala Val Pro
                405                 410                 415
Ser Leu Ala Met Ile Leu Val Asn Ser Phe Gln Leu Leu Tyr Val Val
            420                 425                 430
Asp Ala Leu Trp Asn Glu Glu Ala Leu Leu Thr Thr Met Asp Ile Ile
        435                 440                 445
His Asp Gly Phe Gly Phe Met Leu Ala Phe Gly Asp Leu Val Trp Val
    450                 455                 460
Pro Phe Ile Tyr Ser Phe Gln Ala Phe Tyr Leu Val Ser His Pro Asn
465                 470                 475                 480
Glu Val Ser Trp Pro Met Ala Ser Leu Ile Ile Val Leu Lys Leu Cys
                485                 490                 495
Gly Tyr Val Ile Phe Arg Gly Ala Asn Ser Gln Lys Asn Ala Phe Arg
            500                 505                 510
Lys Asn Pro Ser Asp Pro Lys Leu Ala His Leu Lys Thr Ile His Thr
        515                 520                 525
Ser Ser Gly Lys Asn Leu Leu Val Ser Gly Trp Trp Gly Phe Val Arg
    530                 535                 540
His Pro Asn Tyr Leu Gly Asp Leu Ile Met Ala Leu Ala Trp Ser Leu
545                 550                 555                 560
Pro Cys Gly Phe Asn His Ile Leu Pro Tyr Phe Tyr Ile Ile Tyr Phe
                565                 570                 575
Thr Met Leu Leu Val His Arg Glu Ala Arg Asp Glu Tyr His Cys Lys
            580                 585                 590
Lys Lys Tyr Gly Val Ala Trp Glu Lys Tyr Cys Gln Arg Val Pro Tyr
        595                 600                 605
Arg Ile Phe Pro Tyr Ile Tyr
    610                 615

<210> SEQ ID NO 89
<211> LENGTH: 660
<212> TYPE: PRT
<213> ORGANISM: Homo Sapiens

<400> SEQUENCE: 89

Met Glu Ala Leu Met Ala Arg Gly Ala Leu Thr Gly Pro Leu Arg Ala
1               5                   10                  15
Leu Cys Leu Leu Gly Cys Leu Leu Ser His Ala Ala Ala Ala Pro Ser
            20                  25                  30
Pro Ile Ile Lys Phe Pro Gly Asp Val Ala Pro Lys Thr Asp Lys Glu
        35                  40                  45
Leu Ala Val Gln Tyr Leu Asn Thr Phe Tyr Gly Cys Pro Lys Glu Ser
    50                  55                  60
Cys Asn Leu Phe Val Leu Lys Asp Thr Leu Lys Met Gln Lys Phe
65                  70                  75                  80
Phe Gly Leu Pro Gln Thr Gly Asp Leu Asp Gln Asn Thr Ile Glu Thr
                85                  90                  95
Met Arg Lys Pro Arg Cys Gly Asn Pro Asp Val Ala Asn Tyr Asn Phe
            100                 105                 110
Phe Pro Arg Lys Pro Lys Trp Asp Lys Asn Gln Ile Thr Tyr Arg Ile
```

-continued

```
            115                 120                     125
Ile Gly Tyr Thr Pro Asp Leu Asp Pro Glu Thr Val Asp Asp Ala Phe
130                     135                 140
Ala Arg Ala Phe Gln Val Trp Ser Asp Val Thr Pro Leu Arg Phe Ser
145                 150                     155                 160
Arg Ile His Asp Gly Glu Ala Asp Ile Met Ile Asn Phe Gly Arg Trp
                    165                 170                 175
Glu His Gly Asp Gly Tyr Pro Phe Asp Gly Lys Asp Gly Leu Leu Ala
                180                 185                 190
His Ala Phe Ala Pro Gly Thr Gly Val Gly Gly Asp Ser His Phe Asp
            195                 200                 205
Asp Asp Glu Leu Trp Thr Leu Gly Glu Gly Gln Val Val Arg Val Lys
210                     215                 220
Tyr Gly Asn Ala Asp Gly Glu Tyr Cys Lys Phe Pro Phe Leu Phe Asn
225                 230                     235                 240
Gly Lys Glu Tyr Asn Ser Cys Thr Asp Thr Gly Arg Ser Asp Gly Phe
                    245                 250                 255
Leu Trp Cys Ser Thr Thr Tyr Asn Phe Glu Lys Asp Gly Lys Tyr Gly
                260                 265                 270
Phe Cys Pro His Glu Ala Leu Phe Thr Met Gly Gly Asn Ala Glu Gly
            275                 280                 285
Gln Pro Cys Lys Phe Pro Phe Arg Phe Gln Gly Thr Ser Tyr Asp Ser
290                     295                 300
Cys Thr Thr Glu Gly Arg Thr Asp Gly Tyr Arg Trp Cys Gly Thr Thr
305                 310                     315                 320
Glu Asp Tyr Asp Arg Asp Lys Lys Tyr Gly Phe Cys Pro Glu Thr Ala
                    325                 330                 335
Met Ser Thr Val Gly Gly Asn Ser Glu Gly Ala Pro Cys Val Phe Pro
                340                 345                 350
Phe Thr Phe Leu Gly Asn Lys Tyr Glu Ser Cys Thr Ser Ala Gly Arg
            355                 360                 365
Ser Asp Gly Lys Met Trp Cys Ala Thr Thr Ala Asn Tyr Asp Asp Asp
370                     375                 380
Arg Lys Trp Gly Phe Cys Pro Asp Gln Gly Tyr Ser Leu Phe Leu Val
385                 390                     395                 400
Ala Ala His Glu Phe Gly His Ala Met Gly Leu Glu His Ser Gln Asp
                    405                 410                 415
Pro Gly Ala Leu Met Ala Pro Ile Tyr Thr Tyr Thr Lys Asn Phe Arg
                420                 425                 430
Leu Ser Gln Asp Asp Ile Lys Gly Ile Gln Glu Leu Tyr Gly Ala Ser
            435                 440                 445
Pro Asp Ile Asp Leu Gly Thr Gly Pro Thr Pro Thr Leu Gly Pro Val
450                     455                 460
Thr Pro Glu Ile Cys Lys Gln Asp Ile Val Phe Asp Gly Ile Ala Gln
465                 470                     475                 480
Ile Arg Gly Glu Ile Phe Phe Phe Lys Asp Arg Phe Ile Trp Arg Thr
                    485                 490                 495
Val Thr Pro Arg Asp Lys Pro Met Gly Pro Leu Leu Val Ala Thr Phe
                500                 505                 510
Trp Pro Glu Leu Pro Glu Lys Ile Asp Ala Val Tyr Glu Ala Pro Gln
            515                 520                 525
Glu Glu Lys Ala Val Phe Phe Ala Gly Asn Glu Tyr Trp Ile Tyr Ser
530                     535                 540
```

-continued

```
Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
        610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 90
<211> LENGTH: 430
<212> TYPE: PRT
<213> ORGANISM: Homo Sapiens

<400> SEQUENCE: 90

Leu Arg Tyr Gln Gln Leu Ile Lys Glu Asn Leu Lys Glu Ile Ala Lys
1               5                   10                  15

Leu Ile Thr Leu Glu Gln Gly Lys Thr Leu Ala Asp Ala Glu Gly Asp
            20                  25                  30

Val Phe Arg Gly Leu Gln Val Val Glu His Ala Cys Ser Val Thr Ser
        35                  40                  45

Leu Met Met Gly Glu Thr Met Pro Ser Ile Thr Lys Asp Met Asp Leu
    50                  55                  60

Tyr Ser Tyr Arg Leu Pro Leu Gly Val Cys Ala Gly Ile Ala Pro Phe
65                  70                  75                  80

Asn Phe Pro Ala Met Ile Pro Leu Trp Met Phe Pro Met Ala Met Val
                85                  90                  95

Cys Gly Asn Thr Phe Leu Met Lys Pro Ser Glu Arg Val Pro Gly Ala
                100                 105                 110

Thr Met Leu Leu Ala Lys Leu Leu Gln Asp Ser Gly Ala Pro Asp Gly
            115                 120                 125

Thr Leu Asn Ile Ile His Gly Gln His Glu Ala Val Asn Phe Ile Cys
        130                 135                 140

Asp His Pro Asp Ile Lys Ala Ile Ser Phe Val Gly Ser Asn Lys Ala
145                 150                 155                 160

Gly Glu Tyr Ile Phe Glu Arg Gly Ser Arg His Gly Lys Arg Val Gln
                165                 170                 175

Ala Asn Met Gly Ala Lys Asn His Gly Val Val Met Pro Asp Ala Asn
            180                 185                 190

Lys Glu Asn Thr Leu Asn Gln Leu Val Gly Ala Ala Phe Gly Ala Ala
        195                 200                 205

Gly Gln Arg Cys Met Ala Leu Ser Thr Ala Val Leu Val Gly Glu Ala
    210                 215                 220

Lys Lys Trp Leu Pro Glu Leu Val Glu His Ala Lys Asn Leu Arg Val
225                 230                 235                 240

Asn Ala Gly Asp Gln Pro Gly Ala Asp Leu Gly Pro Leu Ile Thr Pro
                245                 250                 255
```

-continued

```
Gln Ala Lys Glu Arg Val Cys Asn Leu Ile Asp Ser Gly Thr Lys Glu
        260                 265                 270
Gly Ala Ser Ile Leu Leu Asp Gly Arg Lys Ile Lys Val Lys Gly Tyr
    275                 280                 285
Glu Asn Gly Asn Phe Val Gly Pro Thr Ile Ile Ser Asn Val Lys Pro
290                 295                 300
Asn Met Thr Cys Tyr Lys Glu Glu Ile Phe Gly Pro Val Leu Val Val
305                 310                 315                 320
Leu Glu Thr Glu Thr Leu Asp Glu Ala Ile Gln Ile Val Asn Asn Asn
                325                 330                 335
Pro Tyr Gly Asn Gly Thr Ala Ile Phe Thr Thr Asn Gly Ala Thr Ala
            340                 345                 350
Arg Lys Tyr Ala His Leu Val Asp Val Gly Gln Val Gly Val Asn Val
        355                 360                 365
Pro Ile Pro Val Pro Leu Pro Met Phe Ser Phe Thr Gly Ser Arg Ser
    370                 375                 380
Ser Phe Arg Gly Asp Thr Asn Phe Tyr Gly Lys Gln Gly Ile Gln Phe
385                 390                 395                 400
Tyr Thr Gln Leu Lys Thr Ile Thr Ser Gln Trp Lys Glu Glu Asp Ala
                405                 410                 415
Thr Leu Ser Ser Pro Ala Val Val Met Pro Thr Met Gly Arg
            420                 425                 430

<210> SEQ ID NO 91
<211> LENGTH: 1857
<212> TYPE: PRT
<213> ORGANISM: Homo Sapiens

<400> SEQUENCE: 91

Thr Tyr Ser Gly Leu Phe Cys Val Val Asn Pro Tyr Lys His Leu
1               5                   10                  15
Pro Ile Tyr Ser Glu Lys Ile Val Asp Met Tyr Lys Gly Lys Lys Arg
            20                  25                  30
His Glu Met Pro Pro His Ile Tyr Ala Ile Ala Asp Thr Ala Tyr Arg
        35                  40                  45
Ser Met Leu Gln Asp Arg Glu Asp Gln Ser Ile Leu Cys Thr Gly Glu
    50                  55                  60
Ser Gly Ala Gly Lys Thr Glu Asn Thr Lys Lys Val Ile Gln Tyr Leu
65                  70                  75                  80
Ala Val Val Ala Ser Ser His Lys Gly Lys Lys Asp Thr Ser Ile Thr
                85                  90                  95
Gly Glu Leu Glu Lys Gln Leu Leu Gln Ala Asn Pro Ile Leu Glu Ala
            100                 105                 110
Phe Gly Asn Ala Lys Thr Val Lys Asn Asp Asn Ser Ser Arg Phe Gly
        115                 120                 125
Lys Phe Ile Arg Ile Asn Phe Asp Val Thr Gly Tyr Ile Val Gly Ala
    130                 135                 140
Asn Ile Glu Thr Tyr Leu Leu Glu Lys Ser Arg Ala Ile Arg Gln Ala
145                 150                 155                 160
Arg Asp Glu Arg Thr Phe His Ile Phe Tyr Tyr Met Ile Ala Gly Ala
                165                 170                 175
Lys Glu Lys Met Arg Ser Asp Leu Leu Leu Glu Gly Phe Asn Asn Tyr
            180                 185                 190
Thr Phe Leu Ser Asn Gly Phe Val Pro Ile Pro Ala Ala Gln Asp Asp
```

-continued

```
            195                 200                 205
Glu Met Phe Gln Glu Thr Val Glu Ala Met Ala Ile Met Gly Phe Ser
    210                 215                 220
Glu Glu Glu Gln Leu Ser Ile Leu Lys Val Val Ser Ser Val Leu Gln
225                 230                 235                 240
Leu Gly Asn Ile Val Phe Lys Lys Glu Arg Asn Thr Asp Gln Ala Ser
                245                 250                 255
Met Pro Asp Asn Thr Ala Ala Gln Lys Val Cys His Leu Met Gly Ile
                260                 265                 270
Asn Val Thr Asp Phe Thr Arg Ser Ile Leu Thr Pro Arg Ile Lys Val
            275                 280                 285
Gly Arg Asp Val Val Gln Lys Ala Gln Thr Lys Glu Gln Ala Asp Phe
            290                 295                 300
Ala Val Glu Ala Leu Ala Lys Ala Thr Tyr Glu Arg Leu Phe Arg Trp
305                 310                 315                 320
Ile Leu Thr Arg Val Asn Lys Ala Leu Asp Lys Thr His Arg Gln Gly
                325                 330                 335
Ala Ser Phe Leu Gly Ile Leu Asp Ile Ala Gly Phe Glu Ile Phe Glu
                340                 345                 350
Val Asn Ser Phe Glu Gln Leu Cys Ile Asn Tyr Thr Asn Glu Lys Leu
            355                 360                 365
Gln Gln Leu Phe Asn His Thr Met Phe Ile Leu Glu Gln Glu Glu Tyr
370                 375                 380
Gln Arg Glu Gly Ile Glu Trp Asn Phe Ile Asp Phe Gly Leu Asp Leu
385                 390                 395                 400
Gln Pro Cys Ile Glu Leu Ile Glu Arg Pro Asn Asn Pro Gly Val
                405                 410                 415
Leu Ala Leu Leu Asp Glu Glu Cys Trp Phe Pro Lys Ala Thr Asp Lys
                420                 425                 430
Ser Phe Val Glu Lys Leu Cys Thr Glu Gln Gly Ser His Pro Lys Phe
            435                 440                 445
Gln Lys Pro Lys Gln Leu Lys Asp Lys Thr Glu Phe Ser Ile Ile His
450                 455                 460
Tyr Ala Gly Lys Val Asp Tyr Asn Ala Ser Ala Trp Leu Thr Lys Asn
465                 470                 475                 480
Met Asp Pro Leu Asn Asp Asn Val Thr Ser Leu Leu Asn Ala Ser Ser
                485                 490                 495
Asp Lys Phe Val Ala Asp Leu Trp Lys Asp Val Asp Arg Ile Val Gly
                500                 505                 510
Leu Asp Gln Met Ala Lys Met Thr Glu Ser Ser Leu Pro Ser Ala Ser
            515                 520                 525
Lys Thr Lys Lys Gly Met Phe Arg Thr Val Gly Gln Leu Tyr Lys Glu
530                 535                 540
Gln Leu Gly Lys Leu Met Thr Thr Leu Arg Asn Thr Thr Pro Asn Phe
545                 550                 555                 560
Val Arg Cys Ile Ile Pro Asn His Glu Lys Arg Ser Gly Lys Leu Asp
                565                 570                 575
Ala Phe Leu Val Leu Glu Gln Leu Arg Cys Asn Gly Val Leu Glu Gly
                580                 585                 590
Ile Arg Ile Cys Arg Gln Gly Phe Pro Asn Arg Ile Val Phe Gln Glu
            595                 600                 605
Phe Arg Gln Arg Tyr Glu Ile Leu Ala Ala Asn Ala Ile Pro Lys Gly
610                 615                 620
```

```
Phe Met Asp Gly Lys Gln Ala Cys Ile Leu Met Ile Lys Ala Leu Glu
625                 630                 635                 640

Leu Asp Pro Asn Leu Tyr Arg Ile Gly Gln Ser Lys Ile Phe Phe Arg
            645                 650                 655

Thr Gly Val Leu Ala His Leu Glu Glu Glu Arg Asp Leu Lys Ile Thr
            660                 665                 670

Asp Val Ile Met Ala Phe Gln Ala Met Cys Arg Gly Tyr Leu Ala Arg
        675                 680                 685

Lys Ala Phe Ala Lys Arg Gln Gln Leu Thr Ala Met Lys Val Ile
    690                 695                 700

Gln Arg Asn Cys Ala Ala Tyr Leu Lys Leu Arg Asn Trp Gln Trp Trp
705                 710                 715                 720

Arg Leu Phe Thr Lys Val Lys Pro Leu Leu Gln Val Thr Arg Gln Glu
            725                 730                 735

Glu Glu Met Gln Ala Lys Glu Asp Glu Leu Gln Lys Thr Lys Glu Arg
            740                 745                 750

Gln Gln Lys Ala Glu Asn Glu Leu Lys Glu Leu Glu Gln Lys His Ser
        755                 760                 765

Gln Leu Thr Glu Glu Lys Asn Leu Leu Gln Glu Gln Leu Gln Ala Glu
770                 775                 780

Thr Glu Leu Tyr Ala Glu Ala Glu Glu Met Arg Val Arg Leu Ala Ala
785                 790                 795                 800

Lys Lys Gln Glu Leu Glu Glu Ile Leu His Glu Met Glu Ala Arg Leu
            805                 810                 815

Glu Glu Glu Glu Asp Arg Gly Gln Gln Leu Gln Ala Glu Arg Lys Lys
            820                 825                 830

Met Ala Gln Gln Met Leu Asp Leu Glu Glu Gln Leu Glu Glu Glu Glu
        835                 840                 845

Ala Ala Arg Gln Lys Leu Gln Leu Glu Lys Val Thr Ala Glu Ala Lys
    850                 855                 860

Ile Lys Lys Leu Glu Asp Glu Ile Leu Val Met Asp Asp Gln Asn Asn
865                 870                 875                 880

Lys Leu Ser Lys Glu Arg Lys Leu Leu Glu Glu Arg Ile Ser Asp Leu
            885                 890                 895

Thr Thr Asn Leu Ala Glu Glu Glu Lys Ala Lys Asn Leu Thr Lys
            900                 905                 910

Leu Lys Asn Lys His Glu Ser Met Ile Ser Glu Leu Glu Val Arg Leu
        915                 920                 925

Lys Lys Glu Glu Lys Ser Arg Gln Glu Leu Glu Lys Leu Lys Arg Lys
930                 935                 940

Leu Glu Gly Asp Ala Ser Asp Phe His Glu Gln Ile Ala Asp Leu Gln
945                 950                 955                 960

Ala Gln Ile Ala Glu Leu Lys Met Gln Leu Ala Lys Lys Glu Glu Glu
            965                 970                 975

Leu Gln Ala Ala Leu Ala Arg Leu Asp Asp Glu Ile Ala Gln Lys Asn
        980                 985                 990

Asn Ala Leu Lys Lys Ile Arg Glu Leu Glu Gly His Ile Ser Asp Leu
    995                 1000                1005

Gln Glu Asp Leu Asp Ser Glu Arg Ala Ala Arg Asn Lys Ala Glu
    1010                1015                1020

Lys Gln Lys Arg Asp Leu Gly Glu Glu Leu Glu Ala Leu Lys Thr
    1025                1030                1035
```

-continued

```
Glu Leu Glu Asp Thr Leu Asp Ser Thr Ala Thr Gln Gln Glu Leu
    1040                1045                1050

Arg Ala Lys Arg Glu Gln Glu Val Thr Val Leu Lys Lys Ala Leu
    1055                1060                1065

Asp Glu Glu Thr Arg Ser His Glu Ala Gln Val Gln Glu Met Arg
    1070                1075                1080

Gln Lys His Ala Gln Ala Val Glu Glu Leu Thr Glu Gln Leu Glu
    1085                1090                1095

Gln Phe Lys Arg Ala Lys Ala Asn Leu Asp Lys Asn Lys Gln Thr
    1100                1105                1110

Leu Glu Lys Glu Asn Ala Asp Leu Ala Gly Glu Leu Arg Val Leu
    1115                1120                1125

Gly Gln Ala Lys Gln Glu Val Glu His Lys Lys Lys Lys Leu Glu
    1130                1135                1140

Ala Gln Val Gln Glu Leu Gln Ser Lys Cys Ser Asp Gly Glu Arg
    1145                1150                1155

Ala Arg Ala Glu Leu Asn Asp Lys Val His Lys Leu Gln Asn Glu
    1160                1165                1170

Val Glu Ser Val Thr Gly Met Leu Asn Glu Ala Glu Gly Lys Ala
    1175                1180                1185

Ile Lys Leu Ala Lys Asp Val Ala Ser Leu Ser Ser Gln Leu Gln
    1190                1195                1200

Asp Thr Gln Glu Leu Leu Gln Glu Glu Thr Arg Gln Lys Leu Asn
    1205                1210                1215

Val Ser Thr Lys Leu Arg Gln Leu Glu Glu Glu Arg Asn Ser Leu
    1220                1225                1230

Gln Asp Gln Leu Asp Glu Glu Met Glu Ala Lys Gln Asn Leu Glu
    1235                1240                1245

Arg His Ile Ser Thr Leu Asn Ile Gln Leu Ser Asp Ser Lys Lys
    1250                1255                1260

Lys Leu Gln Asp Phe Ala Ser Thr Val Glu Ala Leu Glu Glu Gly
    1265                1270                1275

Lys Lys Arg Phe Gln Lys Glu Ile Glu Asn Leu Thr Gln Gln Tyr
    1280                1285                1290

Glu Glu Lys Ala Ala Ala Tyr Asp Lys Leu Glu Lys Thr Lys Asn
    1295                1300                1305

Arg Leu Gln Gln Glu Leu Asp Asp Leu Val Val Asp Leu Asp Asn
    1310                1315                1320

Gln Arg Gln Leu Val Ser Asn Leu Glu Lys Lys Gln Arg Lys Phe
    1325                1330                1335

Asp Gln Leu Leu Ala Glu Glu Lys Asn Ile Ser Ser Lys Tyr Ala
    1340                1345                1350

Asp Glu Arg Asp Arg Ala Glu Ala Glu Ala Arg Glu Lys Glu Thr
    1355                1360                1365

Lys Ala Leu Ser Leu Ala Arg Ala Leu Glu Glu Ala Leu Glu Ala
    1370                1375                1380

Lys Glu Glu Leu Glu Arg Thr Asn Lys Met Leu Lys Ala Glu Met
    1385                1390                1395

Glu Asp Leu Val Ser Ser Lys Asp Asp Val Gly Lys Asn Val His
    1400                1405                1410

Glu Leu Glu Lys Ser Lys Arg Ala Leu Glu Thr Gln Met Glu Glu
    1415                1420                1425

Met Lys Thr Gln Leu Glu Glu Leu Glu Asp Glu Leu Gln Ala Thr
```

```
                      1430              1435               1440

Glu  Asp  Ala  Lys  Leu  Arg  Leu  Glu  Val  Asn  Met  Gln  Ala  Leu  Lys
1445                1450                    1455

Gly  Gln  Phe  Glu  Arg  Asp  Leu  Gln  Ala  Arg  Asp  Glu  Gln  Asn  Glu
1460                1465                    1470

Glu  Lys  Arg  Arg  Gln  Leu  Gln  Arg  Gln  Leu  His  Glu  Tyr  Glu  Thr
1475                1480                    1485

Glu  Leu  Glu  Asp  Glu  Arg  Lys  Gln  Arg  Ala  Leu  Ala  Ala  Ala  Ala
1490                1495                    1500

Lys  Lys  Lys  Leu  Glu  Gly  Asp  Leu  Lys  Asp  Leu  Glu  Leu  Gln  Ala
1505                1510                    1515

Asp  Ser  Ala  Ile  Lys  Gly  Arg  Glu  Glu  Ala  Ile  Lys  Gln  Leu  Arg
1520                1525                    1530

Lys  Leu  Gln  Ala  Gln  Met  Lys  Asp  Phe  Gln  Arg  Glu  Leu  Glu  Asp
1535                1540                    1545

Ala  Arg  Ala  Ser  Arg  Asp  Glu  Ile  Phe  Ala  Thr  Ala  Lys  Glu  Asn
1550                1555                    1560

Glu  Lys  Lys  Ala  Lys  Ser  Leu  Glu  Ala  Asp  Leu  Met  Gln  Leu  Gln
1565                1570                    1575

Glu  Asp  Leu  Ala  Ala  Ala  Glu  Arg  Ala  Arg  Lys  Gln  Ala  Asp  Leu
1580                1585                    1590

Glu  Lys  Glu  Glu  Leu  Ala  Glu  Glu  Leu  Ala  Ser  Ser  Leu  Ser  Gly
1595                1600                    1605

Arg  Asn  Ala  Leu  Gln  Asp  Glu  Lys  Arg  Arg  Leu  Glu  Ala  Arg  Ile
1610                1615                    1620

Ala  Gln  Leu  Glu  Glu  Glu  Leu  Glu  Glu  Glu  Gln  Gly  Asn  Met  Glu
1625                1630                    1635

Ala  Met  Ser  Asp  Arg  Val  Arg  Lys  Ala  Thr  Gln  Ala  Glu  Gln
1640                1645                    1650

Leu  Ser  Asn  Glu  Leu  Ala  Thr  Glu  Arg  Ser  Thr  Ala  Gln  Lys  Asn
1655                1660                    1665

Glu  Ser  Ala  Arg  Gln  Gln  Leu  Glu  Arg  Gln  Asn  Lys  Glu  Leu  Arg
1670                1675                    1680

Ser  Lys  Leu  His  Glu  Met  Glu  Gly  Ala  Val  Lys  Ser  Lys  Phe  Lys
1685                1690                    1695

Ser  Thr  Ile  Ala  Ala  Leu  Glu  Ala  Lys  Ile  Ala  Gln  Leu  Glu  Glu
1700                1705                    1710

Gln  Val  Glu  Gln  Glu  Ala  Arg  Glu  Lys  Gln  Ala  Ala  Thr  Lys  Ser
1715                1720                    1725

Leu  Lys  Gln  Lys  Asp  Lys  Lys  Leu  Lys  Glu  Ile  Leu  Leu  Gln  Val
1730                1735                    1740

Glu  Asp  Glu  Arg  Lys  Met  Ala  Glu  Gln  Tyr  Lys  Glu  Gln  Ala  Glu
1745                1750                    1755

Lys  Gly  Asn  Ala  Arg  Val  Lys  Gln  Leu  Lys  Arg  Gln  Leu  Glu  Glu
1760                1765                    1770

Ala  Glu  Glu  Glu  Ser  Gln  Arg  Ile  Asn  Ala  Asn  Arg  Arg  Lys  Leu
1775                1780                    1785

Gln  Arg  Glu  Leu  Asp  Glu  Ala  Thr  Glu  Ser  Asn  Glu  Ala  Met  Gly
1790                1795                    1800

Arg  Glu  Val  Asn  Ala  Leu  Lys  Ser  Lys  Leu  Arg  Arg  Gly  Asn  Glu
1805                1810                    1815

Thr  Ser  Phe  Val  Pro  Ser  Arg  Arg  Ser  Gly  Gly  Arg  Arg  Val  Ile
1820                1825                    1830
```

-continued

Glu Asn Ala Asp Gly Ser Glu Glu Thr Asp Thr Arg Asp Ala
    1835                1840                1845

Asp Phe Asn Gly Thr Lys Ala Ser Glu
    1850                1855

<210> SEQ ID NO 92
<211> LENGTH: 1953
<212> TYPE: PRT
<213> ORGANISM: Homo Sapiens

<400> SEQUENCE: 92

Gly Cys Leu Cys Cys Ser Ser Glu Gln Leu Gln Glu Leu Pro Ser Arg
1               5                   10                  15

Glu Leu Gln Asp Ala Phe Pro Val Pro Leu Ala Gln Leu Pro Gln Gln
            20                  25                  30

Thr Thr Glu Lys Thr Val Thr Met Gly Asp Val Lys Leu Val Ala Ser
        35                  40                  45

Ser His Ile Ser Lys Thr Ser Leu Ser Val Asp Pro Ser Arg Val Asp
    50                  55                  60

Ser Met Pro Leu Thr Glu Ala Pro Ala Phe Ile Leu Pro Pro Arg Asn
65                  70                  75                  80

Leu Cys Ile Lys Glu Gly Ala Thr Ala Lys Phe Glu Gly Arg Val Arg
                85                  90                  95

Gly Tyr Pro Glu Pro Gln Val Thr Trp His Arg Asn Gly Gln Pro Ile
            100                 105                 110

Thr Ser Gly Gly Arg Phe Leu Leu Asp Cys Gly Ile Arg Gly Thr Phe
        115                 120                 125

Ser Leu Val Ile His Ala Val His Glu Glu Asp Arg Gly Lys Tyr Thr
    130                 135                 140

Cys Glu Ala Thr Asn Gly Ser Gly Ala Arg Gln Val Thr Val Glu Leu
145                 150                 155                 160

Thr Val Glu Gly Ser Phe Ala Lys Gln Leu Gly Gln Pro Val Val Ser
                165                 170                 175

Lys Thr Leu Gly Asp Arg Phe Ser Ala Ser Ala Val Glu Thr Arg Pro
            180                 185                 190

Ser Ile Trp Gly Glu Cys Pro Pro Lys Phe Ala Thr Lys Leu Gly Arg
        195                 200                 205

Val Val Val Lys Glu Gly Gln Met Gly Arg Phe Ser Cys Lys Ile Thr
    210                 215                 220

Gly Arg Pro Gln Pro Gln Val Thr Trp Leu Lys Gly Asn Val Pro Leu
225                 230                 235                 240

Gln Pro Ser Ala Arg Val Ser Val Ser Glu Lys Asn Gly Met Gln Val
                245                 250                 255

Leu Glu Ile His Gly Val Asn Gln Asp Asp Val Gly Val Tyr Thr Cys
            260                 265                 270

Leu Val Val Asn Gly Ser Gly Lys Ala Ser Met Ser Ala Glu Leu Ser
        275                 280                 285

Ile Gln Gly Leu Asp Ser Ala Asn Arg Ser Phe Val Arg Glu Thr Lys
    290                 295                 300

Ala Thr Asn Ser Asp Val Arg Lys Glu Val Thr Asn Val Ile Ser Lys
305                 310                 315                 320

Glu Ser Lys Leu Asp Ser Leu Glu Ala Ala Lys Ser Lys Asn Cys
                325                 330                 335

Ser Ser Pro Gln Arg Gly Gly Ser Pro Pro Trp Ala Ala Asn Ser Gln

-continued

```
                340                  345                  350
Pro Gln Pro Pro Arg Glu Ser Lys Leu Glu Ser Cys Lys Asp Ser Pro
        355                  360                  365
Arg Thr Ala Pro Gln Thr Pro Val Leu Gln Lys Thr Ser Ser Ile
370                  375                  380
Thr Leu Gln Ala Ala Arg Val Gln Pro Glu Pro Arg Ala Pro Gly Leu
385                  390                  395                  400
Gly Val Leu Ser Pro Ser Gly Glu Glu Arg Lys Arg Pro Ala Pro Pro
                405                  410                  415
Arg Pro Ala Thr Phe Pro Thr Arg Gln Pro Gly Leu Gly Ser Gln Asp
                420                  425                  430
Val Val Ser Lys Ala Ala Asn Arg Arg Ile Pro Met Glu Gly Gln Arg
                435                  440                  445
Asp Ser Ala Phe Pro Lys Phe Glu Ser Lys Pro Gln Ser Gln Glu Val
        450                  455                  460
Lys Glu Asn Gln Thr Val Lys Phe Arg Cys Glu Val Ser Gly Ile Pro
465                  470                  475                  480
Lys Pro Glu Val Ala Trp Phe Leu Glu Gly Thr Pro Val Arg Arg Gln
                485                  490                  495
Glu Gly Ser Ile Glu Val Tyr Glu Asp Ala Gly Ser His Tyr Leu Cys
            500                  505                  510
Leu Leu Lys Ala Arg Thr Arg Asp Ser Gly Thr Tyr Ser Cys Thr Ala
            515                  520                  525
Ser Asn Ala Gln Gly Gln Val Ser Cys Ser Trp Thr Leu Gln Val Glu
        530                  535                  540
Arg Leu Ala Val Met Glu Val Ala Pro Ser Phe Ser Ser Val Leu Lys
545                  550                  555                  560
Asp Cys Ala Val Ile Glu Gly Gln Asp Phe Val Leu Gln Cys Ser Val
                565                  570                  575
Arg Gly Thr Pro Val Pro Arg Ile Thr Trp Leu Leu Asn Gly Gln Pro
            580                  585                  590
Ile Gln Tyr Ala Arg Ser Thr Cys Glu Ala Gly Val Ala Glu Leu His
            595                  600                  605
Ile Gln Asp Ala Leu Pro Glu Asp His Gly Thr Tyr Thr Cys Leu Ala
        610                  615                  620
Glu Asn Ala Leu Gly Gln Val Ser Cys Ser Ala Trp Val Thr Val His
625                  630                  635                  640
Glu Lys Lys Ser Ser Arg Lys Ser Glu Tyr Leu Leu Pro Val Ala Pro
                645                  650                  655
Ser Lys Pro Thr Ala Pro Ile Phe Leu Gln Gly Leu Ser Asp Leu Lys
                660                  665                  670
Val Met Asp Gly Ser Gln Val Thr Met Thr Val Gln Val Ser Gly Asn
            675                  680                  685
Pro Pro Pro Glu Val Ile Trp Leu His Asn Gly Asn Glu Ile Gln Glu
        690                  695                  700
Ser Glu Asp Phe His Phe Glu Gln Arg Gly Thr Gln His Ser Leu Trp
705                  710                  715                  720
Ile Gln Glu Val Phe Pro Glu Asp Thr Gly Thr Tyr Thr Cys Glu Ala
                725                  730                  735
Trp Asn Ser Ala Gly Glu Val Arg Thr Gln Ala Val Leu Thr Val Gln
            740                  745                  750
Glu Pro His Asp Gly Thr Gln Pro Trp Phe Ile Ser Lys Pro Arg Ser
            755                  760                  765
```

```
Val Thr Ala Ser Leu Gly Gln Ser Val Leu Ile Ser Cys Ala Ile Ala
    770                 775                 780

Gly Asp Pro Phe Pro Thr Val His Trp Leu Arg Asp Gly Lys Ala Leu
785                 790                 795                 800

Cys Lys Asp Thr Gly His Phe Glu Val Leu Gln Asn Glu Asp Val Phe
                805                 810                 815

Thr Leu Val Leu Lys Lys Val Gln Pro Trp His Ala Gly Gln Tyr Glu
                820                 825                 830

Ile Leu Leu Lys Asn Arg Val Gly Glu Cys Ser Cys Gln Val Ser Leu
                835                 840                 845

Met Leu Gln Asn Ser Ser Ala Arg Ala Leu Pro Arg Gly Arg Glu Pro
850                 855                 860

Ala Ser Cys Glu Asp Leu Cys Gly Gly Val Gly Ala Asp Gly Gly
865                 870                 875                 880

Gly Ser Asp Arg Tyr Gly Ser Leu Arg Pro Gly Trp Pro Ala Arg Gly
                885                 890                 895

Gln Gly Trp Leu Glu Glu Glu Asp Gly Glu Asp Val Arg Gly Val Leu
                900                 905                 910

Lys Arg Arg Val Glu Thr Arg Gln His Thr Glu Glu Ala Ile Arg Gln
                915                 920                 925

Gln Glu Val Glu Gln Leu Asp Phe Arg Asp Leu Leu Gly Lys Lys Val
930                 935                 940

Ser Thr Lys Thr Leu Ser Glu Asp Asp Leu Lys Glu Ile Pro Ala Glu
945                 950                 955                 960

Gln Met Asp Phe Arg Ala Asn Leu Gln Arg Gln Val Lys Pro Lys Thr
                965                 970                 975

Val Ser Glu Glu Glu Arg Lys Val His Ser Pro Gln Gln Val Asp Phe
                980                 985                 990

Arg Ser Val Leu Ala Lys Lys Gly Thr Ser Lys Thr Pro Val Pro Glu
                995                 1000                1005

Lys Val Pro Pro Pro Lys Pro Ala Thr Pro Asp Phe Arg Ser Val
    1010                1015                1020

Leu Gly Gly Lys Lys Lys Leu Pro Ala Glu Asn Gly Ser Ser Ser
    1025                1030                1035

Ala Glu Thr Leu Asn Ala Lys Ala Val Glu Ser Ser Lys Pro Leu
    1040                1045                1050

Ser Asn Ala Gln Pro Ser Gly Pro Leu Lys Pro Val Gly Asn Ala
    1055                1060                1065

Lys Pro Ala Glu Thr Leu Lys Pro Met Gly Asn Ala Lys Pro Ala
    1070                1075                1080

Glu Thr Leu Lys Pro Met Gly Asn Ala Lys Pro Asp Glu Asn Leu
    1085                1090                1095

Lys Ser Ala Ser Lys Glu Glu Leu Lys Lys Asp Val Lys Asn Asp
    1100                1105                1110

Val Asn Cys Lys Arg Gly His Ala Gly Thr Thr Asp Asn Glu Lys
    1115                1120                1125

Arg Ser Glu Ser Gln Gly Thr Ala Pro Ala Phe Lys Gln Lys Leu
    1130                1135                1140

Gln Asp Val His Val Ala Glu Gly Lys Lys Leu Leu Leu Gln Cys
    1145                1150                1155

Gln Val Ser Ser Asp Pro Pro Ala Thr Ile Ile Trp Thr Leu Asn
    1160                1165                1170
```

-continued

```
Gly Lys Thr Leu Lys Thr Thr Lys Phe Ile Ile Leu Ser Gln Glu
    1175                1180                1185

Gly Ser Leu Cys Ser Val Ser Ile Glu Lys Ala Leu Pro Glu Asp
    1190                1195                1200

Arg Gly Leu Tyr Lys Cys Val Ala Lys Asn Asp Ala Gly Gln Ala
    1205                1210                1215

Glu Cys Ser Cys Gln Val Thr Val Asp Asp Ala Pro Ala Ser Glu
    1220                1225                1230

Asn Thr Lys Ala Pro Glu Met Lys Ser Arg Arg Pro Lys Ser Ser
    1235                1240                1245

Leu Pro Pro Val Leu Gly Thr Glu Ser Asp Ala Thr Val Lys Lys
    1250                1255                1260

Lys Pro Ala Pro Lys Thr Pro Pro Lys Ala Ala Met Pro Pro Gln
    1265                1270                1275

Ile Ile Gln Phe Pro Glu Asp Gln Lys Val Arg Ala Gly Glu Ser
    1280                1285                1290

Val Glu Leu Phe Gly Lys Val Thr Gly Thr Gln Pro Ile Thr Cys
    1295                1300                1305

Thr Trp Met Lys Phe Arg Lys Gln Ile Gln Glu Ser Glu His Met
    1310                1315                1320

Lys Val Glu Asn Ser Glu Asn Gly Ser Lys Leu Thr Ile Leu Ala
    1325                1330                1335

Ala Arg Gln Glu His Cys Gly Cys Tyr Thr Leu Leu Val Glu Asn
    1340                1345                1350

Lys Leu Gly Ser Arg Gln Ala Gln Val Asn Leu Thr Val Val Asp
    1355                1360                1365

Lys Pro Asp Pro Pro Ala Gly Thr Pro Cys Ala Ser Asp Ile Arg
    1370                1375                1380

Ser Ser Ser Leu Thr Leu Ser Trp Tyr Gly Ser Ser Tyr Asp Gly
    1385                1390                1395

Gly Ser Ala Val Gln Ser Tyr Ser Ile Glu Ile Trp Asp Ser Ala
    1400                1405                1410

Asn Lys Thr Trp Lys Glu Leu Ala Thr Cys Arg Ser Thr Ser Phe
    1415                1420                1425

Asn Val Gln Asp Leu Leu Pro Asp His Glu Tyr Lys Phe Arg Val
    1430                1435                1440

Arg Ala Ile Asn Val Tyr Gly Thr Ser Glu Pro Ser Gln Glu Ser
    1445                1450                1455

Glu Leu Thr Thr Val Gly Glu Lys Pro Glu Pro Lys Asp Glu
    1460                1465                1470

Val Glu Val Ser Asp Asp Asp Glu Lys Glu Pro Glu Val Asp Tyr
    1475                1480                1485

Arg Thr Val Thr Ile Asn Thr Glu Gln Lys Val Ser Asp Phe Tyr
    1490                1495                1500

Asp Ile Glu Glu Arg Leu Gly Ser Gly Lys Phe Gly Gln Val Phe
    1505                1510                1515

Arg Leu Val Glu Lys Lys Thr Arg Lys Val Trp Ala Gly Lys Phe
    1520                1525                1530

Phe Lys Ala Tyr Ser Ala Lys Glu Lys Glu Asn Ile Arg Gln Glu
    1535                1540                1545

Ile Ser Ile Met Asn Cys Leu His His Pro Lys Leu Val Gln Cys
    1550                1555                1560

Val Asp Ala Phe Glu Glu Lys Ala Asn Ile Val Met Val Leu Glu
```

-continued

```
              1565                1570                1575

Ile Val Ser Gly Gly Glu Leu Phe Glu Arg Ile Ile Asp Glu Asp
    1580                1585                1590

Phe Glu Leu Thr Glu Arg Cys Ile Lys Tyr Met Arg Gln Ile
    1595                1600                1605

Ser Glu Gly Val Glu Tyr Ile His Lys Gln Gly Ile Val His Leu
    1610                1615                1620

Asp Leu Lys Pro Glu Asn Ile Met Cys Val Asn Lys Thr Gly Thr
    1625                1630                1635

Arg Ile Lys Leu Ile Asp Phe Gly Leu Ala Arg Arg Leu Glu Asn
    1640                1645                1650

Ala Gly Ser Leu Lys Val Leu Phe Gly Thr Pro Glu Phe Val Ala
    1655                1660                1665

Pro Glu Val Ile Asn Tyr Glu Pro Ile Gly Tyr Ala Thr Asp Met
    1670                1675                1680

Trp Ser Ile Gly Val Ile Cys Tyr Ile Leu Val Ser Gly Leu Ser
    1685                1690                1695

Pro Phe Met Gly Asp Asn Asp Asn Glu Thr Leu Ala Asn Val Thr
    1700                1705                1710

Ser Ala Thr Trp Asp Phe Asp Asp Glu Ala Phe Asp Glu Ile Ser
    1715                1720                1725

Asp Asp Ala Lys Asp Phe Ile Ser Asn Leu Leu Lys Lys Asp Met
    1730                1735                1740

Lys Asn Arg Leu Asp Cys Thr Gln Cys Leu Gln His Pro Trp Leu
    1745                1750                1755

Met Lys Asp Thr Lys Asn Met Glu Ala Lys Lys Leu Ser Lys Asp
    1760                1765                1770

Arg Met Lys Lys Tyr Met Ala Arg Arg Lys Trp Gln Lys Thr Gly
    1775                1780                1785

Asn Ala Val Arg Ala Ile Gly Arg Leu Ser Ser Met Ala Met Ile
    1790                1795                1800

Ser Gly Leu Ser Gly Arg Lys Ser Ser Thr Gly Ser Pro Thr Ser
    1805                1810                1815

Pro Leu Asn Ala Glu Lys Leu Glu Ser Glu Glu Asp Val Ser Gln
    1820                1825                1830

Ala Phe Leu Glu Ala Val Ala Glu Glu Lys Pro His Val Lys Pro
    1835                1840                1845

Tyr Phe Ser Lys Thr Ile Arg Asp Leu Glu Val Val Glu Gly Ser
    1850                1855                1860

Ala Ala Arg Phe Asp Cys Lys Ile Glu Gly Tyr Pro Asp Pro Glu
    1865                1870                1875

Val Val Trp Phe Lys Asp Asp Gln Ser Ile Arg Glu Ser Arg His
    1880                1885                1890

Phe Gln Ile Asp Tyr Asp Glu Asp Gly Asn Cys Ser Leu Ile Ile
    1895                1900                1905

Ser Asp Val Cys Gly Asp Asp Asp Ala Lys Tyr Thr Cys Lys Ala
    1910                1915                1920

Val Asn Ser Leu Gly Glu Ala Thr Cys Thr Ala Glu Leu Ile Val
    1925                1930                1935

Glu Thr Met Glu Glu Gly Glu Gly Glu Gly Glu Glu Glu Glu Glu
    1940                1945                1950
```

```
<210> SEQ ID NO 93
<211> LENGTH: 901
<212> TYPE: PRT
<213> ORGANISM: Homo Sapiens

<400> SEQUENCE: 93

Val Gly Arg Ala Arg Ala Pro Gly Ala Gln Val Gly Ala Gly Ala Met
1               5                   10                  15

Glu Pro Pro Thr Val Pro Ser Glu Arg Ser Leu Ser Leu Ser Leu Pro
            20                  25                  30

Gly Pro Arg Glu Gly Gln Ala Thr Leu Lys Pro Pro Gln His Leu
        35                  40                  45

Trp Arg Gln Pro Arg Thr Pro Ile Arg Ile Gln Gln Arg Gly Tyr Ser
    50                  55                  60

Asp Ser Ala Glu Arg Ala Glu Arg Glu Arg Gln Pro His Arg Pro Ile
65              70                  75                  80

Glu Arg Ala Asp Ala Met Asp Thr Ser Asp Arg Pro Gly Leu Arg Thr
                85                  90                  95

Thr Arg Met Ser Trp Pro Ser Ser Phe His Gly Thr Gly Thr Gly Ser
            100                 105                 110

Gly Gly Ala Gly Gly Gly Ser Ser Arg Arg Phe Glu Ala Glu Asn Gly
        115                 120                 125

Pro Thr Pro Ser Pro Gly Arg Ser Pro Leu Asp Ser Gln Ala Ser Pro
    130                 135                 140

Gly Leu Val Leu His Ala Gly Ala Ala Thr Ser Gln Arg Arg Glu Ser
145                 150                 155                 160

Phe Leu Tyr Arg Ser Asp Ser Asp Tyr Asp Met Ser Pro Lys Thr Met
                165                 170                 175

Ser Arg Asn Ser Ser Val Thr Ser Glu Ala His Ala Glu Asp Leu Ile
            180                 185                 190

Val Thr Pro Phe Ala Gln Val Leu Ala Ser Leu Arg Ser Val Arg Ser
        195                 200                 205

Asn Phe Ser Leu Leu Thr Asn Val Pro Val Pro Ser Asn Lys Arg Ser
    210                 215                 220

Pro Leu Gly Gly Pro Thr Pro Val Cys Lys Ala Thr Leu Ser Glu Glu
225                 230                 235                 240

Thr Cys Gln Gln Leu Ala Arg Glu Thr Leu Glu Glu Leu Asp Trp Cys
                245                 250                 255

Leu Glu Gln Leu Glu Thr Met Gln Thr Tyr Arg Ser Val Ser Glu Met
            260                 265                 270

Ala Ser His Lys Phe Lys Arg Met Leu Asn Arg Glu Leu Thr His Leu
        275                 280                 285

Ser Glu Met Ser Arg Ser Gly Asn Gln Val Ser Glu Tyr Ile Ser Thr
    290                 295                 300

Thr Phe Leu Asp Lys Gln Asn Glu Val Glu Ile Pro Ser Pro Thr Met
305                 310                 315                 320

Lys Glu Arg Glu Lys Gln Gln Ala Pro Arg Pro Arg Pro Ser Gln Pro
                325                 330                 335

Pro Pro Pro Pro Val Pro His Leu Gln Pro Met Ser Gln Ile Thr Gly
            340                 345                 350

Leu Lys Lys Leu Met His Ser Asn Ser Leu Asn Asn Ser Asn Ile Pro
        355                 360                 365

Arg Phe Gly Val Lys Thr Asp Gln Glu Glu Leu Leu Ala Gln Glu Leu
    370                 375                 380
```

-continued

```
Glu Asn Leu Asn Lys Trp Gly Leu Asn Ile Phe Cys Val Ser Asp Tyr
385                 390                 395                 400

Ala Gly Gly Arg Ser Leu Thr Cys Ile Met Tyr Met Ile Phe Gln Glu
                405                 410                 415

Arg Asp Leu Leu Lys Lys Phe Arg Ile Pro Val Asp Thr Met Val Thr
            420                 425                 430

Tyr Met Leu Thr Leu Glu Asp His Tyr His Ala Asp Val Ala Tyr His
        435                 440                 445

Asn Ser Leu His Ala Ala Asp Val Leu Gln Ser Thr His Val Leu Leu
    450                 455                 460

Ala Thr Pro Ala Leu Asp Ala Val Phe Thr Asp Leu Glu Ile Leu Ala
465                 470                 475                 480

Ala Leu Phe Ala Ala Ile His Asp Val Asp His Pro Gly Val Ser
                485                 490                 495

Asn Gln Phe Leu Ile Asn Thr Asn Ser Glu Leu Ala Leu Met Tyr Asn
                500                 505                 510

Asp Glu Ser Val Leu Glu Asn His His Leu Ala Val Gly Phe Lys Leu
            515                 520                 525

Leu Gln Glu Asp Asn Cys Asp Ile Phe Gln Asn Leu Ser Lys Arg Gln
    530                 535                 540

Arg Gln Ser Leu Arg Lys Met Val Ile Asp Met Val Leu Ala Thr Asp
545                 550                 555                 560

Met Ser Lys His Met Thr Leu Leu Ala Asp Leu Lys Thr Met Val Glu
                565                 570                 575

Thr Lys Lys Val Thr Ser Ser Gly Val Leu Leu Leu Asp Asn Tyr Ser
            580                 585                 590

Asp Arg Ile Gln Val Leu Arg Asn Met Val His Cys Ala Asp Leu Ser
        595                 600                 605

Asn Pro Thr Lys Pro Leu Glu Leu Tyr Arg Gln Trp Thr Asp Arg Ile
    610                 615                 620

Met Ala Glu Phe Phe Gln Gln Gly Asp Arg Glu Arg Glu Arg Gly Met
625                 630                 635                 640

Glu Ile Ser Pro Met Cys Asp Lys His Thr Ala Ser Val Glu Lys Ser
                645                 650                 655

Gln Val Gly Phe Ile Asp Tyr Ile Val His Pro Leu Trp Glu Thr Trp
            660                 665                 670

Ala Asp Leu Val His Pro Asp Ala Gln Glu Ile Leu Asp Thr Leu Glu
        675                 680                 685

Asp Asn Arg Asp Trp Tyr Tyr Ser Ala Ile Arg Gln Ser Pro Ser Pro
    690                 695                 700

Pro Pro Glu Glu Glu Ser Arg Gly Pro Gly His Pro Pro Leu Pro Asp
705                 710                 715                 720

Lys Phe Gln Phe Glu Leu Thr Leu Glu Glu Glu Glu Glu Glu Glu Ile
                725                 730                 735

Ser Met Ala Gln Ile Pro Cys Thr Ala Gln Glu Ala Leu Thr Ala Gln
                740                 745                 750

Gly Leu Ser Gly Val Glu Glu Ala Leu Asp Ala Thr Ile Ala Trp Glu
            755                 760                 765

Ala Ser Pro Ala Gln Glu Ser Leu Glu Val Met Ala Gln Glu Ala Ser
        770                 775                 780

Leu Glu Ala Glu Leu Glu Ala Val Tyr Leu Thr Gln Gln Ala Gln Ser
785                 790                 795                 800

Thr Gly Ser Ala Pro Val Ala Pro Asp Glu Phe Ser Ser Arg Glu Glu
```

```
                        805                 810                 815
Phe Val Val Ala Val Ser His Ser Ser Pro Ser Ala Leu Ala Leu Gln
                820                 825                 830

Ser Pro Leu Leu Pro Ala Trp Arg Thr Leu Ser Val Ser Glu His Ala
            835                 840                 845

Pro Gly Leu Pro Gly Leu Pro Ser Thr Ala Ala Glu Val Glu Ala Gln
850                 855                 860

Arg Glu His Gln Ala Ala Lys Arg Ala Cys Ser Ala Cys Ala Gly Thr
865                 870                 875                 880

Phe Gly Glu Asp Thr Ser Ala Leu Pro Ala Pro Gly Gly Gly Gly Ser
                885                 890                 895

Gly Gly Asp Pro Thr
            900

<210> SEQ ID NO 94
<211> LENGTH: 702
<212> TYPE: PRT
<213> ORGANISM: Homo Sapiens

<400> SEQUENCE: 94

Pro Ala Ser Gly Arg Ala Pro Gln Pro Gly Arg Cys Thr Cys Gln Gly
1               5                   10                  15

Asn Lys Leu Glu Glu Gln Asp Pro Arg Pro Leu Gln Pro Ile Pro Gly
            20                  25                  30

Leu Met Glu Gly Asn Lys Leu Glu Glu Gln Asp Ser Ser Pro Pro Gln
        35                  40                  45

Ser Thr Pro Gly Leu Met Lys Gly Asn Lys Arg Glu Glu Gln Gly Leu
50                  55                  60

Gly Pro Glu Pro Ala Ala Pro Gln Gln Pro Thr Ala Glu Glu Glu Ala
65                  70                  75                  80

Leu Ile Glu Phe His Arg Ser Tyr Arg Glu Leu Phe Glu Phe Phe Cys
                85                  90                  95

Asn Asn Thr Thr Ile His Gly Ala Ile Arg Leu Val Cys Ser Gln His
            100                 105                 110

Asn Arg Met Lys Thr Ala Phe Trp Ala Val Leu Trp Leu Cys Thr Phe
        115                 120                 125

Gly Met Met Tyr Trp Gln Phe Gly Leu Leu Phe Gly Glu Tyr Phe Ser
    130                 135                 140

Tyr Pro Val Ser Leu Asn Ile Asn Leu Asn Ser Asp Lys Leu Val Phe
145                 150                 155                 160

Pro Ala Val Thr Ile Cys Thr Leu Asn Pro Tyr Arg Tyr Pro Glu Ile
                165                 170                 175

Lys Glu Glu Leu Glu Glu Leu Asp Arg Ile Thr Glu Gln Thr Leu Phe
            180                 185                 190

Asp Leu Tyr Lys Tyr Ser Ser Phe Thr Thr Leu Val Ala Gly Ser Arg
        195                 200                 205

Ser Arg Arg Asp Leu Arg Gly Thr Leu Pro His Pro Leu Gln Arg Leu
    210                 215                 220

Arg Val Pro Pro Pro His Gly Ala Arg Ala Arg Ser Val Ala
225                 230                 235                 240

Ser Ser Leu Arg Asp Asn Asn Pro Gln Val Asp Trp Lys Asp Trp Lys
                245                 250                 255

Ile Gly Phe Gln Leu Cys Asn Gln Asn Lys Ser Asp Cys Phe Tyr Gln
            260                 265                 270
```

-continued

```
Thr Tyr Ser Ser Gly Val Asp Ala Val Arg Glu Trp Tyr Arg Phe His
        275                 280                 285
Tyr Ile Asn Ile Leu Ser Arg Leu Pro Glu Thr Leu Pro Ser Leu Glu
        290                 295                 300
Glu Asp Thr Leu Gly Asn Phe Ile Phe Ala Cys Arg Phe Asn Gln Val
305                 310                 315                 320
Ser Cys Asn Gln Ala Asn Tyr Ser His Phe His His Pro Met Tyr Gly
                325                 330                 335
Asn Cys Tyr Thr Phe Asn Asp Lys Asn Asn Ser Asn Leu Trp Met Ser
                340                 345                 350
Ser Met Pro Gly Ile Asn Asn Gly Leu Ser Leu Met Leu Arg Ala Glu
                355                 360                 365
Gln Asn Asp Phe Ile Pro Leu Leu Ser Thr Val Thr Gly Ala Arg Val
        370                 375                 380
Met Val His Gly Gln Asp Glu Pro Ala Phe Met Asp Asp Gly Gly Phe
385                 390                 395                 400
Asn Leu Arg Pro Gly Val Glu Thr Ser Ile Ser Met Arg Lys Glu Thr
                405                 410                 415
Leu Asp Arg Leu Gly Gly Asp Tyr Gly Asp Cys Thr Lys Asn Gly Ser
                420                 425                 430
Asp Val Pro Val Glu Asn Leu Tyr Pro Ser Lys Tyr Thr Gln Gln Val
                435                 440                 445
Cys Ile His Ser Cys Phe Gln Glu Ser Met Ile Lys Glu Cys Gly Cys
        450                 455                 460
Ala Tyr Ile Phe Tyr Pro Arg Pro Gln Asn Val Glu Tyr Cys Asp Tyr
465                 470                 475                 480
Arg Lys His Ser Ser Trp Gly Tyr Cys Tyr Tyr Lys Leu Gln Val Asp
                485                 490                 495
Phe Ser Ser Asp His Leu Gly Cys Phe Thr Lys Cys Arg Lys Pro Cys
                500                 505                 510
Ser Val Thr Ser Tyr Gln Leu Ser Ala Gly Tyr Ser Arg Trp Pro Ser
                515                 520                 525
Val Thr Ser Gln Glu Trp Val Phe Gln Met Leu Ser Arg Gln Asn Asn
        530                 535                 540
Tyr Thr Val Asn Asn Lys Arg Asn Gly Val Ala Lys Val Asn Ile Phe
545                 550                 555                 560
Phe Lys Glu Leu Asn Tyr Lys Thr Asn Ser Glu Ser Pro Ser Val Thr
                565                 570                 575
Met Val Thr Leu Leu Ser Asn Leu Gly Ser Gln Trp Ser Leu Trp Phe
                580                 585                 590
Gly Ser Ser Val Leu Ser Val Val Glu Met Ala Glu Leu Val Phe Asp
        595                 600                 605
Leu Leu Val Ile Met Phe Leu Met Leu Leu Arg Arg Phe Arg Ser Arg
        610                 615                 620
Tyr Trp Ser Pro Gly Arg Gly Arg Gly Ala Gln Glu Val Ala Ser
625                 630                 635                 640
Thr Leu Ala Ser Ser Pro Ser His Phe Cys Pro His Pro Met Ser
                645                 650                 655
Leu Ser Leu Ser Gln Pro Gly Pro Ala Pro Ser Pro Ala Leu Thr Ala
                660                 665                 670
Pro Pro Pro Ala Tyr Ala Thr Leu Gly Pro Arg Pro Ser Pro Gly Gly
                675                 680                 685
Ser Ala Gly Ala Ser Ser Ser Thr Cys Pro Leu Gly Gly Pro
```

690        695        700

<210> SEQ ID NO 95
<211> LENGTH: 109
<212> TYPE: PRT
<213> ORGANISM: Homo Sapiens

<400> SEQUENCE: 95

Ala Tyr Ser Arg Gly Thr Ser Ser Leu Ser Thr Met Asn Gln Thr Ala
1               5                   10                  15

Ile Leu Ile Cys Cys Leu Ile Phe Leu Thr Leu Ser Gly Ile Gln Gly
            20                  25                  30

Val Pro Leu Ser Arg Thr Val Arg Cys Thr Cys Ile Ser Ile Ser Asn
        35                  40                  45

Gln Pro Val Asn Pro Arg Ser Leu Glu Lys Leu Glu Ile Ile Pro Ala
    50                  55                  60

Ser Gln Phe Cys Pro Arg Val Glu Ile Ile Ala Thr Met Lys Lys Lys
65                  70                  75                  80

Gly Glu Lys Arg Cys Leu Asn Pro Glu Ser Lys Ala Ile Lys Asn Leu
                85                  90                  95

Leu Lys Ala Val Ser Lys Glu Met Ser Lys Arg Ser Pro
            100                 105

<210> SEQ ID NO 96
<211> LENGTH: 249
<212> TYPE: PRT
<213> ORGANISM: Homo Sapiens

<400> SEQUENCE: 96

Glu Phe Pro Glu Glu Ala Asn Pro Ala Gly Ile Arg Ala Ile Arg Thr
1               5                   10                  15

Ala Thr Met Thr Val Gly Lys Ser Ser Lys Met Leu Gln His Ile Asp
            20                  25                  30

Tyr Arg Met Arg Cys Ile Leu Gln Asp Gly Arg Ile Phe Ile Gly Thr
        35                  40                  45

Phe Lys Ala Phe Asp Lys His Met Asn Leu Ile Leu Cys Asp Cys Asp
    50                  55                  60

Glu Phe Arg Lys Ile Lys Pro Lys Asn Ser Lys Gln Ala Glu Arg Glu
65                  70                  75                  80

Glu Lys Arg Val Leu Gly Leu Val Leu Leu Arg Gly Glu Asn Leu Val
                85                  90                  95

Ser Met Thr Val Glu Gly Pro Pro Lys Asp Thr Gly Ile Ala Arg
            100                 105                 110

Val Pro Leu Ala Gly Ala Ala Gly Pro Gly Ile Gly Arg Ala Ala
        115                 120                 125

Gly Arg Gly Ile Pro Ala Gly Val Pro Met Pro Gln Ala Pro Ala Gly
    130                 135                 140

Leu Ala Gly Pro Val Arg Gly Val Gly Pro Ser Gln Gln Val Met
145                 150                 155                 160

Thr Pro Gln Gly Arg Gly Thr Val Ala Ala Ala Ala Ala Thr
            165                 170                 175

Ala Ser Ile Ala Gly Ala Pro Thr Gln Tyr Pro Pro Arg Gly Gly
        180                 185                 190

Pro Pro Pro Pro Met Gly Arg Gly Ala Pro Pro Gly Met Met Gly
    195                 200                 205

Pro Pro Pro Gly Met Arg Pro Pro Met Gly Pro Pro Met Gly Ile Pro

-continued

```
            210                 215                 220
Pro Gly Arg Gly Thr Pro Met Gly Met Pro Pro Gly Met Arg Pro
225                 230                 235                 240

Pro Pro Pro Gly Met Arg Gly Leu Leu
                245

<210> SEQ ID NO 97
<211> LENGTH: 729
<212> TYPE: PRT
<213> ORGANISM: Homo Sapiens

<400> SEQUENCE: 97

Leu Leu Leu Trp Leu Asn Pro Gln Ala Leu Val Gly Ala Gln Gly Gly
1               5                   10                  15

Arg Met Ser Gln Trp Tyr Glu Leu Gln Gln Leu Asp Ser Lys Phe Leu
                20                  25                  30

Glu Gln Val His Gln Leu Tyr Asp Asp Ser Phe Pro Met Glu Ile Arg
            35                  40                  45

Gln Tyr Leu Ala Gln Trp Leu Glu Lys Gln Asp Trp Glu His Ala Ala
        50                  55                  60

Asn Asp Val Ser Phe Ala Thr Ile Arg Phe His Asp Leu Leu Ser Gln
65                  70                  75                  80

Leu Asp Asp Gln Tyr Ser Arg Phe Ser Leu Glu Asn Asn Phe Leu Leu
                85                  90                  95

Gln His Asn Ile Arg Lys Ser Lys Arg Asn Leu Gln Asp Asn Phe Gln
            100                 105                 110

Glu Asp Pro Ile Gln Met Ser Met Ile Ile Tyr Ser Cys Leu Lys Glu
        115                 120                 125

Glu Arg Lys Ile Leu Glu Asn Ala Gln Arg Phe Asn Gln Ala Gln Ser
    130                 135                 140

Gly Asn Ile Gln Ser Thr Val Met Leu Asp Lys Gln Lys Glu Leu Asp
145                 150                 155                 160

Ser Lys Val Arg Asn Val Lys Asp Lys Val Met Cys Ile Glu His Glu
                165                 170                 175

Ile Lys Ser Leu Glu Asp Leu Gln Asp Glu Tyr Asp Phe Lys Cys Lys
            180                 185                 190

Thr Leu Gln Asn Arg Glu His Glu Thr Asn Gly Val Ala Lys Ser Asp
        195                 200                 205

Gln Lys Gln Glu Gln Leu Leu Leu Lys Lys Met Tyr Leu Met Leu Asp
    210                 215                 220

Asn Lys Arg Lys Glu Val Val His Lys Ile Ile Glu Leu Leu Asn Val
225                 230                 235                 240

Thr Glu Leu Thr Gln Asn Ala Leu Ile Asn Asp Glu Leu Val Glu Trp
                245                 250                 255

Lys Arg Arg Gln Gln Ser Ala Cys Ile Gly Gly Pro Pro Asn Ala Cys
            260                 265                 270

Leu Asp Gln Leu Gln Asn Trp Phe Thr Ile Val Ala Glu Ser Leu Gln
        275                 280                 285

Gln Val Arg Gln Gln Leu Lys Lys Leu Glu Glu Leu Glu Gln Lys Tyr
    290                 295                 300

Thr Tyr Glu His Asp Pro Ile Thr Lys Asn Lys Gln Val Leu Trp Asp
305                 310                 315                 320

Arg Thr Phe Ser Leu Phe Gln Gln Leu Ile Gln Ser Ser Phe Val Val
                325                 330                 335
```

-continued

```
Glu Arg Gln Pro Cys Met Pro Thr His Pro Gln Arg Pro Leu Val Leu
            340                 345                 350
Lys Thr Gly Val Gln Phe Thr Val Lys Leu Arg Leu Leu Val Lys Leu
        355                 360                 365
Gln Glu Leu Asn Tyr Asn Leu Lys Val Lys Val Leu Phe Asp Lys Asp
    370                 375                 380
Val Asn Glu Arg Asn Thr Val Lys Gly Phe Arg Lys Phe Asn Ile Leu
385                 390                 395                 400
Gly Thr His Thr Lys Val Met Asn Met Glu Glu Ser Thr Asn Gly Ser
                405                 410                 415
Leu Ala Ala Glu Phe Arg His Leu Gln Leu Lys Glu Gln Lys Asn Ala
            420                 425                 430
Gly Thr Arg Thr Asn Glu Gly Pro Leu Ile Val Thr Glu Glu Leu His
        435                 440                 445
Ser Leu Ser Phe Glu Thr Gln Leu Cys Gln Pro Gly Leu Val Ile Asp
    450                 455                 460
Leu Glu Thr Thr Ser Leu Pro Val Val Ile Ser Asn Val Ser Gln
465                 470                 475                 480
Leu Pro Ser Gly Trp Ala Ser Ile Leu Trp Tyr Asn Met Leu Val Ala
                485                 490                 495
Glu Pro Arg Asn Leu Ser Phe Phe Leu Thr Pro Cys Ala Arg Trp
            500                 505                 510
Ala Gln Leu Ser Glu Val Leu Ser Trp Gln Phe Ser Ser Val Thr Lys
        515                 520                 525
Arg Gly Leu Asn Val Asp Gln Leu Asn Met Leu Gly Glu Lys Leu Leu
    530                 535                 540
Gly Pro Asn Ala Ser Pro Asp Gly Leu Ile Pro Trp Thr Arg Phe Cys
545                 550                 555                 560
Lys Glu Asn Ile Asn Asp Lys Asn Phe Pro Phe Trp Leu Trp Ile Glu
                565                 570                 575
Ser Ile Leu Glu Leu Ile Lys Lys His Leu Leu Pro Leu Trp Asn Asp
            580                 585                 590
Gly Cys Ile Met Gly Phe Ile Ser Lys Glu Arg Glu Arg Ala Leu Leu
        595                 600                 605
Lys Asp Gln Gln Pro Gly Thr Phe Leu Leu Arg Phe Ser Glu Ser Ser
    610                 615                 620
Arg Glu Gly Ala Ile Thr Phe Thr Trp Val Glu Arg Ser Gln Asn Gly
625                 630                 635                 640
Gly Glu Pro Asp Phe His Ala Val Glu Pro Tyr Thr Lys Lys Glu Leu
                645                 650                 655
Ser Ala Val Thr Phe Pro Asp Ile Ile Arg Asn Tyr Lys Val Met Ala
            660                 665                 670
Ala Glu Asn Ile Pro Glu Asn Pro Leu Lys Tyr Leu Tyr Pro Asn Ile
        675                 680                 685
Asp Lys Asp His Ala Phe Gly Lys Tyr Tyr Ser Arg Pro Lys Glu Ala
    690                 695                 700
Pro Glu Pro Met Glu Leu Asp Gly Pro Lys Gly Thr Gly Tyr Ile Lys
705                 710                 715                 720
Thr Glu Leu Ile Ser Val Ser Glu Val
                725

<210> SEQ ID NO 98
<211> LENGTH: 1575
<212> TYPE: PRT
```

-continued

```
<213> ORGANISM: Homo Sapiens

<400> SEQUENCE: 98

Arg Gly Arg Leu Leu Gly Leu Leu Asn Pro Ser Val Ser Leu Gly Arg
1               5                   10                  15

Pro Lys Val Arg Val Met Tyr Arg Asp Glu Cys Lys Lys His Leu Ala
            20                  25                  30

Gly Leu Gly Ala Leu Gly Leu Gly Ser Leu Ile Thr Glu Leu Thr Ala
        35                  40                  45

Asn Glu Glu Leu Thr Gly Thr Asp Gly Ala Leu Val Asn Asp Glu Gly
    50                  55                  60

Trp Val Arg Ser Thr Glu Asp Ala Val Asp Tyr Ser Asp Ile Asn Glu
65                  70                  75                  80

Val Ala Glu Asp Glu Ser Arg Arg Tyr Gln Gln Thr Met Gly Ser Leu
                85                  90                  95

Gln Pro Leu Cys His Ser Asp Tyr Asp Glu Asp Tyr Asp Ala Asp
            100                 105                 110

Cys Glu Asp Ile Asp Cys Lys Leu Met Pro Pro Pro Pro Pro Pro
            115                 120                 125

Gly Pro Met Lys Lys Asp Lys Asp Gln Asp Ser Ile Thr Gly Glu Lys
        130                 135                 140

Val Asp Phe Ser Ser Ser Ser Asp Ser Glu Ser Glu Met Gly Pro Gln
145                 150                 155                 160

Glu Ala Thr Gln Ala Glu Ser Glu Asp Gly Lys Leu Thr Leu Pro Leu
                165                 170                 175

Ala Gly Ile Met Gln His Asp Ala Thr Lys Leu Leu Pro Ser Val Thr
            180                 185                 190

Glu Leu Phe Pro Glu Phe Arg Pro Gly Lys Val Leu Arg Phe Leu Arg
        195                 200                 205

Leu Phe Gly Pro Gly Lys Asn Val Pro Ser Val Trp Arg Ser Ala Arg
    210                 215                 220

Arg Lys Arg Lys Lys Lys His Arg Glu Leu Ile Gln Glu Glu Gln Ile
225                 230                 235                 240

Gln Glu Val Glu Cys Ser Val Glu Ser Glu Val Ser Gln Lys Ser Leu
                245                 250                 255

Trp Asn Tyr Asp Tyr Ala Pro Pro Pro Pro Glu Gln Cys Leu Ser
            260                 265                 270

Asp Asp Glu Ile Thr Met Met Ala Pro Val Ser Lys Phe Ser Gln
            275                 280                 285

Ser Thr Gly Asp Ile Asp Lys Val Thr Asp Thr Lys Pro Arg Val Ala
        290                 295                 300

Glu Trp Arg Tyr Gly Pro Ala Arg Leu Trp Tyr Asp Met Leu Gly Val
305                 310                 315                 320

Pro Glu Asp Gly Ser Gly Phe Asp Tyr Gly Phe Lys Leu Arg Lys Thr
            325                 330                 335

Glu His Glu Pro Val Ile Lys Ser Arg Met Ile Glu Glu Phe Arg Lys
            340                 345                 350

Leu Glu Glu Asn Asn Gly Thr Asp Leu Leu Ala Asp Glu Asn Phe Leu
            355                 360                 365

Met Val Thr Gln Leu His Trp Glu Asp Ile Ile Trp Asp Gly Glu
    370                 375                 380

Asp Val Lys His Lys Gly Thr Lys Pro Gln Arg Ala Ser Leu Ala Gly
385                 390                 395                 400
```

-continued

```
Trp Leu Pro Ser Ser Met Thr Arg Asn Ala Met Ala Tyr Asn Val Gln
            405                 410                 415

Gln Gly Phe Ala Ala Thr Leu Asp Asp Lys Pro Trp Tyr Ser Ile
        420                 425                 430

Phe Pro Ile Asp Asn Glu Asp Leu Val Tyr Gly Arg Trp Glu Asp Asn
        435                 440                 445

Ile Ile Trp Asp Ala Gln Ala Met Pro Arg Leu Leu Glu Pro Pro Val
    450                 455                 460

Leu Thr Leu Asp Pro Asn Asp Glu Asn Leu Ile Leu Glu Ile Pro Asp
465                 470                 475                 480

Glu Lys Glu Glu Ala Thr Ser Asn Ser Pro Ser Lys Glu Ser Lys Lys
                485                 490                 495

Glu Ser Ser Leu Lys Lys Ser Arg Ile Leu Leu Gly Lys Thr Gly Val
            500                 505                 510

Ile Lys Glu Glu Pro Gln Gln Asn Met Ser Gln Pro Glu Val Lys Asp
        515                 520                 525

Pro Trp Asn Leu Ser Asn Asp Glu Tyr Tyr Tyr Pro Lys Gln Gln Gly
    530                 535                 540

Leu Arg Gly Thr Phe Gly Gly Asn Ile Ile Gln His Ser Ile Pro Ala
545                 550                 555                 560

Val Glu Leu Arg Gln Pro Phe Phe Pro Thr His Met Gly Pro Ile Lys
                565                 570                 575

Leu Arg Gln Phe His Arg Pro Pro Leu Lys Lys Tyr Ser Phe Gly Ala
            580                 585                 590

Leu Ser Gln Pro Gly Pro His Ser Val Gln Pro Leu Leu Lys His Ile
        595                 600                 605

Lys Lys Lys Ala Lys Met Arg Glu Gln Glu Arg Gln Ala Ser Gly Gly
    610                 615                 620

Gly Glu Met Phe Phe Met Arg Thr Pro Gln Asp Leu Thr Gly Lys Asp
625                 630                 635                 640

Gly Asp Leu Ile Leu Ala Glu Tyr Ser Glu Glu Asn Gly Pro Leu Met
                645                 650                 655

Met Gln Val Gly Met Ala Thr Lys Ile Lys Asn Tyr Lys Arg Lys
            660                 665                 670

Pro Gly Lys Asp Pro Gly Ala Pro Asp Cys Lys Tyr Gly Glu Thr Val
        675                 680                 685

Tyr Cys His Thr Ser Pro Phe Leu Gly Ser Leu His Pro Gly Gln Leu
    690                 695                 700

Leu Gln Ala Phe Glu Asn Asn Leu Phe Arg Ala Pro Ile Tyr Leu His
705                 710                 715                 720

Lys Met Pro Glu Thr Asp Phe Leu Ile Ile Arg Thr Arg Gln Gly Tyr
                725                 730                 735

Tyr Ile Arg Glu Leu Val Asp Ile Phe Val Val Gly Gln Gln Cys Pro
            740                 745                 750

Leu Phe Glu Val Pro Gly Pro Asn Ser Lys Arg Ala Asn Thr His Ile
        755                 760                 765

Arg Asp Phe Leu Gln Val Phe Ile Tyr Arg Leu Phe Trp Lys Ser Lys
    770                 775                 780

Asp Arg Pro Arg Arg Ile Arg Met Glu Asp Ile Lys Lys Ala Phe Pro
785                 790                 795                 800

Ser His Ser Glu Ser Ser Ile Arg Lys Arg Leu Lys Leu Cys Ala Asp
                805                 810                 815

Phe Lys Arg Thr Gly Met Asp Ser Asn Trp Trp Val Leu Lys Ser Asp
```

-continued

```
                    820                 825                 830
Phe Arg Leu Pro Thr Glu Glu Ile Arg Ala Met Val Ser Pro Glu
            835                 840                 845
Gln Cys Cys Ala Tyr Tyr Ser Met Ile Ala Ala Glu Gln Arg Leu Lys
        850                 855                 860
Asp Ala Gly Tyr Gly Glu Lys Ser Phe Phe Ala Pro Glu Glu Asn
865                 870                 875                 880
Glu Glu Asp Phe Gln Met Lys Ile Asp Asp Glu Val Arg Thr Ala Pro
                885                 890                 895
Trp Asn Thr Thr Arg Ala Phe Ile Ala Ala Met Lys Gly Lys Cys Leu
                900                 905                 910
Leu Glu Val Thr Gly Val Ala Asp Pro Thr Gly Cys Gly Glu Gly Phe
            915                 920                 925
Ser Tyr Val Lys Ile Pro Asn Lys Pro Thr Gln Gln Lys Asp Asp Lys
        930                 935                 940
Glu Pro Gln Pro Val Lys Lys Thr Val Thr Gly Thr Asp Ala Asp Leu
945                 950                 955                 960
Arg Arg Leu Ser Leu Lys Asn Ala Lys Gln Leu Leu Arg Lys Phe Gly
                965                 970                 975
Val Pro Glu Glu Glu Ile Lys Lys Leu Ser Arg Trp Glu Val Ile Asp
                980                 985                 990
Val Val Arg Thr Met Ser Thr Glu  Gln Ala Arg Ser Gly  Glu Gly Pro
            995                 1000                1005
Met Ser  Lys Phe Ala Arg Gly  Ser Arg Phe Ser Val  Ala Glu His
    1010                1015                1020
Gln Glu  Arg Tyr Lys Glu Glu  Cys Gln Arg Ile Phe  Asp Leu Gln
    1025                1030                1035
Asn Lys  Val Leu Ser Ser Thr  Glu Val Leu Ser Thr  Asp Thr Asp
    1040                1045                1050
Ser Ser  Ser Ala Glu Asp Ser  Asp Phe Glu Glu Met  Gly Lys Asn
    1055                1060                1065
Ile Glu  Asn Met Leu Gln Asn  Lys Lys Thr Ser Ser  Gln Leu Ser
    1070                1075                1080
Arg Glu  Arg Glu Glu Gln Glu  Arg Lys Glu Leu Gln  Arg Met Leu
    1085                1090                1095
Leu Ala  Ala Gly Ser Ala Ala  Ser Gly Asn Asn His  Arg Asp Asp
    1100                1105                1110
Asp Thr  Ala Ser Val Thr Ser  Leu Asn Ser Ser Ala  Thr Gly Arg
    1115                1120                1125
Cys Leu  Lys Ile Tyr Arg Thr  Phe Arg Asp Glu Glu  Gly Lys Glu
    1130                1135                1140
Tyr Val  Arg Cys Glu Thr Val  Arg Lys Pro Ala Val  Ile Asp Ala
    1145                1150                1155
Tyr Val  Arg Ile Arg Thr Thr  Lys Asp Glu Glu Phe  Ile Arg Lys
    1160                1165                1170
Phe Ala  Leu Phe Asp Glu Gln  His Arg Glu Glu Met  Arg Lys Glu
    1175                1180                1185
Arg Arg  Arg Ile Gln Glu Gln  Leu Arg Arg Leu Lys  Arg Asn Gln
    1190                1195                1200
Glu Lys  Glu Lys Leu Lys Gly  Pro Pro Glu Lys Lys  Pro Lys Lys
    1205                1210                1215
Met Lys  Glu Arg Pro Asp Leu  Lys Leu Lys Cys Gly  Ala Cys Gly
    1220                1225                1230
```

-continued

```
Ala Ile Gly His Met Arg Thr Asn Lys Phe Cys Pro Leu Tyr Tyr
    1235                1240                1245

Gln Thr Asn Ala Pro Pro Ser Asn Pro Val Ala Met Thr Glu Glu
    1250                1255                1260

Gln Glu Glu Glu Leu Glu Lys Thr Val Ile His Asn Asp Asn Glu
    1265                1270                1275

Glu Leu Ile Lys Val Glu Gly Thr Lys Ile Val Leu Gly Lys Gln
    1280                1285                1290

Leu Ile Glu Ser Ala Asp Glu Val Arg Arg Lys Ser Leu Val Leu
    1295                1300                1305

Lys Phe Pro Lys Gln Gln Leu Pro Pro Lys Lys Arg Arg Val
    1310                1315                1320

Gly Thr Thr Val His Cys Asp Tyr Leu Asn Arg Pro His Lys Ser
    1325                1330                1335

Ile His Arg Arg Arg Thr Asp Pro Met Val Thr Leu Ser Ser Ile
    1340                1345                1350

Leu Glu Ser Ile Ile Asn Asp Met Arg Asp Leu Pro Asn Thr Tyr
    1355                1360                1365

Pro Phe His Thr Pro Val Asn Ala Lys Val Val Lys Asp Tyr Tyr
    1370                1375                1380

Lys Ile Ile Thr Arg Pro Met Asp Leu Gln Thr Leu Arg Glu Asn
    1385                1390                1395

Val Arg Lys Arg Leu Tyr Pro Ser Arg Glu Glu Phe Arg Glu His
    1400                1405                1410

Leu Glu Leu Ile Val Lys Asn Ser Ala Thr Tyr Asn Gly Pro Lys
    1415                1420                1425

His Ser Leu Thr Gln Ile Ser Gln Ser Met Leu Asp Leu Cys Asp
    1430                1435                1440

Glu Lys Leu Lys Glu Lys Glu Asp Lys Leu Ala Arg Leu Glu Lys
    1445                1450                1455

Ala Ile Asn Pro Leu Leu Asp Asp Asp Gln Val Ala Phe Ser
    1460                1465                1470

Phe Ile Leu Asp Asn Ile Val Thr Gln Lys Met Met Ala Val Pro
    1475                1480                1485

Asp Ser Trp Pro Phe His His Pro Val Asn Lys Lys Phe Val Pro
    1490                1495                1500

Asp Tyr Tyr Lys Val Ile Val Asn Pro Met Asp Leu Glu Thr Ile
    1505                1510                1515

Arg Lys Asn Ile Ser Lys His Lys Tyr Gln Ser Arg Glu Ser Phe
    1520                1525                1530

Leu Asp Asp Val Asn Leu Ile Leu Ala Asn Ser Val Lys Tyr Asn
    1535                1540                1545

Asp Asn Glu Cys Ser Ser Lys Ala Asn Asp Ile Val Cys Leu Ile
    1550                1555                1560

Gln Tyr Cys Ser Ser Gln Ile Glu Glu Leu Arg Phe
    1565                1570                1575

<210> SEQ ID NO 99
<211> LENGTH: 166
<212> TYPE: PRT
<213> ORGANISM: Homo Sapiens

<400> SEQUENCE: 99

Leu Cys Leu Lys Lys Lys Ile Pro Asn Met Asp Lys Pro Arg Lys Glu
1               5                   10                  15
```

-continued

```
Asn Glu Glu Pro Gln Ser Arg Pro Arg Pro Met Arg Arg Gly Leu
             20                  25                  30

Arg Trp Ser Thr Leu Pro Lys Ser Ser Pro Pro Arg Ser Ser Leu Arg
         35                  40                  45

Arg Ser Ser Pro Arg Arg Ser Ser Phe Leu Arg Ser Ser Cys Leu
 50                  55                  60

Ser Ser Cys Leu Arg Cys Ser Ser Arg Arg Thr Pro Ser Ala Gly Leu
 65                  70                  75                  80

Ser Arg Lys Asp Leu Phe Glu Val Arg Pro Pro Met Glu Gln Pro Pro
             85                  90                  95

Cys Gly Val Gly Lys His Asn Leu Glu Glu Gly Ile Phe Lys Glu Arg
             100                 105                 110

Leu Ala Arg Ser Arg Pro Gln Phe Arg Gly Asp Ile His Gly Arg Asn
             115                 120                 125

Leu Ser Asn Glu Glu Met Ile Gln Ala Ala Asp Glu Leu Glu Glu Met
             130                 135                 140

Lys Arg Val Arg Asn Lys Leu Met Ile Met His Trp Arg Ala Lys Arg
145                 150                 155                 160

Gly Gly Pro Tyr Pro Ile
             165

<210> SEQ ID NO 100
<211> LENGTH: 245
<212> TYPE: PRT
<213> ORGANISM: Homo Sapiens

<400> SEQUENCE: 100

Thr Lys Met Leu Lys Ser Trp Arg Ser Gly Arg Gln Ile Thr Gln Lys
1               5                   10                  15

Gly Thr Glu Asp Glu Leu Asp Lys Tyr Ser Glu Ala Leu Lys Asp Ala
             20                  25                  30

Gln Glu Lys Leu Glu Leu Ala Glu Lys Ala Thr Asp Ala Glu Ala
         35                  40                  45

Asp Val Ala Ser Leu Asn Arg Arg Ile Gln Leu Val Glu Glu Glu Leu
 50                  55                  60

Asp Arg Ala Gln Glu Arg Leu Ala Thr Ala Leu Gln Lys Leu Glu Glu
 65                  70                  75                  80

Ala Glu Lys Ala Ala Asp Glu Ser Glu Arg Gly Met Lys Val Ile Glu
             85                  90                  95

Ser Arg Ala Gln Lys Asp Glu Glu Lys Met Glu Ile Gln Glu Ile Gln
             100                 105                 110

Leu Lys Glu Ala Lys His Ile Ala Glu Asp Ala Asp Arg Lys Tyr Glu
             115                 120                 125

Glu Val Ala Arg Lys Leu Val Ile Ile Glu Ser Asp Leu Glu Arg Ala
             130                 135                 140

Glu Glu Arg Ala Glu Leu Ser Glu Gly Gln Val Arg Gln Leu Glu Glu
145                 150                 155                 160

Gln Leu Arg Ile Met Asp Gln Thr Leu Lys Ala Leu Met Ala Ala Glu
             165                 170                 175

Asp Lys Tyr Ser Gln Lys Glu Asp Arg Tyr Glu Glu Ile Lys Val
             180                 185                 190

Leu Ser Asp Lys Leu Lys Glu Ala Glu Thr Arg Ala Glu Phe Ala Glu
             195                 200                 205

Arg Ser Val Thr Lys Leu Glu Lys Ser Ile Asp Asp Leu Glu Glu Lys
```

```
              210                 215                 220
Val Leu Met Pro Lys Lys Thr Leu Val Cys Ile Arg Cys Trp Ile
225                 230                 235                 240

Arg Leu Tyr Trp Ser
                245
```

<210> SEQ ID NO 101
<211> LENGTH: 267
<212> TYPE: PRT
<213> ORGANISM: Homo Sapiens

<400> SEQUENCE: 101

```
Leu Pro Val Leu Ala Ser Arg Ala Tyr Ala Pro Ala Pro Gly Gln
1               5                   10                  15

Ala Leu Gln Arg Val Gly Ile Val Gly Gln Glu Ala Pro Arg Ser
                20                  25                  30

Lys Trp Pro Trp Gln Val Ser Leu Arg Val Arg Asp Arg Tyr Trp Met
                35                  40                  45

His Phe Cys Gly Gly Ser Leu Ile His Pro Gln Trp Val Leu Thr Ala
            50                  55                  60

Ala His Cys Val Gly Pro Asp Val Lys Asp Leu Ala Ala Leu Arg Val
65                  70                  75                  80

Gln Leu Arg Glu Gln His Leu Tyr Tyr Gln Asp Gln Leu Leu Pro Val
                85                  90                  95

Ser Arg Ile Ile Val His Pro Gln Phe Tyr Thr Ala Gln Ile Gly Ala
                100                 105                 110

Asp Ile Ala Leu Leu Glu Leu Glu Glu Pro Val Lys Val Ser Ser His
                115                 120                 125

Val His Thr Val Thr Leu Pro Pro Ala Ser Glu Thr Phe Pro Pro Gly
                130                 135                 140

Met Pro Cys Trp Val Thr Gly Trp Gly Asp Val Asp Asn Asp Glu Arg
145                 150                 155                 160

Leu Pro Pro Pro Phe Pro Leu Lys Gln Val Lys Val Pro Ile Met Glu
                165                 170                 175

Asn His Ile Cys Asp Ala Lys Tyr His Leu Gly Ala Tyr Thr Gly Asp
                180                 185                 190

Asp Val Arg Ile Val Arg Asp Met Leu Cys Ala Gly Asn Thr Arg
                195                 200                 205

Arg Asp Ser Cys Gln Gly Asp Ser Gly Gly Pro Leu Val Cys Lys Val
                210                 215                 220

Asn Gly Thr Trp Leu Gln Ala Gly Val Val Ser Trp Gly Glu Gly Cys
225                 230                 235                 240

Ala Gln Pro Asn Arg Pro Gly Ile Tyr Thr Arg Val Thr Tyr Tyr Leu
                245                 250                 255

Asp Trp Ile His His Tyr Val Pro Lys Lys Pro
                260                 265
```

<210> SEQ ID NO 102
<211> LENGTH: 192
<212> TYPE: PRT
<213> ORGANISM: Homo Sapiens

<400> SEQUENCE: 102

```
Ala Arg Ala Ser Ser Cys Leu Ser Ala Asn Ala Arg Met Ala Ser
1               5                   10                  15

Gln Asn Arg Asp Pro Ala Ala Thr Ser Val Ala Ala Ala Arg Lys Gly
```

```
                    20                  25                  30
Ala Glu Pro Ser Gly Gly Ala Ala Arg Gly Pro Val Gly Lys Arg Leu
        35                  40                  45
Gln Gln Glu Leu Met Thr Leu Met Met Ser Gly Asp Lys Gly Ile Ser
    50                  55                  60
Ala Phe Pro Glu Ser Asp Asn Leu Phe Lys Trp Val Gly Thr Ile His
65                  70                  75                   80
Gly Ala Ala Gly Thr Val Tyr Glu Asp Leu Arg Tyr Lys Leu Ser Leu
            85                  90                  95
Glu Phe Pro Ser Gly Tyr Pro Tyr Asn Ala Pro Thr Val Lys Phe Leu
            100                 105                 110
Thr Pro Cys Tyr His Pro Asn Val Asp Thr Gln Gly Asn Ile Cys Leu
        115                 120                 125
Asp Ile Leu Lys Glu Lys Trp Ser Ala Leu Tyr Asp Val Arg Thr Ile
    130                 135                 140
Leu Leu Ser Ile Gln Ser Leu Leu Gly Glu Pro Asn Ile Asp Ser Pro
145                 150                 155                 160
Leu Asn Thr His Ala Ala Glu Leu Trp Lys Asn Pro Thr Ala Phe Lys
            165                 170                 175
Lys Tyr Leu Gln Glu Thr Tyr Ser Lys Gln Val Thr Ser Gln Glu Pro
            180                 185                 190
```